United States Patent
Han et al.

(10) Patent No.: US 10,784,447 B2
(45) Date of Patent: *Sep. 22, 2020

(54) ORGANIC COMPOUND, COMPOSITION, AND ORGANIC OPTOELECTRONIC DIODE

(71) Applicant: SAMSUNG SDI CO., LTD., Yongin-si, Gyeonggi-do (KR)

(72) Inventors: Sujin Han, Suwon-si (KR); Dong Min Kang, Suwon-si (KR); Soohyun Min, Suwon-si (KR); Eun Sun Yu, Suwon-si (KR); Byoungkwan Lee, Suwon-si (KR); Hanill Lee, Suwon-si (KR); Sung-Hyun Jung, Suwon-si (KR); Ho Kuk Jung, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/567,491

(22) PCT Filed: Nov. 18, 2015

(86) PCT No.: PCT/KR2015/012412
§ 371 (c)(1),
(2) Date: Oct. 18, 2017

(87) PCT Pub. No.: WO2016/171356
PCT Pub. Date: Oct. 27, 2016

(65) Prior Publication Data
US 2018/0114918 A1 Apr. 26, 2018

(30) Foreign Application Priority Data
Apr. 24, 2015 (KR) .................. 10-2015-0058116

(51) Int. Cl.
| | |
|---|---|
| H01L 51/00 | (2006.01) |
| C07D 213/16 | (2006.01) |
| C07D 239/24 | (2006.01) |
| C07D 239/26 | (2006.01) |
| C07D 251/24 | (2006.01) |
| C07D 401/10 | (2006.01) |
| C07D 401/14 | (2006.01) |

(Continued)

(52) U.S. Cl.
CPC ........ *H01L 51/0067* (2013.01); *C07D 209/86* (2013.01); *C07D 213/16* (2013.01); *C07D 213/22* (2013.01); *C07D 239/26* (2013.01); *C07D 251/24* (2013.01); *C07D 401/14* (2013.01); *C07D 487/04* (2013.01); *C09K 11/06* (2013.01); *H01L 51/005* (2013.01); *H01L 51/0054* (2013.01); *C09K 2211/1007* (2013.01); *C09K 2211/1018* (2013.01); *C09K 2211/1029* (2013.01); *C09K 2211/185* (2013.01); *H01L 51/0052* (2013.01); *H01L 51/0072* (2013.01); *H01L 51/508* (2013.01); *H01L 51/5016* (2013.01); *H01L 2251/5384* (2013.01)

(58) Field of Classification Search
CPC . H01L 51/0067; C07D 213/16; C07D 239/24; C07D 239/26; C07D 251/24
See application file for complete search history.

(56) References Cited

U.S. PATENT DOCUMENTS

| | | | |
|---|---|---|---|
| 6,057,048 A | 5/2000 | Hu et al. | |
| 6,225,467 B1 | 5/2001 | Esteghamatian et al. | |

(Continued)

FOREIGN PATENT DOCUMENTS

| | | |
|---|---|---|
| CN | 1010510585 A | 8/2009 |
| CN | 101656301 A | 2/2010 |

(Continued)

OTHER PUBLICATIONS

Su, Shi-Jian et al., Novel Four-Pyridylbenzene-Armed Biphenyls as Electron-Transport Materials for Phosphorescent OLEDs, Organic Letters, 2008, vol. 10, No. 5, p. 941-944.

(Continued)

*Primary Examiner* — Emily A Bernhardt
*Assistant Examiner* — Laura M Daniel
(74) *Attorney, Agent, or Firm* — Lee IP Law, P.C.

(57) ABSTRACT

The present invention relates to: an organic compound represented by Chemical Formula 1; a composition for an organic optoelectronic diode containing the organic compound; and an organic optoelectronic diode to which the organic compound or the composition is applied.

[Chemical Formula 1]

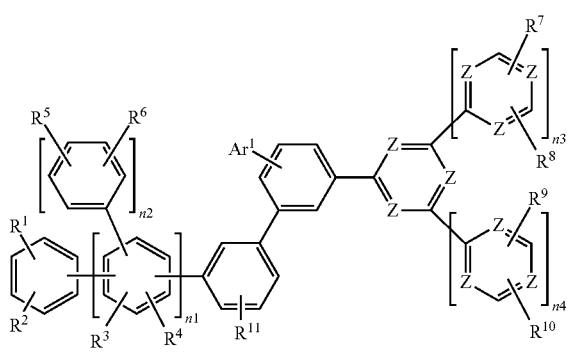

In Chemical Formula 1, Z, $R^1$ to $R^{11}$, and n1 to n4 are the same as those defined in the specification.

12 Claims, 2 Drawing Sheets

(51) Int. Cl.
*C09K 11/06* (2006.01)
*C07D 213/22* (2006.01)
*C07D 209/86* (2006.01)
*C07D 487/04* (2006.01)
*H01L 51/50* (2006.01)

(56) References Cited

U.S. PATENT DOCUMENTS

| | | | |
|---|---|---|---|
| 6,821,643 | B1 | 11/2004 | Hu et al. |
| 2003/0166920 | A1 | 9/2003 | Lu et al. |
| 2007/0190355 | A1 | 8/2007 | Ikeda et al. |
| 2010/0039026 | A1 | 2/2010 | Yang et al. |
| 2011/0278555 | A1 | 11/2011 | Inoue et al. |
| 2013/0241904 | A1 | 9/2013 | Lo et al. |
| 2014/0131665 | A1 | 5/2014 | Xia et al. |
| 2016/0301012 | A1* | 10/2016 | Han .............. H01L 51/0067 |
| 2017/0098778 | A1* | 4/2017 | Oh .................. C07D 209/86 |
| 2018/0114918 | A1 | 4/2018 | Han et al. |

FOREIGN PATENT DOCUMENTS

| | | |
|---|---|---|
| CN | 10-2036957 A | 4/2011 |
| CN | 102272122 | 12/2011 |
| CN | 102439004 A | 5/2012 |
| CN | 103391922 A | 11/2013 |
| EP | 2 091 095 A2 | 8/2009 |
| JP | 2005-302657 A | 10/2005 |
| JP | 2007-223929 A | 9/2007 |
| JP | 2007-534722 A | 11/2007 |
| JP | 4106974 B2 | 6/2008 |
| JP | 2008-280330 A | 11/2008 |
| JP | 2009-224512 A | 10/2009 |
| JP | 4474493 B1 | 6/2010 |
| JP | 2012-149059 A | 9/2012 |
| JP | 5206907 B1 | 6/2013 |
| JP | 2013-183113 A | 9/2013 |
| JP | 5312824 B2 | 10/2013 |
| JP | 2015-027986 A | 2/2015 |
| KR | 2000-0052560 A | 8/2000 |
| KR | 10-2007-0009074 A | 1/2007 |
| KR | 10-0721565 B1 | 5/2007 |
| KR | 10-2007-0090952 A | 9/2007 |
| KR | 10-2008-0039941 A | 5/2008 |
| KR | 10-2009-0047547 A | 5/2009 |
| KR | 10-2009-0101954 A | 9/2009 |
| KR | 10-2009-0130008 A | 12/2009 |
| KR | 10-2010-0021908 A | 2/2010 |
| KR | 10-0958641 B1 | 5/2010 |
| KR | 10-2011-0017392 A | 2/2011 |
| KR | 10-2011-0049012 A | 5/2011 |
| KR | 10-2011-0049554 A | 5/2011 |
| KR | 10-2011-0106325 A | 9/2011 |
| KR | 10-2012-0025006 A | 3/2012 |
| KR | 10-2012-0046778 A | 5/2012 |
| KR | 10-2012-0082938 A | 7/2012 |
| KR | 10-2013-0130788 A | 12/2013 |
| KR | 10-2014-0010133 A | 1/2014 |
| KR | 10-20140135524 A | 11/2014 |
| KR | 10-2014-0145000 A | 12/2014 |
| KR | 10-2015-0088712 A | 3/2015 |
| KR | 10-1502316 B1 | 3/2015 |
| KR | 10-2015-0036736 A | 4/2015 |
| KR | 10-2015-0117173 A | 10/2015 |
| KR | 10-2015-0120875 A | 10/2015 |
| KR | 10-2015-0129282 A | 11/2015 |
| KR | 10-2016-0049842 A | 5/2016 |
| KR | 10-2016-0051133 A | 5/2016 |
| KR | 10-2016-0051142 A | 5/2016 |
| KR | 10-1829745 B1 | 2/2018 |
| TW | 2010-33176 | 9/2010 |
| WO | WO 2005-003783 A | 1/2005 |
| WO | WO 2005-085387 A | 9/2005 |
| WO | WO 2006-067976 A | 6/2006 |
| WO | WO 2007-023840 A | 1/2007 |
| WO | WO 2010-080471 A | 7/2010 |
| WO | WO 2012-059600 A | 5/2012 |
| WO | WO 2012-087960 A1 | 6/2012 |
| WO | WO 2012-137958 A | 10/2012 |
| WO | WO 2014-171541 A1 | 10/2014 |
| WO | WO 2015-111848 A1 | 7/2015 |

OTHER PUBLICATIONS

Su, Shi-Jian, et al., "Pyridine-Containing Triphenylbenzene Derivatives with High Electron Mobility for Highly Efficient Phosphorescent OLEDs." Advanced Materials, 2008, vol. 20, No. 11, pp. 2125-2130.
Su, Shi-Jian, et al., "Structure-Property Relationship of Pyridine-Containing Triphenyl Benzene Electron-Transport Materials for Highly Efficient Blue Phosphorescent OLEDs." Advanced Functional Materials, 2009, vol. 19, No. 9, pp. 1260-1267.
Daisuke Yokoyama, et al., "Molecular stacking induced by intermolecular C—H—N hydrogen bonds leading to high carrier mobility in vacuum-deposited organic films", Advanced Functional Materials, 2011, vol. 21, No. 8, pp. 1375-1382.
International Search Report for PCT/KR2015/012412 filed on Nov. 18, 2015.
Kimura et al. A Rigid 1,3,5,-phenylene-based metallodendrimer containing a ruthenium bis(terpyridyl) complex, Oct. 26, 1999, The Royal Society of Chemistry 2000.
Chinese Office Action dated Oct. 9, 2019.
U.S. Appl. No. 15/037,419, filed May 18, 2016, Alexander Kollias.
Chinese Search Report dated Jun. 28, 2017.
Search Report dated Feb. 27, 2018, which was attached to the Office Action dated Mar. 7, 2018, of the corresponding Chinese Patent Application No. 201480073378.2.
Provisional double patenting rejection over claims of the above-identified application; USPTO Office action dated Dec. 17, 2018, in U.S. Appl. No. 15/316,720.
USPTO rejection dated Jul. 24, 2017 for U.S. Appl. No. 15/037,419.
USPTO Final rejection dated Nov. 2, 2017 for U.S. Appl. No. 15/037,419.
USPTO rejection dated Sep. 24, 2018 for U.S. Appl. No. 15/037,419.
USPTO Final rejection dated Feb. 5, 2019 for U.S. Appl. No. 15/037,419.
USPTO rejection dated Nov. 8, 2019 for U.S. Appl. No. 15/037,420.
Provisional double patenting rejection over claims of the above-identified application; USPTO Office action dated Nov. 8, 2019, in U.S. Appl. No. 15/037,419.

* cited by examiner

【Figure 1】
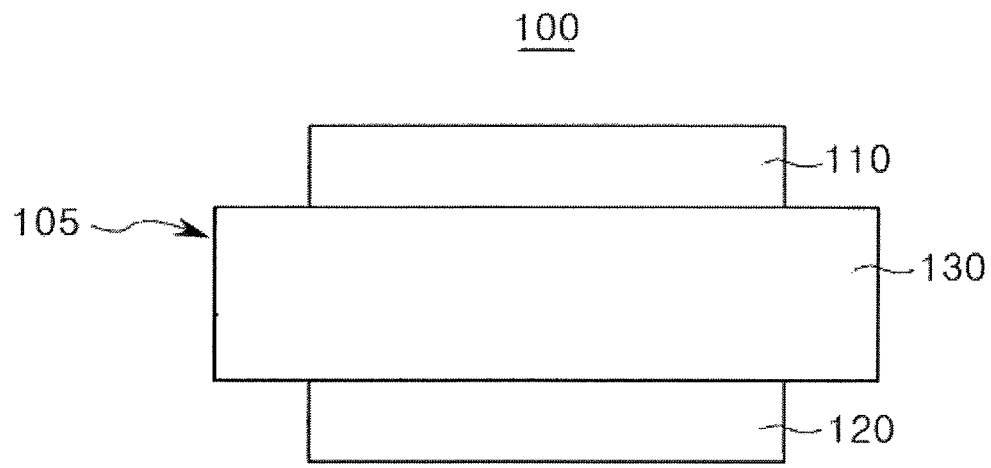
【Figure 2】
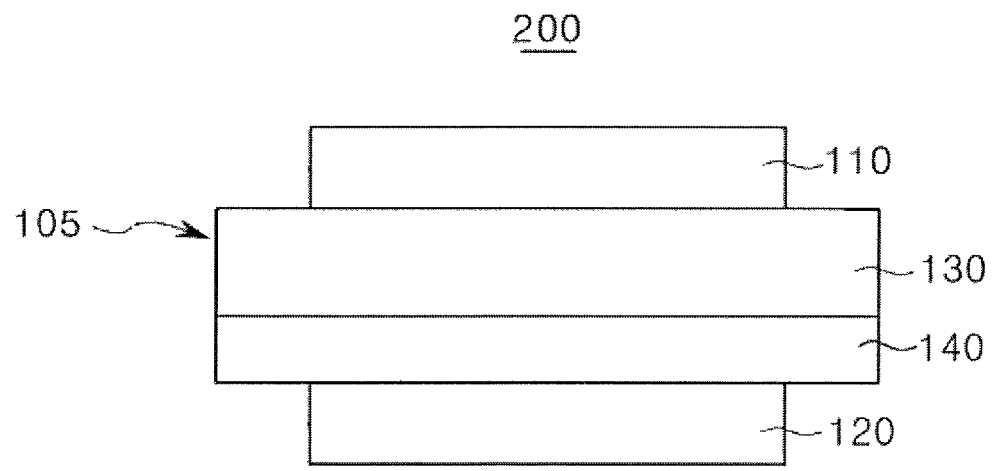

[Figure 3]
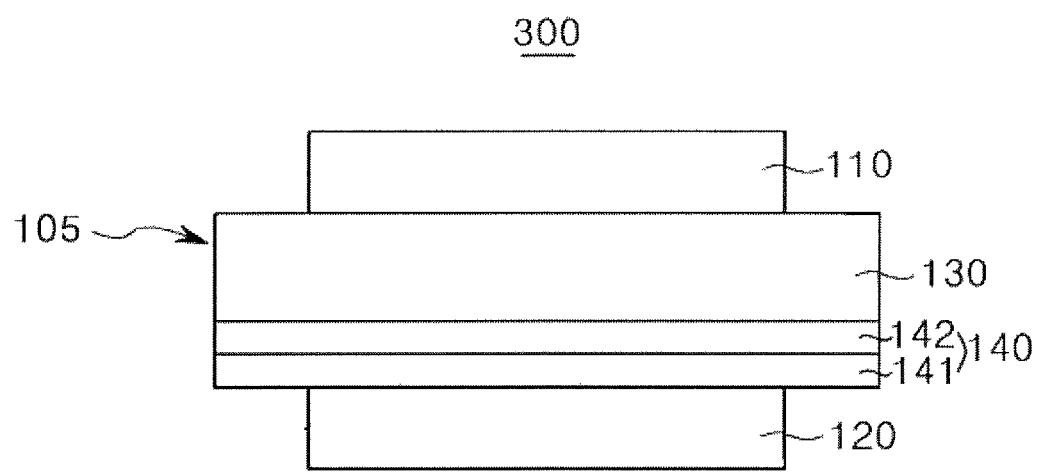

ORGANIC COMPOUND, COMPOSITION, AND ORGANIC OPTOELECTRONIC DIODE

CROSS REFERENCE TO RELATED APPLICATIONS

This is the U.S. national phase application based on PCT/KR2015/012412 filed Nov. 18, 2015, which is based on Korean Patent Application No. 10-2015-0058116 filed Apr. 24, 2015, the entire contents of all of which are hereby incorporated by reference.

TECHNICAL FIELD

An organic compound, a composition, and organic optoelectronic diode are disclosed.

BACKGROUND ART

An organic optoelectronic diode is a device that converts electrical energy into photoenergy, and vice versa.

An organic optoelectronic diode may be classified as follows in accordance with its driving principles. One is a photoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectronic diode may be an organic photoelectric diode, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron transport auxiliary layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides an organic compound capable of realizing an organic optoelectronic diode having high efficiency and a long life-span.

Another embodiment provides a composition for an organic optoelectronic diode containing the organic compound.

Yet another embodiment provides an organic optoelectronic diode including the organic compound.

Technical Solution

According to an embodiment, an organic compound represented by Chemical Formula 1 is provided.

[Chemical Formula 1]

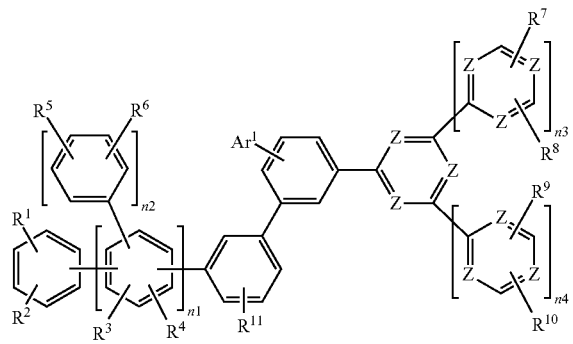

In Chemical Formula I,
Z is independently N, C, or $CR^a$,
at least one of Z's is N,
$Ar^1$ is a substituted or unsubstituted C6 to C12 aryl group or a substituted or unsubstituted C3 to C12 nitrogen-containing six-membered ring,
$R^1$ to $R^6$, $R^{11}$ and $R^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof,
$R^7$ to $R^{10}$ are independently hydrogen, deuterium, a substituted or unsubstituted C6 to C10 aryl group or a substituted or unsubstituted C3 to C12 heterocyclic group,
$R^1$ and $R^2$ are independently present or linked with each other to form a ring,
$R^5$ and $R^6$ are independently present or linked with each other to form a ring,
$R^7$ and $R^8$ are independently present or linked with each other to form a ring,
$R^9$ and $R^{10}$ are independently present or linked with each other to form a ring,
n1 is an integer ranging from 1 to 5,
n2 is an integer ranging from 0 to 2, and
n3 and n4 are independently 0 or 1.

According to another embodiment, a composition for an organic optoelectronic diode includes a first organic compound that is the organic compound and at least one second organic compound having a carbazole moiety.

According to another embodiment, an organic optoelectronic diode includes an anode and a cathode facing each other and at least one organic layer between the anode and the cathode, wherein the organic layer includes the organic compound or the composition for an organic optoelectronic diode.

Advantageous Effects

An organic optoelectronic diode having high efficiency and a long life-span may be realized.

DESCRIPTION OF DRAWINGS

FIG. 1 is a cross-sectional view of an organic light emitting diode according to an embodiment.

FIG. 2 is a cross-sectional view of an organic light emitting diode according to another embodiment.

FIG. 3 is a cross-sectional view of an organic light emitting diode according to another embodiment.

DETAILED DESCRIPTION

Hereinafter, embodiments of the present invention are described in detail. However, these embodiments are exemplary, the present invention is not limited thereto and the present invention is defined by the scope of claims.

In the present specification when a definition is not otherwise provided, "substituted" refers to replacement of at least one hydrogen of a substituent or a compound by deuterium, a halogen, a hydroxy group, an amino group, a C1 to C30 amine group, a nitro group, a C1 to C40 silyl group, a C1 to C30 alkyl group, a C1 to C10 alkylsilyl group, a C6 to C30 aryl group, a C2 to C30 heterocyclic group, a C1 to C20 alkoxy group, a C1 to C10 trifluoroalkyl group such as a trifluoromethyl group, or a cyano group.

In addition, two adjacent substituents of the substituted halogen, a hydroxy group, an amino group, C1 to C20 amine group, a nitro group. C3 to C40 silyl group, C1 to C30 alkyl group, C1 to C10 alkylsilyl group, C6 to C30 aryl group, C3 to C30 heterocyclic group, C1 to C20 alkoxy group, C1 to C10 trifluoroalkyl group such as trifluoromethyl group, or cyano group may be fused to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including at least one heteroatom and remaining carbons in one functional group. The heteroatom may be selected from N, O, S, P, and Si.

In the present specification, "an aryl group" refers to a group including at least one hydrocarbon aromatic moiety, and includes hydrocarbon aromatic moieties linked by a single bond and hydrocarbon aromatic moieties fused directly or indirectly to provide a non-aromatic fused ring. The aryl group may include a monocyclic, polycyclic or fused polycyclic (i.e., rings sharing adjacent pairs of carbon atoms) functional group.

In the present specification, "a heterocyclic group" is a concept including a heteroaryl group, and may include at least one hetero atom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

More specifically, the substituted or unsubstituted aryl group and/or the substituted or unsubstituted heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted terphenyl group, a substituted or unsubstituted quaterphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridinyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, a combination thereof, or a combined fused ring of the foregoing groups, but is not limited thereto.

In the present specification, the substituted or unsubstituted arylene group or the substituted or unsubstituted heteroarylene group or the substituted or unsubstituted divalent heterocyclic group has two linking groups in the substituted or unsubstituted aryl group or the substituted or unsubstituted heterocyclic group, and may be, for example, a substituted or unsubstituted phenylene group, a substituted or unsubstituted naphthalene group, a substituted or unsubstituted anthracenylene group, a substituted or unsubstituted phenanthrylene group, a substituted or unsubstituted naphthacenylene group, a substituted or unsubstituted pyrenylene group, a substituted or unsubstituted biphenylene group, a substituted or unsubstituted terphenylene group, a substituted or unsubstituted quarterphenylene group, a substituted or unsubstituted chrysenylene group, a substituted or unsubstituted triperylenylene group, a substituted or unsubstituted perylenylene group, a substituted or unsubstituted indenylene group, a substituted or unsubstituted furanylene group, a substituted or unsubstituted thiophenylene group, a substituted or unsubstituted pyrrolylene group, a substituted or unsubstituted pyrazolene group, a substituted or unsubstituted imidazolylene group, a substituted or unsubstituted triazolylene group, a substituted or unsubstituted oxazolylene group, a substituted or unsubstituted thiazolylene group, a substituted or unsubstituted oxadiazolylene group, a substituted or unsubstituted thiadiazolylene group, a substituted or unsubstituted pyridinylene group, a substituted or unsubstituted pyrimidinylene group, a substituted or unsubstituted pyrazinylene group, a substituted or unsubstituted triazinylene group, a substituted or unsubstituted benzofuranylene group, a substituted or unsubstituted benzothiophenylene group, a substituted or unsubstituted benzimidazolylene group, a substituted or unsubstituted indolylene group, a substituted or unsubstituted quinolinylene group, a substituted or unsubstituted isoquinolinylene group, a substituted or unsubstituted quinazolinylene group, a substituted or unsubstituted quinoxalinylene group, a substituted or unsubstituted naphthyridinylene group, a substituted or unsubstituted benzoxazinylene group, a substituted or unsubstituted benzthiazinylene group, a substituted or unsubstituted acridinylene group, a substituted or unsubstituted phenazinylene group, a substituted or unsubstituted phenothiazinylene group, a substituted or unsubstituted phenoxazinylene group, a substituted or unsubstituted fluorenylene group, a substituted or unsubstituted dibenzofuranylene group, a substituted or unsubstituted dibenzothiophenylene group, a substituted or unsubstituted carbazolene group, a combination thereof, or a fused form of combinations thereof, but are not limited thereto.

In one example of the present invention, the substituted or unsubstituted arylene group or the substituted or unsubstituted heteroarylene group or the substituted or unsubstituted divalent heterocyclic group may be one of a substituted or unsubstituted phenylene group, a substituted or unsubstituted biphenylene group, a substituted or unsubstituted terphenylene group, a substituted or unsubstituted quarterphenylene group, a substituted or unsubstituted naphthalene group, and a substituted or unsubstituted pyrimidinylene group, or a combination thereof.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, an organic compound according to an embodiment is described.

An organic compound according to an embodiment is represented by Chemical Formula 1.

[Chemical Formula 1]

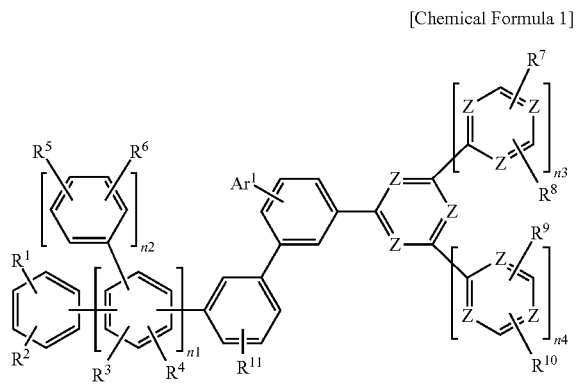

In Chemical Formula 1,
Z is independently N, C, or CR$^a$,
at least one of Z's is N,
Ar$^1$ is a substituted or unsubstituted C6 to C12 aryl group or a substituted or unsubstituted C3 to C12 nitrogen-containing six-membered ring,
R$^1$ to R$^6$, R$^{11}$ and R$^a$ are independently hydrogen, deuterium, a substituted or unsubstituted C 1 to C10 alkyl group, a substituted or unsubstituted C6 to C12 aryl group, a substituted or unsubstituted C3 to C12 heterocyclic group, or a combination thereof, R$^7$ to R$^{10}$ are independently hydrogen, deuterium, a substituted or unsubstituted C6 to C10 aryl group or a substituted or unsubstituted C3 to C12 heterocyclic group,
R$^1$ and R$^2$ are independently present or linked with each other to form a ring,
R$^5$ and R$^6$ are independently present or linked with each other to form a ring.
R$^7$ and R$^8$ are independently present or linked with each other to form a ring,
R$^9$ and R$^{10}$ are independently present or linked with each other to form a ring,
n1 is an integer ranging from 1 to 5,
n2 is an integer ranging from 0 to 2, and
n3 and n4 are independently 0 or 1.

The organic compound represented by Chemical Formula 1 includes consecutively linked substituted or unsubstituted two or more aryl groups and a heteroaryl group having at least one nitrogen as a center of two phenylene groups bound in a meta position.

The organic compound includes a ring having at least one nitrogen and thus may have a structure of easily accepting electrons when an electric field is applied thereto and accordingly, lower a driving voltage of an organic optoelectronic diode.

In addition, the organic compound includes a plurality of substituted or unsubstituted aryl group moieties easily accepting holes and a nitrogen-containing ring moiety easily accepting electrons and thus may form a bipolar structure and may balance flows of the holes and the electrons and resultantly, improve efficiency of an organic optoelectronic diode.

In addition, the organic compound includes two phenylene groups linked in a meta position and thus may appropriately localize the plurality of substituted or unsubstituted aryl group moiety easily accepting holes and the nitrogen-containing ring moiety easily accepting electrons in the above bipolar structure and control a flow of a conjugation system and resultantly, exhibit excellent bipolar characteristics. Accordingly, the organic compound may appropriately improve a life-span of an organic optoelectronic diode.

Herein, one of the two phenylene groups bound in a meta position may be an unsubstituted phenylene group. For example, one of the two phenylene groups bound in a meta position of Chemical Formula 1 may be substituted with Ar$^1$ and Ar$^1$ may be a substituted or unsubstituted C6 to C12 aryl group or a substituted or unsubstituted C3 to C12 nitrogen-containing six-membered ring.

Herein the nitrogen-containing six-membered ring has a structure where in a six-membered ring such as benzene, at least one methine group (=CH—) is replaced by a nitrogen atom, for example a structure including five methine groups and one nitrogen atom, four methine groups or two nitrogen atoms, or three methine groups and three nitrogen atoms in a six-membered ring.

For example, Ar$^1$ of Chemical Formula 1 may be a substituted or unsubstituted phenyl group, a substituted or unsubstituted biphenyl group, a substituted or unsubstituted naphthyl group, a substituted or unsubstituted pyridinyl group, a substituted or unsubstituted pyrimidinyl group, or a substituted or unsubstituted triazinyl group.

In addition, the organic compound may have a substantial linear structure and may be self-arranged during the deposition and thus increase process stability thin film uniformity.

For example, Chemical Formula I may include three phenylene groups that are consecutively bound in a meta position from the nitrogen-containing ring moiety.

For example, n2 of Chemical Formula 1 may be 0 and in this case, life-span may be increased.

For example, the organic compound may be represented by Chemical Formula 1-I according to the position and the number of nitrogen.

[Chemical Formula 1-I]

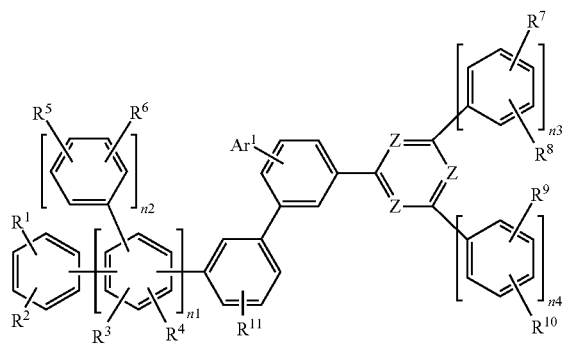

In Chemical Formula 1-I, Z, $Ar^1$, $R^1$ to $R^{11}$, and n1 to n4 are the same as described above.

The compound may have a lower LUMO energy level by directly linking the two phenylene groups bound in a meta position with the nitrogen-containing ring moiety and thus when the compound is applied to an organic optoelectronic diode, electrons may be easily transported from an electron transport layer to a light emitting layer. Accordingly, it is advantageous in terms of a driving voltage and efficiency of an organic light emitting diode.

In Chemical Formula 1-I, for example one of Z's may be nitrogen and two of Z's may be nitrogen. For example, each of $R^7$ to $R^{10}$ may be hydrogen. Each of n3 and n4 may be for example 1 and each of $R^7$ to $R^{10}$ may be hydrogen.

For example, the organic compound may be represented by Chemical Formula 1-II according to the position and the number of nitrogen.

[Chemical Formula 1-II]

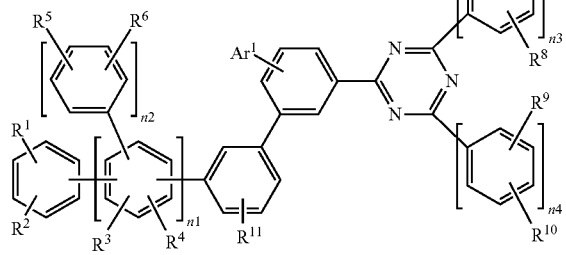

In Chemical Formula 1-II, $Ar^1$, $R^1$ to $R^{11}$, and n1 to n4 are the same as described above.

The compound may have a lower LUMO energy level by directly linking two phenylene groups bound in a meta position with a ring moiety having three nitrogens and thus when the compound is applied to an organic optoelectronic diode, electrons may be easily transported from an electron transport layer to a light emitting layer. Accordingly, it is advantageous in terms of a driving voltage and efficiency of an organic light emitting diode.

In Chemical Formula 1-II for example each of $R^7$ to $R^{10}$ may be hydrogen. Each of n3 and n4 may be for example 1 and each of $R^7$ to $R^{10}$ may be hydrogen.

The organic compound may be for example represented by one of Chemical Formulae 1-A to 1-C.

[Chemical Formula 1-A]

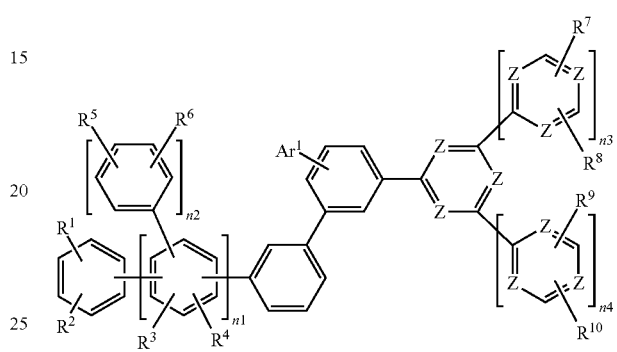

[Chemical Formula 1-B]

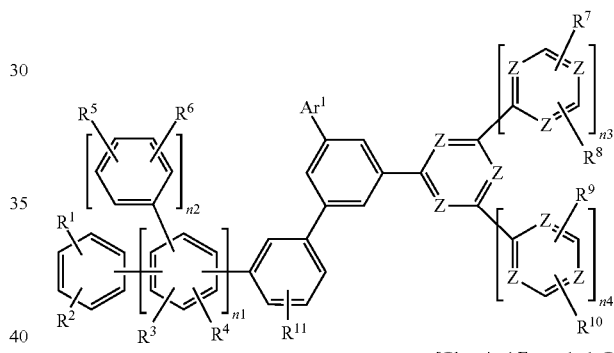

[Chemical Formula 1-C]

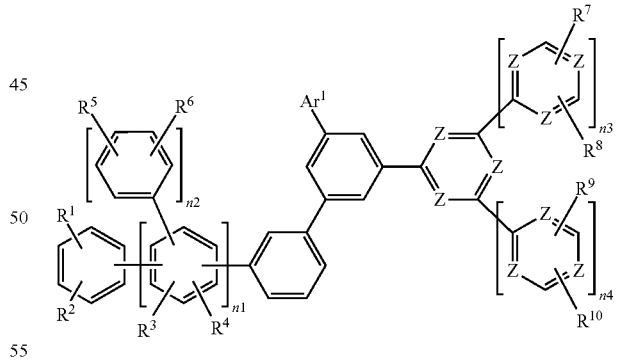

In Chemical Formulae 1-A to 1-C, Z, $Ar^1$, $R^1$ to $R^{11}$, and n1 to n4 are the same as described above.

Chemical Formula 1-A has a structure where one of the two phenylene groups bound in a meta position is a phenylene group substituted with $Ar^1$ and the other is an unsubstituted phenylene group. Chemical Formula 1-B has a structure where $Ar^1$ is substituted at a meta position. Chemical Formula 1-C has a structure where one of the two phenylene groups bound in a meta position is a phenylene group substituted with $Ar^1$ and the other is an unsubstituted phenylene group.

For example, in Chemical Formulae 1-A to 1-C, $Ar^1$ may be a substituted or unsubstituted phenyl group, a substituted or unsubstituted biphenyl group, a substituted or unsubstituted naphthyl group, a substituted or unsubstituted pyridinyl group, a substituted or unsubstituted pyrimidinyl group, or a substituted or unsubstituted triazinyl group.

The compound represented by Chemical Formula 1-A may be for example represented by Chemical Formula 1-A-I or 1-A-II according to the position and the number of nitrogen, but is not limited thereto.

[1-A-I]

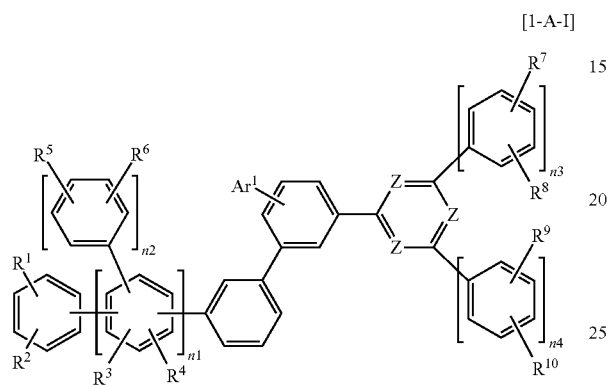

[1-A-II]

In Chemical Formulae 1-A-I and/or 1-A-II, Z, $Ar^1$, $R^1$ to $R^{11}$, and n1 to n4 are the same as described above.

In Chemical Formula 1-A-I, for example one of Z's may be nitrogen and two of Z's may be nitrogen. In Chemical Formulae 1-A-I and 1-A-II, each of $R^7$ to $R^{10}$ may be for example hydrogen. In Chemical Formulae 1-A-I and 1-A-II, each of n3 and n4 may be for example 1 and each of $R^7$ to $R^{10}$ may be hydrogen.

The compound represented by Chemical Formula 1-B may be for example represented by Chemical Formula 1-B-I or 1-B-II according to the position and the number of nitrogen, but is not limited thereto.

[1-B-I]

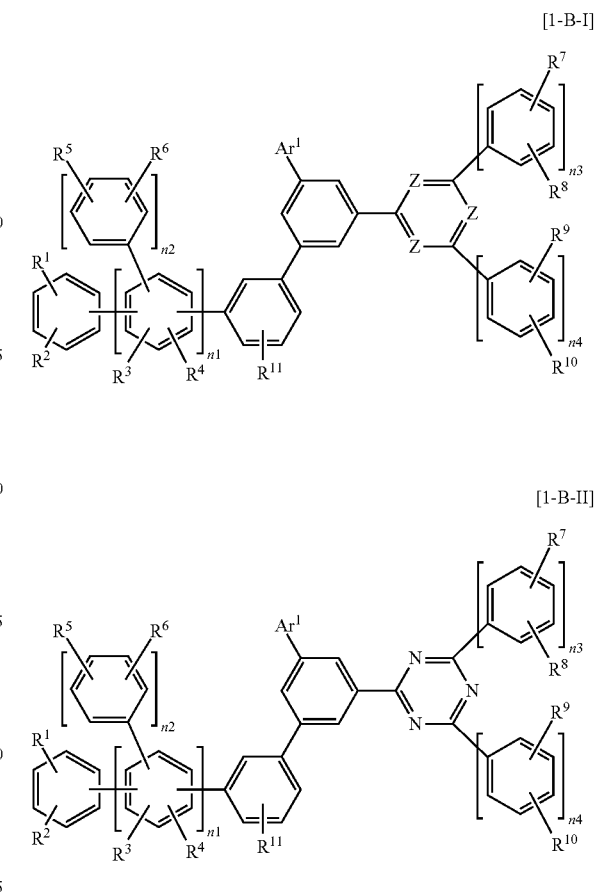

[1-B-II]

In Chemical Formula 1-B-I or 1-B-II, Z, $Ar^1$, $R^1$ to $R^{11}$, and n1 to n4 are the same as described above.

In Chemical Formula 1-B-I, for example one of Z's may be nitrogen and two of Z's may be nitrogen. In Chemical Formulae 1-B-I and 1-B-II, each of $R^7$ to $R^{10}$ are for example hydrogen. In Chemical Formulae 1-B-I and 1-B-II, each of n3 and n4 may be for example 1 and each of $R^7$ to $R^{10}$ may be hydrogen.

The compound represented by Chemical Formula 1-C may be for example represented by Chemical Formula 1-C-I or 1-C-II according to the position and the number of nitrogen, but is not limited thereto.

[1-C-I]

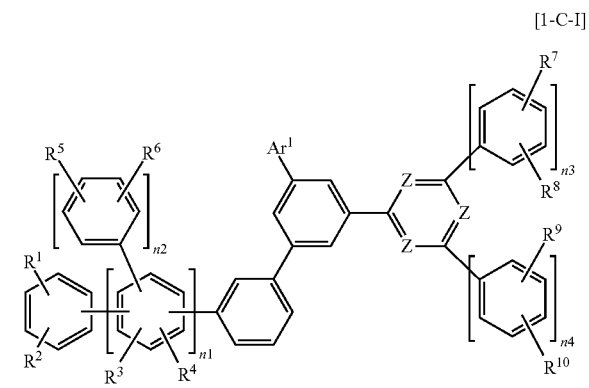

[1-C-II]

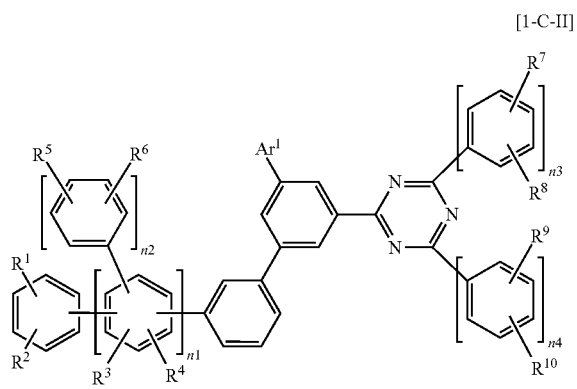

In Chemical Formula 1-C-I or 1-C-II, Z, $R^1$ to $R^{11}$, and n1 to n4 are the same as described above.

In Chemical Formula 1-C-I, for example one of Z's may be nitrogen and two of Z's may be nitrogen. In Chemical Formulae 1-C-I and 1-C-II, each of $R^7$ to $R^{10}$ may be for example hydrogen. In Chemical Formulae 1-C-I and 1-C-II, each of n3 and n4 may be for example 1 and each of $R^7$ to $R^{10}$ may be hydrogen.

The organic compound may be for example represented by one of Chemical Formulae 2 to 4.

[Chemical Formula 2]

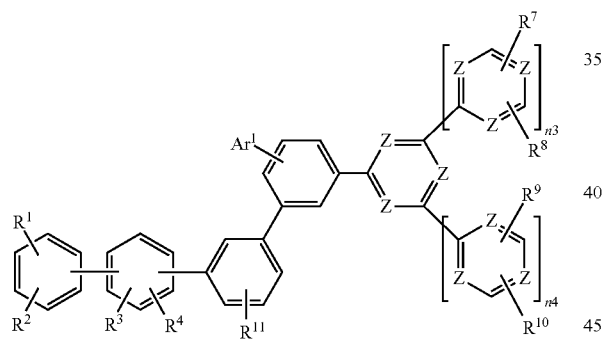

[Chemical Formula 3]

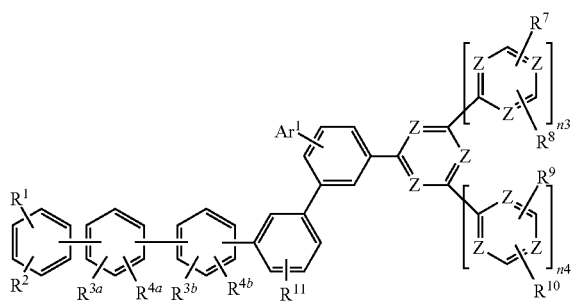

[Chemical Formula 4]

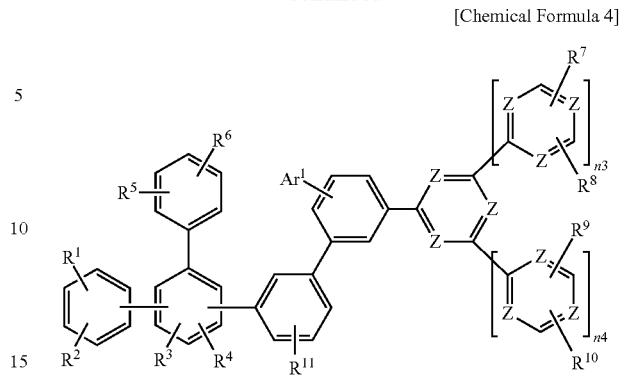

In Chemical Formulae 2 to 4, Z, $R^1$ to $R^{11}$, n3, and n4 are the same as described above, $R^{3a}$ and $R^{3b}$ are the same as $R^3$, and $R^{4a}$ and $R^{4b}$ are the same as $R^4$.

For example, in Chemical Formulae 2 to 4, $Ar^1$ may be bound in a meta position.

For example, in Chemical Formulae 2 to 4, $Ar^1$ may be a substituted or unsubstituted phenyl group, a substituted or unsubstituted biphenyl group, a substituted or unsubstituted naphthyl group, a substituted or unsubstituted pyridinyl group, a substituted or unsubstituted pyrimidinyl group, or a substituted or unsubstituted triazinyl group.

The compound represented by Chemical Formula 2 may be for example represented by Chemical Formula 2-I or 2-II according to the position and the number of nitrogen.

[Chemical Formula 2-I]

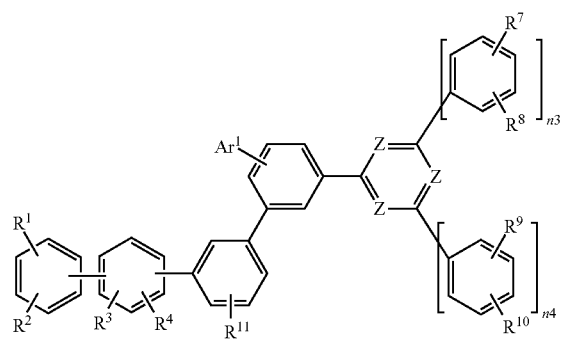

[Chemical Formula 2-II]

In Chemical Formula 2-I or 2-II, Z, $Ar^1$, $R^1$ to $R^4$, $R^7$ to $R^{11}$, n3, and n4 are the same as described above.

In Chemical Formula 2-I, for example one of Z's may be nitrogen and two of Z's may be nitrogen. In Chemical Formulae 2-I and 2-II, each of $R^7$ to $R^{10}$ may be for example hydrogen. In Chemical Formulae 2-I and 2-II, each of n3 and n4 may be for example 1 and each of $R^7$ to $R^{10}$ may be hydrogen.

The compound represented by Chemical Formula 2 may be for example represented by Chemical Formula 2a or 2b according to a linking position.

[Chemical Formula 2a]

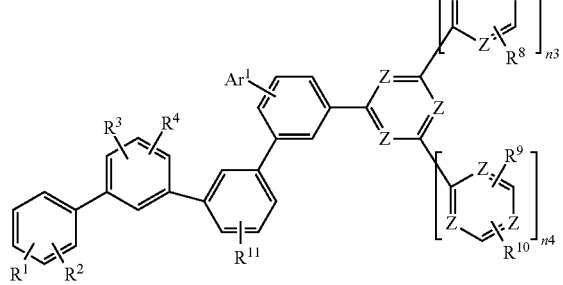

[Chemical Formula 2b]

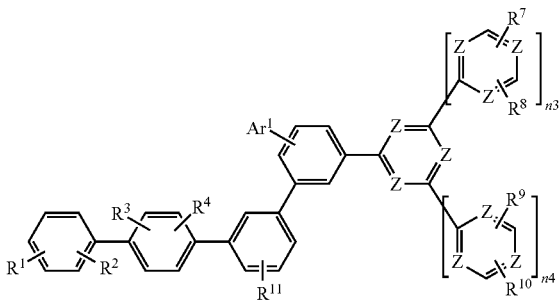

In Chemical Formulae 2a and 2b, Z, $Ar^1$ $R^1$ to $R^4$, $R^7$ to $R^{11}$, n3, and n4 are the same as described above.

For example, in Chemical Formulae 2-I, 2-II, 2a, and 2b, $Ar^1$ may be bound in a meta position.

For example, in Chemical Formulae 2-I, 2-II, 2a, and 2b, $Ar^1$ may be a substituted or unsubstituted phenyl group, a substituted or unsubstituted biphenyl group, a substituted or unsubstituted naphthyl group, a substituted or unsubstituted pyridinyl group, a substituted or unsubstituted pyrimidinyl group, or a substituted or unsubstituted triazinyl group.

The compound represented by Chemical Formula 3 may be for example represented by Chemical Formula 3-I or 3-II according to the position and the number of nitrogen.

[Chemical Formula 3-I]

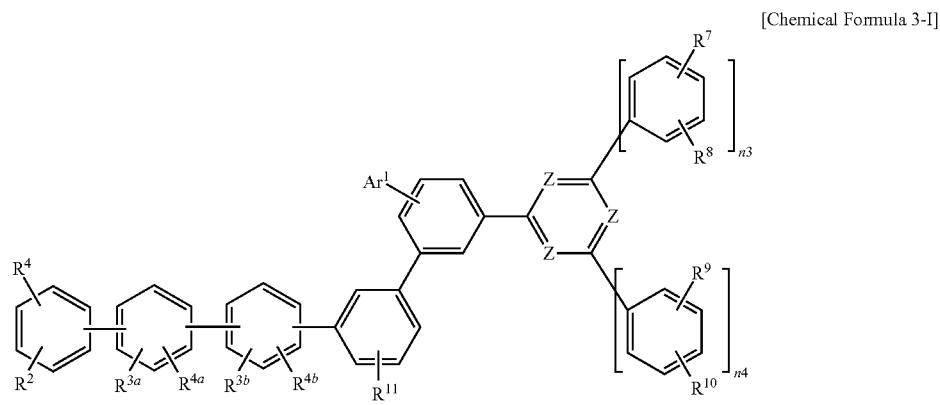

[Chemical Formula 3-II]

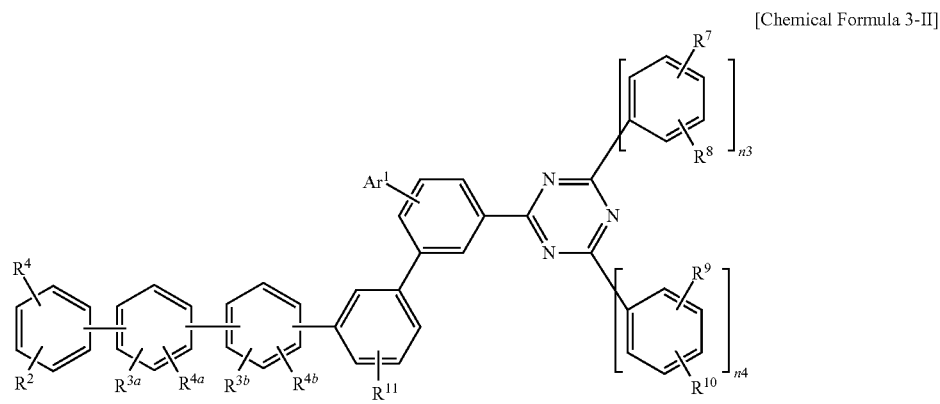

In Chemical Formula 3-I or 3-II, Z, $Ar^1$, $R^1$ to $R^4$, $R^7$ to $R^{11}$, n3, and n4 are the same as described above, $R^{3a}$ and $R^{3b}$ are the same as $R^3$, and $R^{4a}$ and $R^{4b}$ are the same as $R^4$. In Chemical Formula 3-I, for example one of Z's may be nitrogen and two of Z's may be nitrogen. In Chemical Formulae 3-I and 3-II, for example each of $R^7$ to $R^{10}$ may be hydrogen. In Chemical Formulae 3-I and 3-II, each of n3 and n4 may be for example 1 and each of $R^7$ to $R^{10}$ may be hydrogen.

The compound represented by Chemical Formula 3 may be for example represented by Chemical Formulae 3a to 3g according to a linking position.

[Chemical Formula 3a]

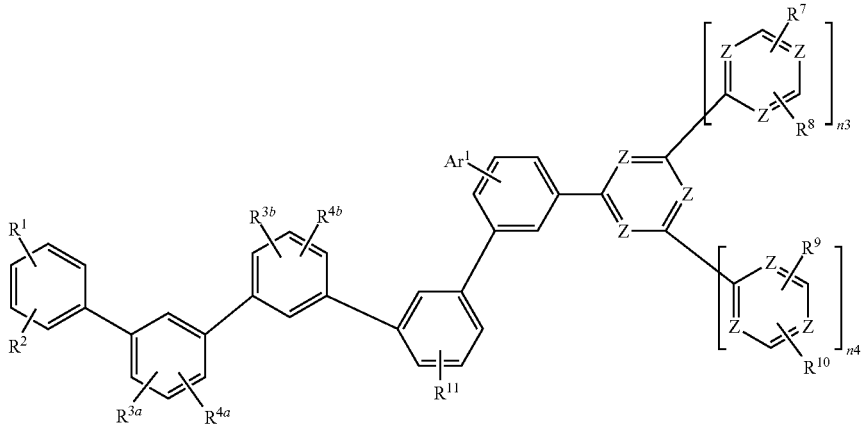

[Chemical Formula 3b]

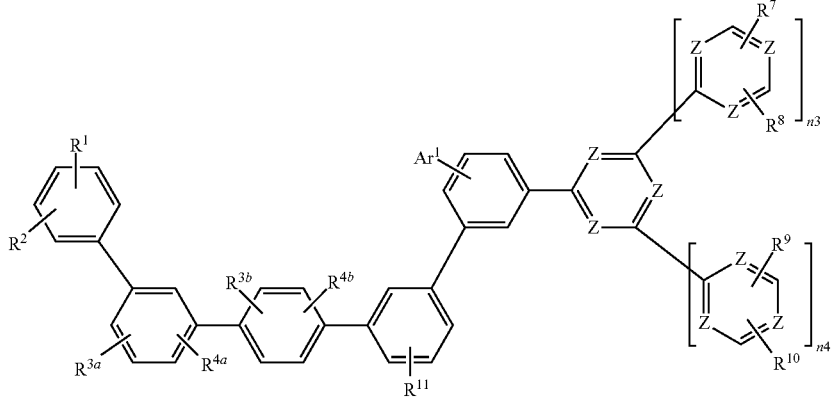

[Chemical Formula 3c]

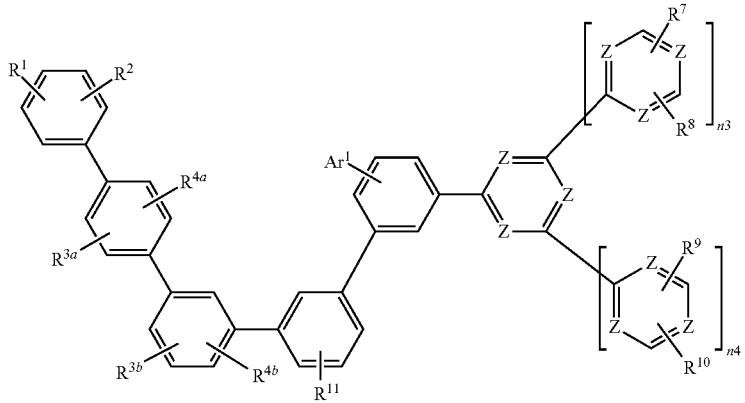

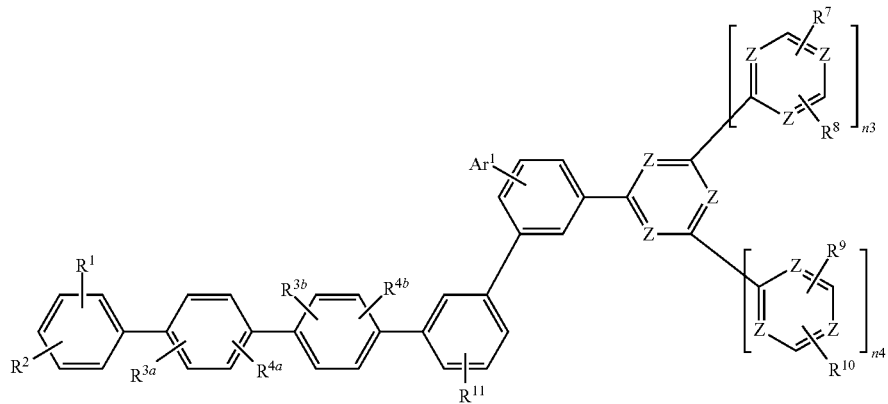
[Chemical Formula 3d]
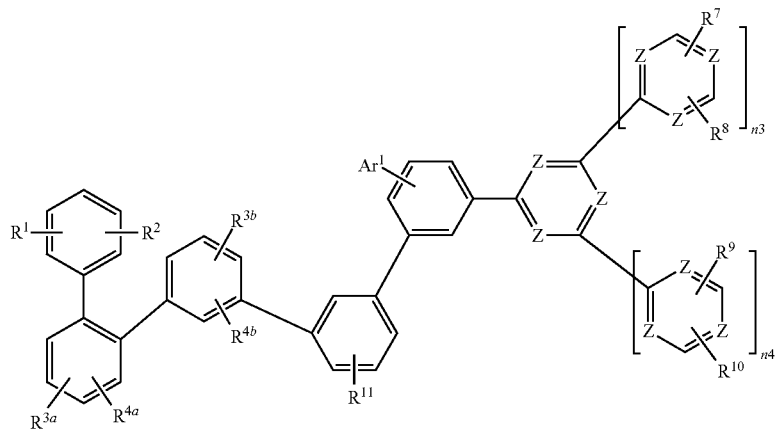
[Chemical Formula 3e]
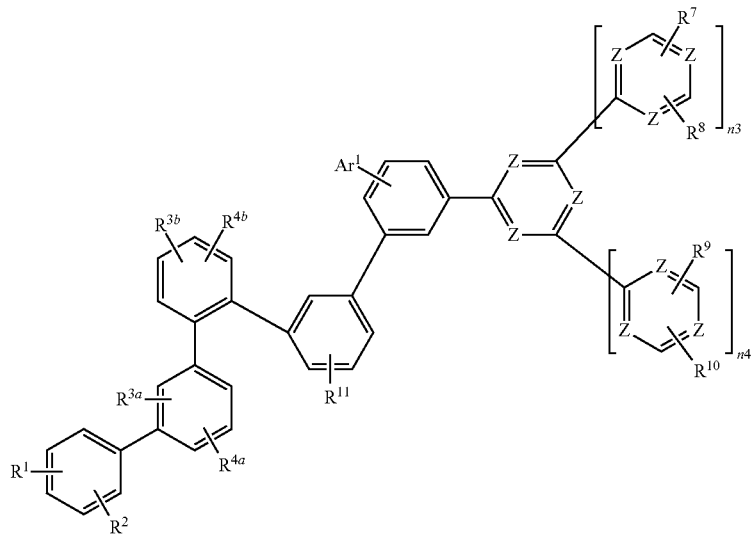
[Chemical Formula 3f]

[Chemical Formula 3g]

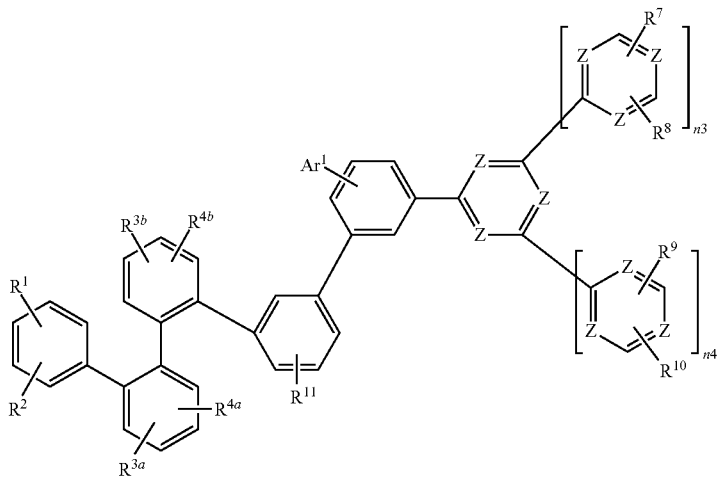

In Chemical Formulae 3a to 3g, Z, $Ar^1$, $R^1$ to $R^4$, $R^7$ to $R^{11}$, n3, and n4 are the same as described above, $R^{3a}$ and $R^{3b}$ are the same as $R^3$, and $R^{4a}$ and $R^{4b}$ are the same as $R^4$.

For example, in Chemical Formulae 3-I, 3-II, and 3a to 3g, $Ar^1$ may be bound in a meta position.

For example, in Chemical Formulae 3-I, 3-II, and 3a to 3g, $Ar^1$ may be a substituted or unsubstituted phenyl group, a substituted or unsubstituted biphenyl group, a substituted or unsubstituted naphthyl group, a substituted or unsubstituted pyridinyl group, a substituted or unsubstituted pyrimidinyl group, or a substituted or unsubstituted triazinyl group.

The compound represented by Chemical Formula 4 may be for example represented by Chemical Formula 4-I or 4-II according to the position and the number of nitrogen.

[Chemical Formula 4-I]

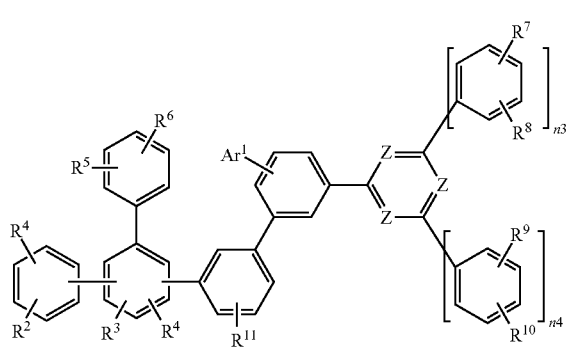

-continued

[Chemical Formula 4-II]

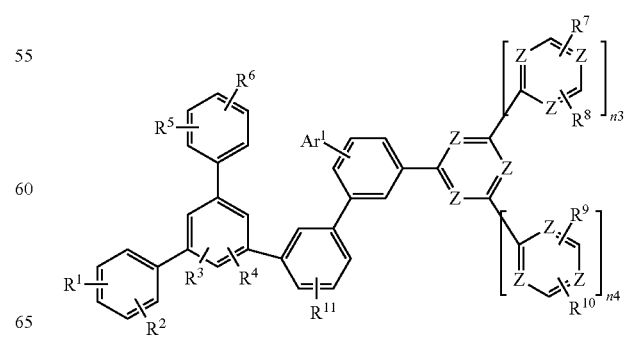

In Chemical Formula 4-I or 4-II, Z, $Ar^1$, $R^1$ to $R^{11}$, n3, and n4 are the same as described above. In Chemical Formula 4-I, for example one of Z's may be nitrogen and two of Z's may be nitrogen. In Chemical Formulae 4-I and 4-II, for example each of $R^7$ to $R^{10}$ may be hydrogen. In Chemical Formulae 4-I and 4-II, each of n3 and n4 may be for example 1 and each of $R^7$ to $R^{10}$ may be hydrogen.

The compound represented by Chemical Formula 4 may be for example represented by Chemical Formula 4a according to a linking position.

[Chemical Formula 4a]

In Chemical Formula 4a, Z, $Ar^1$, $R^1$ to $R^{11}$, n3, and n4 are the same as described above.

For example, in Chemical Formulae 4-I, 4-II, and 4a, $Ar^1$ may be bound in a meta position.

For example, in Chemical Formulae 4-I, 4-II, and 4a, $Ar^1$ may be a substituted or unsubstituted phenyl group, a substituted or unsubstituted biphenyl group, a substituted or unsubstituted naphthyl group, a substituted or unsubstituted pyridinyl group, a substituted or unsubstituted pyrimidinyl group, or a substituted or unsubstituted triazinyl group.

For example, in Chemical Formulae 1 to 4, 1-I, 1-II, 2-I, 2-II, 2a, 2b, 3-I, 3-II, 3a to 3g, 4-I, 4-II, and 4a, $R^7$ to $R^{10}$ may independently be hydrogen or a substituted or unsubstituted C6 to C10 aryl group, for example $R^7$ to $R^{10}$ may independently be hydrogen, a substituted or unsubstituted phenyl group or a substituted or unsubstituted naphthyl group.

For example, in Chemical Formulae 1 to 4, 1-I, 1-II, 2-I, 2-II, 2a, 2b, 3-I, 3-II, 3a to 3g, 4-I, 4-II, and 4a, when at least one of $R^7$ to $R^{10}$ is a substituted or unsubstituted C6 to C10 aryl group, the substituted or unsubstituted C6 to C10 aryl group may not be bound at an ortho position.

For example, in Chemical Formulae 1 to 4, 1-I, 1-II, 2-I, 2-II, 2a, 2b, 3-I, 3-II, 3a to 3g, 4-I, 4-II, and 4a, when at least one of $R^7$ to $R^{10}$ is a substituted or unsubstituted phenyl group, the phenyl group may not be bound at an ortho and para positions.

The organic compound may be for example compounds of Group 1, but is not limited thereto.

[Group 1]

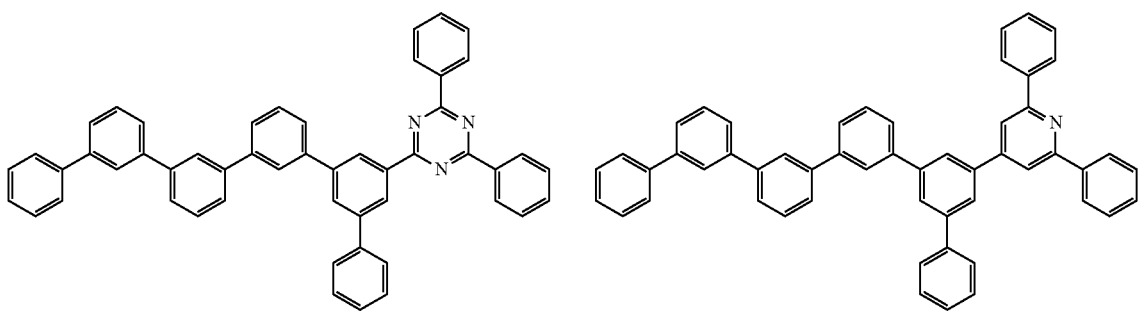

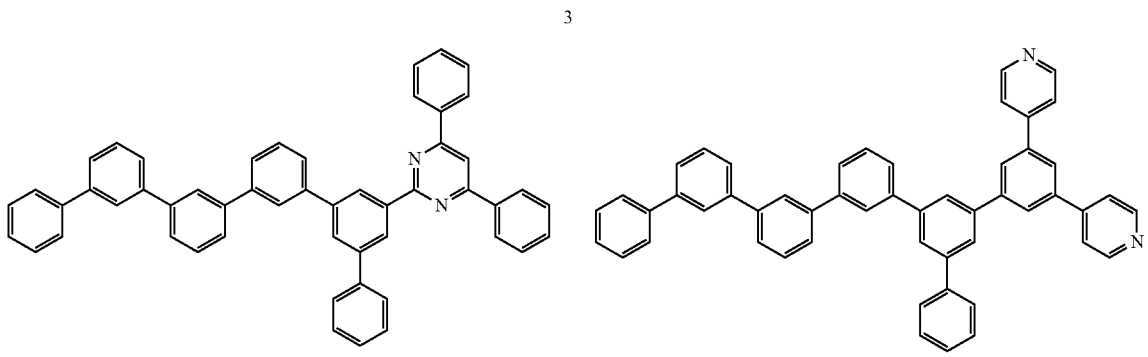

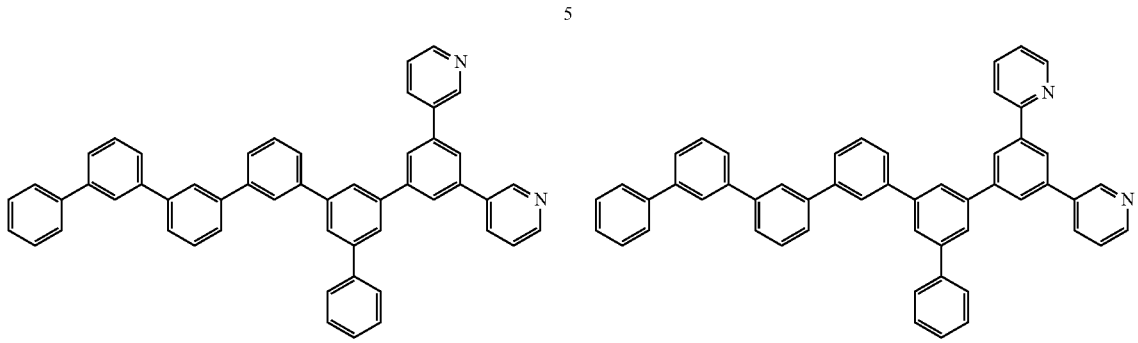

7
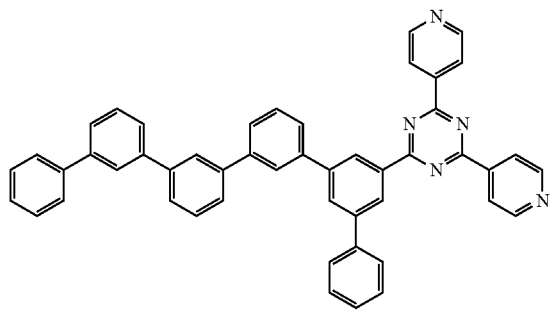
8
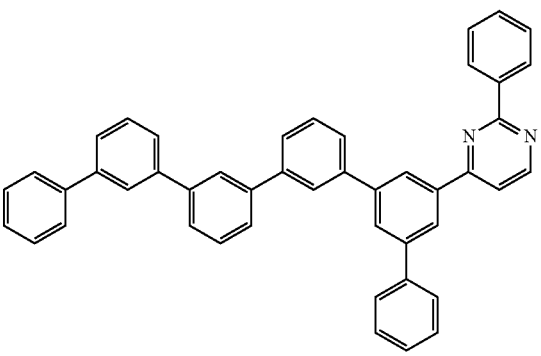
9
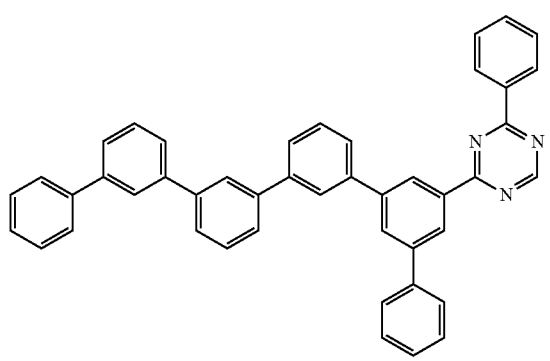
10
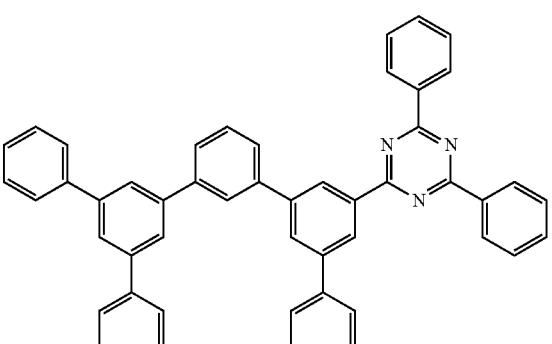
11
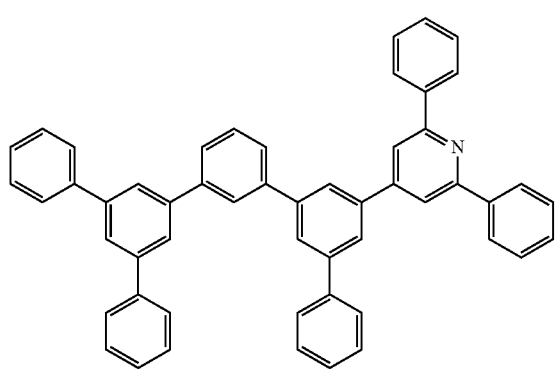
12
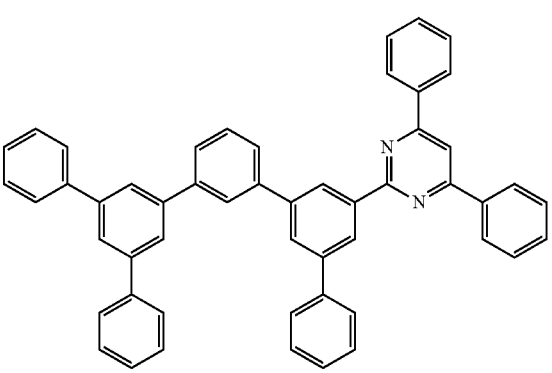
13
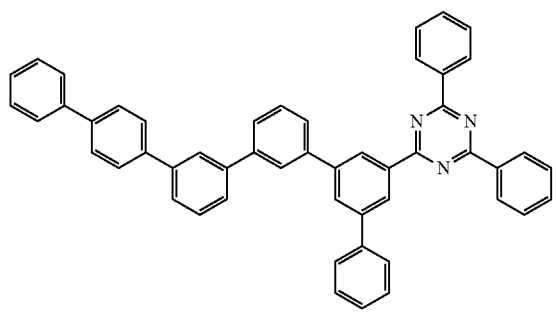
14
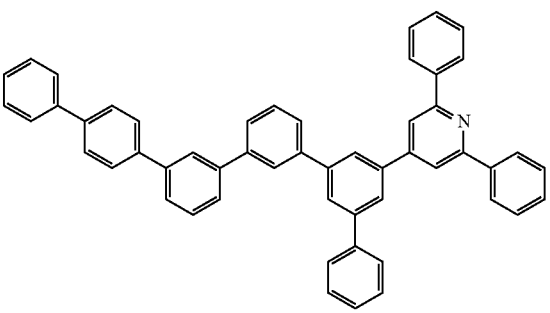

-continued
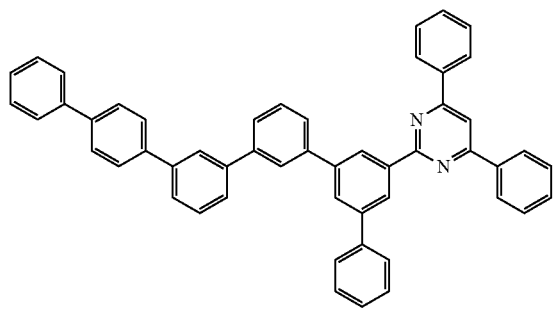
15
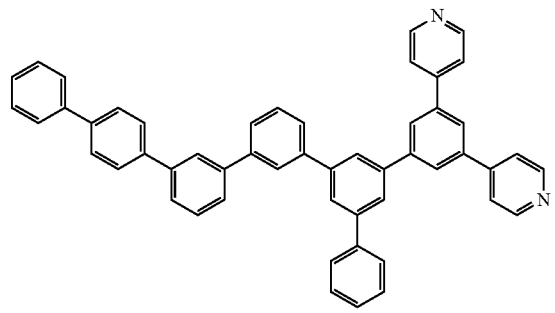
16
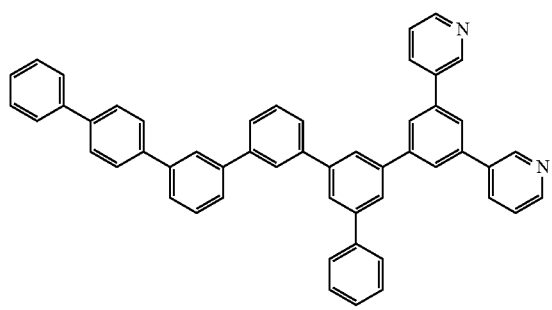
17
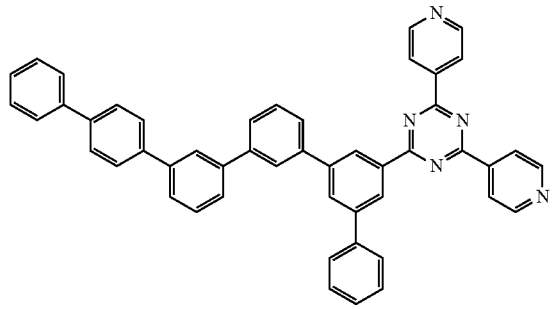
18
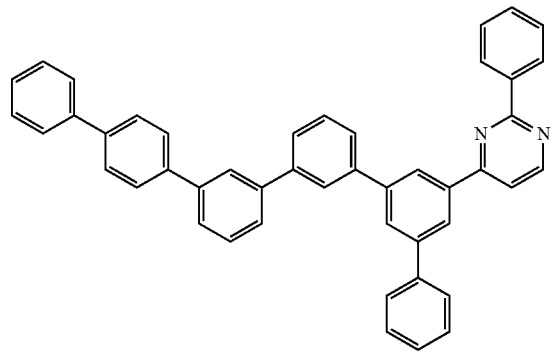
19
20
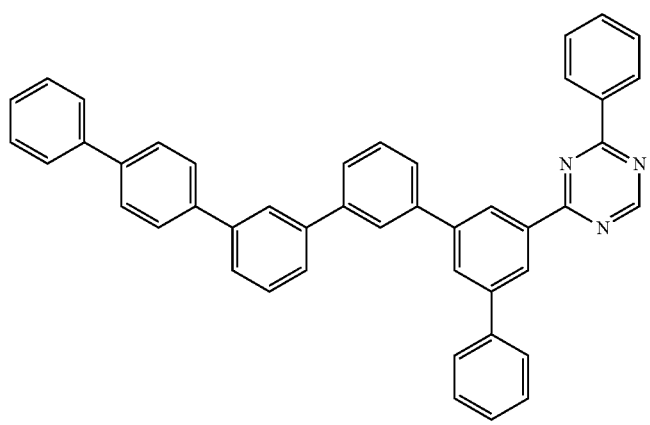
21

22
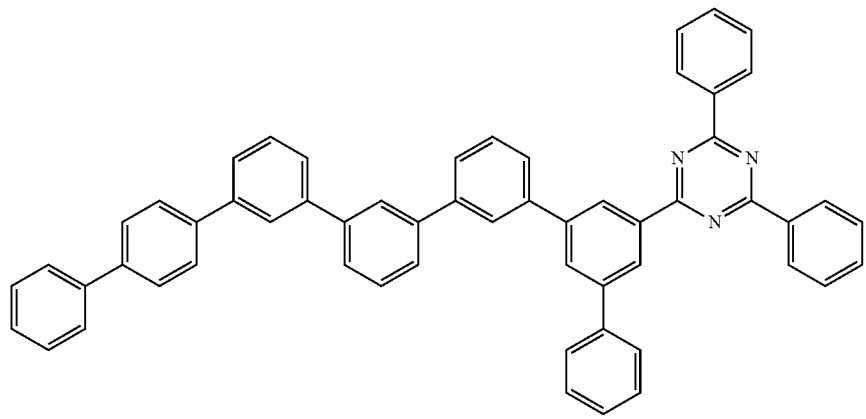
23
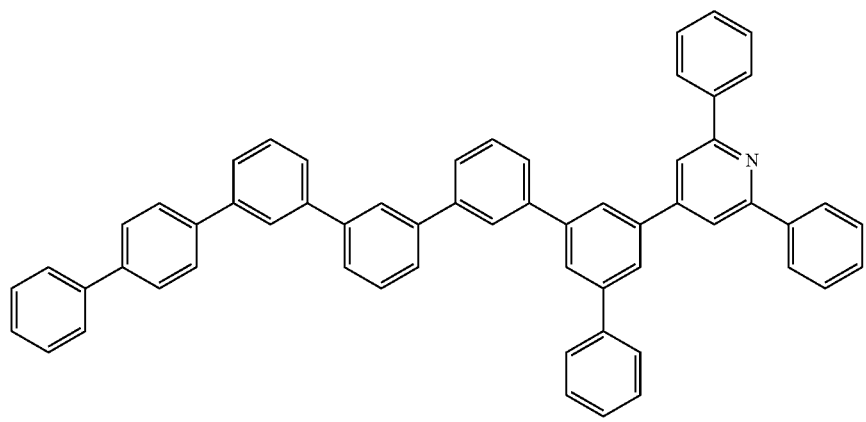
24
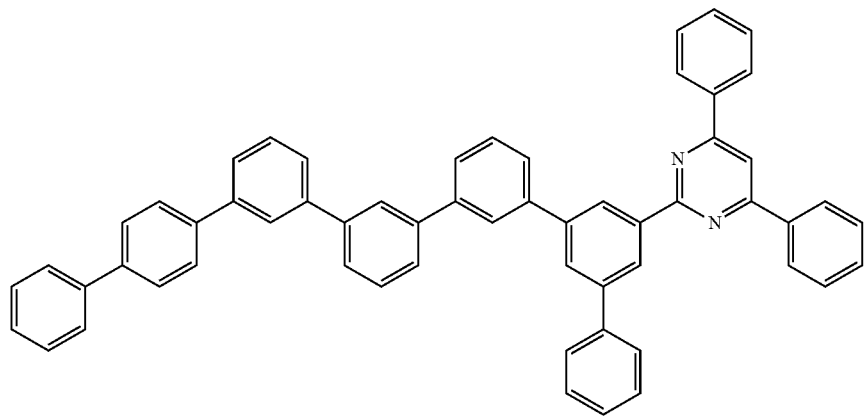

-continued
25
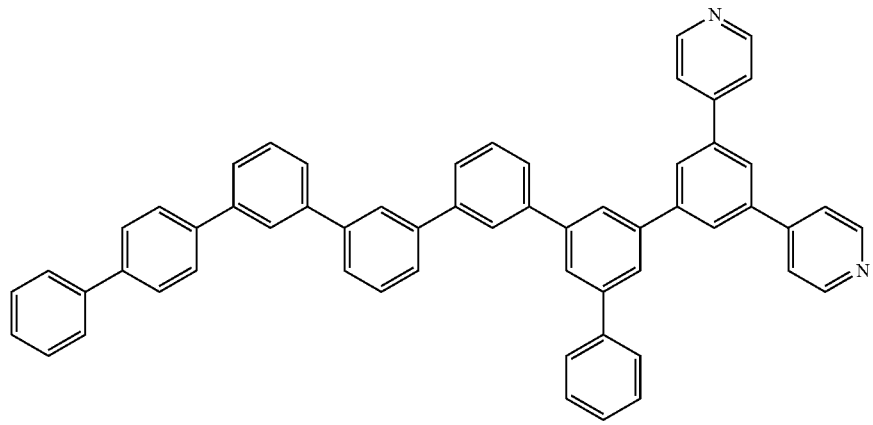
26
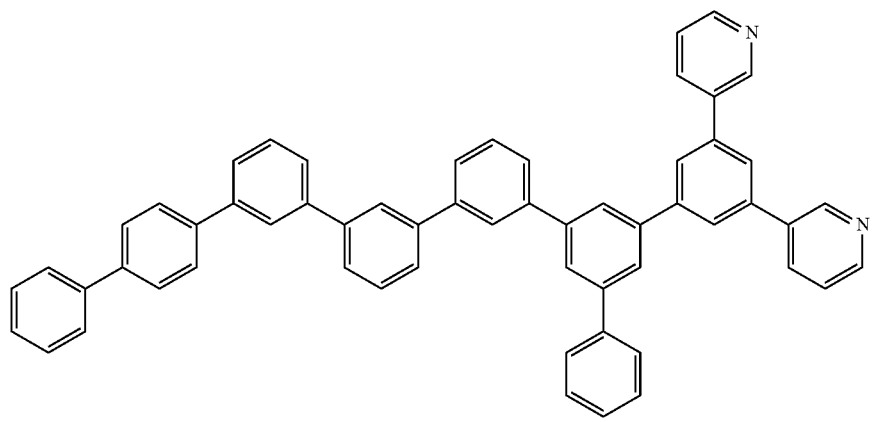
27
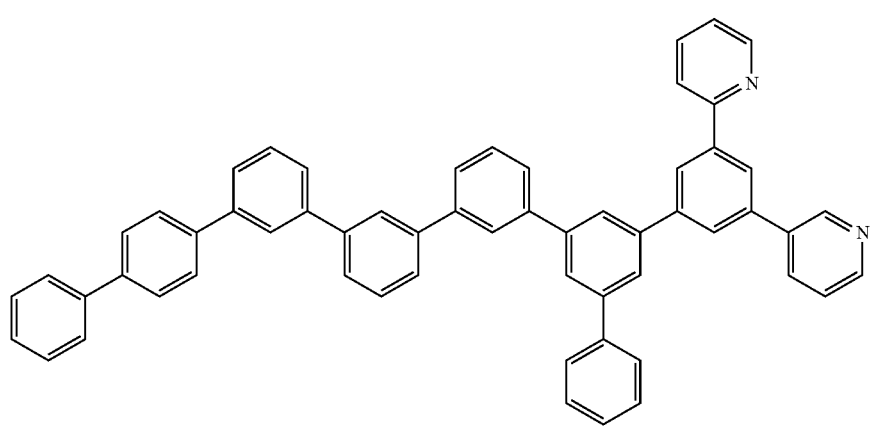

-continued
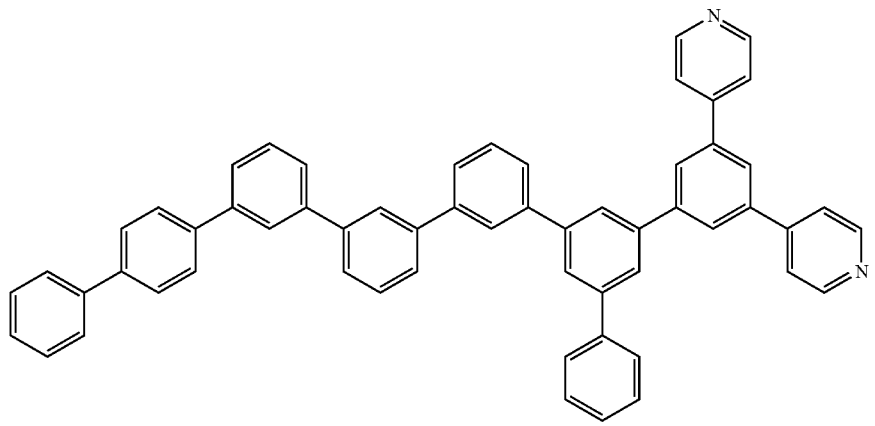
28
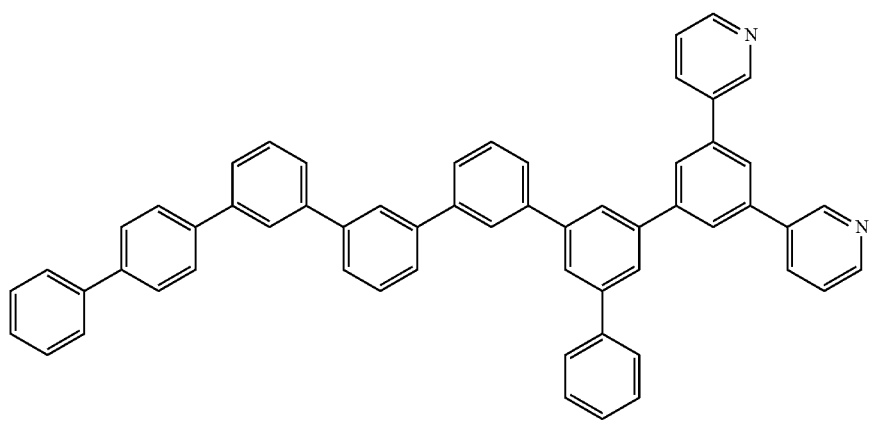
29
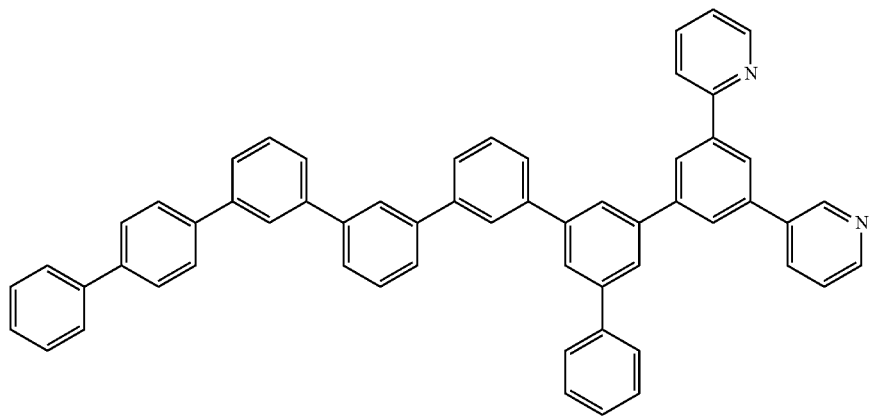
30
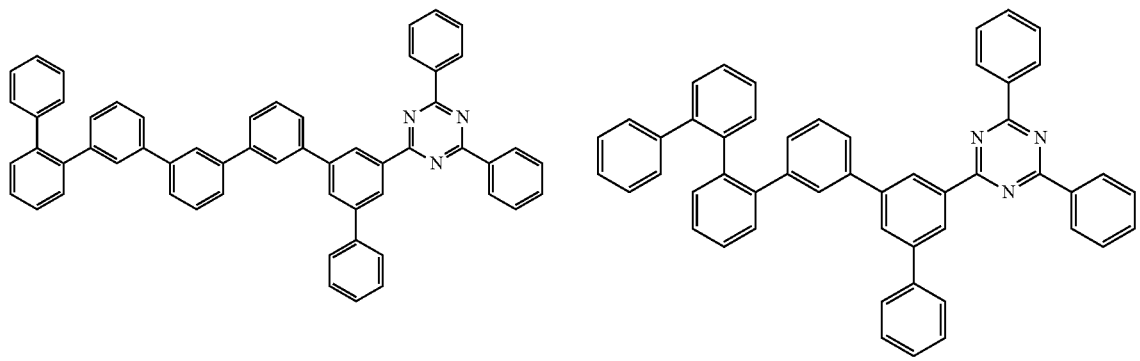
31 32

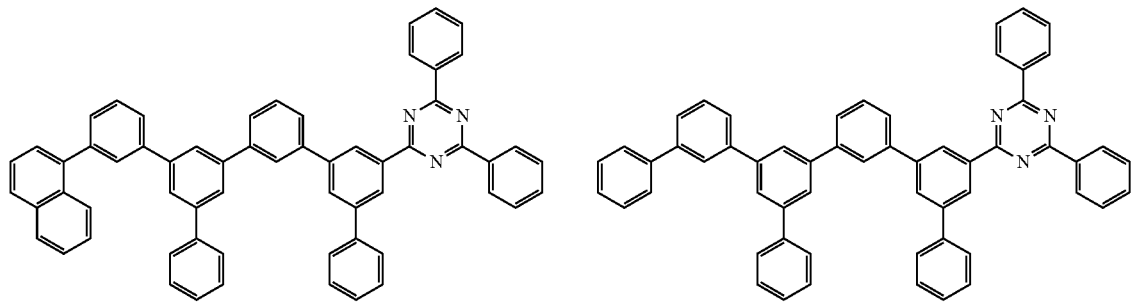
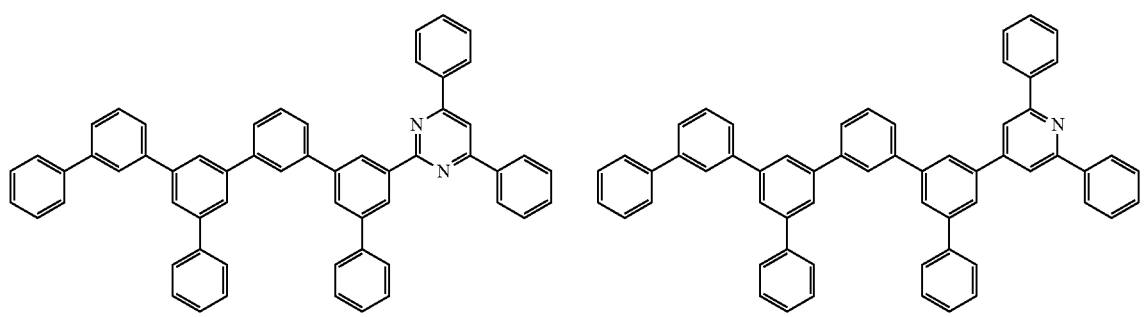
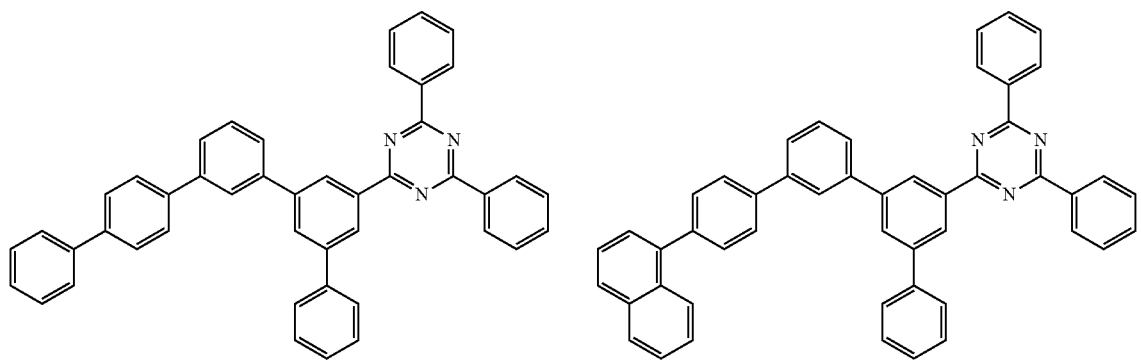
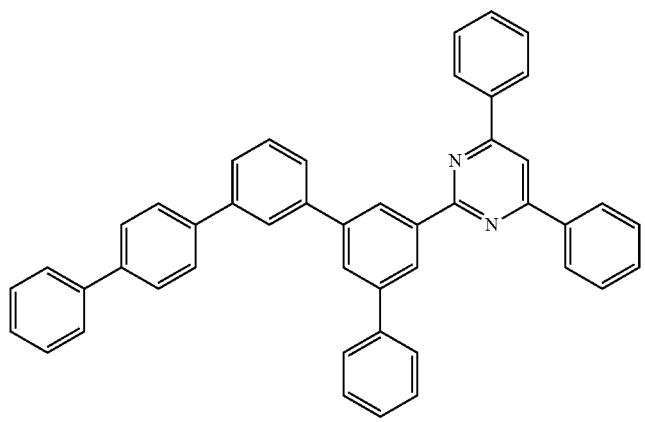

The organic compound may be applied to an organic optoelectronic diode.

The organic compound may be employed in an organic optoelectronic diode alone or with other organic compounds. When the organic compound is employed with other organic compounds, it may be employed in a form of a composition.

Hereinafter, one example of a composition for an organic optoelectronic diode including the organic compound is described.

The composition for an organic optoelectronic diode may be for example a composition of the organic compound and at least one organic compound having a carbazole moiety. Hereinafter, the organic compound is referred to as 'a first organic compound' and the at least one organic compound having a carbazole moiety is referred to as 'a second organic compound'.

The second organic compound may be for example a compound represented by Chemical Formula 5.

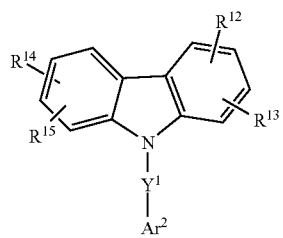

[Chemical Formula 5]

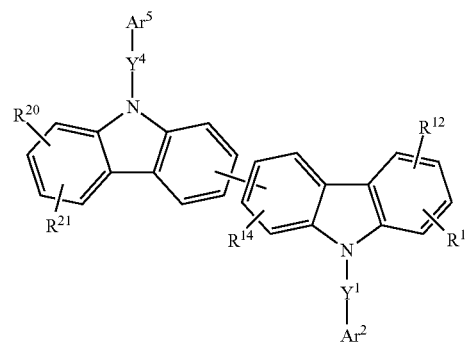

[Chemical Formula 5-I]

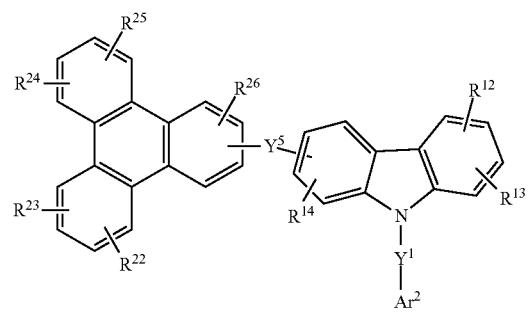

[Chemical Formula 5-II]

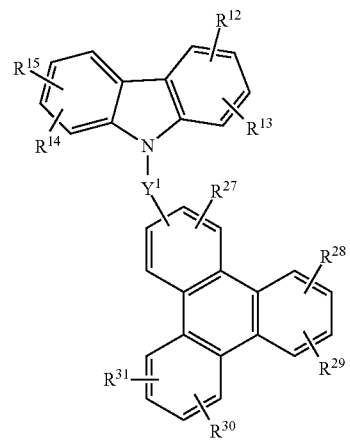

[Chemical Formula 5-III]

In Chemical Formula 5, $Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 divalent heterocyclic group, or a combination thereof, $Ar^2$ is a substituted or unsubstituted C6 to C30 aryl group, a substituted or unsubstituted C2 to C30 heterocyclic group, or a combination thereof, $R^{12}$ to $R^{15}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and at least one of $R^{12}$ to $R^{15}$, and $Ar^2$ includes a substituted or unsubstituted triphenylene group or a substituted or unsubstituted carbazolyl group.

The second organic compound represented by Chemical Formula 5 may be for example represented by at least one of Chemical Formulae 5-I to 5-III.

In Chemical Formulae 5-I to 5-III, $Y^1$, $Y^4$, and $Y^5$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 divalent heterocyclic group, or a combination thereof, $Ar^2$ and $Ar^5$ are independently a substituted or unsubstituted C6 to C30 aryl group, a substituted or unsubstituted C2 to C30 heterocyclic group, or a combination thereof, $R^{12}$ to $R^{15}$ and $R^{20}$ to $R^{31}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof.

The second organic compound represented by Chemical Formula 5 may be for example selected from compounds of Group 2, but is not limited thereto.

[Group 2]
B-10
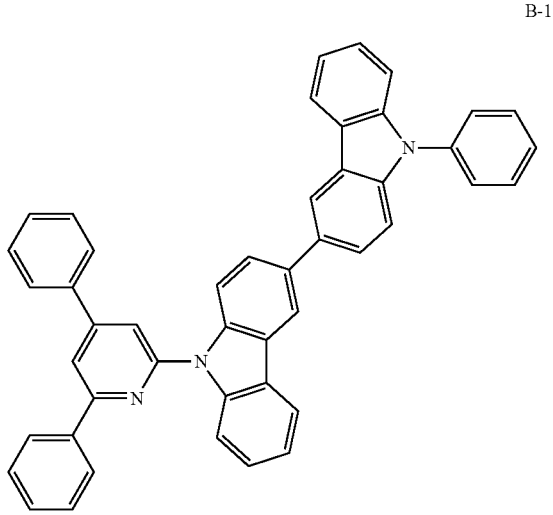
B-11
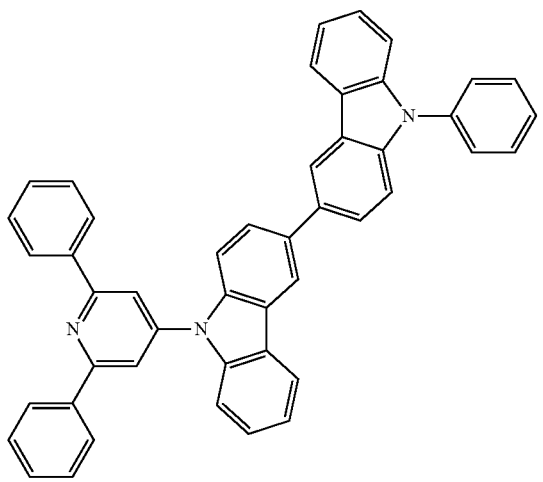
B-12
B-13
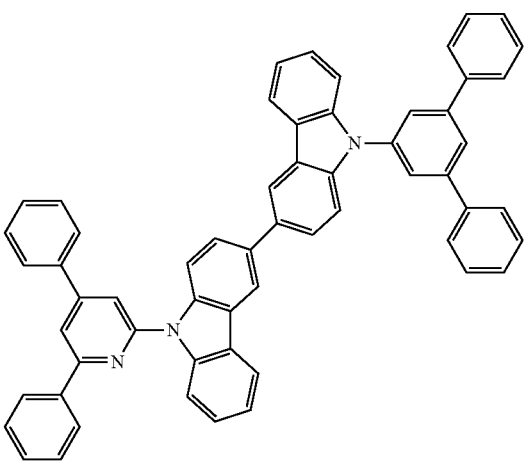
B-14
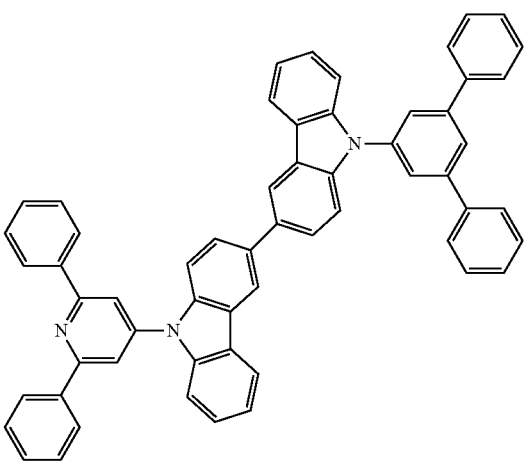
B-15
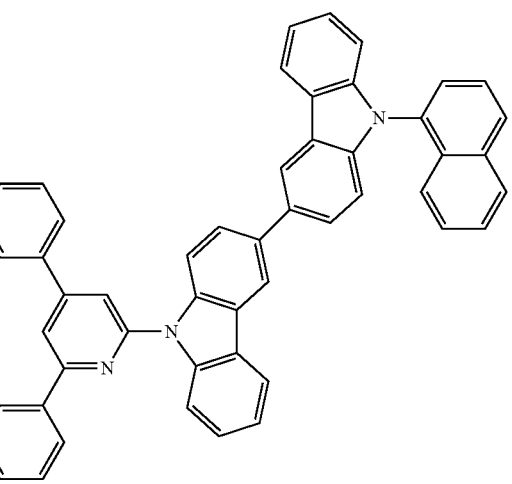

B-16
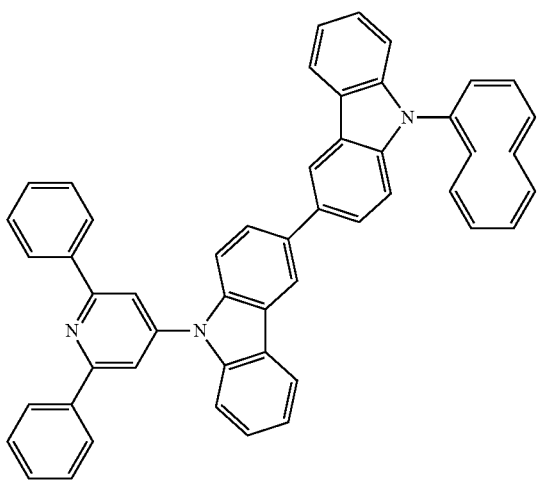
B-17
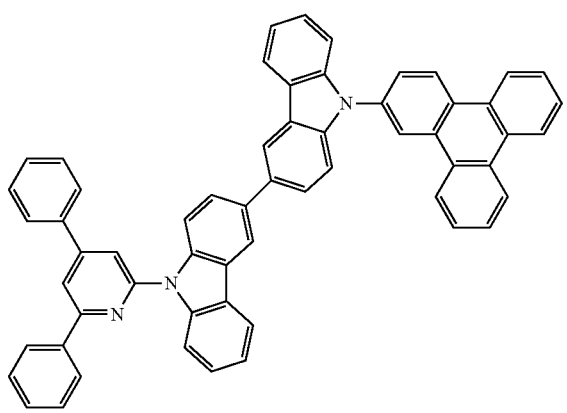
B-18
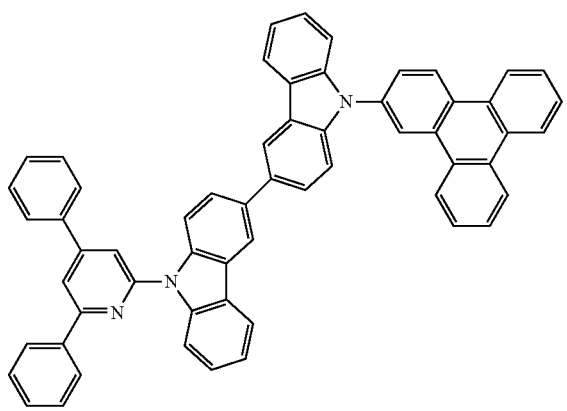
B-19
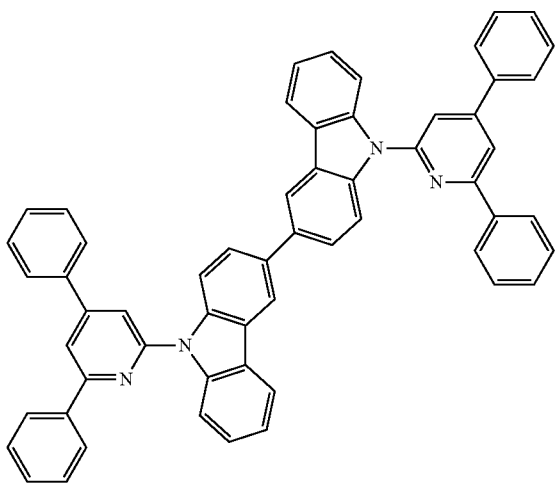
B-20
B-21
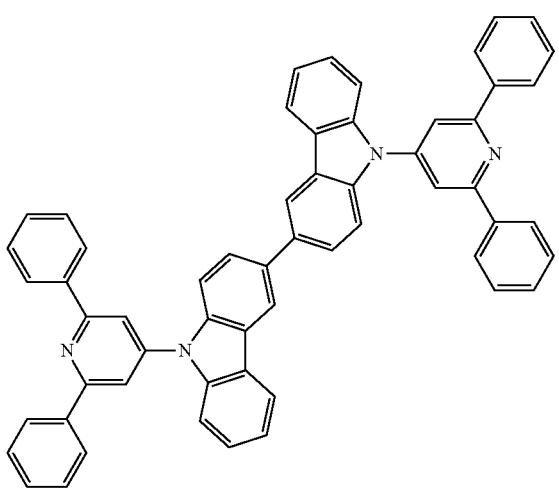

B-22
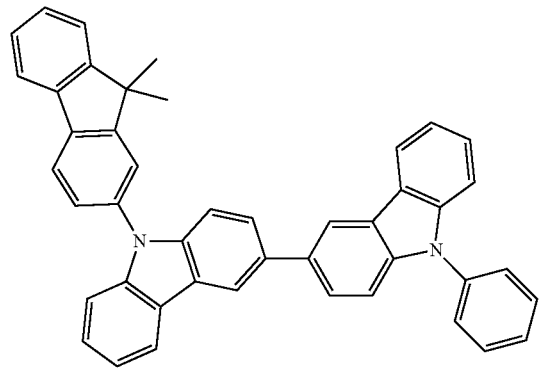
B-23
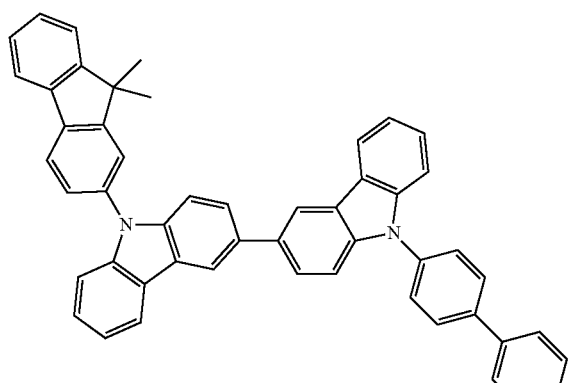
B-24
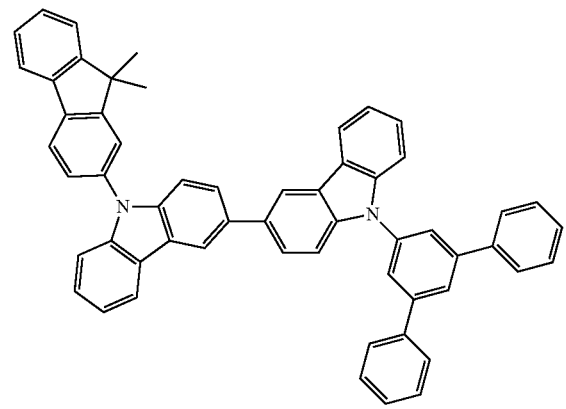
B-25
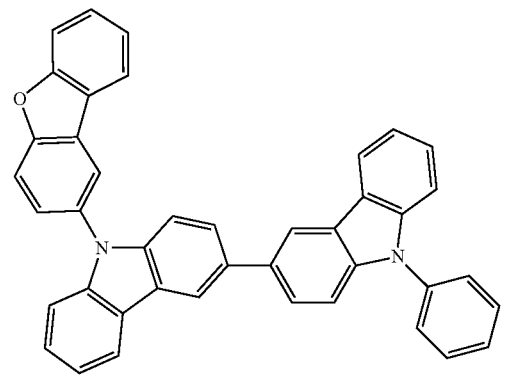
B-26
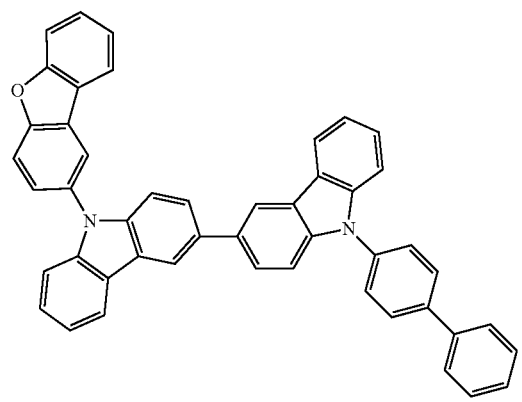
B-27
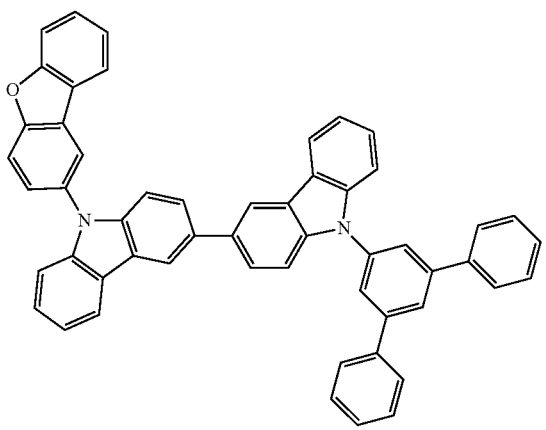
B-28
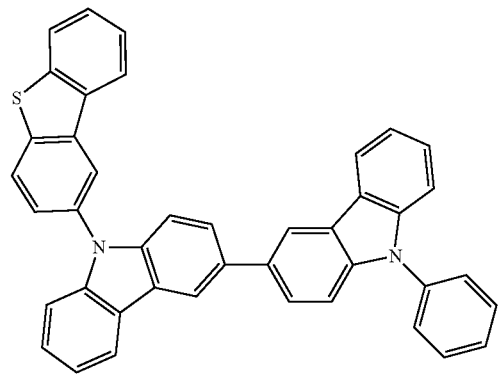

-continued
B-29
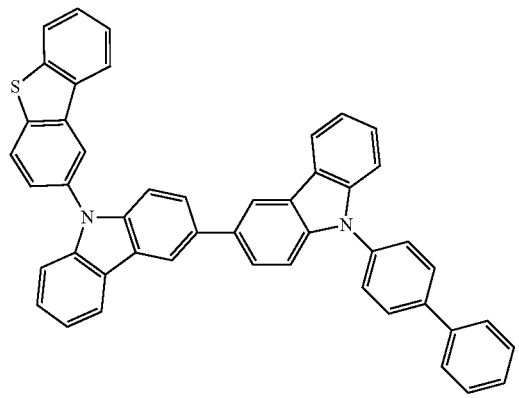
B-30
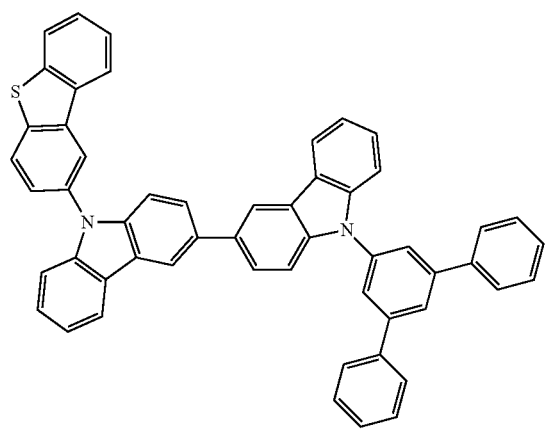
B-31
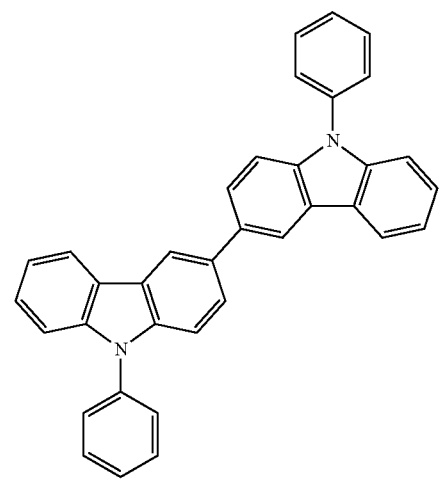
B-32
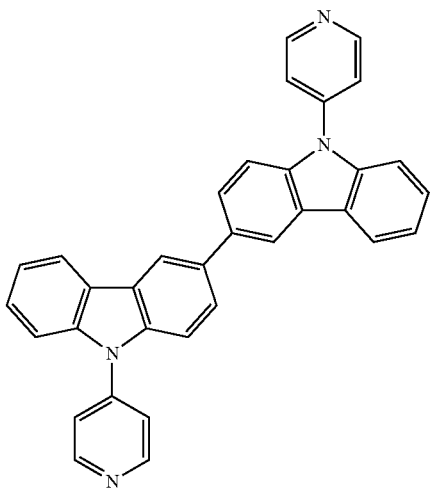
B-33
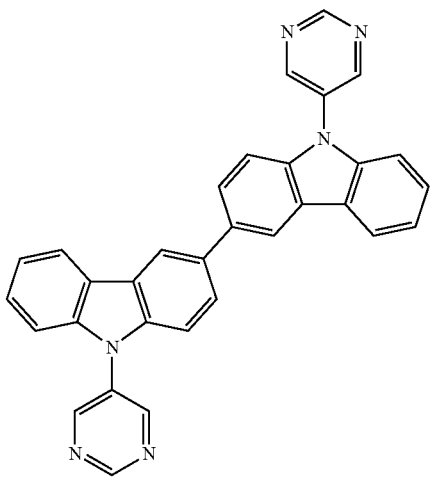
B-34
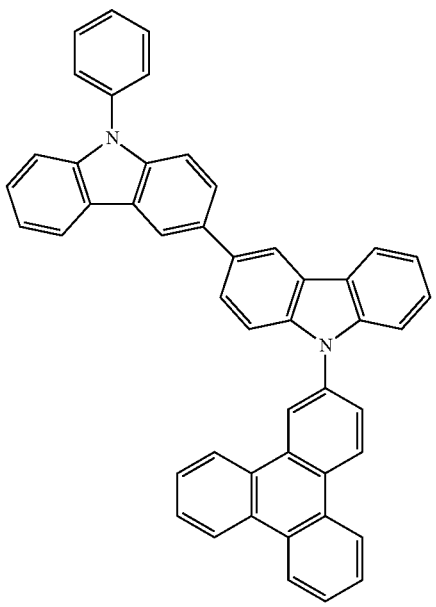

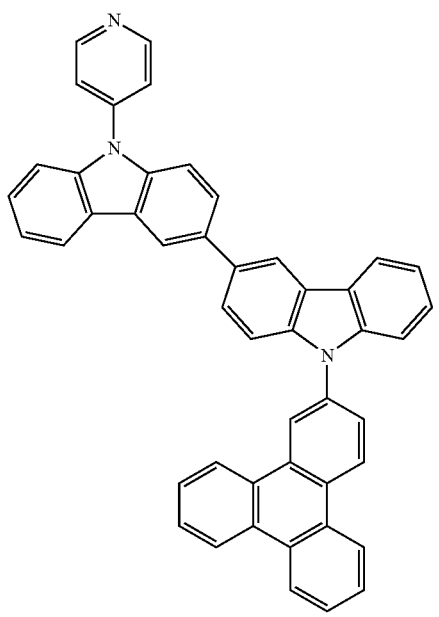
B-35
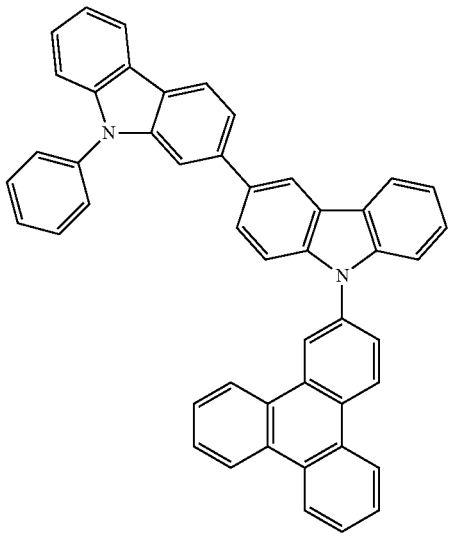
B-40
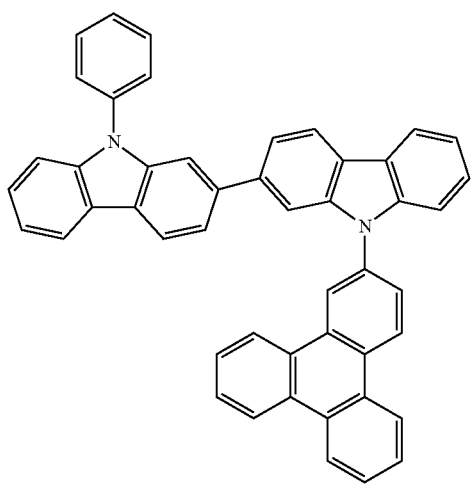
B-37
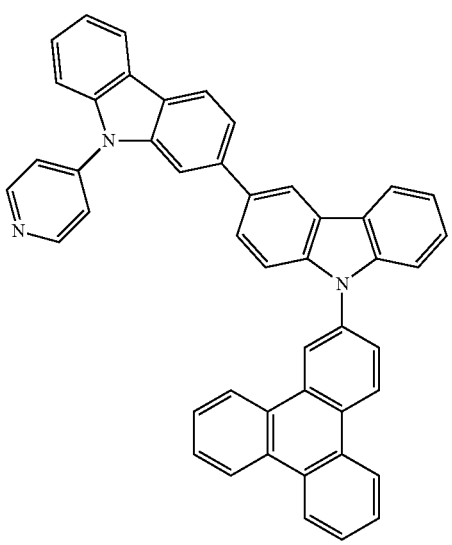
B-41
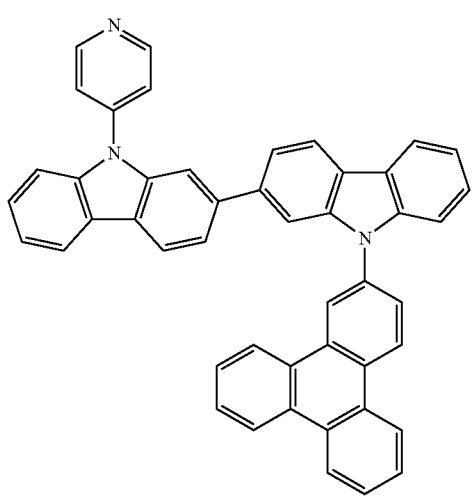
B-38
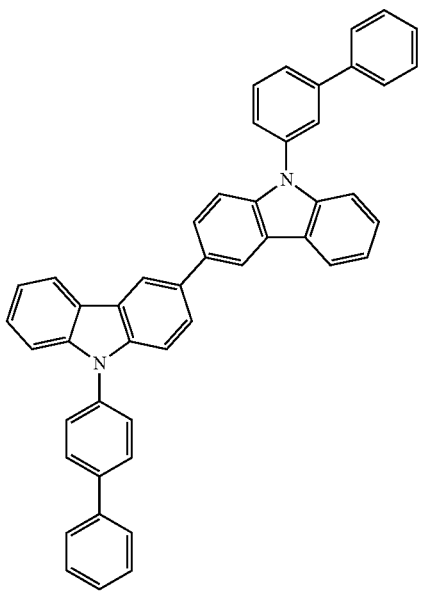
B-43

B-44
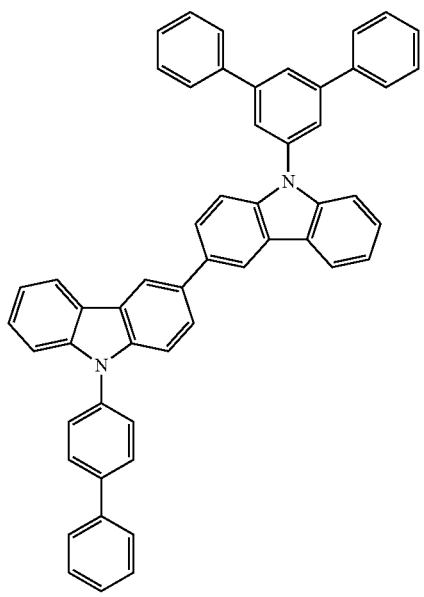
B-46
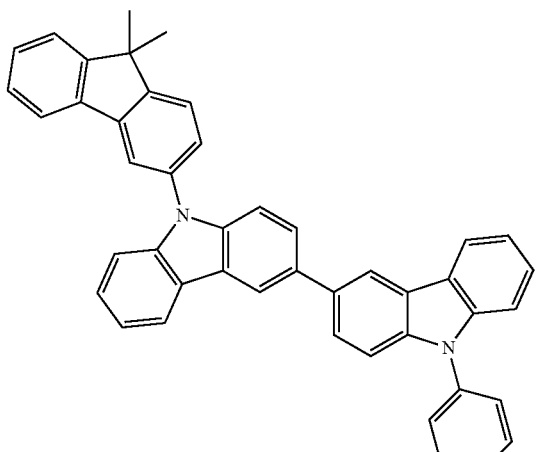
B-47
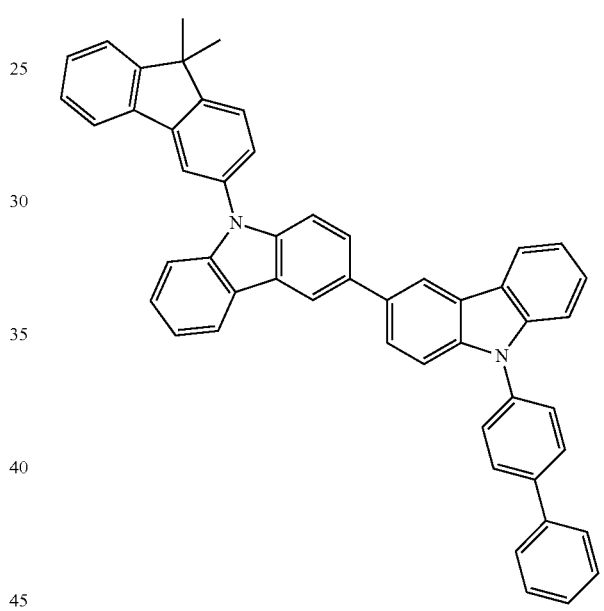
B-45
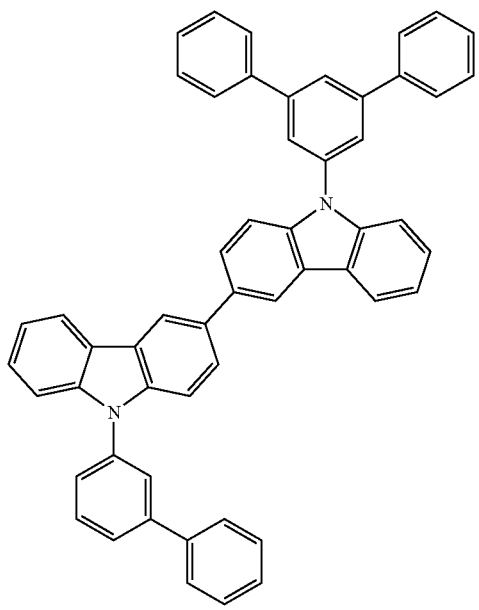
B-48
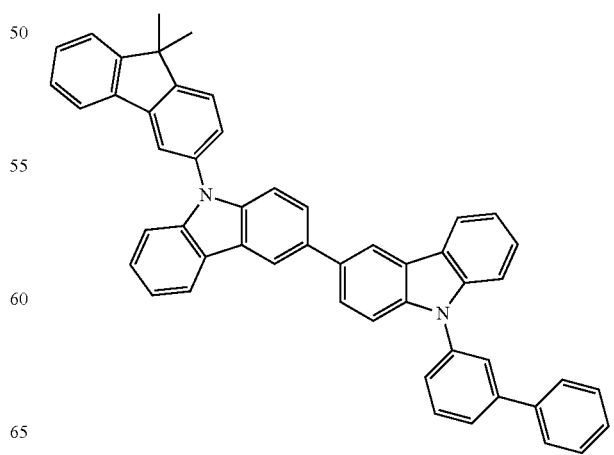

B-49
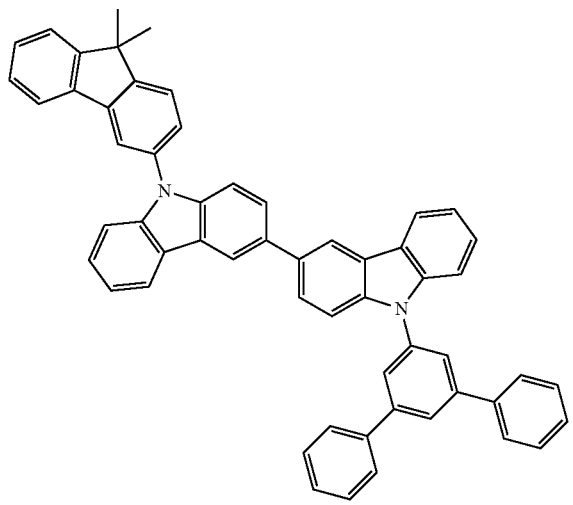
B-52
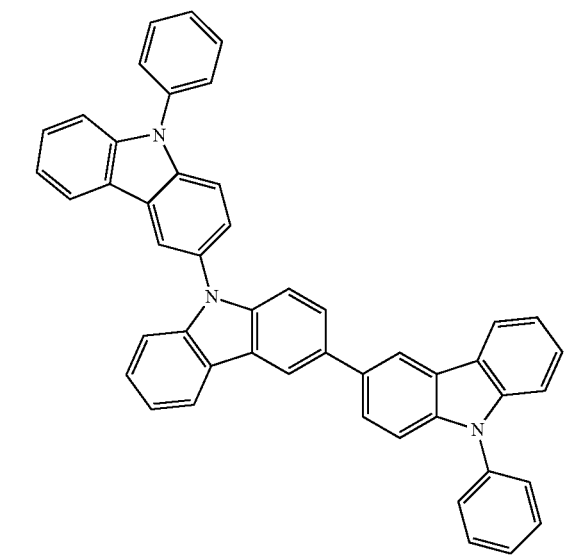
B-50
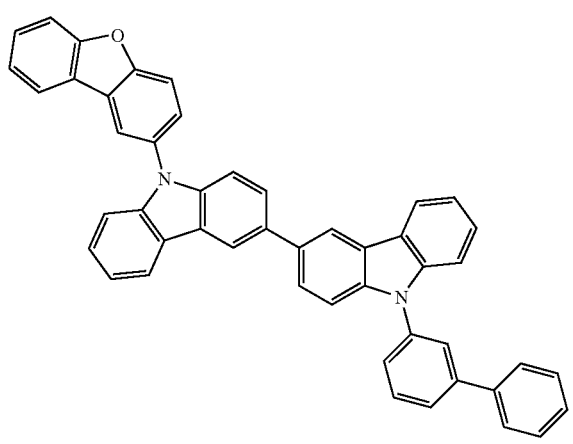
B-53
B-51
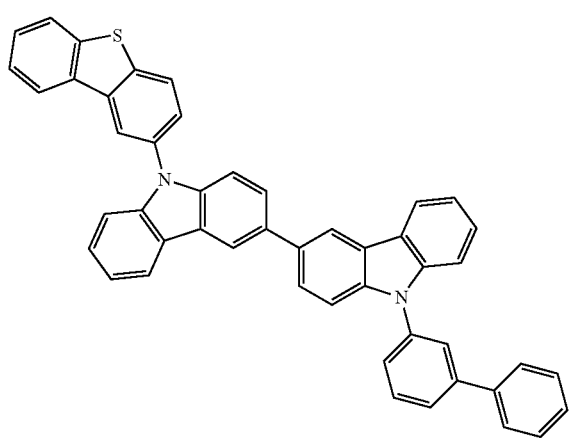
B-54
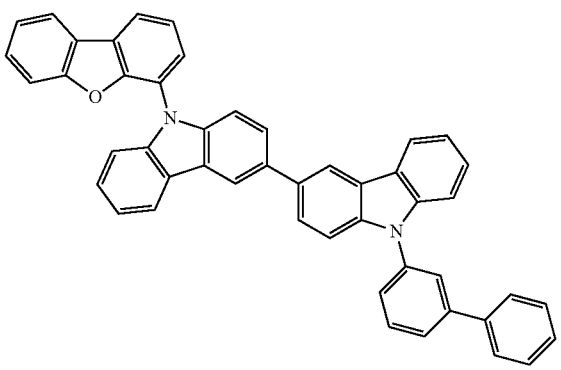

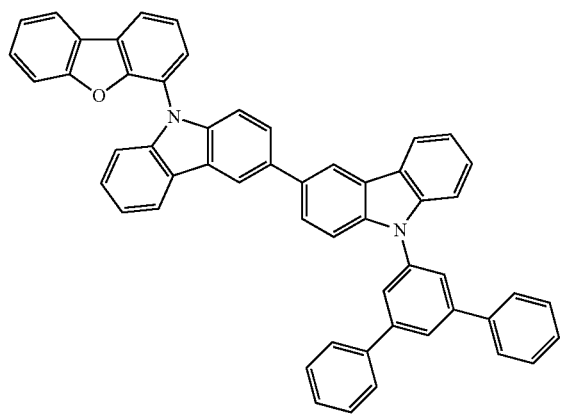
B-55
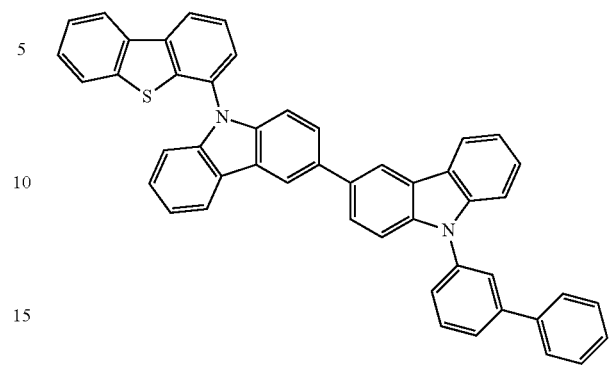
B-58
B-56
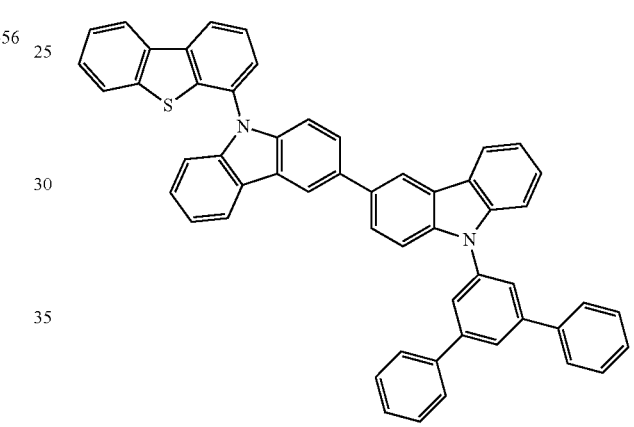
B-59
B-57
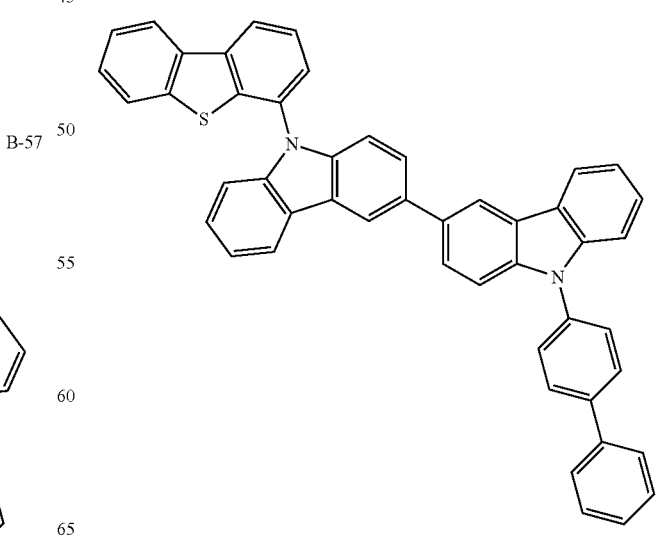
B-60

B-61
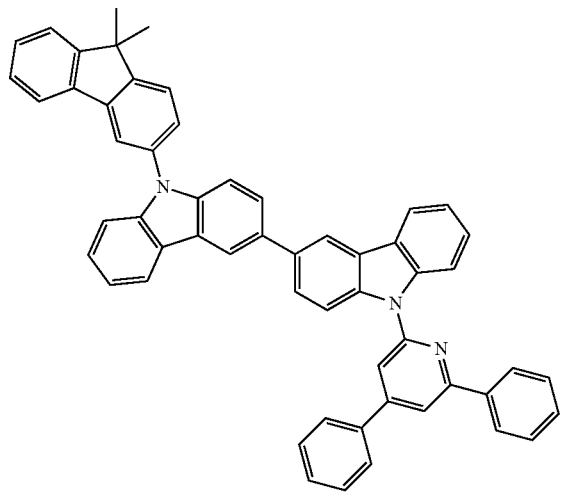
B-64
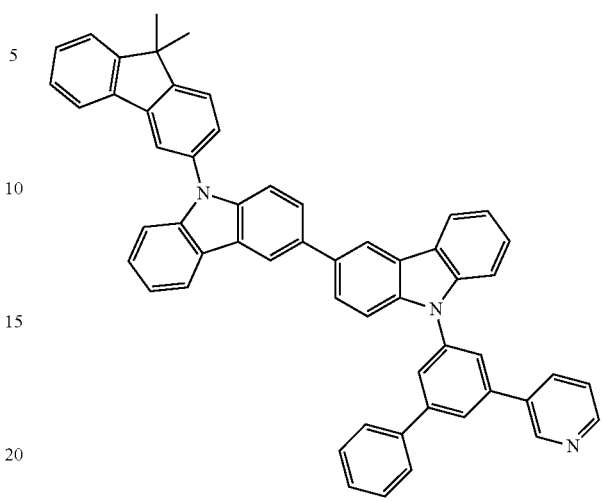
B-62
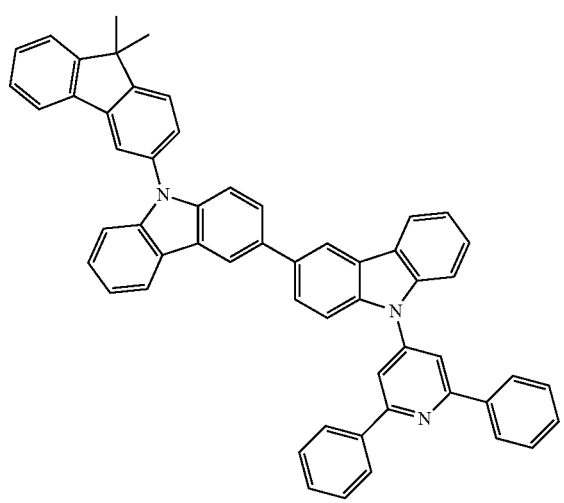
B-65
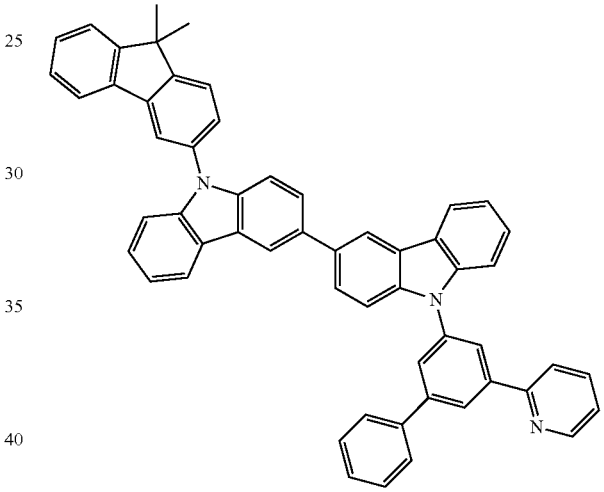
B-63
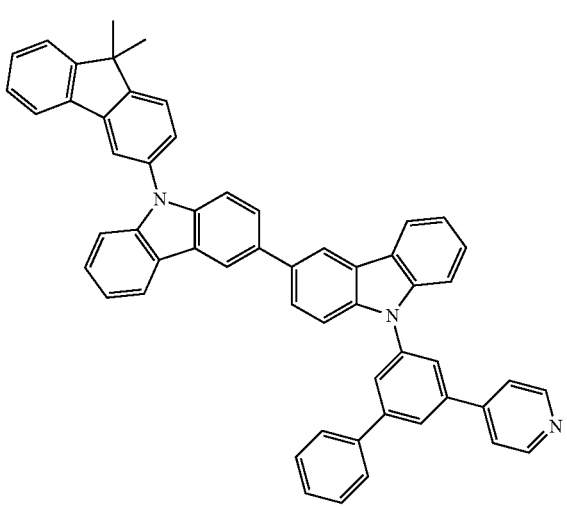
B-66
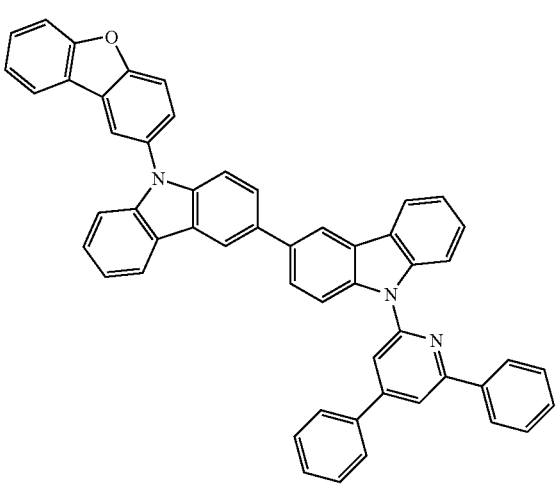

B-67
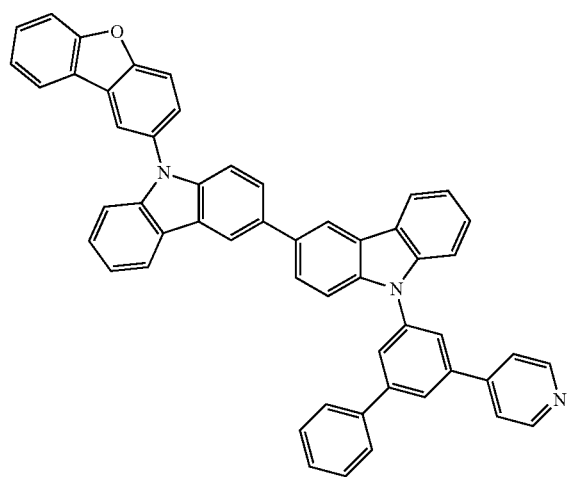
B-68
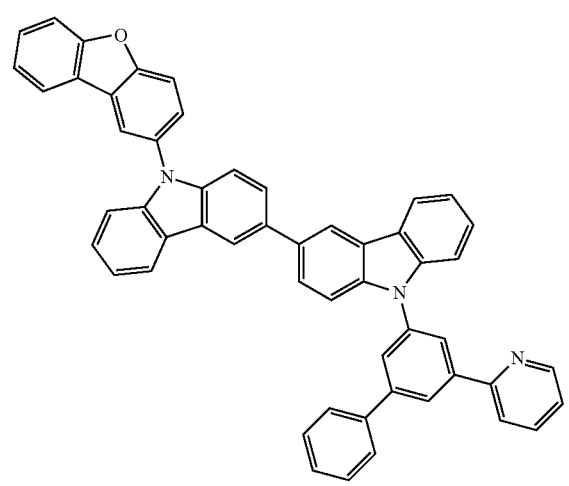
B-69
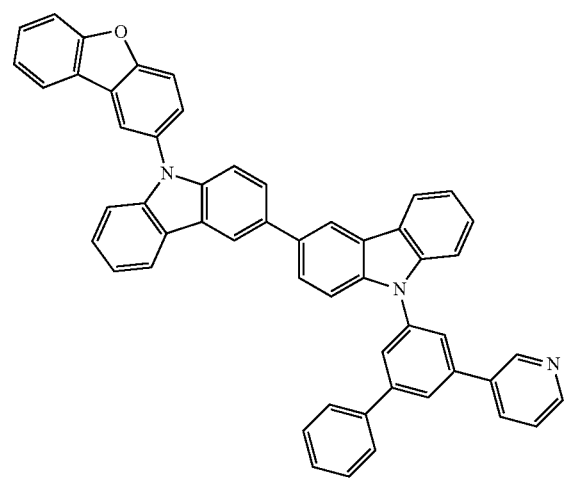
B-70
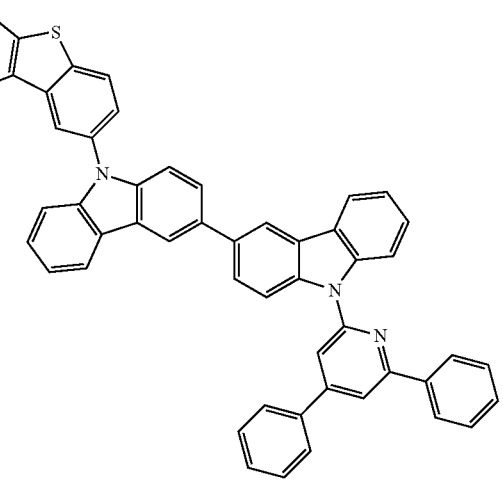
B-71
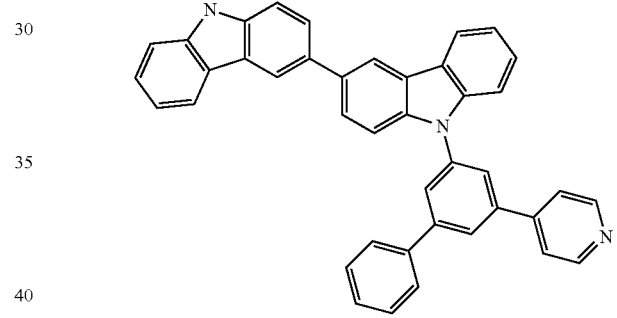
B-72
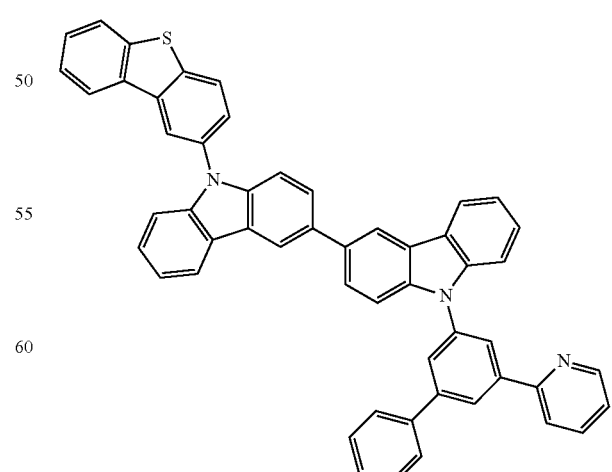

B-73
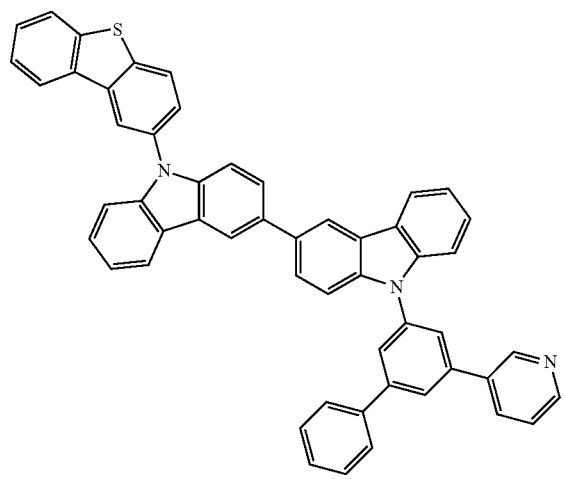
B-74
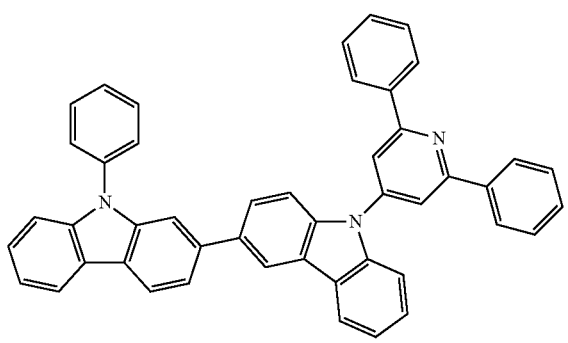
B-75
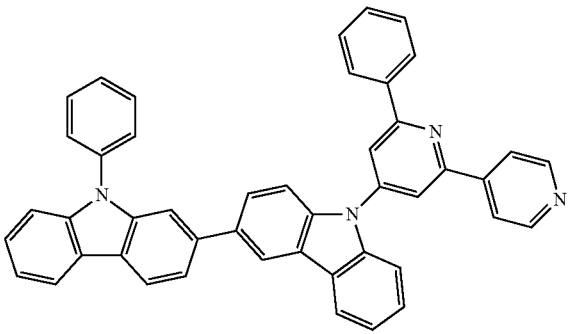
B-76
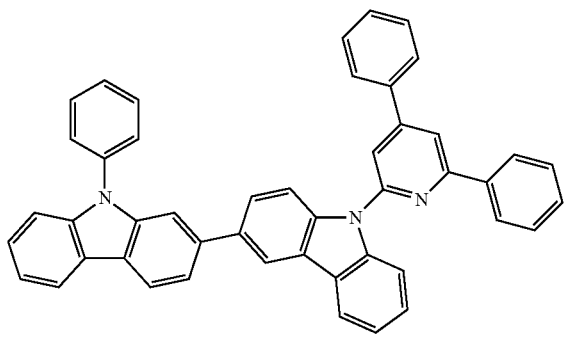
B-77
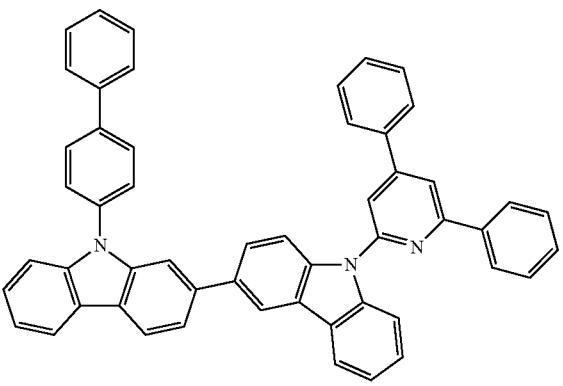
B-78
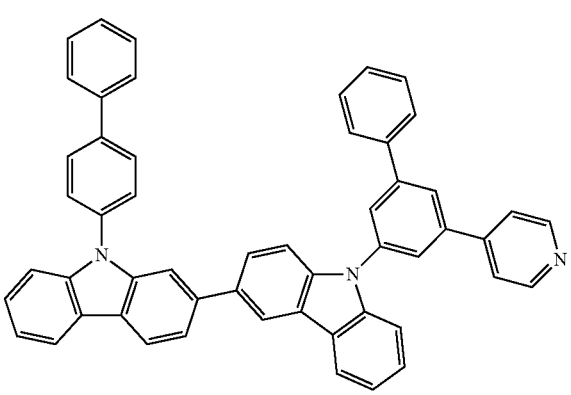
B-79
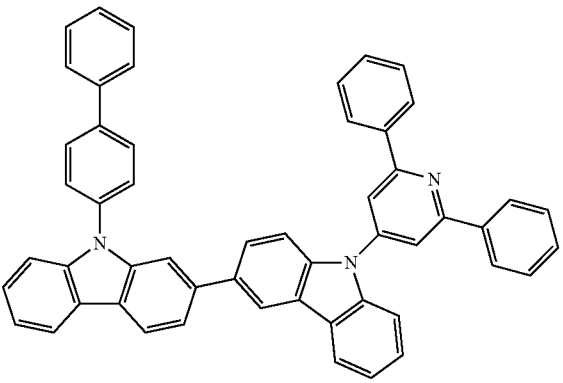
B-80
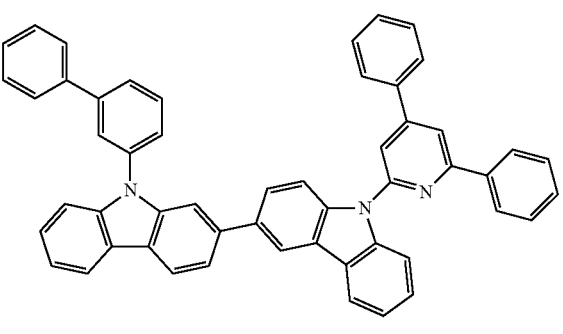

B-81
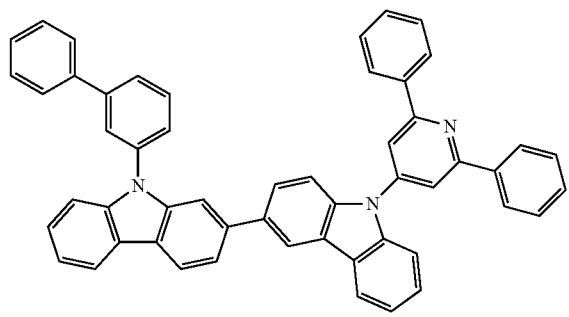
B-85
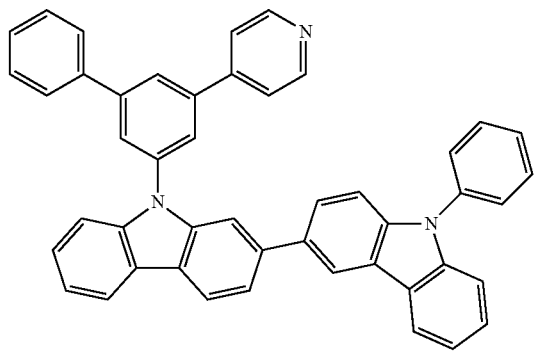
B-82
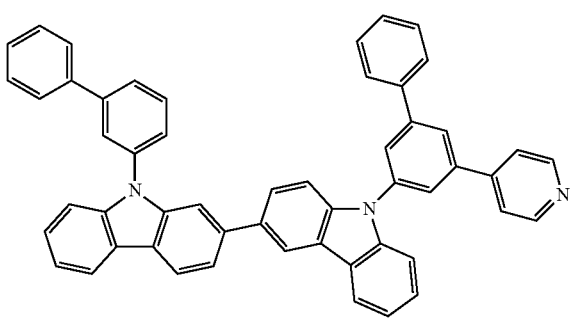
B-86
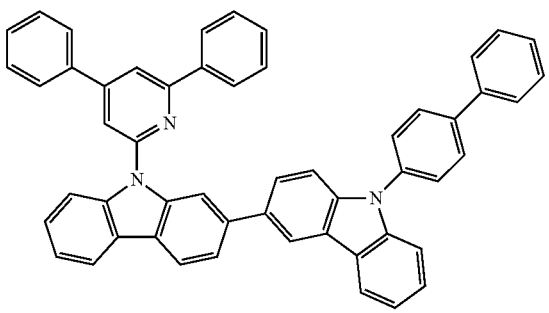
B-83
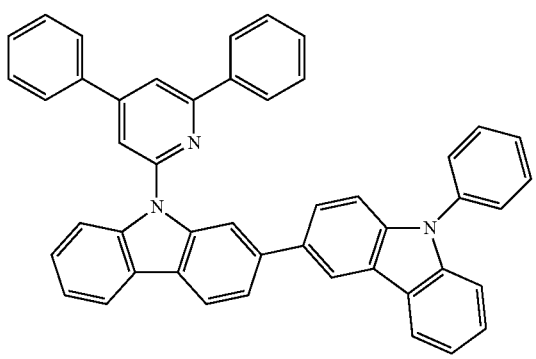
B-87
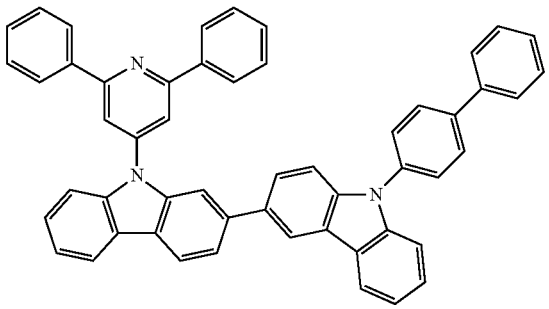
B-84
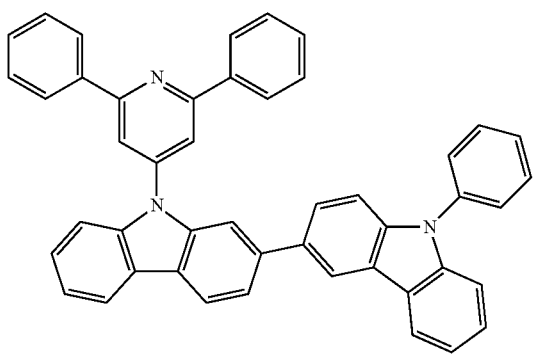
B-88
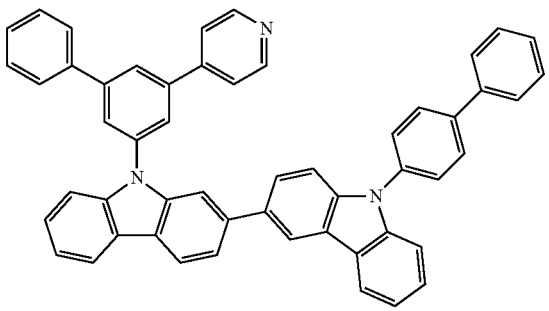

B-89
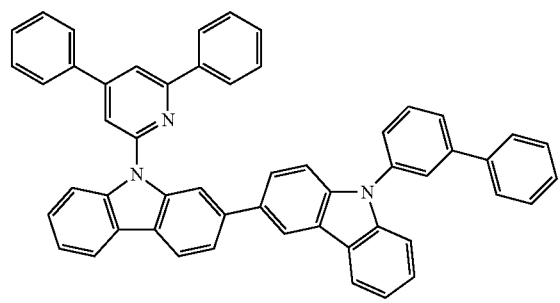
B-93
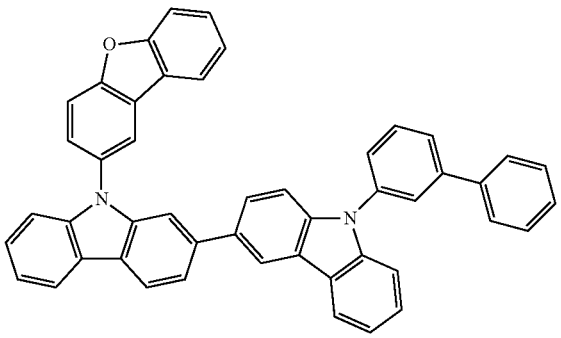
B-90
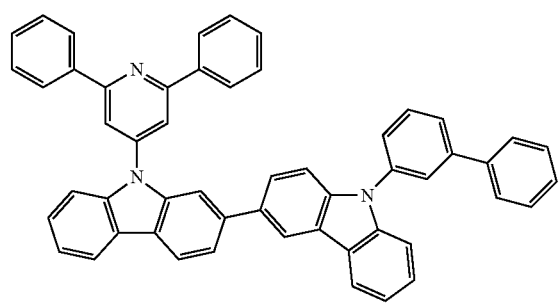
B-94
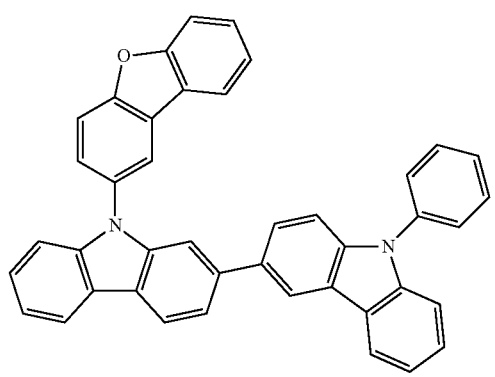
B-91
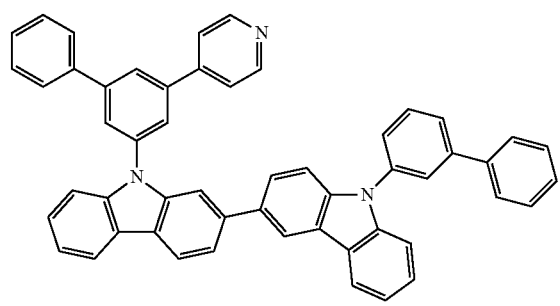
B-95
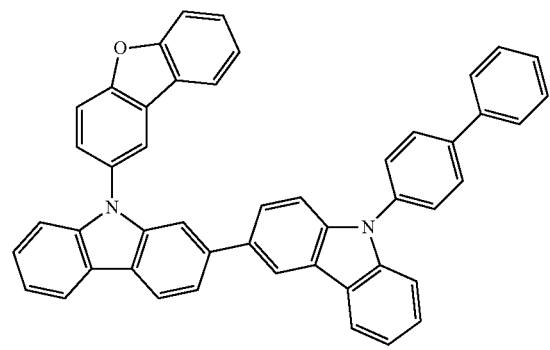
B-92
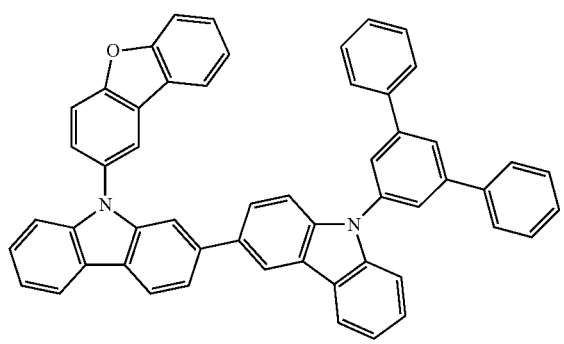
B-96
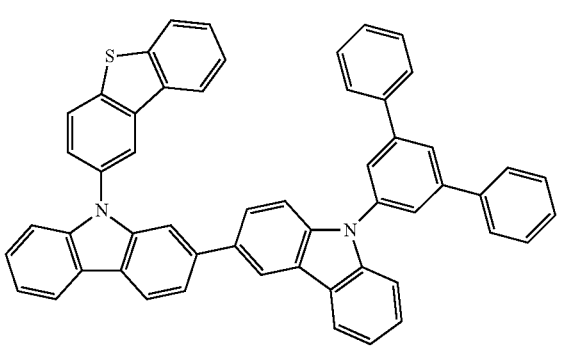

B-97
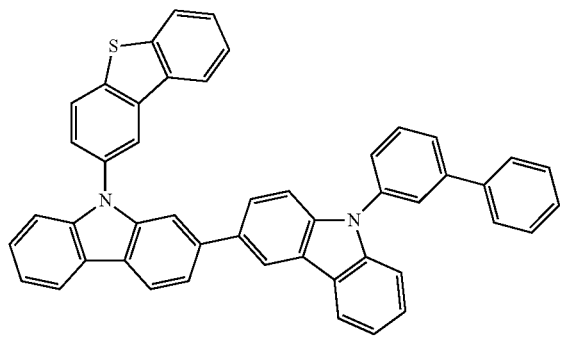
B-101
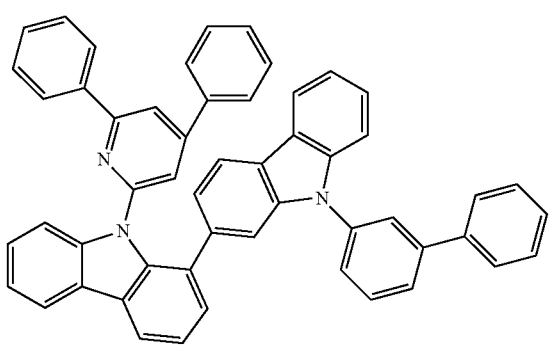
B-98
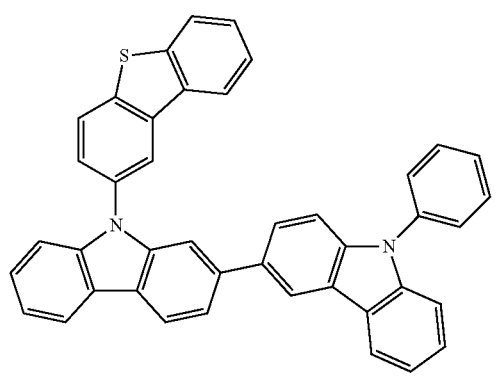
B-102
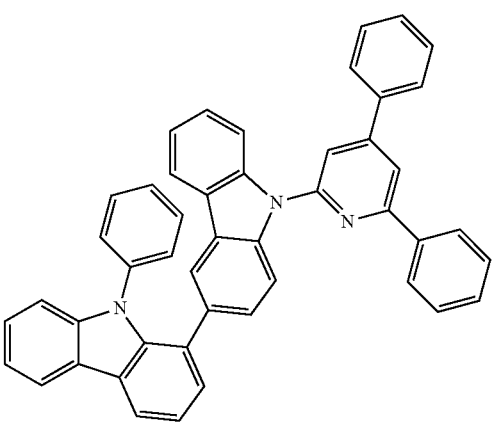
B-99
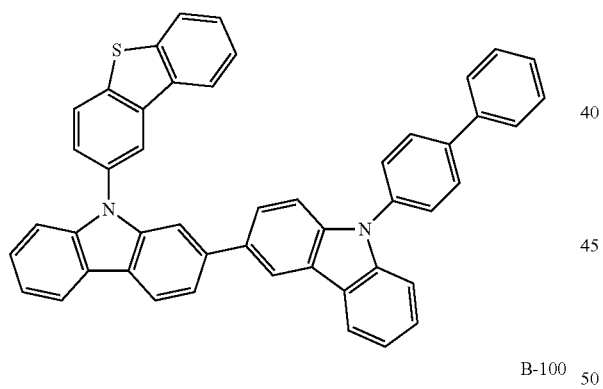
B-103
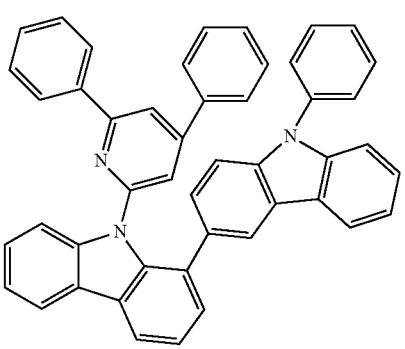
B-100
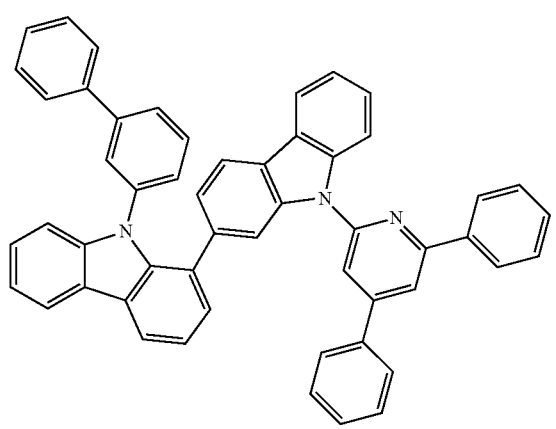
B-104
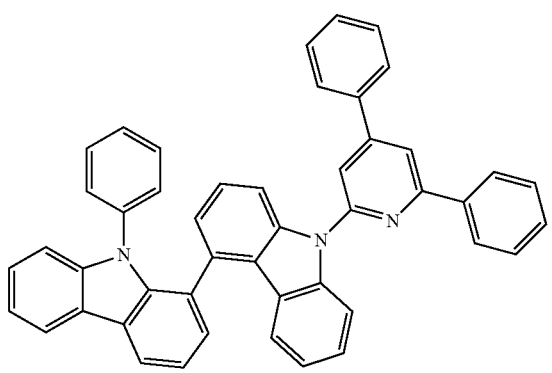

B-105
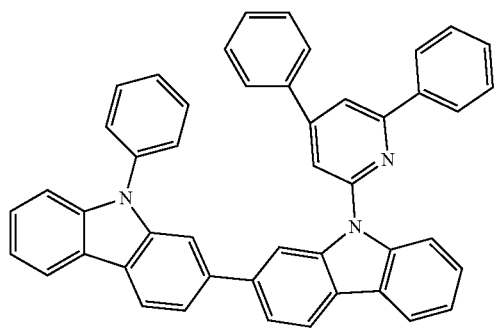
B-109
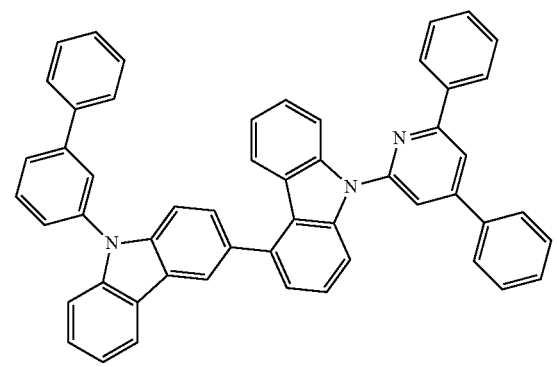
B-106
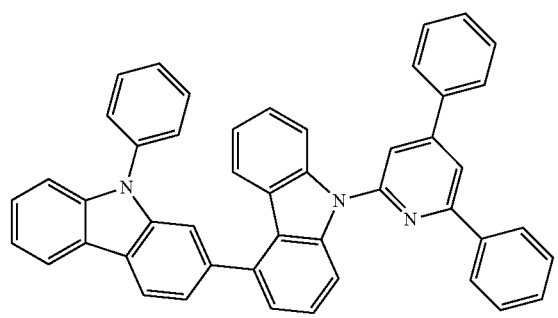
B-110
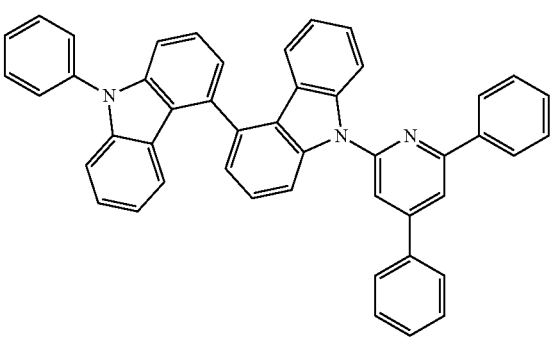
B-107
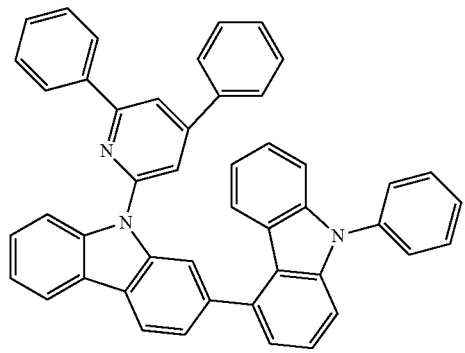
B-111
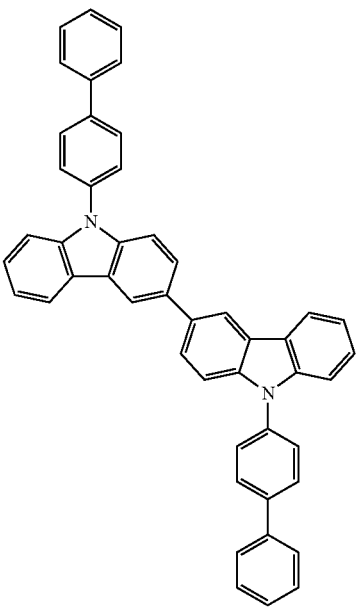
B-108
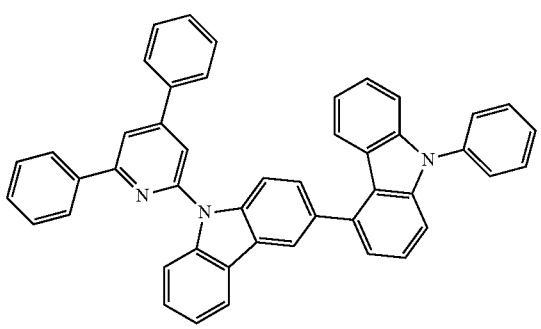

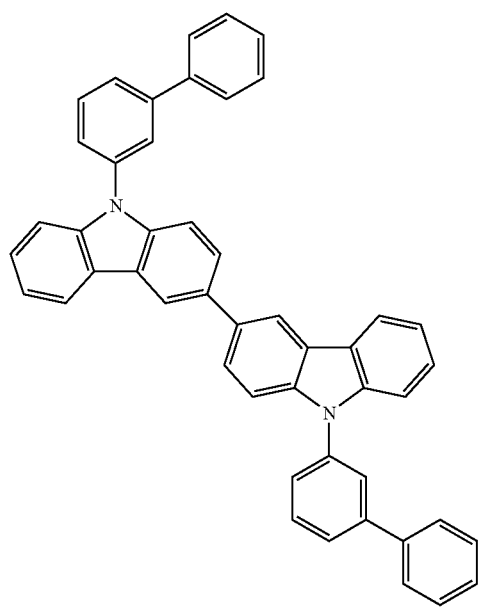
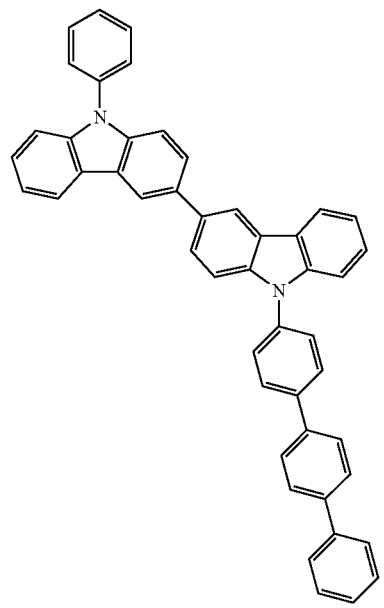

B-116
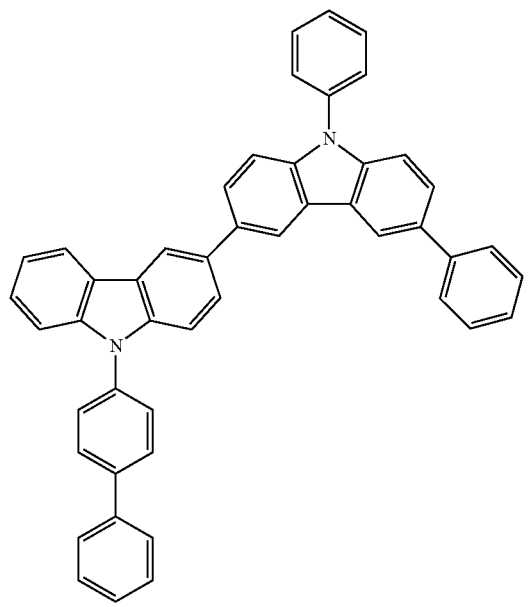
B-117
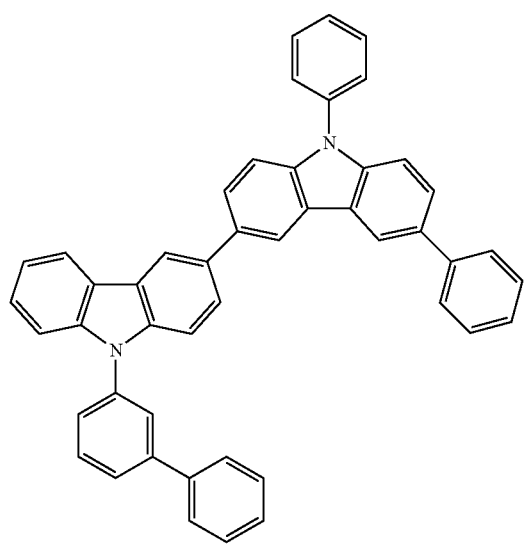
B-118
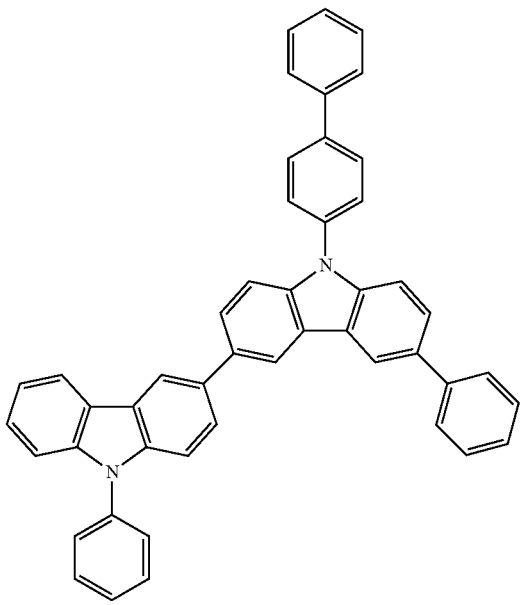
B-119
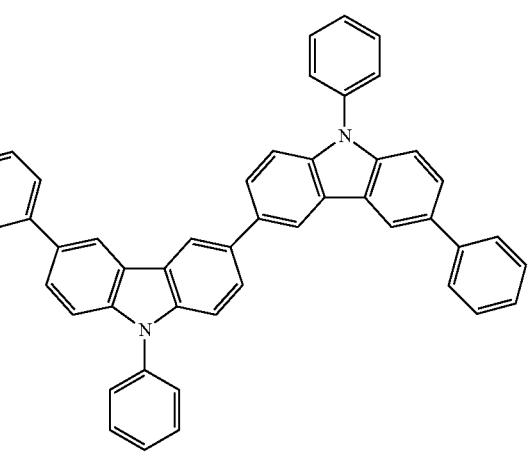
B-120

B-121
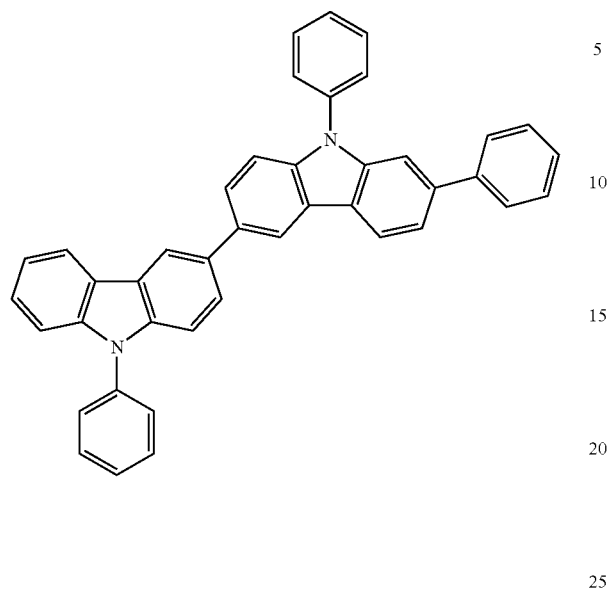
B-122
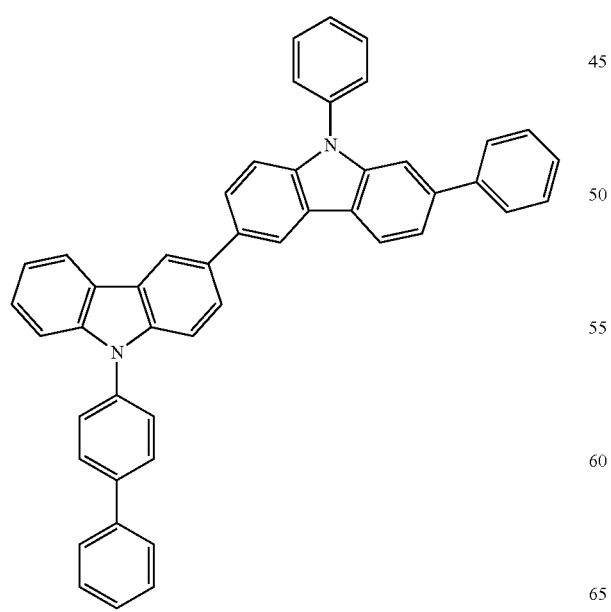
B-123
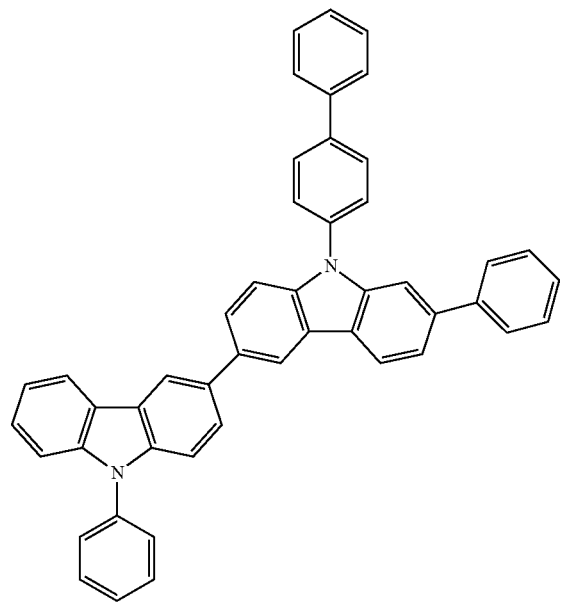
B-124
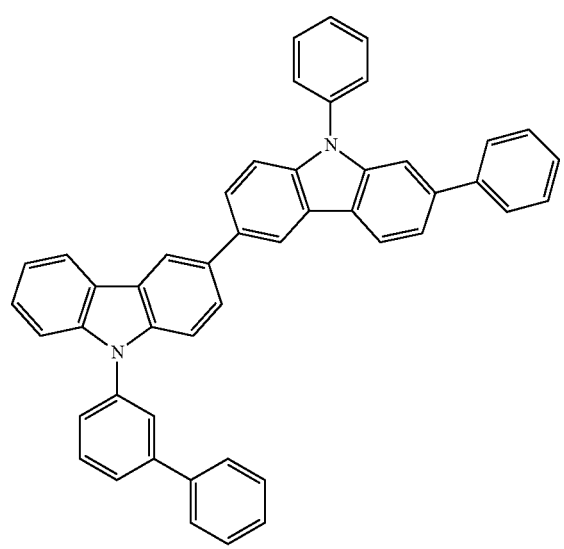

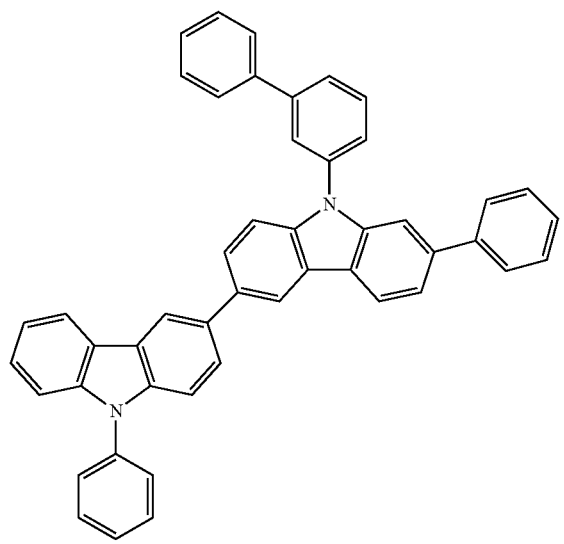
B-125
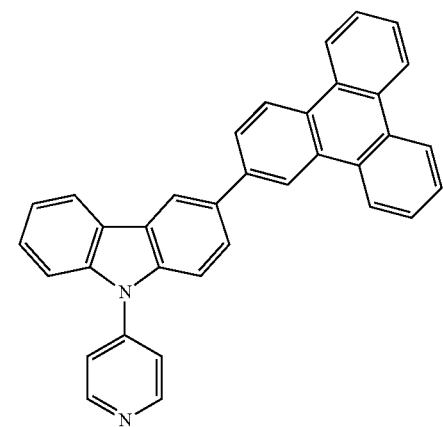
C-10
C-11
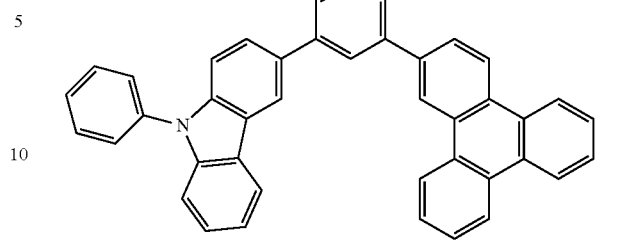
C-12
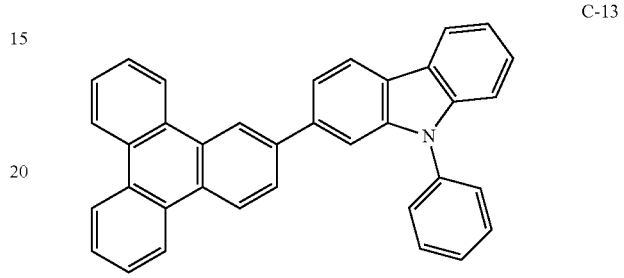
C-13
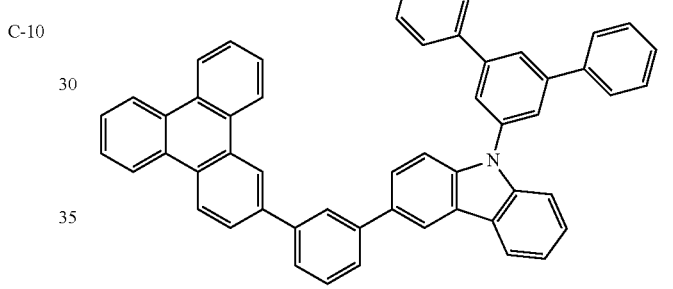
C-14
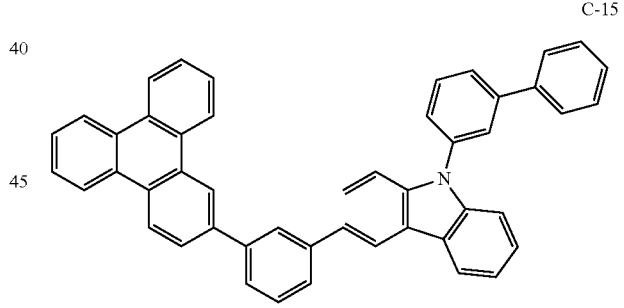
C-15
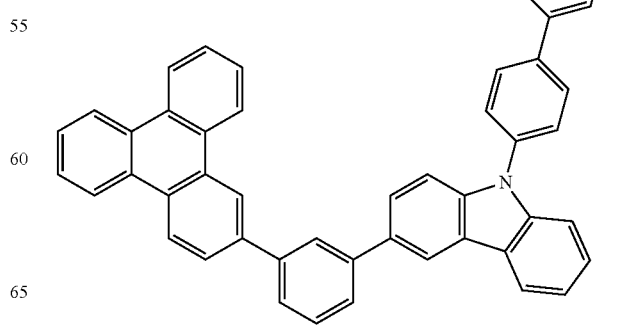
C-16

C-17
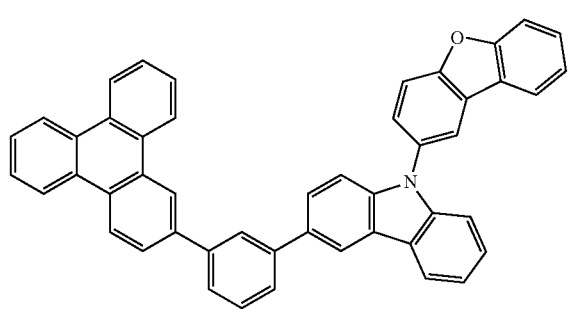
C-18
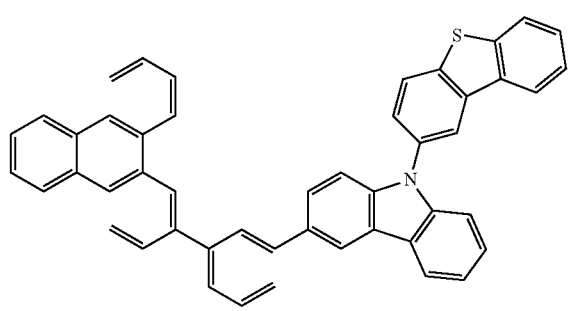
C-19
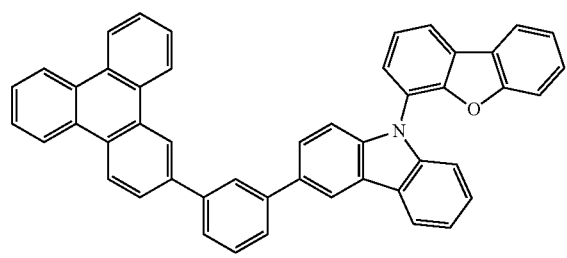
C-20
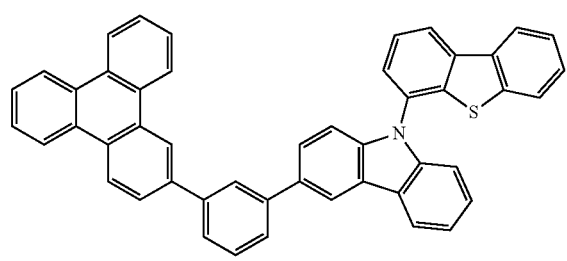
C-21
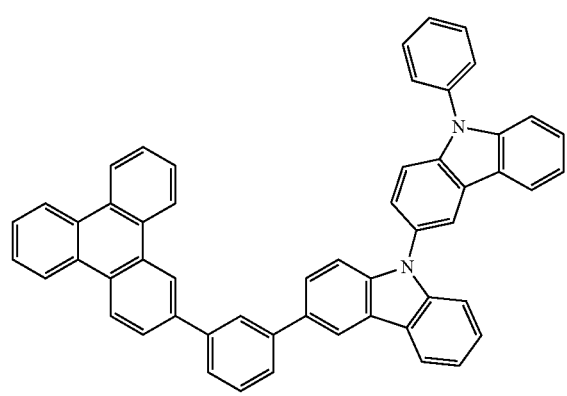
C-22
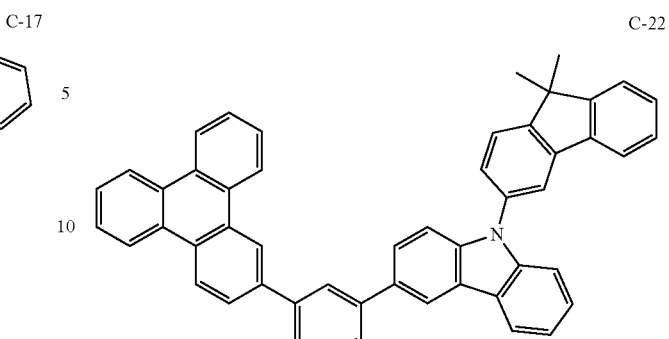
C-23
C-24
C-25

C-26
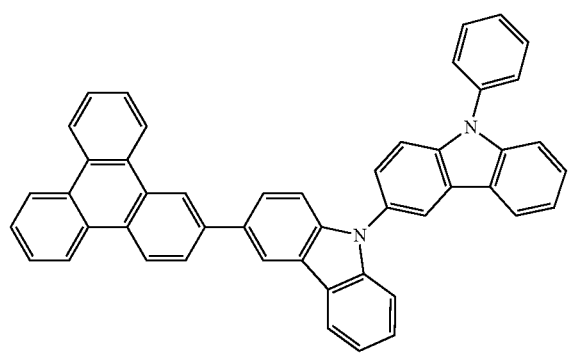
C-27
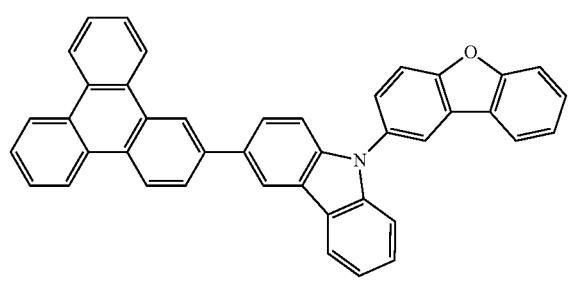
C-28
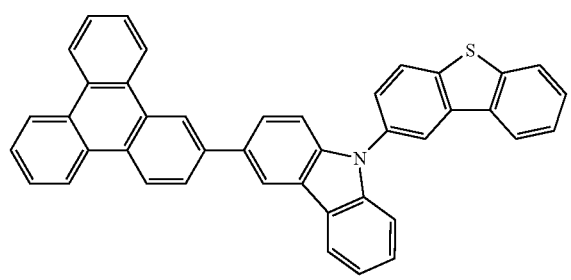
C-29
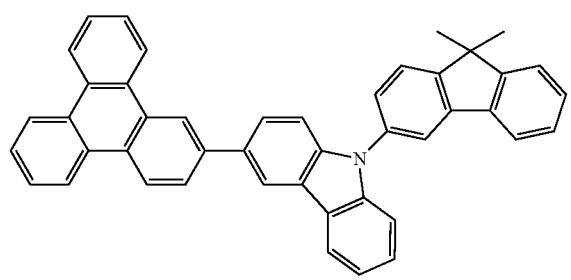
C-30
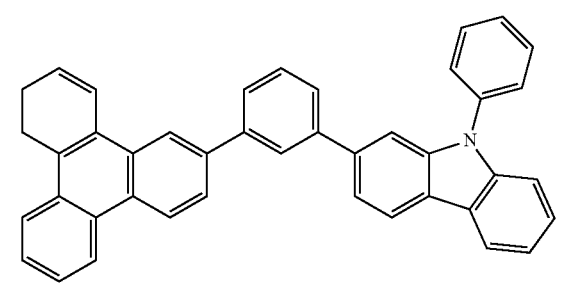
C-31
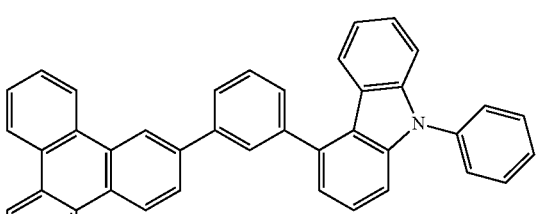
C-32
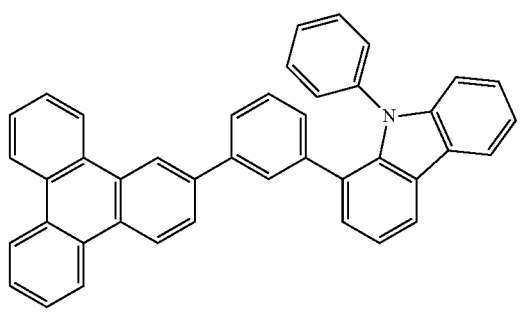
C-33
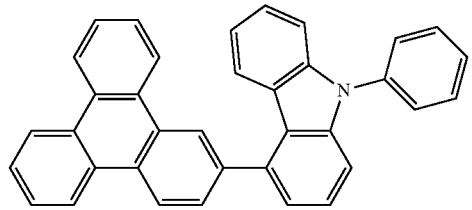
D-10
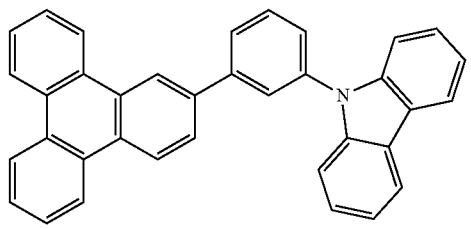
D-11
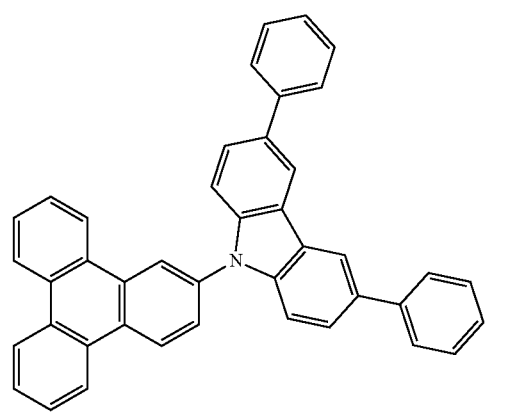

D-12
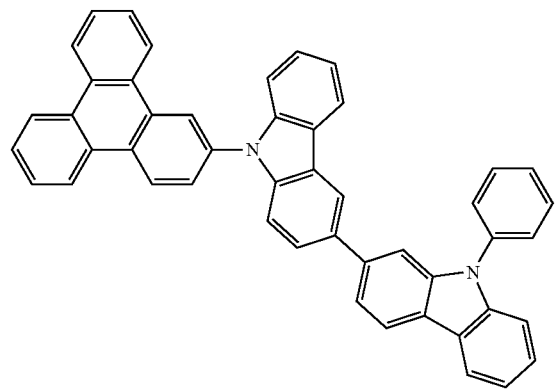
D-13
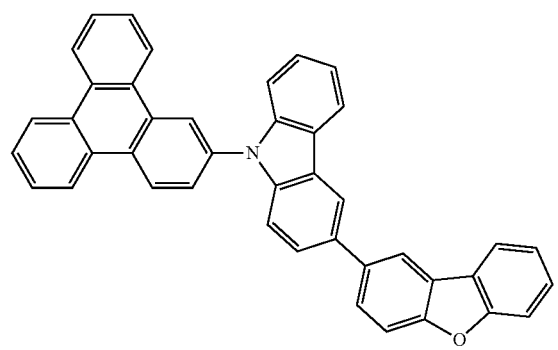
D-14
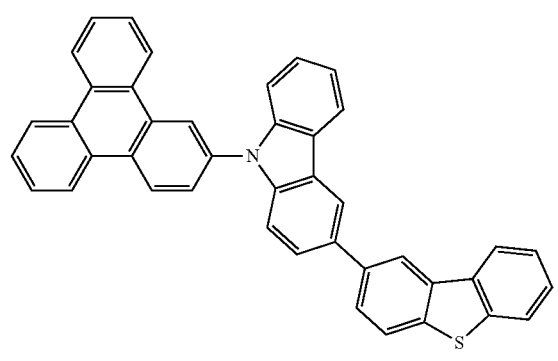
D-15
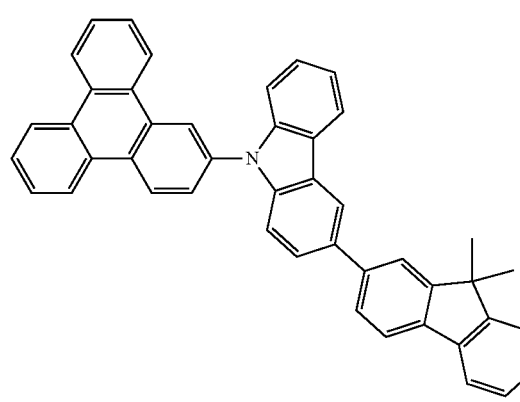
D-16
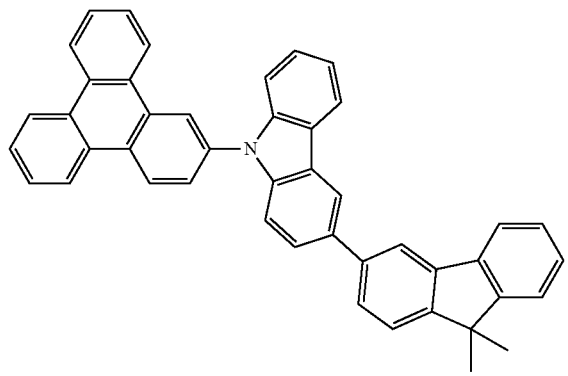
D-17
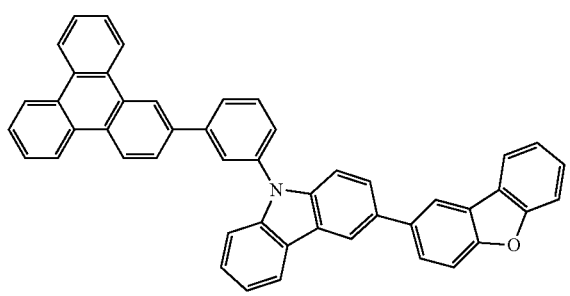
D-18
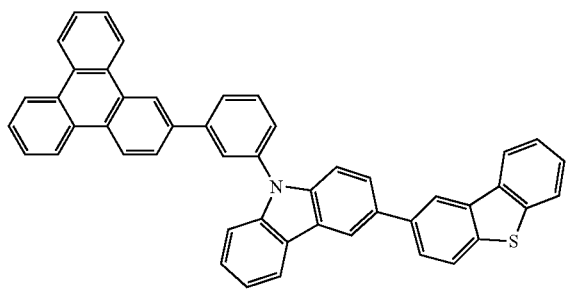
D-19
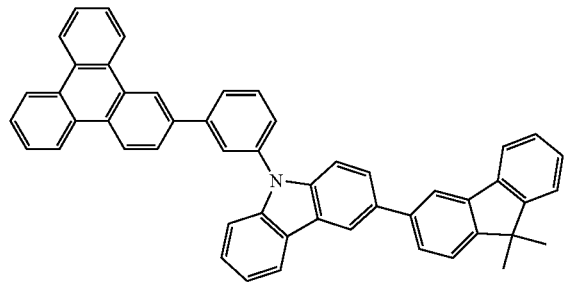

D-20
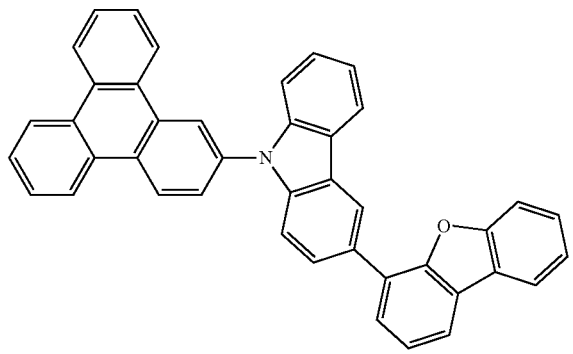
D-21
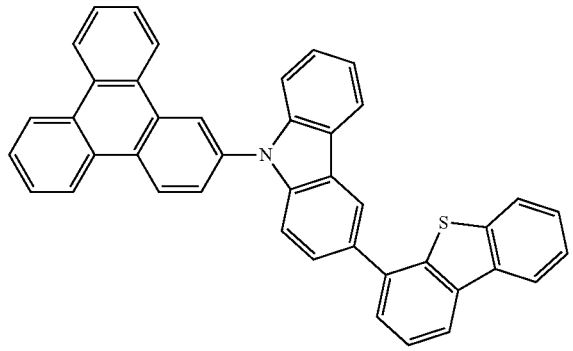
D-22
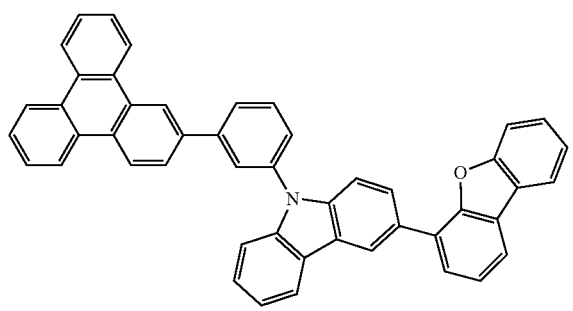
D-23
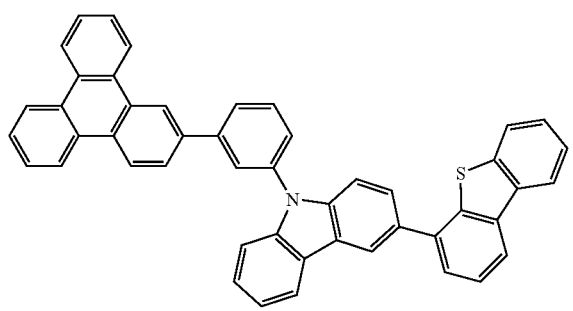
D-24
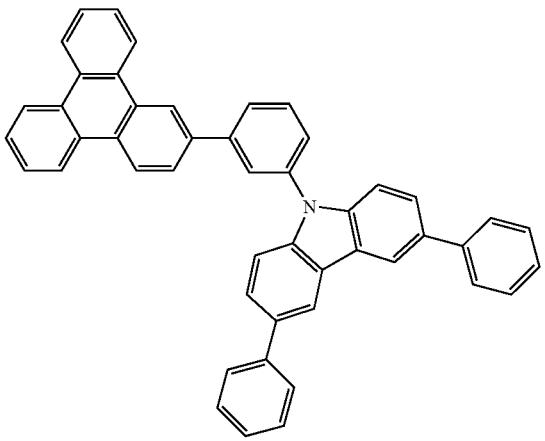
D-25
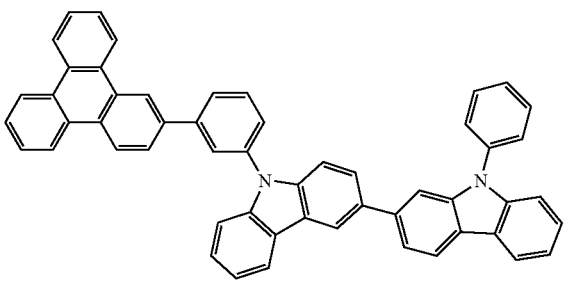
D-26
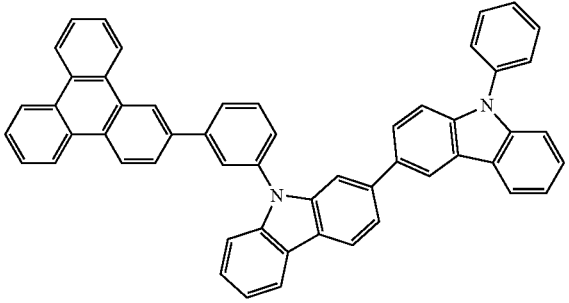
D-27

D-28

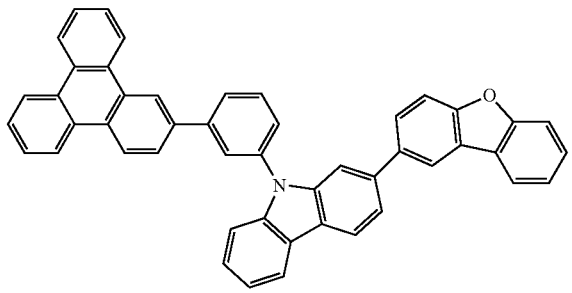

D-29

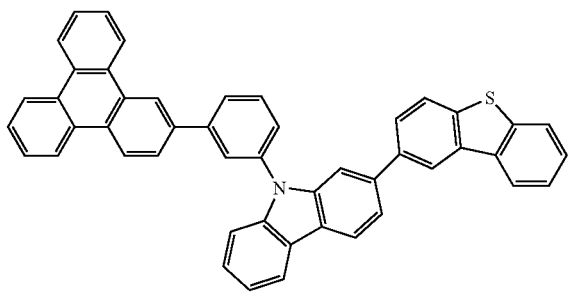

The second organic compound may be for example a compound consisting of a combination of a moiety represented by Chemical Formula 6 and a moiety represented by Chemical Formula 7.

[Chemical Formula 6]

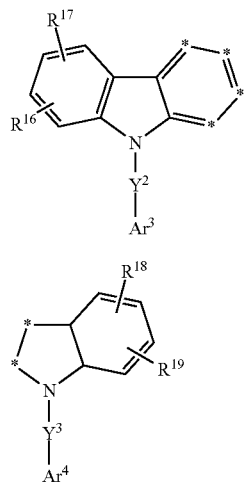

[Chemical Formula 7]

In Chemical Formula 6 or 7, $Y^2$ and $Y^3$ are independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 divalent heterocyclic group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{16}$ to $R^{19}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, and two adjacent *'s of Chemical Formula 6 are bound to two adjacent *'s of Chemical Formula 7 to provide a fused ring, *'s of not providing a fused ring of Chemical Formula 6 are independently $CR^b$ wherein $R^b$ is hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof.

The second organic compound consisting of the moiety represented by Chemical Formula 6 and the moiety represented by Chemical Formula 7 may be, for example selected from compounds of Group 3, but is not limited thereto.

[Group 3]

E-1

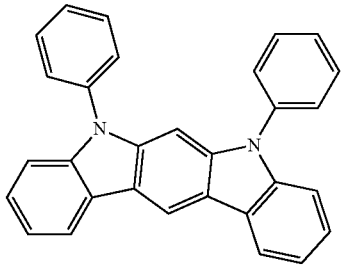

E-2

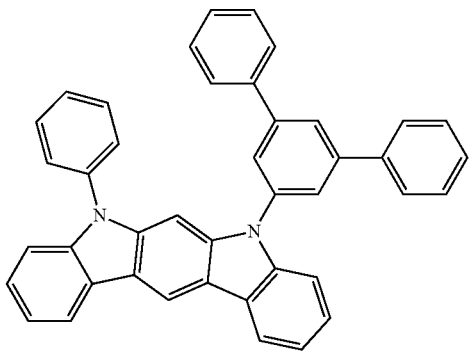

E-3

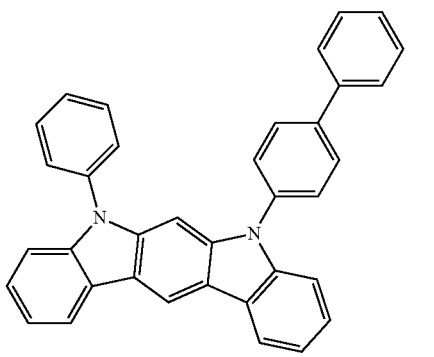

E-4
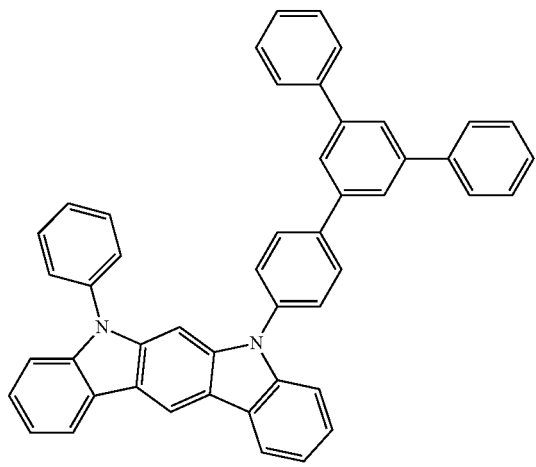
E-5
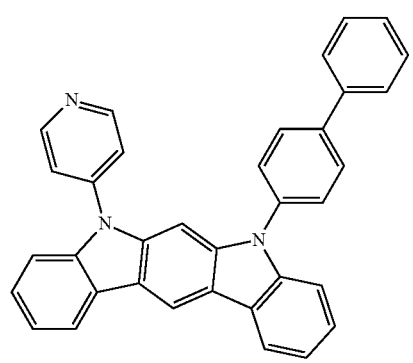
E-6
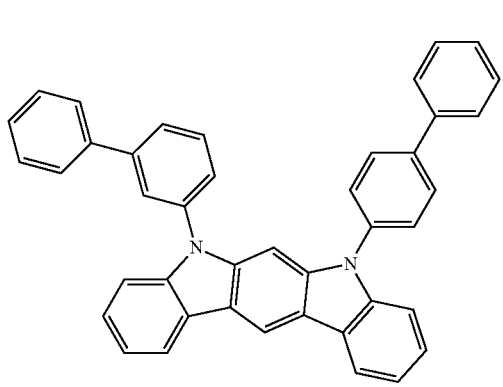
E-7
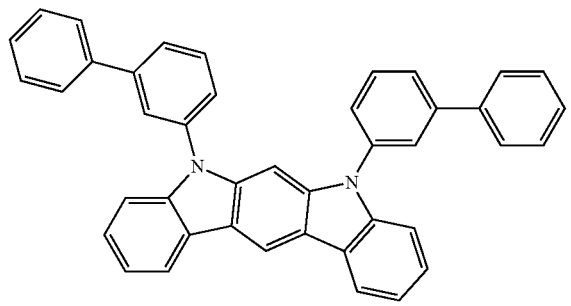
E-8
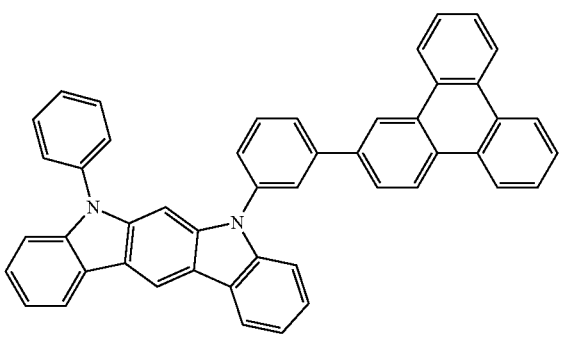
E-9
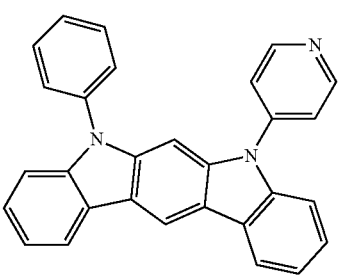
E-10
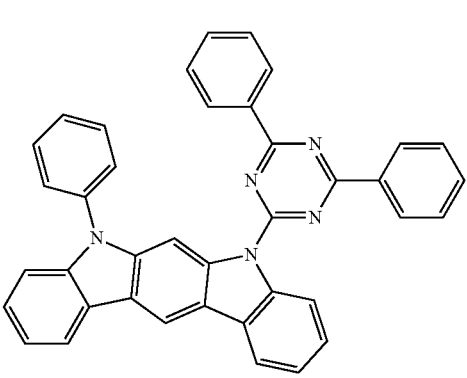
E-11
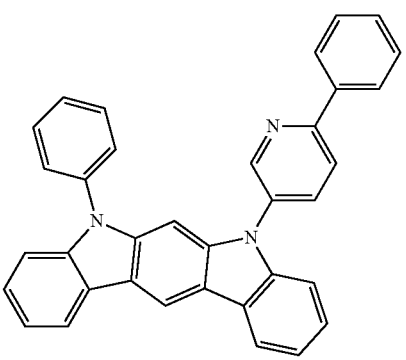

E-12
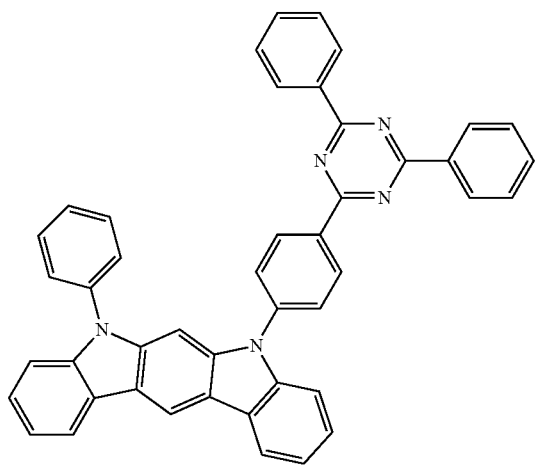
E-13
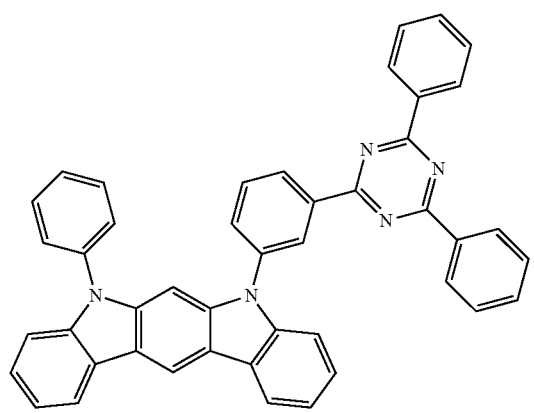
E-14
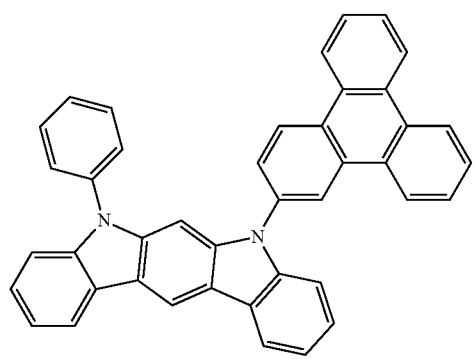
E-15
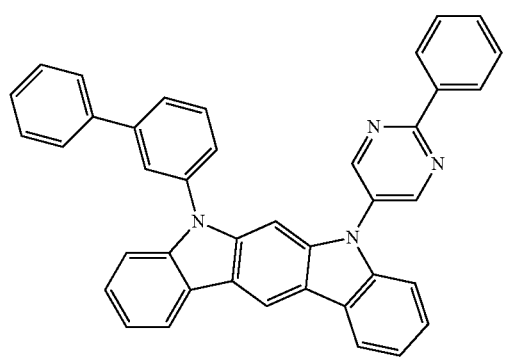
E-16
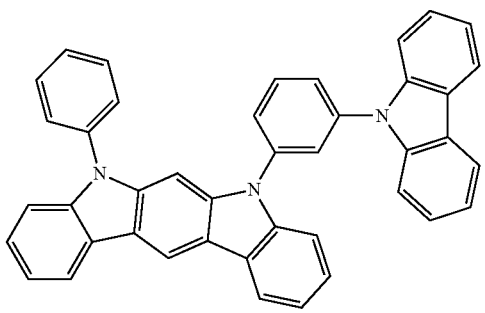
E-17
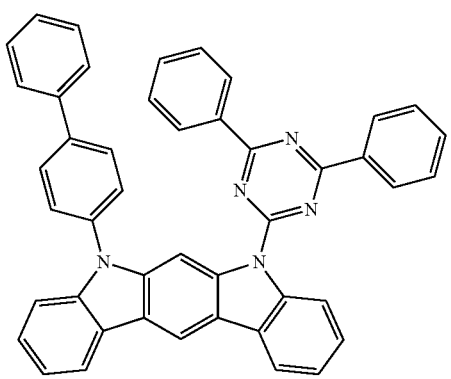
E-18
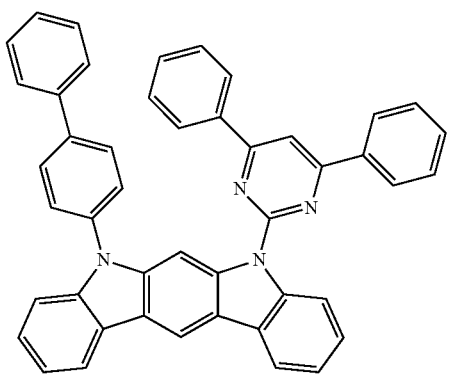
E-19
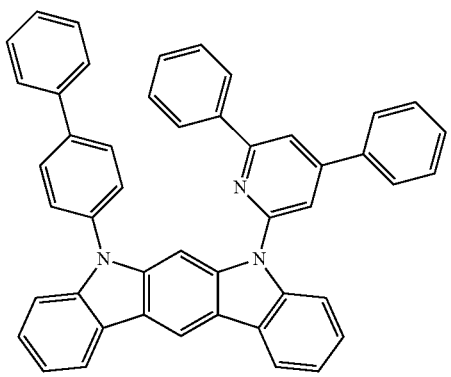

E-20
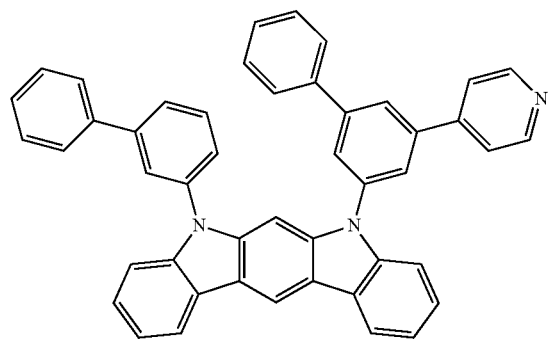
E-25
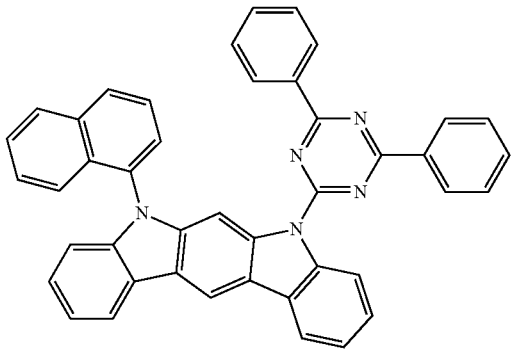
E-21
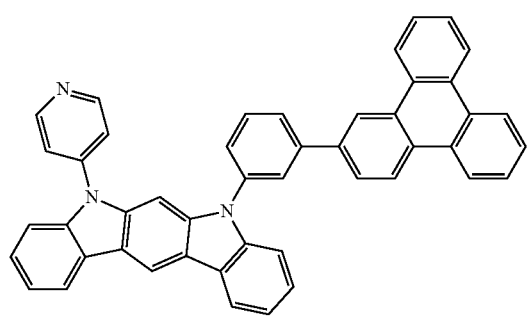
E-26
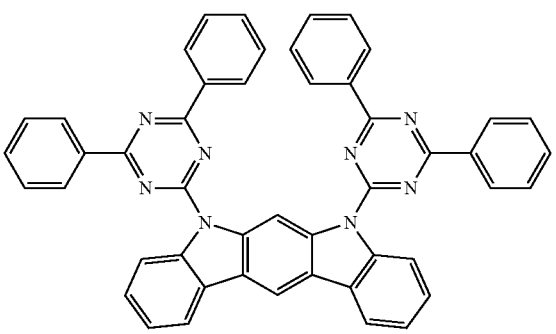
E-22
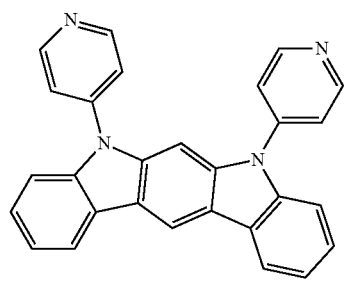
E-23
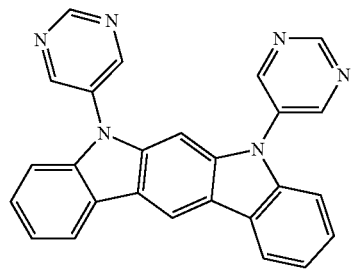
E-27
E-24
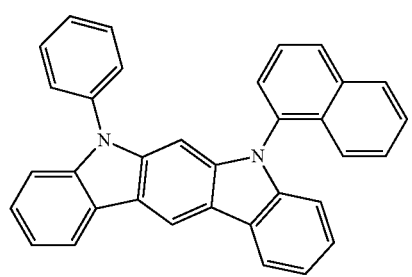
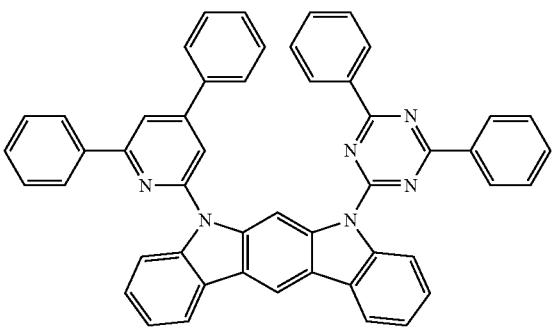

E-29
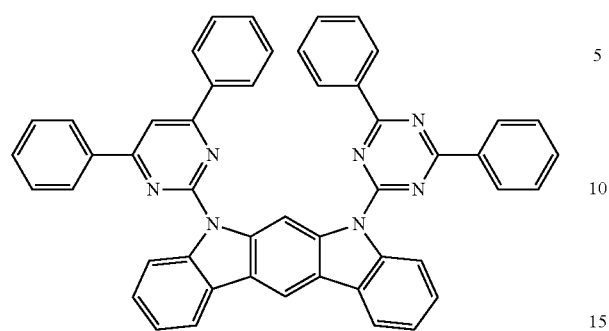
E-33
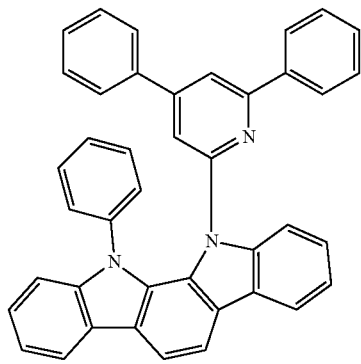
E-30
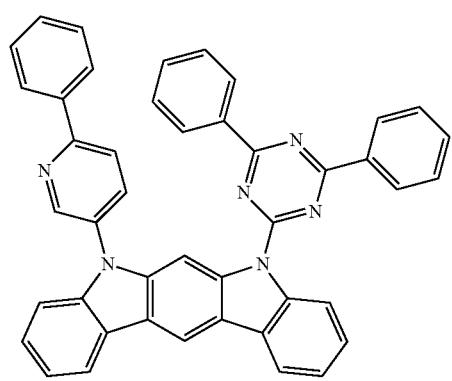
E-34
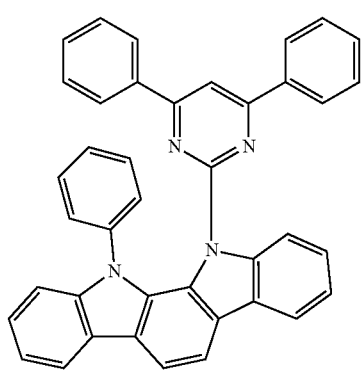
E-31
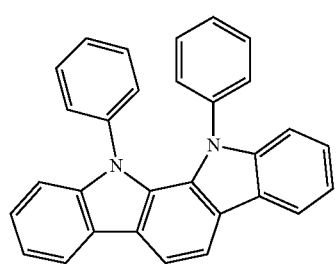
E-35
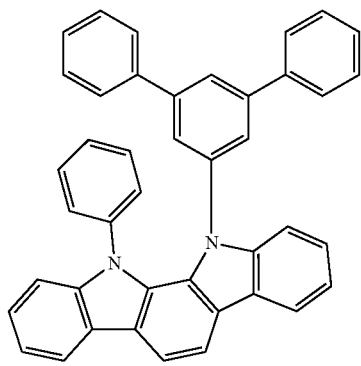
E-32
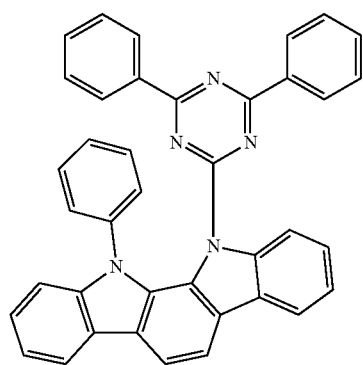
E-36
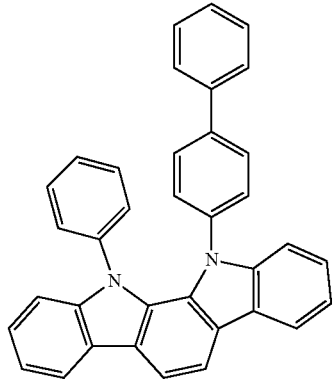

E-37
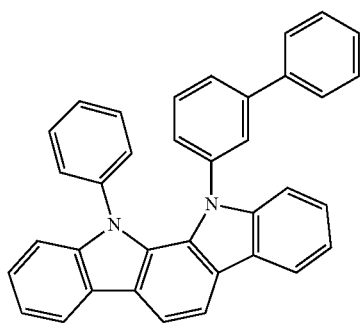
E-38
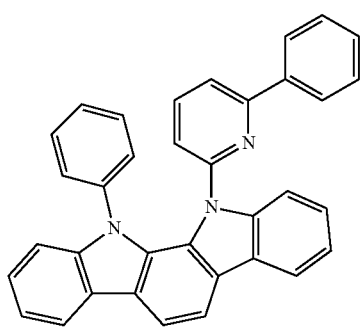
E-39
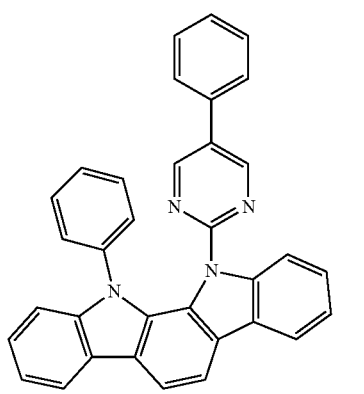
E-40
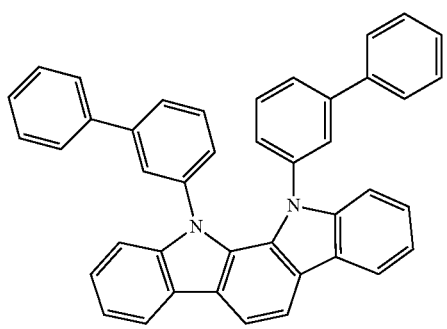
E-41
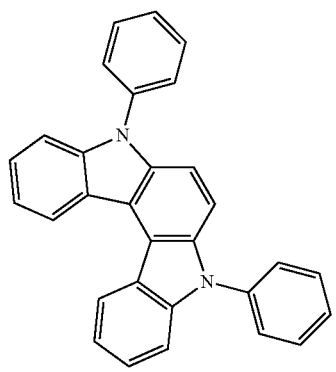
E-42
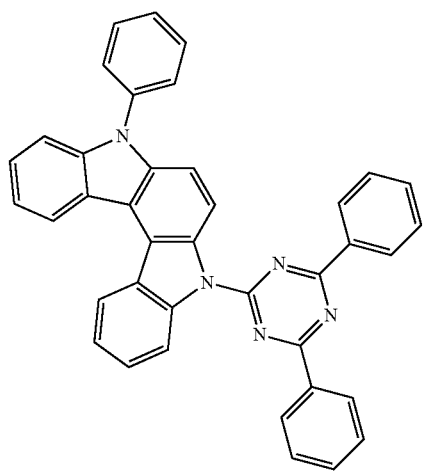
E-43
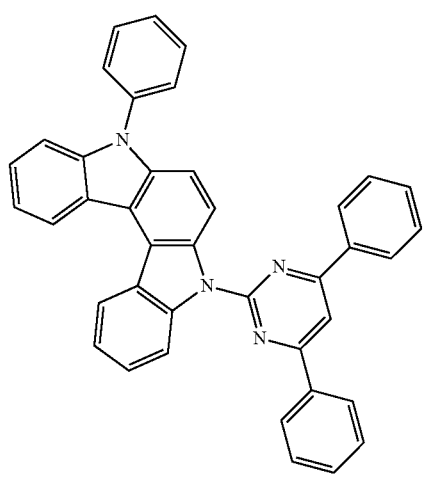

E-44
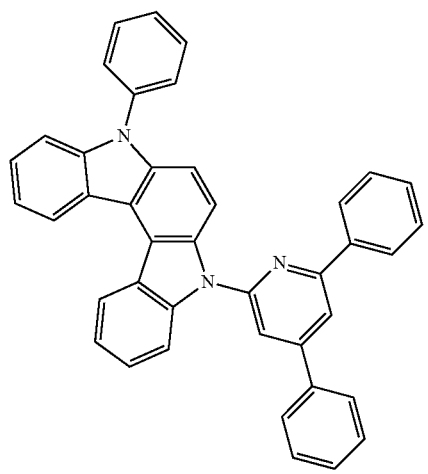
E-45
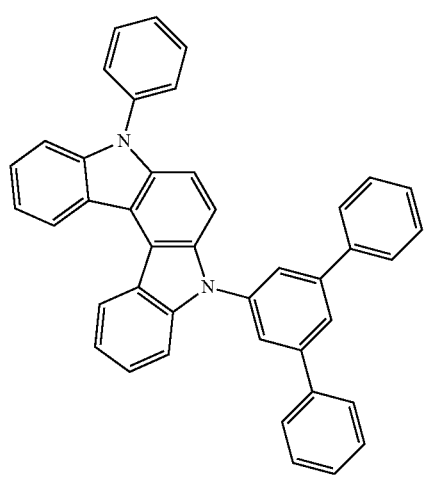
E-46
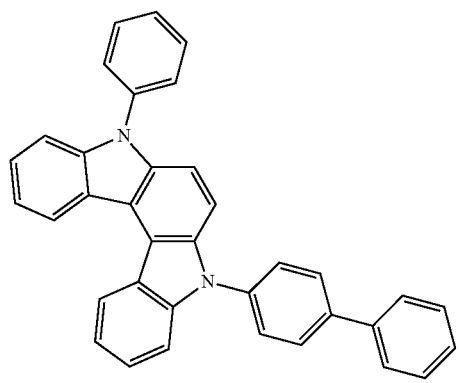
E-47
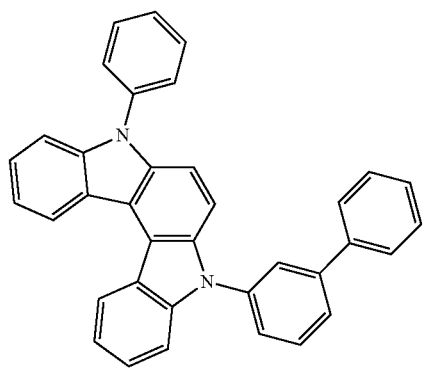
E-48
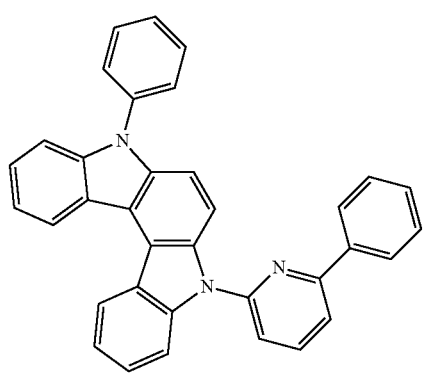
E-49
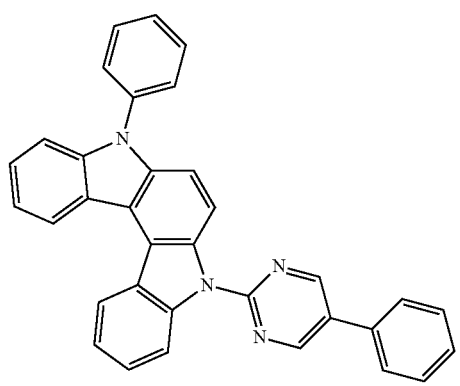

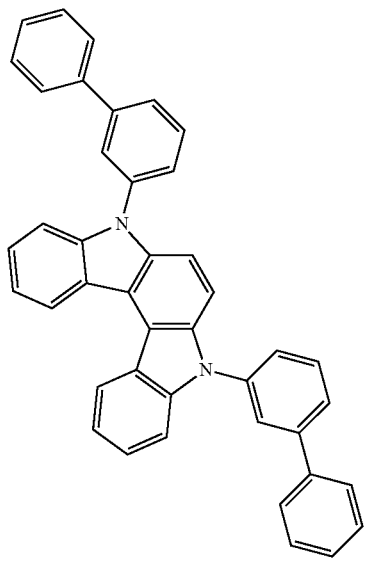
E-50
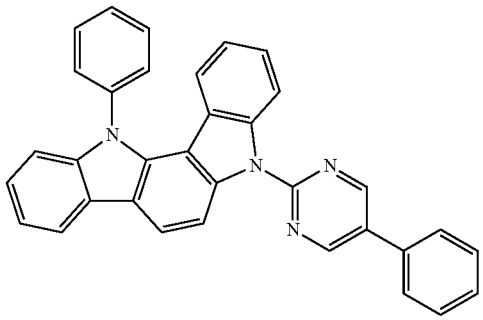
E-54
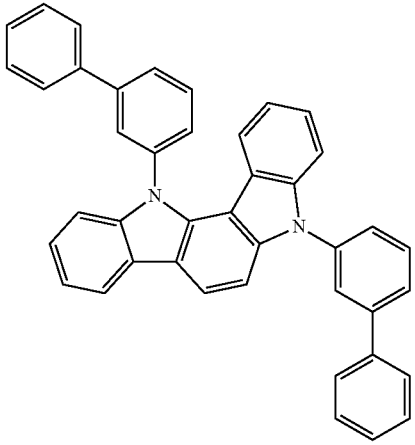
E-55
E-51
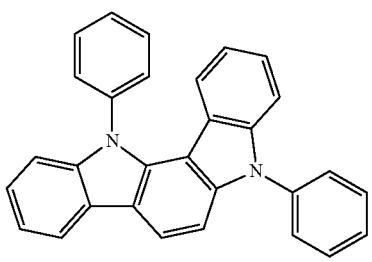
E-56
E-52
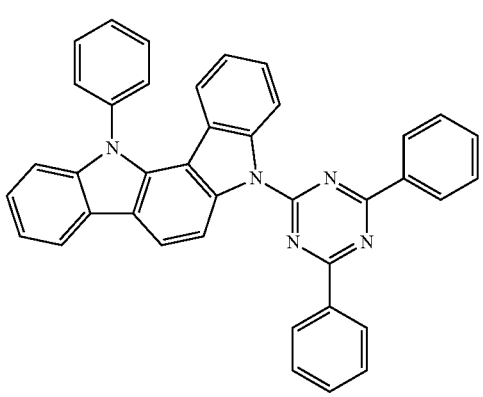
E-57
E-53

E-58
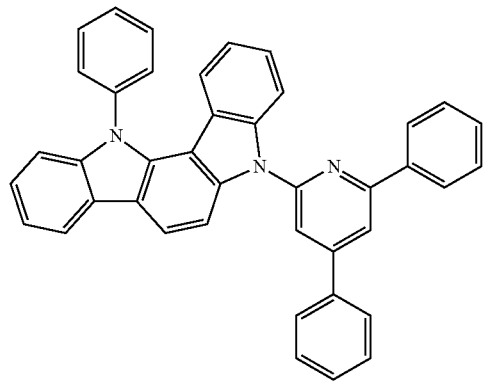
E-59
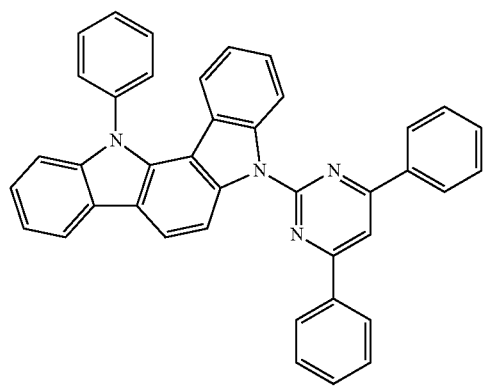
E-60
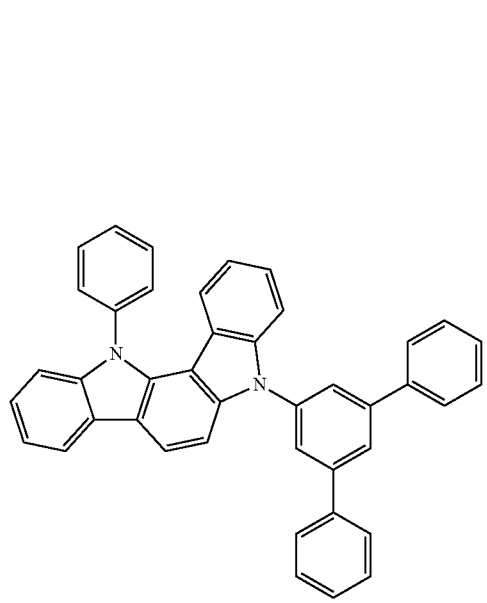
E-61
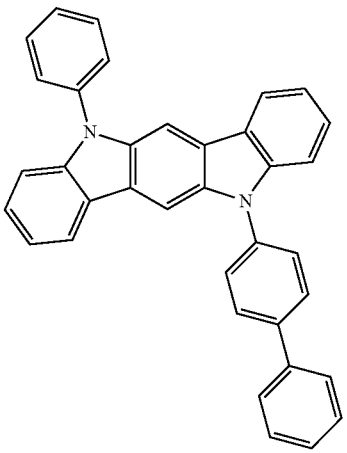
E-62
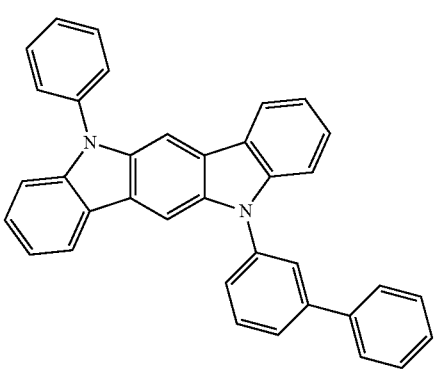
E-63
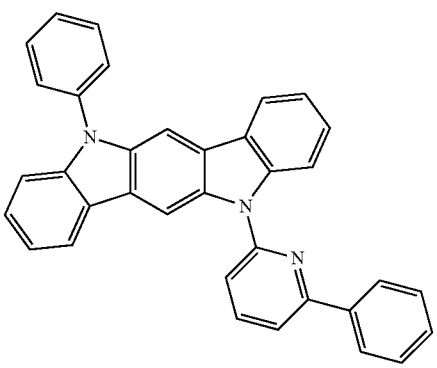
E-64
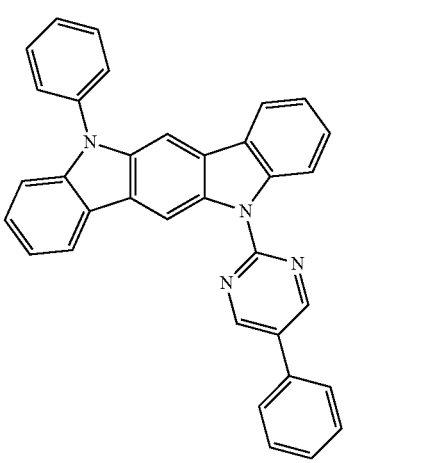

-continued

E-65

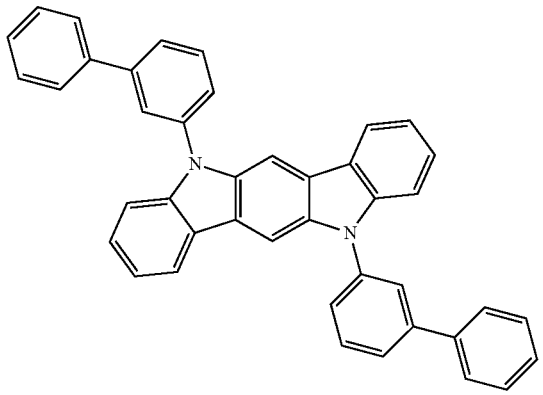

The second organic compound may include at least one of a compound represented by Chemical Formula 5 and a compound consisting of a moiety represented by Chemical Formula 6 and a moiety represented by Chemical Formula 7.

The composition may include the first organic compound and the second organic compound in a weight ratio of about 1:99 to 99:1.

The composition may be applied to an organic layer of an organic optoelectronic diode, and the first organic compound and the second organic compound may act as a host. Herein, the first organic compound may be a compound having bipolar characteristics wherein electron characteristics are relatively strong and the second organic compound may be a compound having bipolar characteristics wherein hole characteristics are relatively strong and may be employed with the first organic compound to heighten charge mobility and stability and thus to improve luminous efficiency and life-span characteristics.

The composition may further include one or more organic compounds besides the first organic compound and the second organic compound.

The composition may further include a dopant. The dopant may be a red, green, or blue dopant, for example a phosphorescent dopant.

The dopant is mixed with the host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

Examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L_2MX$ [Chemical Formula Z]

In Chemical Formula Z, M is a metal, and L and X are the same or different, and are a ligand to form a complex compound with M. The M may be for example Ir, Pt, Os, Ti, Zr, Hf, Eu, Tb, Tm, Fe, Co, Ni, Ru, Rh, Pd, or a combination thereof, and the L and X may be, for example a bidendate ligand.

The composition may be applied to an organic layer of an organic optoelectronic diode, and for example the composition may be applied to an electron transport auxiliary layer between a light emitting layer and an electron transport layer.

The first compound and the second compound are applied to an electron transport auxiliary layer in various ratios, and thereby an electron transport capability to transport electrons from an electron transport layer to a light emitting layer may be controlled and may be balanced with an electron transport capability of a light emitting layer and thus electrons are prevented from being accumulated on the interface of the light emitting layer. In addition, the electron transport auxiliary layer converts holes transported from the anode to the light emitting layer and/or excitons generated in the light emitting layer into excitons having lower energy than the excitons of the light emitting layer, and thus holes and/or excitons may be prevented from passing the light emitting layer and being transported into the electron transport layer. Accordingly, efficiency and life-span of an organic optoelectronic diode may be improved.

The organic compound and/or the composition may be formed to a film using a dry film formation method or a solution process. The dry film formation method may be for example a chemical vapor deposition (CVD) method, sputtering, plasma plating, and ion plating, and two or more compounds may be simultaneously formed into a film or compound having the same deposition temperature may be mixed and formed into a film. The solution process may be for example inkjet printing, spin coating, slit coating, bar coating and/or dip coating.

Hereinafter, an organic optoelectronic diode including the organic compound or the composition is described.

The organic optoelectronic diode may be any device to convert electrical energy into photoenergy and vice versa without particular limitation, and may be, for example an organic photoelectric device, an organic light emitting diode, an organic solar cell, and an organic photo conductor drum.

The organic optoelectronic diode may include an anode and a cathode facing each other, at least one organic layer between the anode and the cathode, and the organic layer includes the organic compound or the composition.

Herein, an organic light emitting diode as one example of an organic optoelectronic diode is described referring to drawings.

FIG. 1 is a cross-sectional view of an organic light emitting diode according to an embodiment.

Referring to FIG. 1, an organic light emitting diode 100 according to an embodiment includes an anode 110 and a cathode 120 and an organic layer 105 between the anode 120 and the cathode 110.

The anode 110 may be made of a conductor having a large work function to help hole injection, and may be for example made of a metal, a metal oxide and/or a conductive polymer. The anode 110 may be for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy) thiophene) (PEDT), polypyrrole, and polyaniline, but is not limited thereto.

The cathode 120 may be made of a conductor having a small work function to help electron injection, and may be for example made of a metal, a metal oxide and/or a conductive polymer. The cathode 120 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO$_2$/Al, LiF/Ca, LiF/Al, and BaF$_2$/Ca, but is not limited thereto.

The organic layer 105 includes a light emitting layer 130 including the organic compound or the composition.

The light emitting layer 130 may include for example the organic compound alone and a mixture of two or more of the organic compounds or the composition.

FIG. 2 is a cross-sectional view of an organic light emitting diode according to another embodiment.

Referring to FIG. 2, an organic light emitting diode 200 of the present embodiment includes an anode 110 and a cathode 120 and an organic layer 105 disposed between the anode 110 and the cathode 120 like the embodiment.

The organic layer 105 includes a light emitting layer 130 and an auxiliary layer 140 disposed between the light emitting layer 130 and the cathode 120. The auxiliary layer 140 may make injection and transport of charges between the cathode 120 and the light emitting layer 130. The auxiliary layer 140 may be for example an electron transport layer, an electron injection layer, and/or an electron transport auxiliary layer.

FIG. 3 is a cross-sectional view of an organic light emitting diode according to another embodiment.

Referring to FIG. 3, an organic light emitting diode 300 of the present embodiment includes an anode 110 and a cathode 120 and an organic layer 105 disposed between the anode 110 and the cathode 120, and the organic layer 105 includes a light emitting layer 130 and an auxiliary layer 140 like the embodiment.

However, the present embodiment includes the auxiliary layer 140 including a first auxiliary layer 142 adjacent to the light emitting layer 130 and a second auxiliary layer 141 adjacent to the cathode 120 unlike the embodiment. The first auxiliary layer 142 may be for example an electron transport auxiliary layer and the second auxiliary layer 141 may be for example an electron transport layer. The organic compound or the composition may be included in the first auxiliary layer 142 adjacent to the light emitting layer 130.

In FIGS. 1 to 3, the organic layer 105 may further include at least one auxiliary layer between the anode 110 and the light emitting layer 130.

The organic light emitting diode may be applied to an organic light emitting display device.

Hereinafter, the embodiments are illustrated in more detail with reference to examples. These examples, however, are not in any sense to be interpreted as limiting the scope of the invention.

Synthesis of Intermediate

Synthesis of Intermediate I-1

[Reaction Scheme 1]

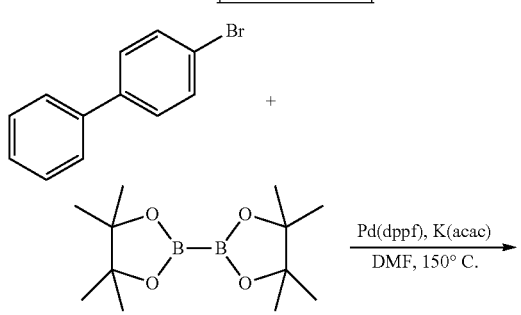

-continued

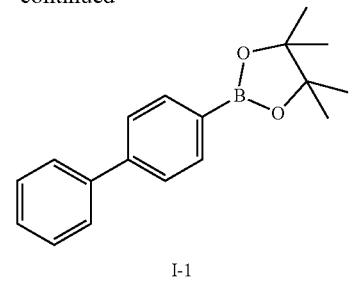

I-1

4-bromo-1,1'-biphenyl (20 g, 86 mmol) was dissolved in dimethylforamide (DMF, 1 L) under a nitrogen environment, bis(pinacolato)diboron (26 g, 103 mmol) and (1,1'-bis(diphenylphosphine)ferrocene)dichloropalladium (II) (Pd(dppf), 0.7 g, 0.86 mmol), and potassium acetate (K(acac), 21 g, 215 mmol) were added thereto, and the mixture is heated and refluxed at 150° C. for 5 hours. When the reaction was complete, water was added to the reaction solution, and the obtained mixture was filtered and dried in a vacuum oven. The obtained residue was separated and purified through flash column chromatography to obtain Intermediate I-1 (20 g and 85%).

HRMS (70 eV, EI+): m/z calcd for C18H21BO2: 280.1635, found: 280

Elemental Analysis: C, 77%; H, 8%

Synthesis of Intermediate I-2

[Reaction Scheme 2]

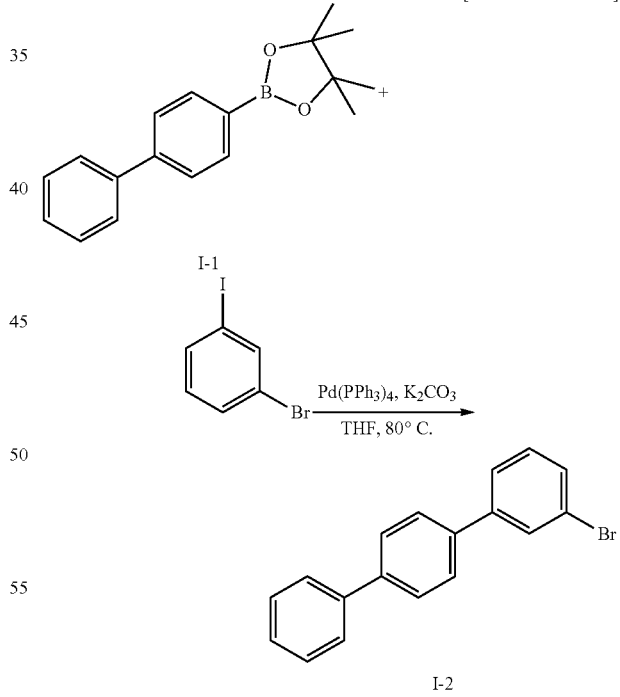

Intermediate I-1 (20 g, 71 mmol) was dissolved in THF (1 L) under a nitrogen environment, 1-bromo-3-iodobenzene (24 g, 85 mmol) and tetrakis(triphenylphosphine)palladium (Pd(PPh$_3$)$_4$, 0.8 mg, 0.7 mmol) were added thereto, and the mixture was stirred. Potassium carbonate (K$_2$CO$_3$, 24.5 g, 177 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO₄, the resultant was filtered and concentrated under a reduced pressure. This obtained residue was separated and purified through flash column chromatography to obtain Intermediate I-2 (30 g and 90%).

HRMS (70 eV, EI+): m/z calcd for C18H13Br: 309.1998, found 309 Elemental Analysis: C, 70%; H, 4%

Synthesis of Intermediate I-3

[Reaction Scheme 3]

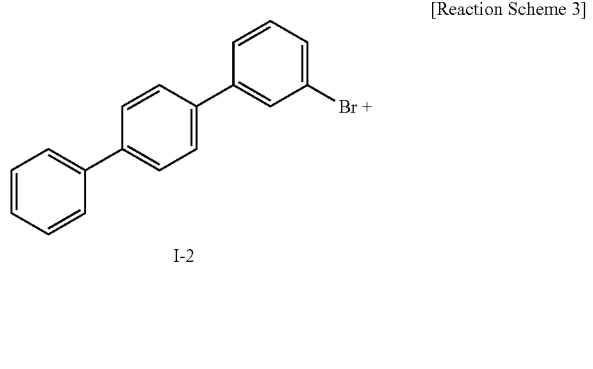

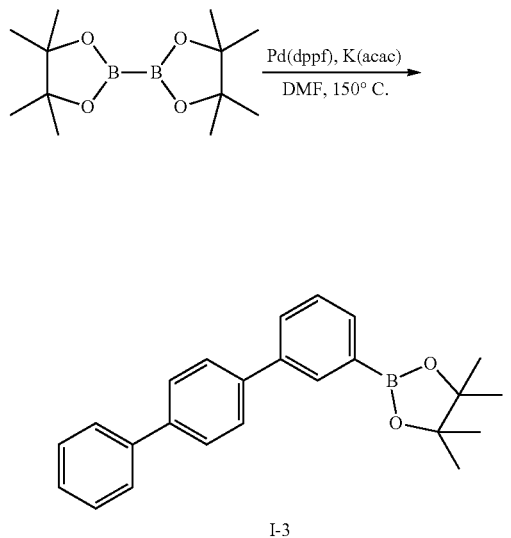

Intermediate I-2 (25 g, 81 mmol) was dissolved in dimethylforamide (DMF, 1 L) under a nitrogen environment, bis(pinacolato)diboron (25 g, 97 mmol), (1,1'-bis(diphenylphosphine)ferrocene)dichloropalladium (II) (Pd(dppf), 0.7 g, 0.81 mmol), and potassium acetate (K(acac), 20 g, 203 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-3 (27 g and 93%).

HRMS (70 eV, EI+): m/z calcd for C24H25BO2: 356.1948, found: 356

Elemental Analysis: C, 81%; H, 7%

Synthesis of Intermediate I-4

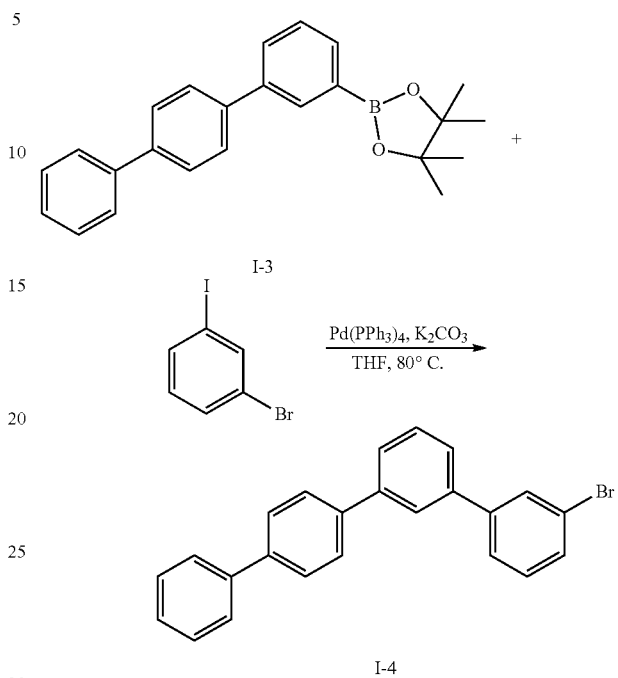

Intermediate I-3 (50 g, 140 mmol) was dissolved in THF (1 L) under a nitrogen environment, 1-bromo-3-iodobenzene (47 g, 168 mmol) and tetrakis(triphenylphosphine)palladium (Pd(PPh₃)₄, 1.6 g, 1.4 mmol) were added thereto, and the mixture was stirred. Potassium carbonate (K₂CO₃, 48 g, 350 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO₄, the resultant was filtered and concentrated under a reduced pressure. The obtained residue was separated and purified through flash column chromatography to obtain Intermediate I-4 (44 g and 89%).

HRMS (70 eV, EI+): m/z calcd for C24H17Br: 384.0514, found 384 Elemental Analysis: C, 75%; H, 4%

Synthesis of Intermediate I-5

[Reaction Scheme 5]

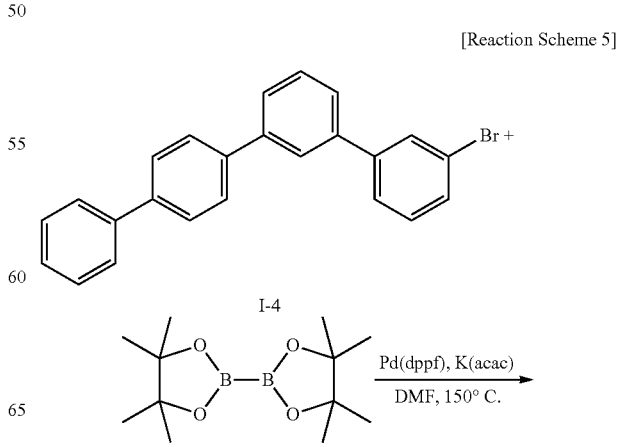

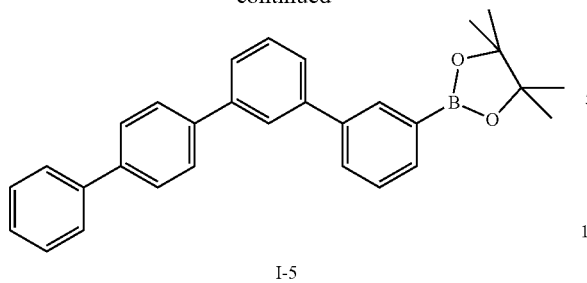

I-5

Intermediate I-4 (20 g, 52 mmol) was dissolved in dimethylforamide (DMF, 1 L) under a nitrogen environment, bis(pinacolato)diboron (16 g, 62.5 mmol), (1,1'-bis(diphenylphosphine)ferrocene)dichloropalladium (II) (Pd(dppf), 0.4 g, 0.52 mmol), and potassium acetate (K(acac), 13 g, 130 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Intermediate I-5 (19 g, 85%).

HRMS (70 eV, EI+): m/z calcd for C30H29BO2: 432.2261, found: 432

Elemental Analysis: C, 83%; H, 7%

Synthesis of Intermediate I-6

[Reaction Scheme 6]

1,3-dibromo-5-chlorobenzene (100 g, 370 mmol) was dissolved in THF (2 L) under a nitrogen environment, phenylboronic acid (47.3 g, 388 mmol) and tetrakis(triphenylphosphine)palladium (Pd(PPh3)4, 1.5 g, 1.36 mmol) were added thereto, and the mixture was stirred. Potassium carbonate (K2CO3, 127 g, 925 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO4, the resultant was filtered and concentrated under a reduced pressure. This obtained residue was separated and purified through flash column chromatography to obtain Intermediate I-6 (49 g, 50%).

HRMS (70 eV, EI+): m/z calcd for C12H8BrCl: 265.9498, found 266 Elemental Analysis: C, 54%; H, 3%

Synthesis of Intermediate I-7

[Reaction Scheme 7]

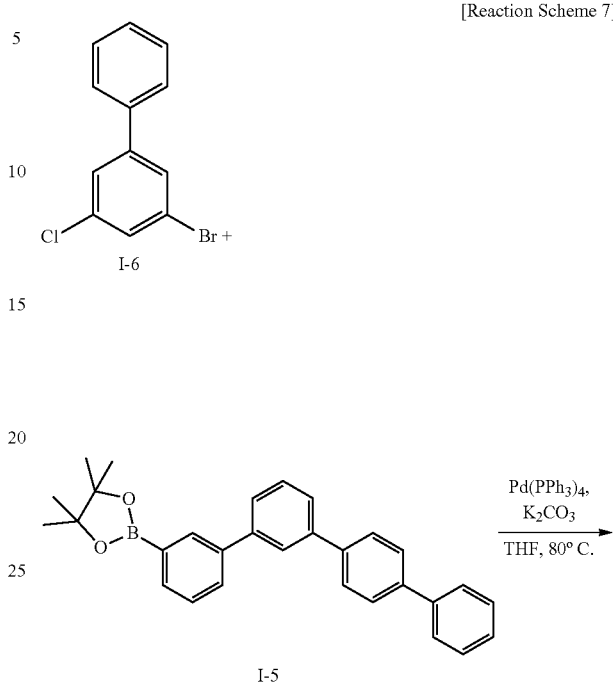

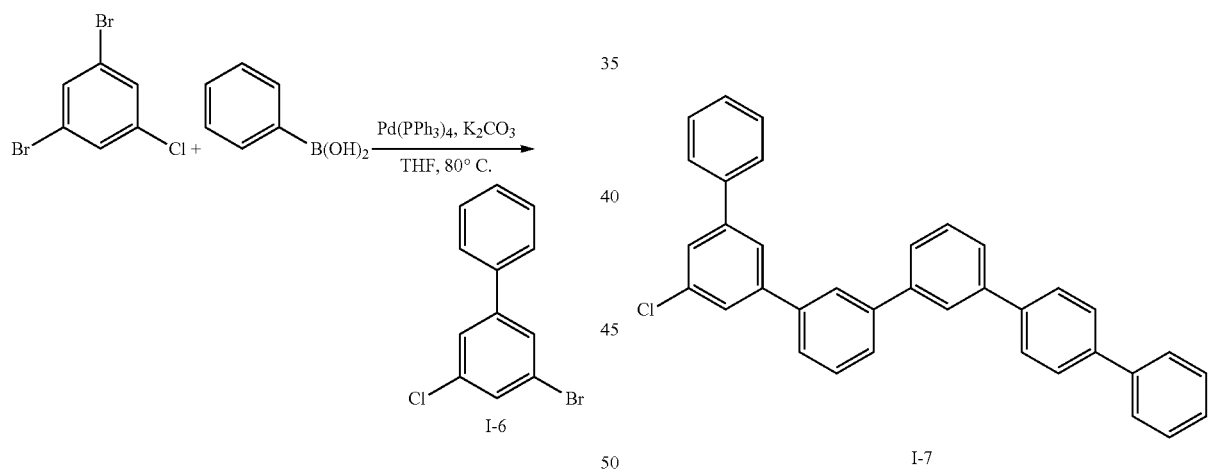

I-7

Intermediate I-6 (22.43 g, 83.83 mmol) was dissolved in THF (500 mL) under a nitrogen environment, Intermediate I-5 (50.7 g, 117.36 mmol) and tetrakis(triphenylphosphine) palladium (Pd(PPh3)4, 2.9 g, 2.5 mmol) were added thereto, and the mixture was stirred. Potassium carbonate (K2CO3, 46 g, 335.31 mmol) saturated in water was added thereto, and the obtained mixture was heated and refluxed at 80° C. for 12 hours. When the reaction was complete, water was added to the reaction solution, the mixture was extracted with dichloromethane (DCM), and moisture was removed with anhydrous MgSO4, followed by filtering and concentrating the resultant under a reduced pressure. This obtained residue was separated and purified through flash column chromatography to obtain Intermediate I-7 (33 g, 81%).

HRMS (70eV, EI+): m/z calcd for C36H25Cl: 492.1645, found 492 Elemental Analysis: C, 88%; H, 5%

Synthesis of Intermediate I-8

[Reaction Scheme 8]

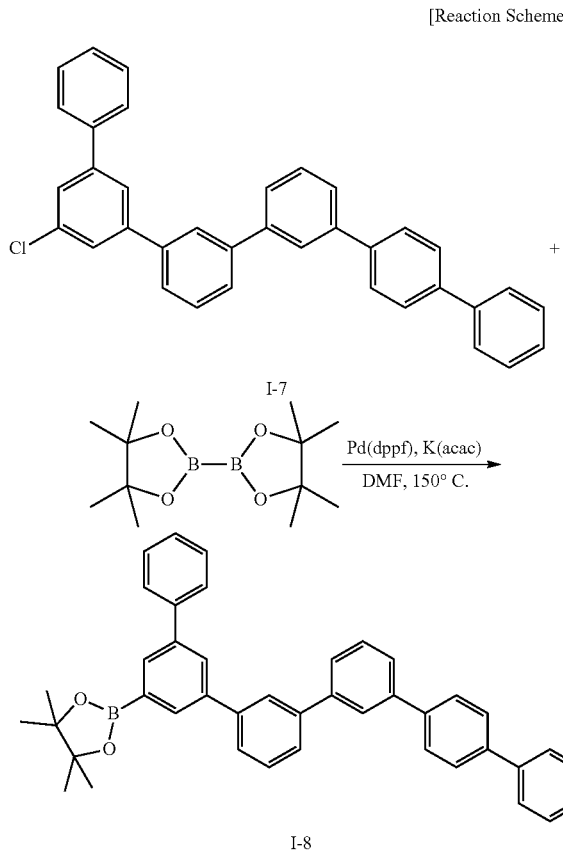

Intermediate I-7 (42 g, 85.8 mmol) was dissolved in dimethylforamide (DMF, 1 L) under a nitrogen environment, bis(pinacolato)diboron (26 g, 103 mmol), (1,1'-bis(diphenylphosphine)ferrocene)dichloropalladium (II) (Pd(dppf), 0.7 g, 0.85 mmol), and potassium acetate (K(acac), 58 g, 595 mmol) were added thereto, and the mixture is heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-8 (42 g, 85%).

HRMS (70 eV, EI+): m/z calcd for C42H37BO2: 584.2887, found: 584.

Elemental Analysis: C, 86%; H, 6%

Synthesis of Intermediate I-9

[Reaction Scheme 9]

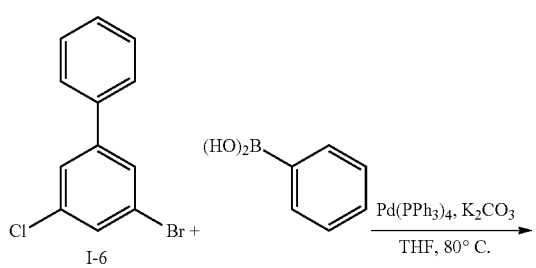

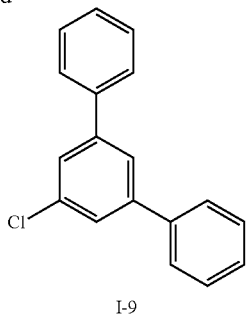

Intermediate I-6 (22.43 g, 83.83 mmol) was dissolved in THF (500 mL) under a nitrogen environment, phenylboronic acid (10 g, 117.36 mmol) and tetrakis(triphenylphosphine)palladium (Pd(PPh$_3$)$_4$, 2.9 g, 2.5 mmol) were added thereto, and the mixture was stirred. Potassium carbonate (K$_2$CO$_3$, 46 g, 335.31 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, and the resultant was filtered and concentrated under a reduced pressure. This obtained residue was separated and purified through flash column chromatography to obtain Intermediate I-9 (19 g, 85%).

HRMS (70 eV, EI+): m/z calcd for C18H13Cl: 264.0706, found 264 Elemental Analysis: C, 82%; H, 5%

Synthesis of Intermediate I-10

[Reaction Scheme 10]

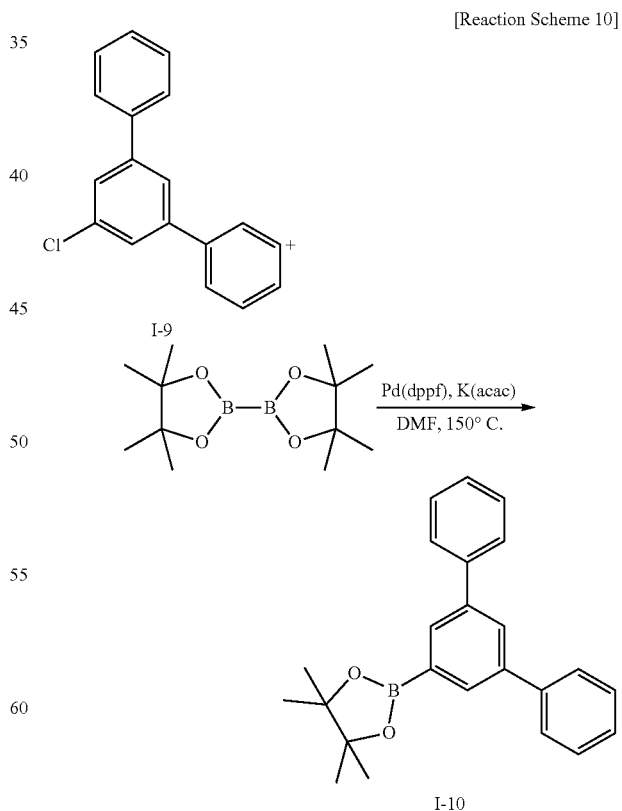

Intermediate I-9 (14 g, 52 mmol) was dissolved in dimethylforamide (DMF, 1 L) under a nitrogen environment, bis(pinacolato)diboron (19.8 g, 78 mmol), (1,1'-bis(diphe-nylphosphine)ferrocene)dichloropalladium (II) (Pd(dppf), 2.55 g, 3.12 mmol), and potassium acetate (K(acac), 15.3 g, 156 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Intermediate I-10 (14 g, 79%).

HRMS (70 eV, EI+): m/z calcd for C24H25BO2: 356.1948, found: 356

Elemental Analysis: C, 81%; H, 7%

Synthesis of Intermediate I-11

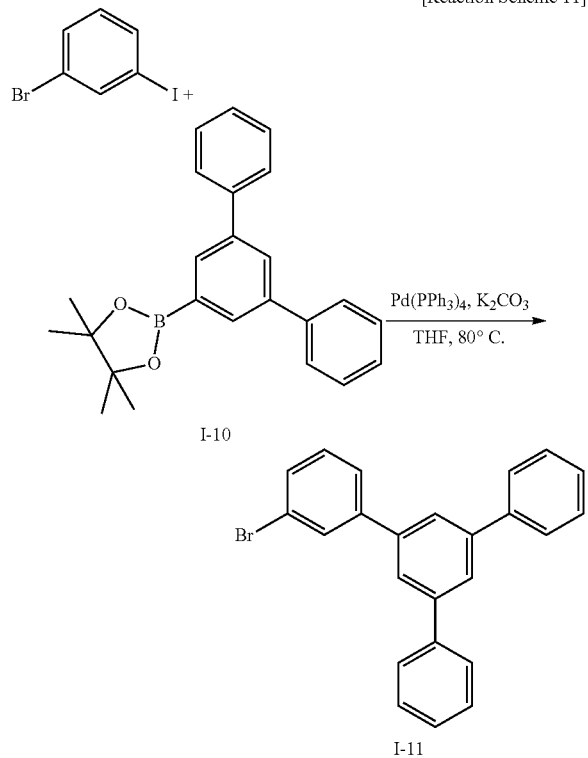

Intermediate I-10 (26.8 g, 62 mmol) was dissolved in THF (1 L) under a nitrogen environment, 1-bromo-3-iodobenzene (22 g, 86.6 mmol) and tetrakis(triphenylphosphine)palladium (Pd(PPh3)4, 2.1 g, 1.86 mmol) were added thereto, and the mixture was stirred. Potassium carbonate (K2CO3, 34.2 g, 247.7 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO4, the resultant was filtered and concentrated under a reduced pressure. This obtained residue was separated and purified through flash column chromatography to obtain Intermediate I-11 (22 g, 77%).

HRMS (70eV, EI+): m/z calcd for C24H17Br: 384.0514, found 384 Elemental Analysis: C, 75%; H, 4%

Synthesis of Intermediate I-12

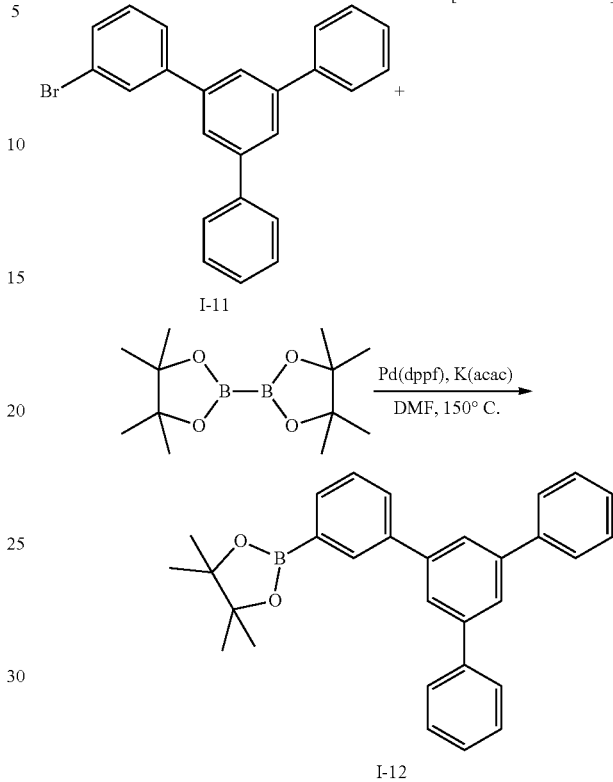

Intermediate I-11 (20 g, 52 mmol) was dissolved in dimethylforamide (DMF, 1 L) under a nitrogen environment, bis(pinacolato)diboron (19.8 g, 78 mmol), (1,1'-bis(diphenylphosphine)ferrocene)dichloropalladium (II) (Pd(dppf), 2.55 g, 3.12 mmol), and potassium acetate (K(acac), 15.3 g, 156 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography to obtain Intermediate I-12 (19 g, 87%).

HRMS (70 eV, EI+): m/z calcd for C30H29BO2: 432.2261, found: 432

Elemental Analysis: C, 83%; H, 7%

Synthesis of Intermediate I-13

[Reaction Scheme 13]

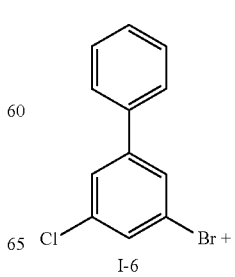

I-6

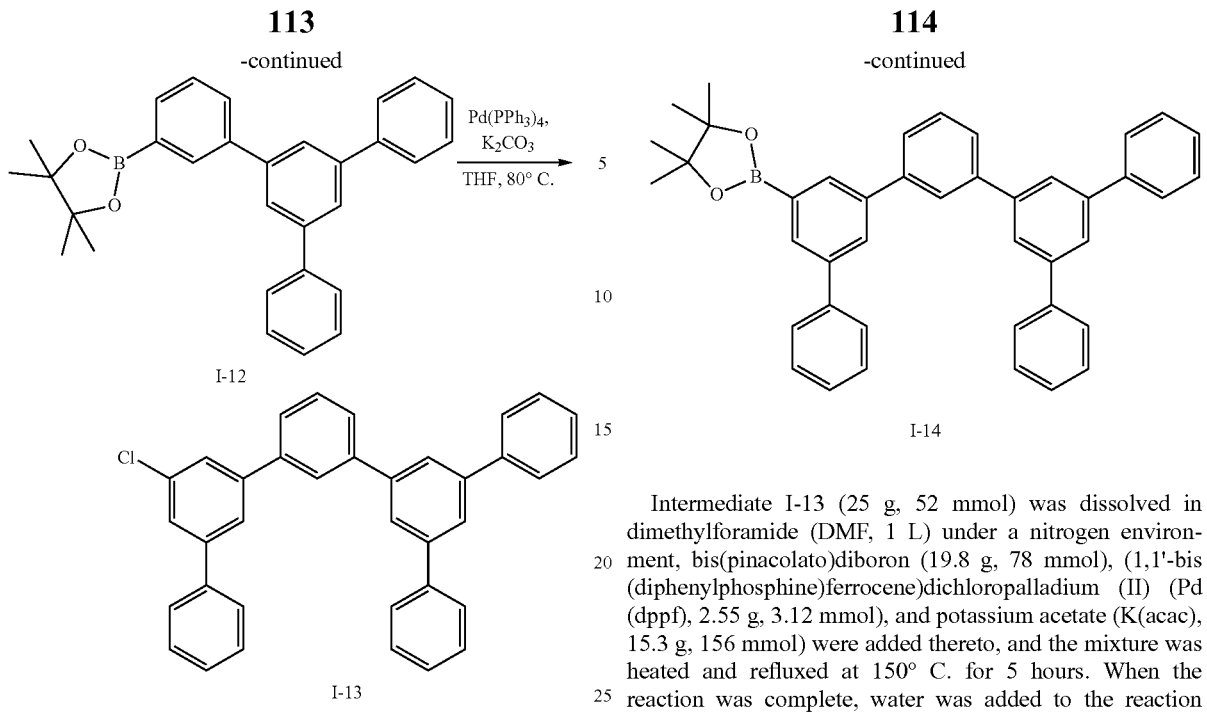

Intermediate I-6 (22.43 g, 83.83 mmol) was dissolved in THF (500 mL) under a nitrogen environment, Intermediate I-12 (50 g, 117.36 mmol) and tetrakis(triphenylphosphine) palladium (Pd(PPh$_3$)$_4$, 2.9 g, 2.5 mmol) were added thereto, and the mixture was stirred. Potassium carbonate (K$_2$CO$_3$, 46 g, 335.31 mmol) saturated in water was added thereto and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Intermediate I-13 (32 g, 78%).

HRMS (70eV, EI+): m/z calcd for C36H25Cl: 492.1645, found 492 Elemental Analysis: C. 88%; H, 5%

Synthesis of Intermediate I-14

Intermediate I-13 (25 g, 52 mmol) was dissolved in dimethylforamide (DMF, 1 L) under a nitrogen environment, bis(pinacolato)diboron (19.8 g, 78 mmol), (1,1'-bis(diphenylphosphine)ferrocene)dichloropalladium (II) (Pd(dppf), 2.55 g, 3.12 mmol), and potassium acetate (K(acac), 15.3 g, 156 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-14 (25 g, 85%).

HRMS (70 eV, EI+): m/z calcd for C42H37BO2: 584.2887, found: 584

Elemental Analysis: C, 86%; H, 6%

Synthesis of Intermediate I-15

[Reaction Scheme 14]

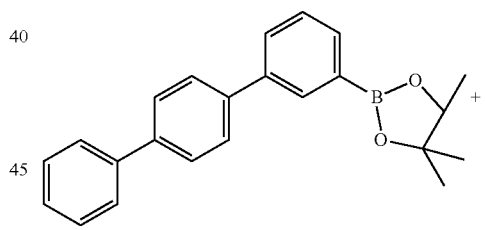

[Reaction Scheme 15]

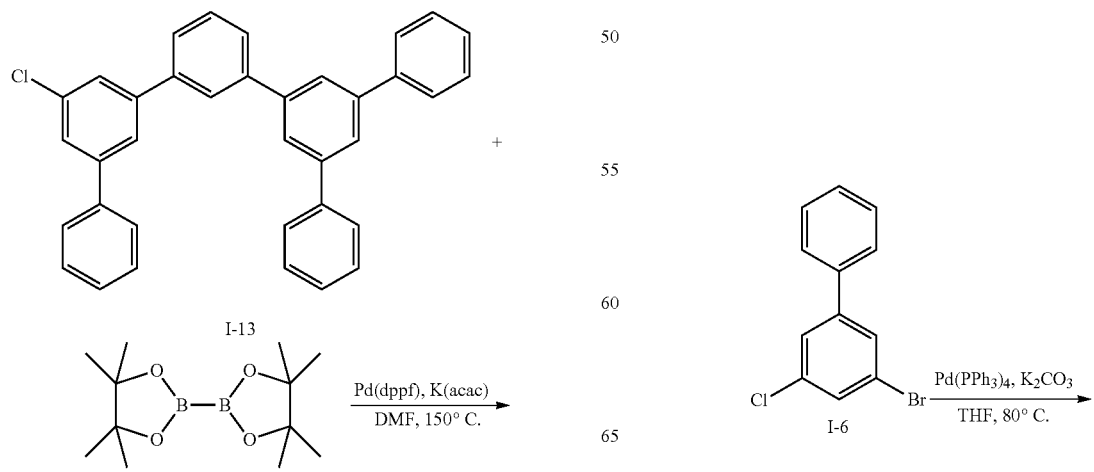

-continued

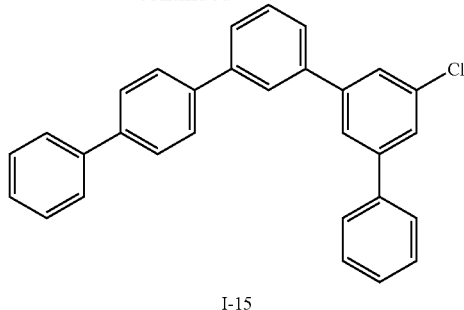

I-15

Intermediate I-3 (28 g, 83.83 mmol) was dissolved in THF (500 mL) under a nitrogen environment, Intermediate I-6 (30 g, 117.36 mmol) and tetrakis(triphenylphosphine)palladium (Pd(PPh$_3$)$_4$, 2.9 g, 2.5 mmol) were added thereto, and the mixture was stirred. Potassium carbonate (K$_2$CO$_3$, 46 g, 335.31 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Intermediate I-15 (28 g, 80%).

HRMS (70eV, EI+): m/z calcd for C30H21Cl: 416.1332, found 416 Elemental Analysis: C, 86%; H, 5%

Synthesis of Intermediate I-16

[Reaction Scheme 16]

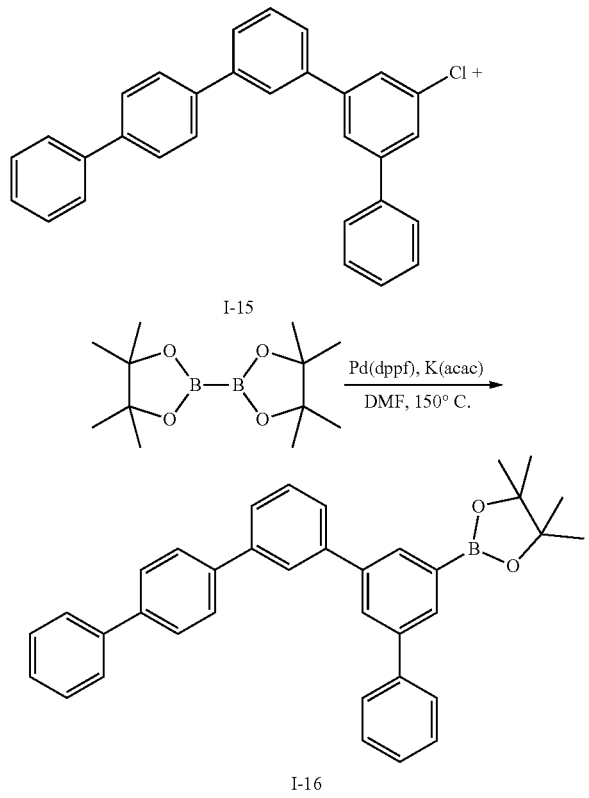

Intermediate I-15 (21 g, 52 mmol) was dissolved in dimethylformamide (DMF, 1 L) under a nitrogen environment, bis(pinacolato)diboron (19.8 g, 78 mmol), (1,1'-bis (diphenylphosphine)ferrocene)dichloropalladium (II) (Pd (dppf), 2.55 g, 3.12 mmol), and potassium acetate (K(acac), 15.3 g, 156 mmol) were added thereto, and the mixture was heated and refluxed at 150° C. for 5 hours. When the reaction was complete, water was added to the reaction solution, and the obtained mixture was filtered, and dried in a vacuum oven. This obtained residue was separated and purified through flash column chromatography to obtain Intermediate I-16 (23 g, 86%).

HRMS (70 eV, EI+): m/z calcd for C36H33BO2: 508.2574, found: 508

Elemental Analysis: C, 85%; H, 7%

Synthesis of Intermediate I-17

[Reaction Scheme 17]

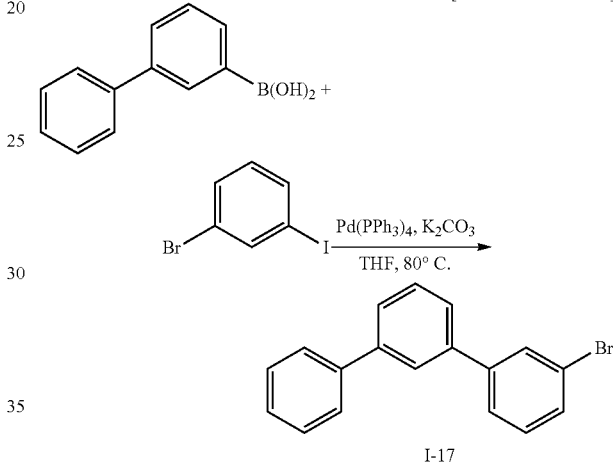

I-17

[1,1'-biphenyl]-3-yl boronic acid (12 g, 62 mmol) was dissolved in THF (1 L) under a nitrogen environment, 1-bromo-3-iodobenzene (22 g, 86.6 mmol) and tetrakis(triphenylphosphine)palladium ((Pd(PPh$_3$)$_4$, 2.1 g, 1.86 mmol) were added thereto, and the mixture was stirred. Potassium carbonate (K$_2$CO$_3$, 34.2 g, 247.7 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Intermediate I-17 (13 g, 70%).

HRMS (70eV, EI+): m/z calcd for C18H13Br: 308.0201, found 308 Elemental Analysis: C, 70%; H, 4%

Synthesis of Intermediate I-18

[Reaction Scheme 18]

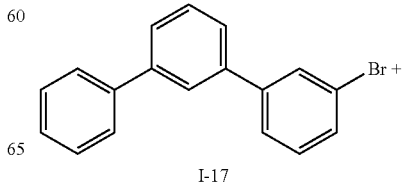

I-17

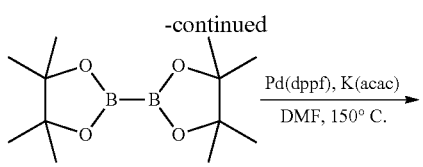

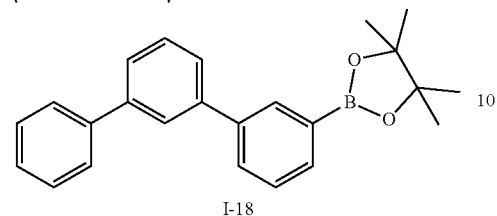

I-18

Intermediate I-17 (16 g, 52 mmol) was dissolved in dimethylforamide (DMF. 1 L) under a nitrogen environment, bis(pinacolato)diboron (19.8 g. 78 mmol), (1,1'-bis(diphenylphosphine)ferrocene)dichloropalladium (II) (Pd(dppf), 2.55 g, 3.12 mmol), and potassium acetate (K(acac), 15.3 g, 156 mmol) were added thereto, and the mixture was heated and refluxed at 150° C. for 5 hours. When the reaction was complete, water was added to the reaction solution, and the obtained mixture was filtered, and dried in a vacuum oven. This obtained residue was separated and purified through flash column chromatography to obtain Intermediate I-18 (17 g, 95%).

HRMS (70 eV, EI+): m/z calcd for C24H25BO2: 356.1948, found: 356

Elemental Analysis: C, 81%; H, 7%

Synthesis of Intermediate I-19

[Reaction Scheme 19]

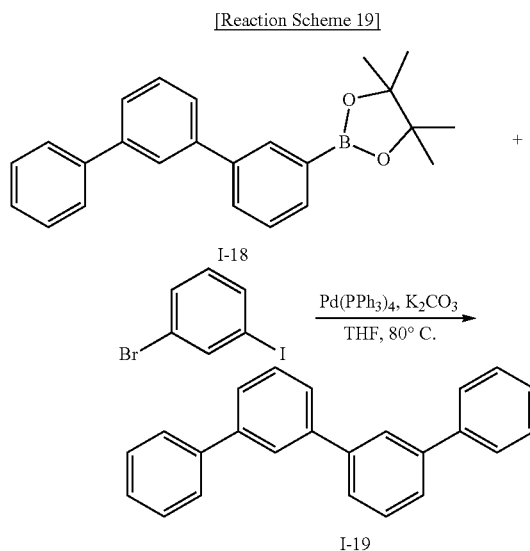

I-19

Intermediate I-18 (22 g, 62 mmol) was dissolved in THF (1 L) under a nitrogen environment, 1-bromo-3-iodobenzene (22 g, 86.6 mmol) and tetrakis(triphenylphosphine)palladium ((Pd(PPh3)4, 2.1 g, 1.86 mmol) were added thereto, and the mixture was stirred. Potassium carbonate (K2CO3, 34.2 g, 247.7 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO4, the resultant was filtered and concentrated under a reduced pressure. This obtained residue was separated and purified through flash column chromatography to obtain Intermediate I-19 (15 g, 65%).

HRMS (70eV, EI+): m/z calcd for C24H17Br: 384.0514, found 384 Elemental Analysis: C, 75%; H, 4%

Synthesis of Intermediate I-20

[Reaction Scheme 20]

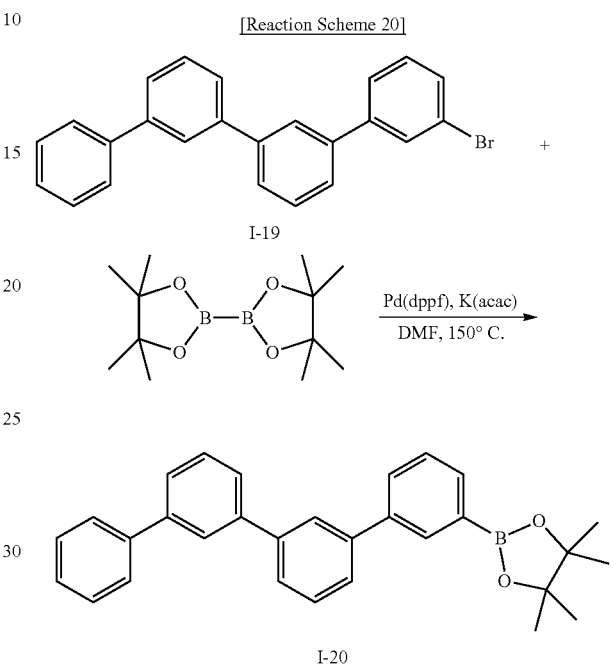

I-20

Intermediate I-19 (66 g, 172 mmol) was dissolved in dimethylforamide (DMF, 1 L) under a nitrogen environment, bis(pinacolato)diboron (52 g, 206 mmol), (1,1'-bis(diphenylphosphine)ferrocene)dichloropalladium (II) (Pd(dppf), 1.4 g, 1.7 mmol), and potassium acetate (K(acac), 42 g, 430 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-20 (20 g, 85%).

HRMS (70 eV, EI+): m/z calcd for C30H29BO2: 432.2261, found: 432

Elemental Analysis: C, 83%; H, 7%

Synthesis of Intermediate I-21

[Reaction Scheme 21]

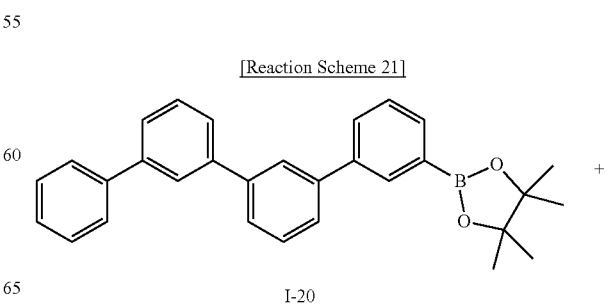

I-20

119
-continued

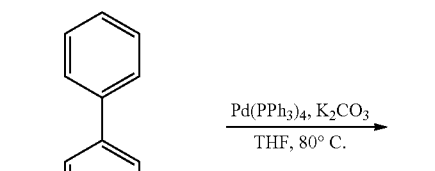

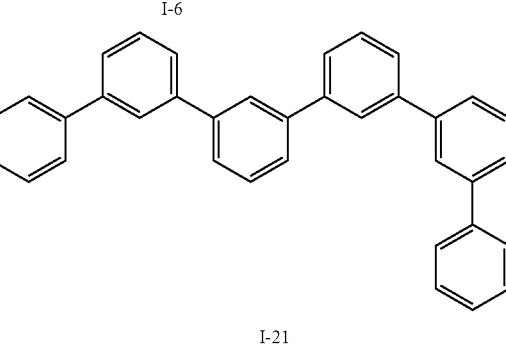

Intermediate I-20 (34 g, 80 mmol) was dissolved in THF (500 mL) under a nitrogen environment, Intermediate I-6 (30 g, 113 mmol) and tetrakis(triphenylphosphine)palladium (2.2 g, 2.3 mmol) were added thereto, and the mixture was stirred. Potassium carbonate (44 g, 319 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Intermediate I-21 (37 g, 95%).

HRMS (70eV, EI+): m/z calcd for C36H25Cl: 492.1645, found 492 Elemental Analysis: C, 88%; H, 5%

Synthesis of Intermediate I-22

[Reaction Scheme 22]

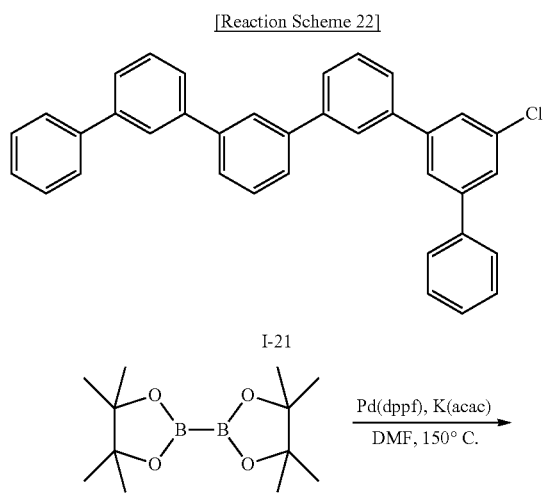

120
-continued

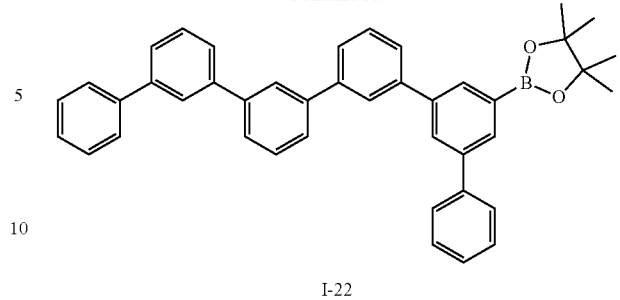

Intermediate I-21 (84 g, 172 mmol) was dissolved in dimethylforamide (DMF, 1 L) under a nitrogen environment, bis(pinacolato)diboron (52 g, 206 mmol), (1,1'-bis(diphenylphosphine)ferrocene)dichloropalladium (II) (Pd(dppf), 1.4 g, 1.7 mmol), and potassium acetate (K(acac), 42 g, 430 mmol) were added thereto, and the mixture was heated and refluxed at 150° C. for 5 hours. When the reaction was complete, water was added to the reaction solution, and the mixture was filtered and then, dried in a vacuum oven. This obtained residue was separated and purified through flash column chromatography to obtain Intermediate I-22 (90 g, 90%).

HRMS (70 eV. EI+): m/z calcd for C42H37BO2: 584.2887, found: 584

Elemental Analysis: C, 86%; H, 6%

Synthesis of Intermediate I-23

[Reaction Scheme 23]

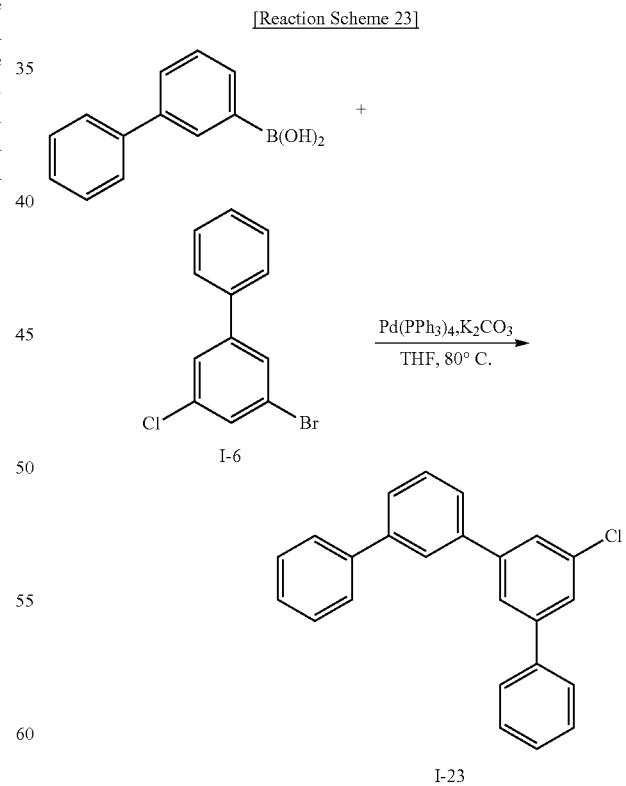

[1,1'-biphenyl]-3-ylboronic acid (16 g, 80 mmol) was dissolved in THF (500 mL) under a nitrogen environment, Intermediate I-6 (30 g, 113 mmol) and tetrakis(triphenylphosphine)palladium (Pd(PPh$_3$)$_4$, 2.2 g, 2.3 mmol) were added thereto, and the mixture was stirred. Potassium carbonate ($K_2CO_3$, 44 g, 319 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Intermediate I-23 (21 g, 80%).

HRMS (70eV, EI+): m/z calcd for C24H17Cl: 340.1019, found 340 Elemental Analysis: C, 85%; H, 5%

Synthesis of Intermediate I-24

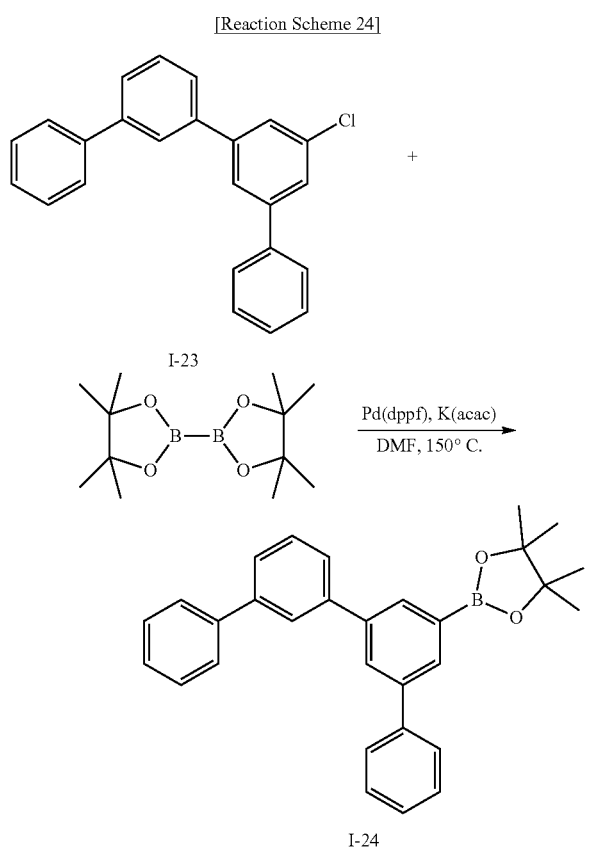

Intermediate I-23 (17 g, 52 mmol) was dissolved in dimethylforamide (DMF, 1 L) under a nitrogen environment, bis(pinacolato)diboron (19.8 g, 78 mmol), (1,1'-bis(diphenylphosphine)ferrocene)dichloropalladium (II) (Pd(dppf), 2.55 g, 3.12 mmol), and potassium acetate (K(acac), 15.3 g, 156 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-24 (20 g, 89%).

HRMS (70 eV, EI+): m/z calcd for C30H29BO2: 432.2261, found: 432

Elemental Analysis: C, 83%; H, 7%

Synthesis of Intermediate I-25

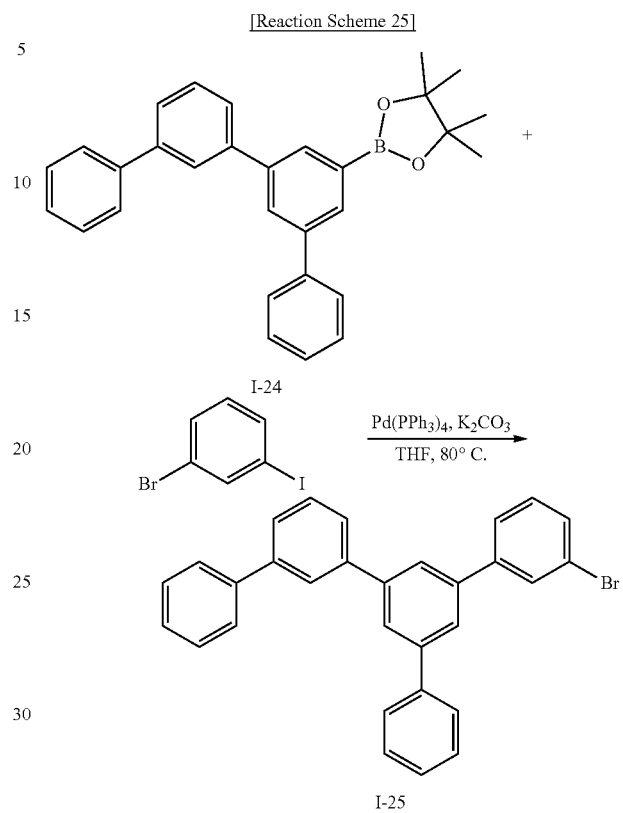

Intermediate I-24 (27 g, 62 mmol) was dissolved in THF (1 L) under a nitrogen environment, 1-bromo-3-iodobenzene (22 g, 86.6 mmol) and tetrakis(triphenylphosphine)palladium ($Pd(PPh_3)_4$, 2.1 g, 1.86 mmol) were added thereto, and the mixture was stirred. Potassium carbonate ($K_2CO_3$, 34.2 g, 247.7 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Intermediate I-25 (19 g, 68%).

HRMS (70eV, EI+): m/z calcd for C30H21Br: 460.0827, found 460 Elemental Analysis: C, 78%; H, 5%

Synthesis of Intermediate I-26

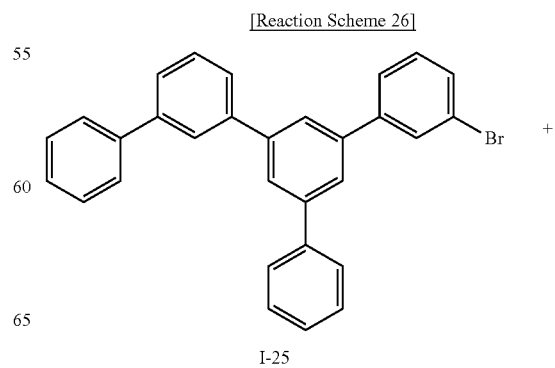

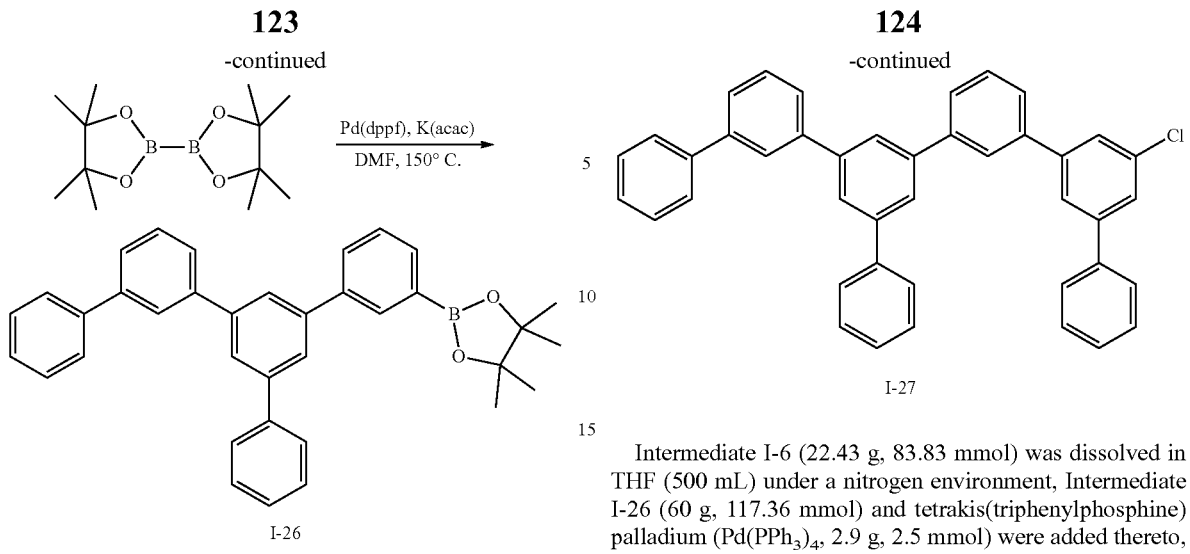

Intermediate I-25 (23 g, 52 mmol) was dissolved in dimethylforamide (DMF, 1 L) under a nitrogen environment, bis(pinacolato)diboron (19.8 g, 78 mmol), (1,1'-bis(diphenylphosphine)ferrocene)dichloropalladium (II) (Pd(dppf), 2.55 g, 3.12 mmol), and potassium acetate (K(acac), 15.3 g, 156 mmol) were added thereto, and the mixture was heated and refluxed at 150° C. for 5 hours. When the reaction was complete, water was added to the reaction solution, and the mixture was filtered and then, dried in a vacuum oven. This obtained residue was separated and purified through flash column chromatography to obtain Intermediate I-26 (26 g, 97%).

HRMS (70 eV, EI+): m/z calcd for C36H33BO2: 508.2574, found: 508

Elemental Analysis: C, 85%; H, 7%

Synthesis of Intermediate I-27

[Reaction Scheme 27]

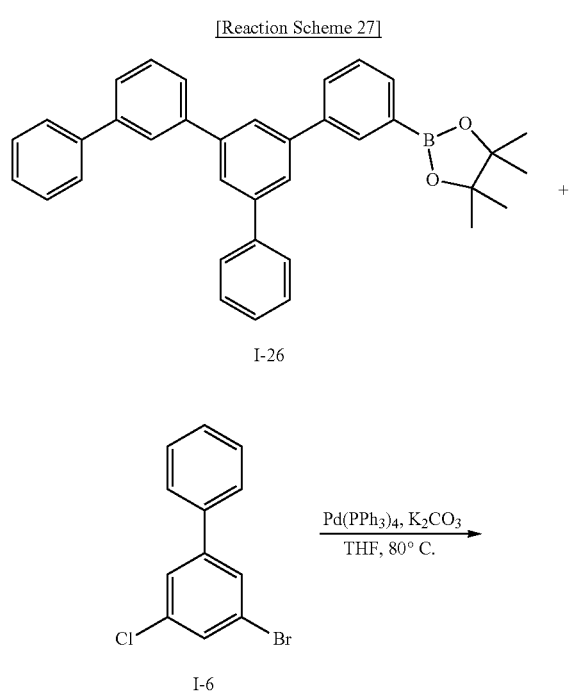

Intermediate I-6 (22.43 g, 83.83 mmol) was dissolved in THF (500 mL) under a nitrogen environment, Intermediate I-26 (60 g, 117.36 mmol) and tetrakis(triphenylphosphine)palladium (Pd(PPh$_3$)$_4$, 2.9 g, 2.5 mmol) were added thereto, and the mixture was stirred. Potassium carbonate (K$_2$CO$_3$, 46 g, 335.31 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Intermediate I-27 (47 g, 80%).

HRMS (70eV, EI+): m/z calcd for C42H29Cl: 568.1958, found 568 Elemental Analysis: C, 89%; H, 5%

Synthesis of Intermediate I-28

[Reaction Scheme 28]

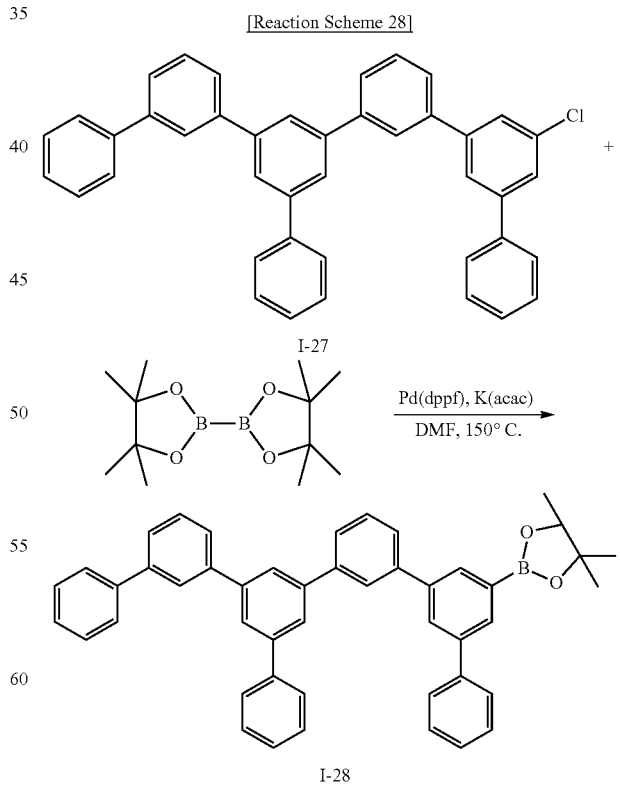

Intermediate I-27 (29 g, 52 mmol) was dissolved in dimethylforamide (DMF, 1 L) under a nitrogen environment, bis(pinacolato)diboron (19.8 g, 78 mmol), (1,1'-bis(diphenylphosphine)ferrocene)dichloropalladium (II) (Pd(dppf), 2.55 g, 3.12 mmol and potassium acetate (K(acac), 15.3 g, 156 mmol) were added thereto, and the mixture was heated and refluxed at 150° C. for 5 hours. When the reaction was complete, water was added to the reaction solution, and the mixture was filtered, and dried in a vacuum oven. The obtained residue was separated and purified through flash column chromatography to obtain Intermediate I-28 (32 g, 94%).

HRMS (70 eV, EI+): m/z calcd for C48H41BO2: 660.3200, found: 660

Elemental Analysis: C, 87%; H, 6%

Synthesis of Intermediate I-29

[Reaction Scheme 29]

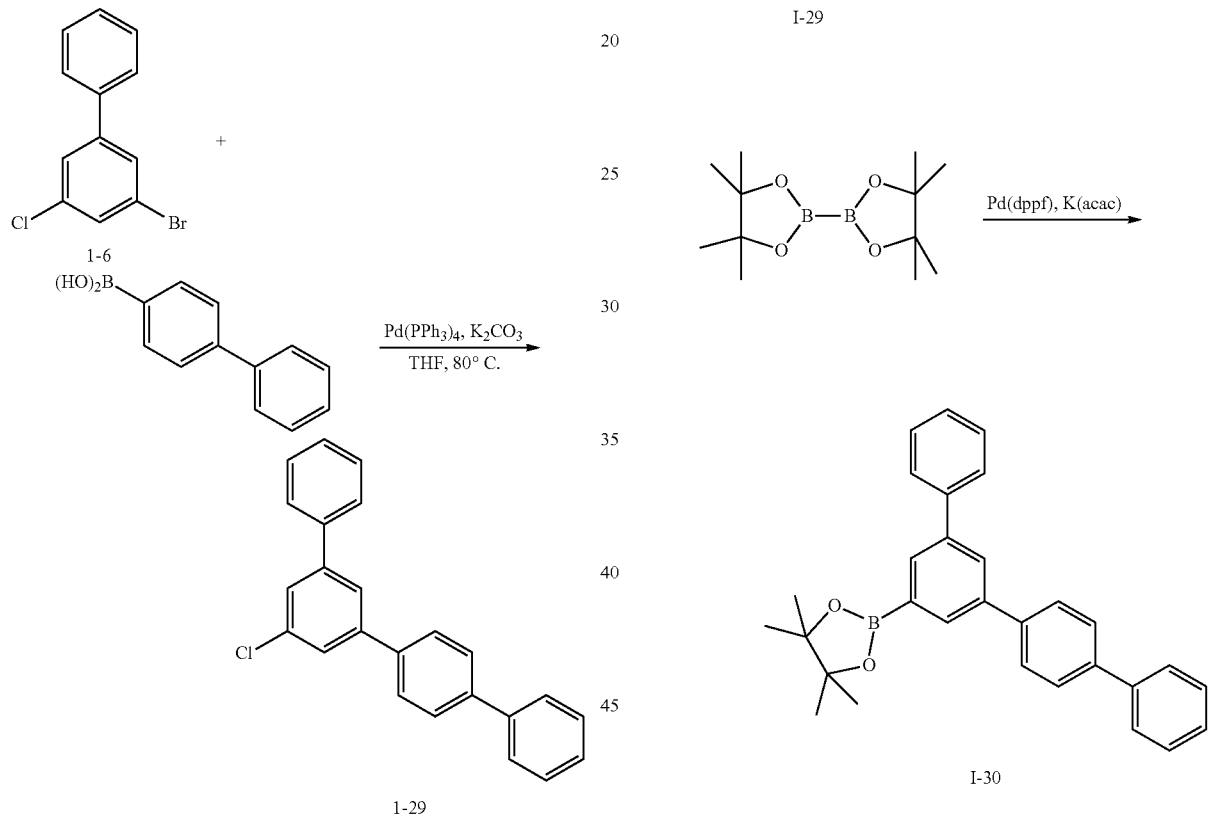

Synthesis of Intermediate I-30

[Reaction Scheme 30]

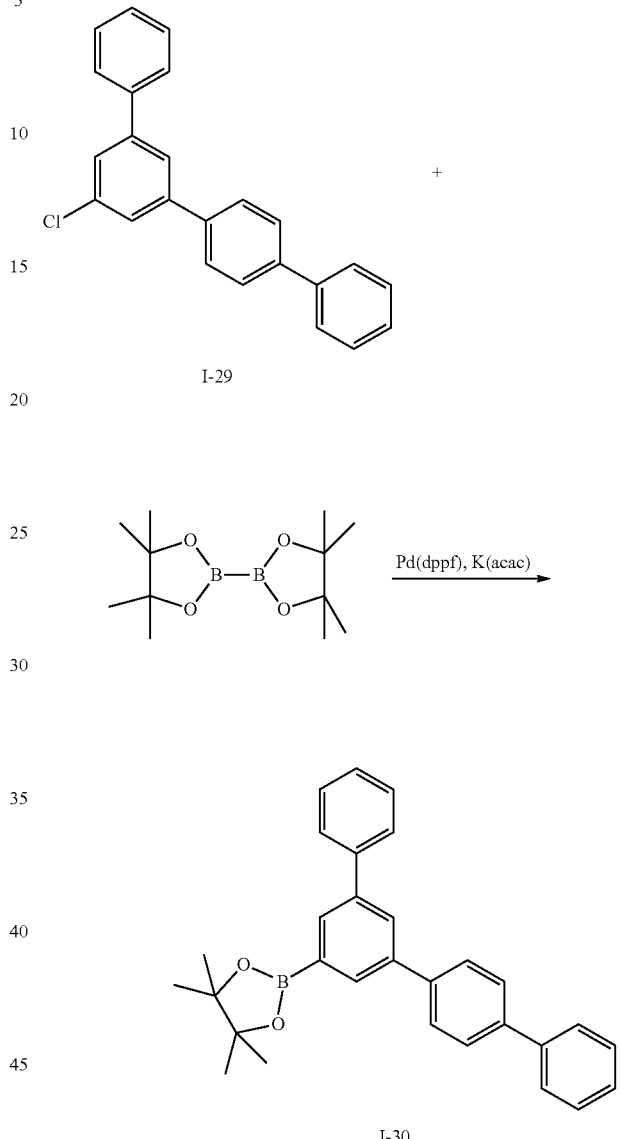

[1,1'-biphenyl]-3-ylboronic acid (16 g, 80 mmol) was dissolved in THF (500 mL) under a nitrogen environment, Intermediate I-6 (30 g, 113 mmol) and tetrakis(triphenylphosphine)palladium (2.2 g, 2.3 mmol) were added thereto, and the mixture was stirred. Potassium carbonate (44 g, 319 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO4, the resultant was filtered and concentrated under a reduced pressure. This obtained residue was separated and purified through flash column chromatography to obtain Intermediate I-29 (23 g, 85%).

HRMS (70eV, EI+): m/z calcd for C24H17Cl: 340.1019, found 340 Elemental Analysis: C, 85%; H, 5%

Intermediate I-29 (17 g, 52 mmol) was dissolved in dimethylforamide (DMF, 1 L) under a nitrogen environment, bis(pinacolato)diboron (19.8 g, 78 mmol), (1,1'-bis(diphenylphosphine)ferrocene)dichloropalladium (II) (Pd(dppf), 2.55 g, 3.12 mmol), and potassium acetate (K(acac), 15.3 g, 156 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-30 (32 g, 95%).

HRMS (70 eV, EI+): m/z calcd for C30H29BO2: 432.2261, found: 432

Elemental Analysis: C, 83%; H, 7%

Synthesis of Intermediate I-31

Synthesis of Intermediate I-32

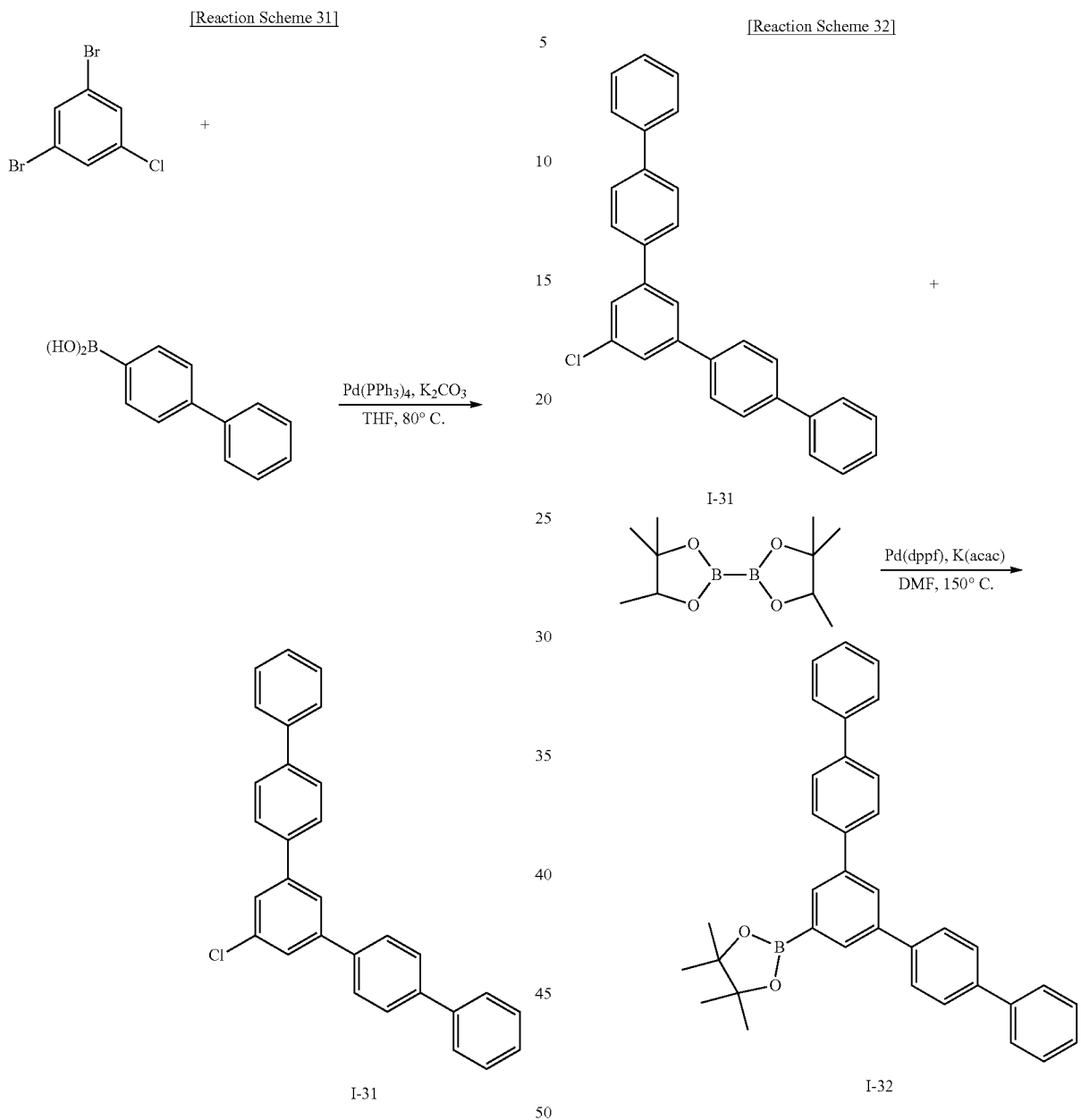

1,3-dibromo-5-chlorobenzene (100 g, 370 mmol) was dissolved in THF (2 L) under a nitrogen environment, [1,1'-biphenyl]-4-ylboronic acid (146 g, 740 mmol) and tetrakis(triphenylphosphine)palladium (3 g, 2.72 mmol) were added thereto, and the mixture was stirred. Potassium carbonate (254 g, 1850 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Intermediate I-31 (76 g, 50%).

HRMS (70 eV, EI+): m/z calcd for C30H21Cl: 416.1332, found 416 Elemental Analysis: C, 77%; H, 5%

Intermediate I-31 (76 g, 185 mmol) was dissolved in dimethylforamide (DMF, 1 L) under a nitrogen environment, bis(pinacolato)diboron (277 g, 288 mmol) and (1,1'-bis(diphenylphosphine)ferrocene)dichloropalladium (II) (Pd(dppf), 13 g, 11.1 mmol), and potassium acetate (K(acac). 54 g, 555 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-32 (89 g, 95%).

HRMS (70 eV, EI+): m/z calcd for C36H33BO2: 508.2574, found: 508

Elemental Analysis: C, 85%; H, 7%

Synthesis of Intermediate I-33

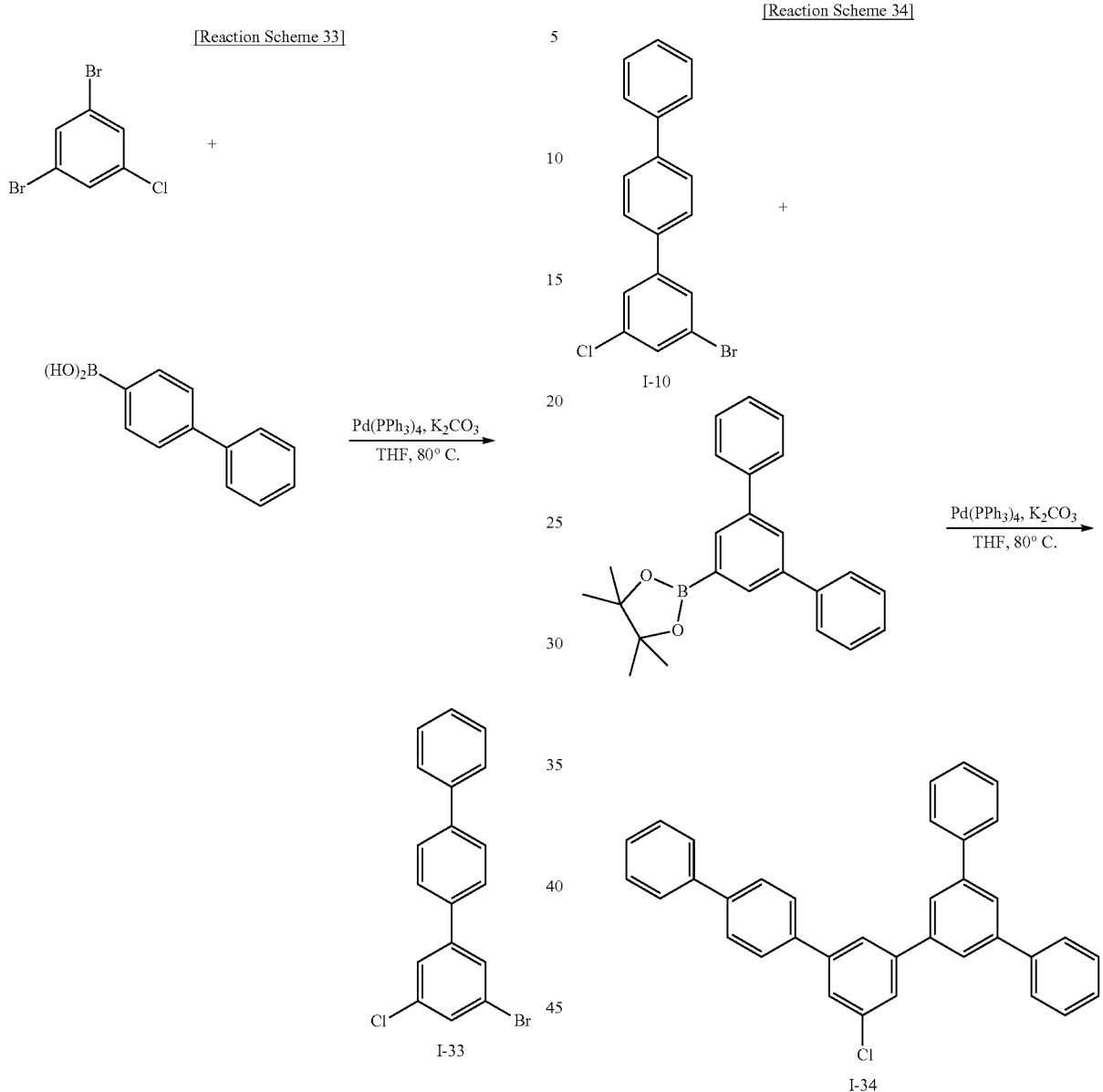

Synthesis of Intermediate I-34

1,3-dibromo-5-chlorobenzene (100 g, 370 mmol) was dissolved in THF (2 L) under a nitrogen environment, [1,1'-biphenyl]-4-ylboronic acid (73 g, 370 mmol) and tetrakis(triphenylphosphine)palladium (1.5 g, 1.36 mmol) were added thereto, and the mixture was stirred. Potassium carbonate (127 g, 925 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Intermediate I-33 (70 g. 55%).

HRMS (70 eV, EI+): m/z calcd for $C18H12BrCl$: 341.9811, found 342 Elemental Analysis: C, 63%; H, 4%

Intermediate I-10 (30 g, 85 mmol) was dissolved in THF (500 mL) under a nitrogen environment, Intermediate I-33 (29 g, 85 mmol) and tetrakis(triphenylphosphine)palladium (0.98 g, 0.85 mmol) were added thereto, and the mixture was stirred. Potassium carbonate (29 g, 212 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Intermediate I-34 (36 g, 85%).

HRMS (70eV, EI+): m/z calcd for $C36H25Cl$: 492.1645, found 492 Elemental Analysis: C, 88%; 5%

Synthesis of Intermediate I-35

[Reaction Scheme 35]

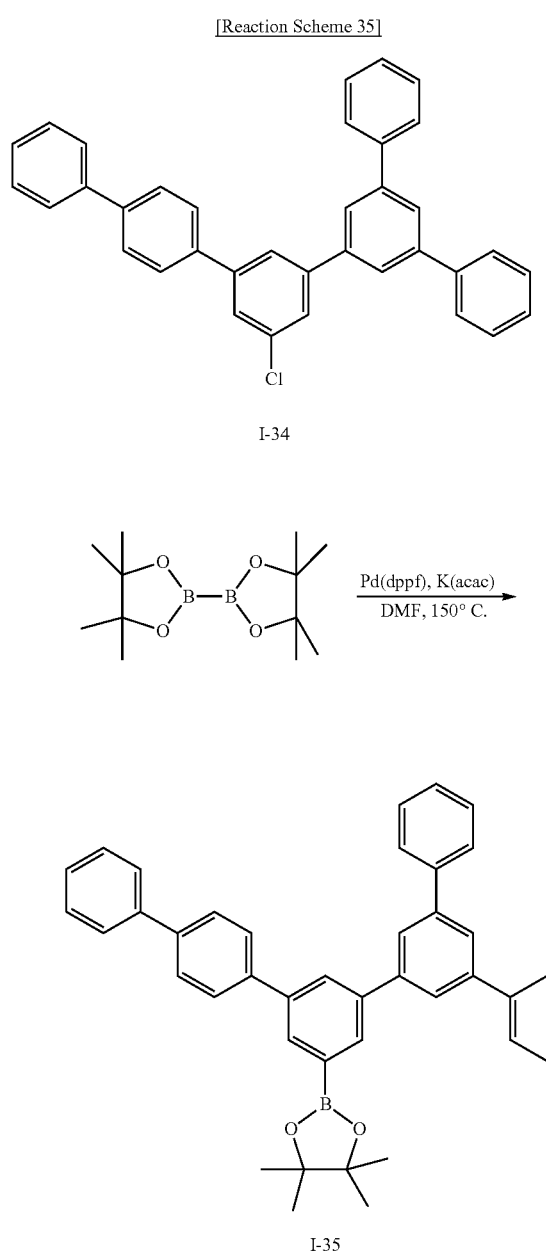

Intermediate I-34 (36 g, 73 mmol) was dissolved in dimethylforamide (DMF, 1 L) under a nitrogen environment, bis(pinacolato)diboron (105 g, 110 mmol), (1,1'-bis(diphenylphosphine)ferrocene)dichloropalladium (II) (Pd(dppf), 0.4 g, 0.73 mmol), and potassium acetate (K(acac), 18 g, 182 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-35 (41 g, 96%).

HRMS (70 eV, EI+): m/z calcd for C42H37BO2: 584.2887, found: 584

Elemental Analysis: C, 86%; H, 6%

SYNTHESIS EXAMPLE 36

Synthesis of Intermediate I-36

[Reaction Scheme 36]

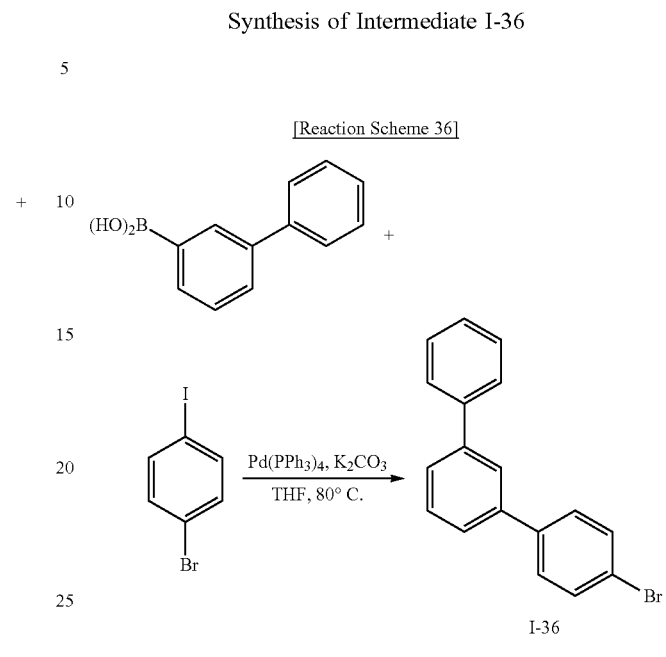

The compound of [1,1'-biphenyl]-3-ylboronic acid (12 g, 62 mmol) was dissolved in THF (1 L) under a nitrogen environment, 1-bromo-3-iodobenzene (22 g, 86.6 mmol) and tetrakis(triphenylphosphine)palladium (2.1 g, 1.86 mmol) were added thereto, and the mixture was stirred. Potassium carbonate (34.2 g, 247.7 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO4, the resultant was filtered and concentrated under a reduced pressure. This obtained residue was separated and purified through flash column chromatography to obtain Intermediate I-36 (13 g, 70%).

HRMS (70eV, EI+): m/z calcd for C18H13Br: 308.0201, found 308 Elemental Analysis: C, 70%; H, 4%

SYNTHESIS EXAMPLE 37

Synthesis of Intermediate I-37

[Reaction Scheme 37]

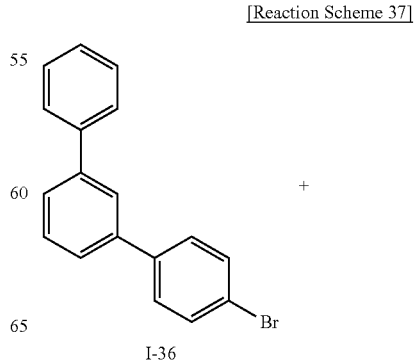

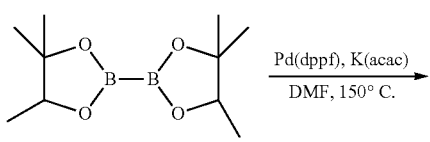

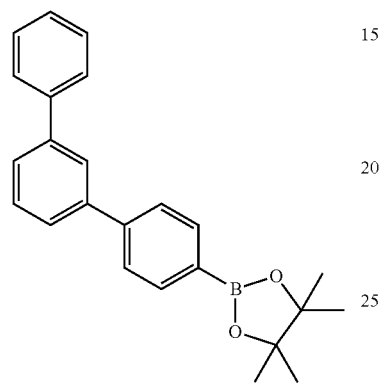

I-37

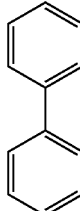

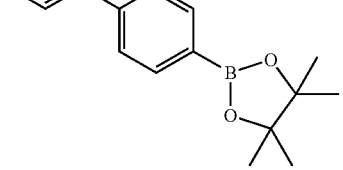

I-37

Intermediate I-36 (16 g, 52 mmol) was dissolved in dimethylforamide (DMF, 1 L) under a nitrogen environment, bis(pinacolato)diboron (19.8 g, 78 mmol), (1,1'-bis(diphenylphosphine)ferrocene)dichloropalladium (II) (2.55 g, 3.12 mmol), and potassium acetate (15.3 g, 156 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-37 (17 g. 95%).

HRMS (70 eV, EI+): m/z calcd for C24H25BO2: 356.1948, found: 356

Elemental Analysis: C, 81%; H, 7%

SYNTHESIS EXAMPLE 38

Synthesis of Intermediate I-38

[Reaction Scheme 38]

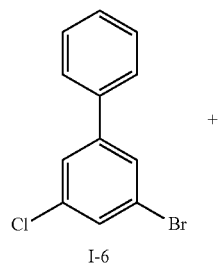

I-6

+

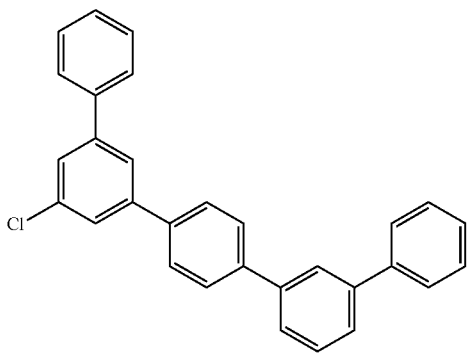

I-38

Intermediate I-37 (20 g, 56 mmol) was dissolved in THF (500 mL) under a nitrogen environment, Intermediate I-6 (22 g, 84 mmol) and tetrakis(triphenylphosphine)palladium (0.65 g, 0.56 mmol) were added thereto, and the mixture was stirred. Potassium carbonate (19 g, 140 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO_4, the resultant was filtered and concentrated under a reduced pressure. This obtained residue was separated and purified through flash column chromatography to obtain Intermediate I-38 (18 g, 80%).

HRMS (70eV, EI+): m/z calcd for C30H21Cl: 416.1332, found 416 Elemental Analysis: C, 86%; H, 5%

135

SYNTHESIS EXAMPLE 39

Synthesis of Intermediate I-39

[Reaction Scheme 39]

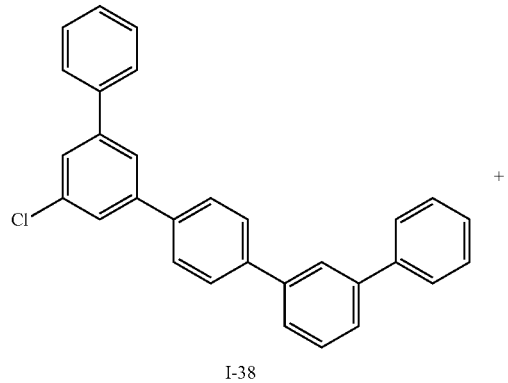

I-38

+

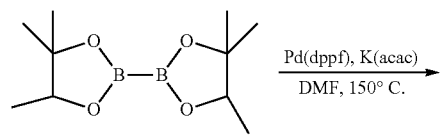

Pd(dppf), K(acac)
DMF, 150° C.

136

-continued

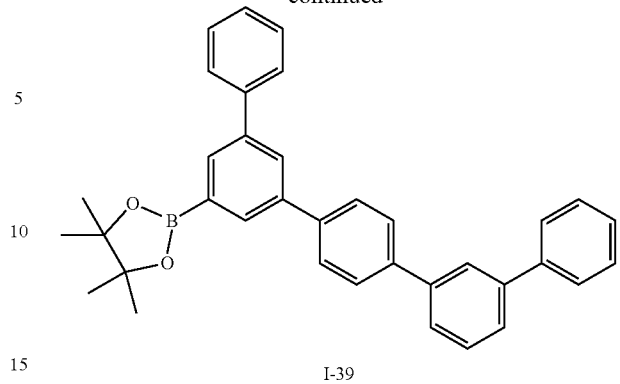

I-39

Intermediate I-38 (18 g, 45 mmol) was dissolved in dimethylforamide (DMF, 1 L) under a nitrogen environment, bis(pinacolato)diboron (17 g, 67 mmol), (1,1'-bis(diphenylphosphine)ferrocene)dichloropalladium (II) (0.25 g, 0.45 mmol), and potassium acetate (11 g, 112 mmol) were added thereto, and the mixture was heated and refluxed at 150° C. for 5 hours. When the reaction was complete, water was added to the reaction solution, and the mixture was filtered, and dried in a vacuum oven. This obtained residue was separated and purified through flash column chromatography to obtain Intermediate I-39 (17 g, 95%).

HRMS (70 eV, EI+): m/z calcd for $C_{36}H_{33}BO_2$: 508.2574, found: 508

Elemental Analysis: C, 85%; H, 7%

Synthesis of Final Compound

SYNTHESIS EXAMPLE 1

Synthesis of Compound 13

[Reaction Scheme 29]

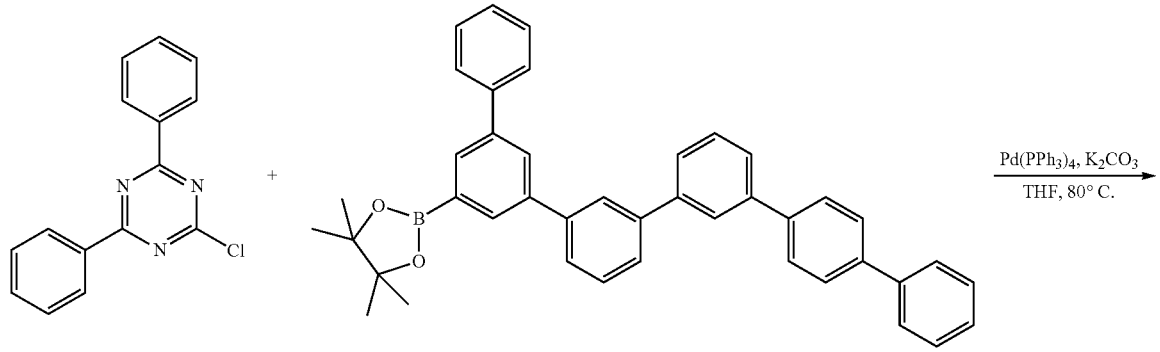

Pd(PPh$_3$)$_4$, K$_2$CO$_3$
THF, 80° C.

I-8

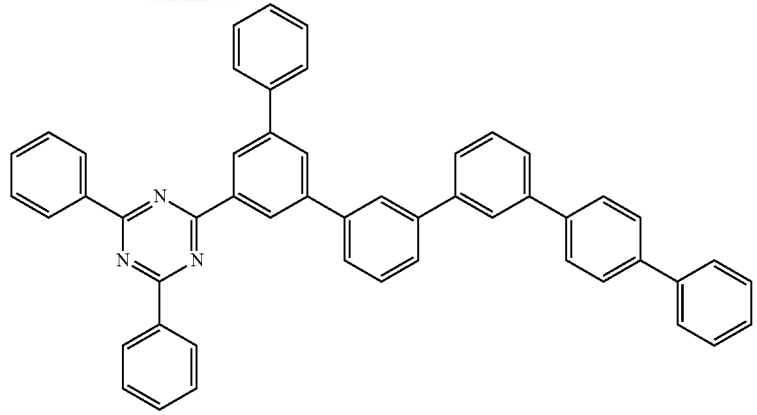

13

2-chloro-4,6-diphenyl-1,3,5-triazine (32 g, 76 mmol) was dissolved in THF (1 L) under a nitrogen environment. Intermediate I-8 (44 g, 76 mmol), tetrakis(triphenylphosphine)palladium (Pd(PPh$_3$)$_4$, 0.88 g, 0.76 mmol) was added thereto, and the mixture was stirred. Potassium carbonate (K$_2$CO$_3$, 26 g, 190 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Compound 13 (41 g, 80%).

HRMS (70 eV, EI+): m/z calcd for C51H35N3: 689.2831, found 689 Elemental Analysis: C, 89%; H, 5%

SYNTHESIS EXAMPLE 2

Synthesis of Compound 10

[Reaction Scheme 30]

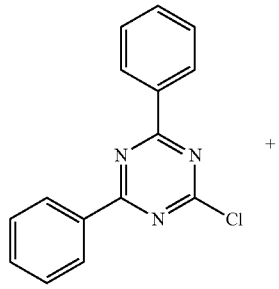

+

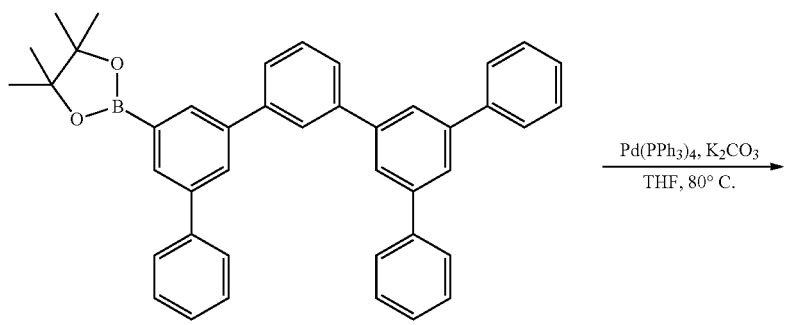

I-14

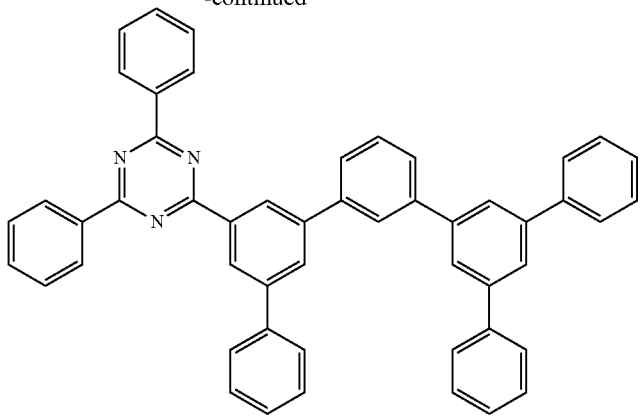

10

2-chloro-4,6-diphenyl-1,3,5-triazine (32 g, 76 mmol) was dissolved in THF (1 L) under a nitrogen environment, Intermediate I-14 (44 g, 76 mmol) and tetrakis(triphenylphosphine)palladium (Pd(PPh$_3$)$_4$, 0.88 g, 0.76 mmol) were added thereto, and the mixture was stirred. Potassium carbonate (K$_2$CO$_3$, 26 g, 190 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Compound 10 (40 g, 78%).

HRMS (70 eV, EI+): m/z calcd for C51H35N3: 689.2831, found 689 Elemental Analysis: C, 89%; H, 5%

SYNTHESIS EXAMPLE 3

Synthesis of Compound 1

[Reaction Scheme 31]

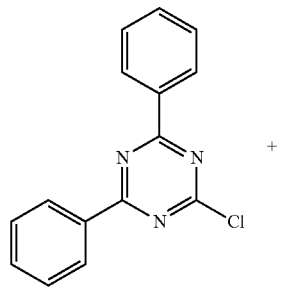

+

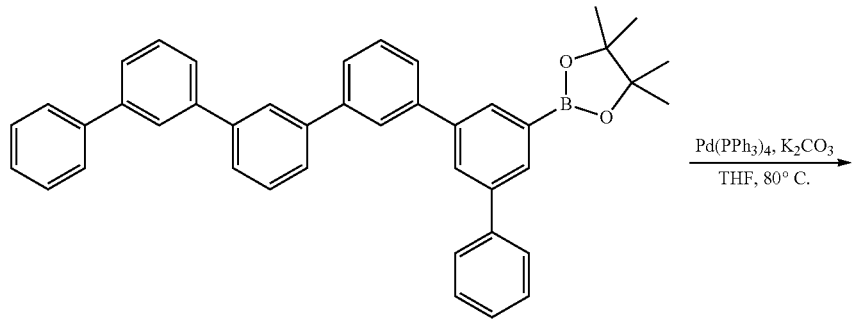

I-22

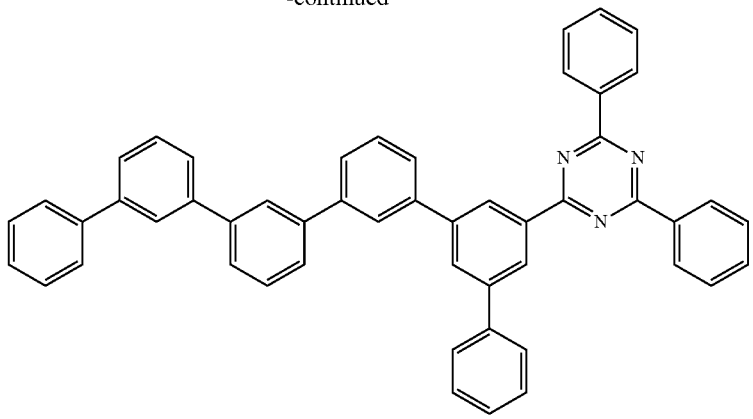

1

2-chloro-4,6-diphenyl-1,3,5-triazine (32 g, 76 mmol) was dissolved in THF (1 L) under a nitrogen environment, Intermediate I-22 (45 g, 76 mmol) and tetrakis(triphenylphosphine)palladium (Pd(PPh$_3$)$_4$, 0.88 g, 0.76 mmol) were added thereto, and the mixture was stirred. Potassium carbonate (K$_2$CO$_3$, 26 g, 190 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Compound 1 (39 g, 75%).

HRMS (70 eV, EI+): m/z calcd for C51H35N3: 689.2831, found 689 Elemental Analysis: C, 89%; H, 5%

SYNTHESIS EXAMPLE 4

Synthesis of Compound 34

[Reaction Scheme 32]

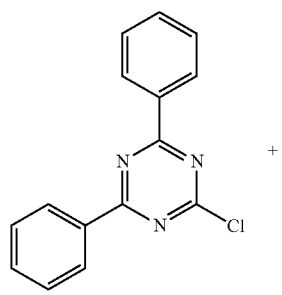

+

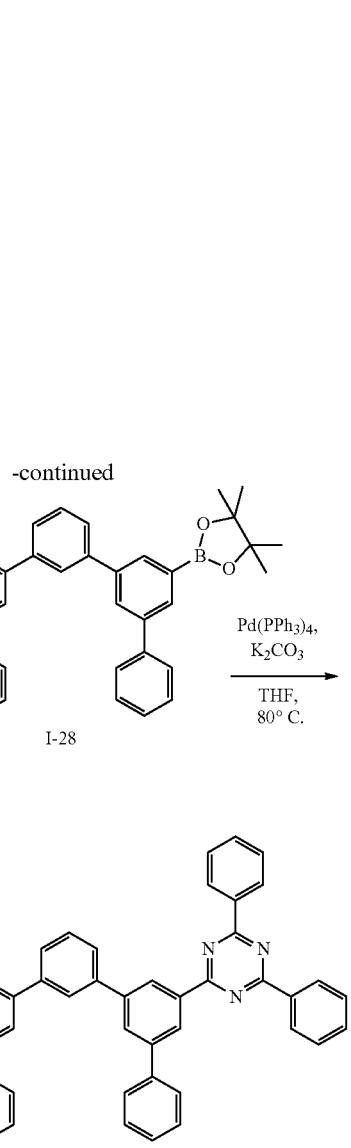

2-chloro-4,6-diphenyl-1,3,5-triazine (32 g, 76 mmol) was dissolved in THF (1 L) under a nitrogen environment, Intermediate I-28 (50 g, 76 mmol) and tetrakis(triphenylphosphine)palladium (Pd(PPh$_3$)$_4$, 0.88 g, 0.76 mmol) were added thereto, and the mixture was stirred. Potassium carbonate (K$_2$CO$_3$, 26 g, 190 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Compound 34 (43 g, 80%).

HRMS (70 eV, EI+): m/z calcd for C57H39N3: 765.3144, found 765 Elemental Analysis: C, 89%; H, 5%

SYNTHESIS EXAMPLE 5

Synthesis of Compound 37

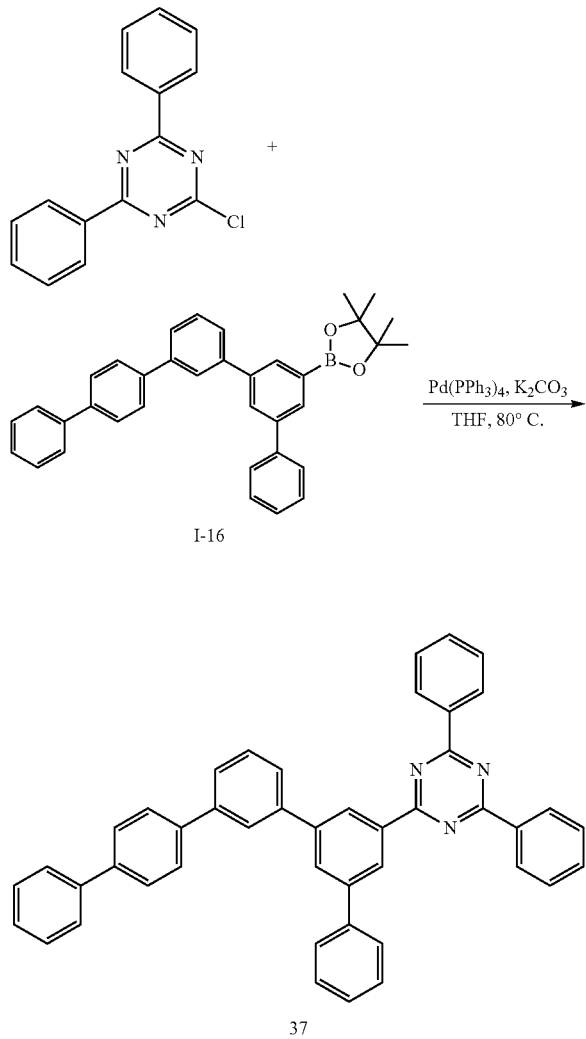

COMPARATIVE SYNTHESIS EXAMPLE 1

HOST 1

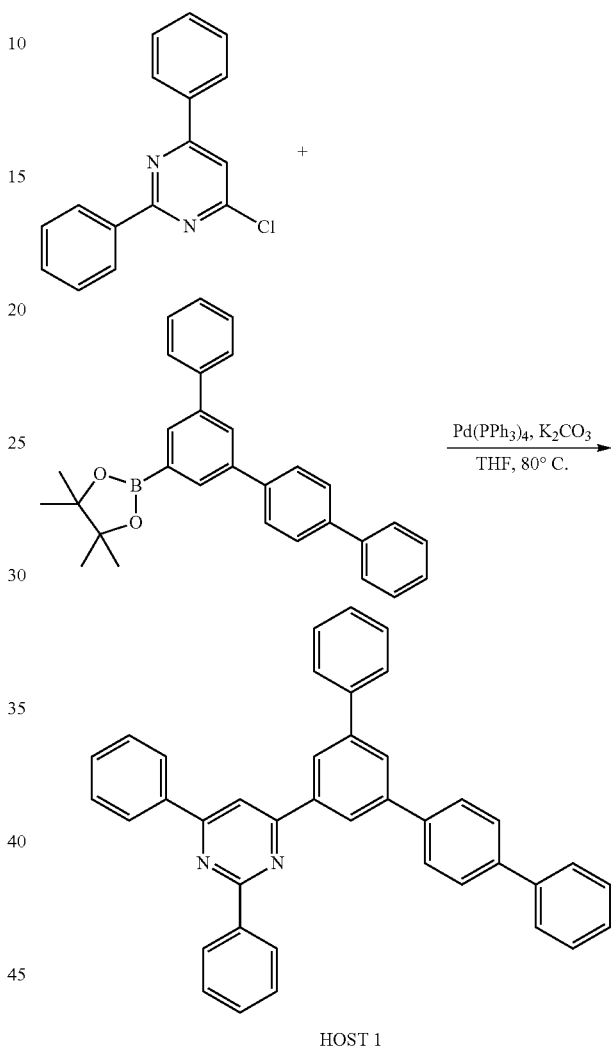

2-chloro-4,6-diphenyl-1,3,5-triazine (32 g, 76 mmol) was dissolved in THF (1 L) under a nitrogen environment, Intermediate I-16 (38 g, 76 mmol) and tetrakis(triphenylphosphine)palladium (Pd(PPh$_3$)$_4$, 0.88 g, 0.76 mmol) were added thereto, and the mixture was stirred. Potassium carbonate (K$_2$CO$_3$, 26 g, 190 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Compound 37 (38 g, 83%).

HRMS (70 eV, EI+): m/z calcd for C$_{45}$H$_{31}$N$_3$: 613.2518, found 613 Elemental Analysis: C, 88%; H, 5%

4-chloro-2,6-diphenylpyrimidine (13.5 g, 60 mmol) was dissolved in THF (1 L) under a nitrogen environment, Intermediate I-30 (26 g, 60 mmol) and tetrakis(triphenylphosphine)palladium (Pd(PPh$_3$)$_4$, 0.7 g, 0.6 mmol) were added thereto, and the mixture was stirred. Potassium carbonate (K$_2$CO$_3$, 20 g, 150 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain HOST 1 (26 g, 80%).

HRMS (70 eV, EI+): m/z calcd for C$_{40}$H$_{28}$N$_2$: 536.2252, found 536 Elemental Analysis: C, 90%; H, 5%

COMPARATIVE SYNTHESIS EXAMPLE 2

HOST 2

[Reaction Scheme 35]

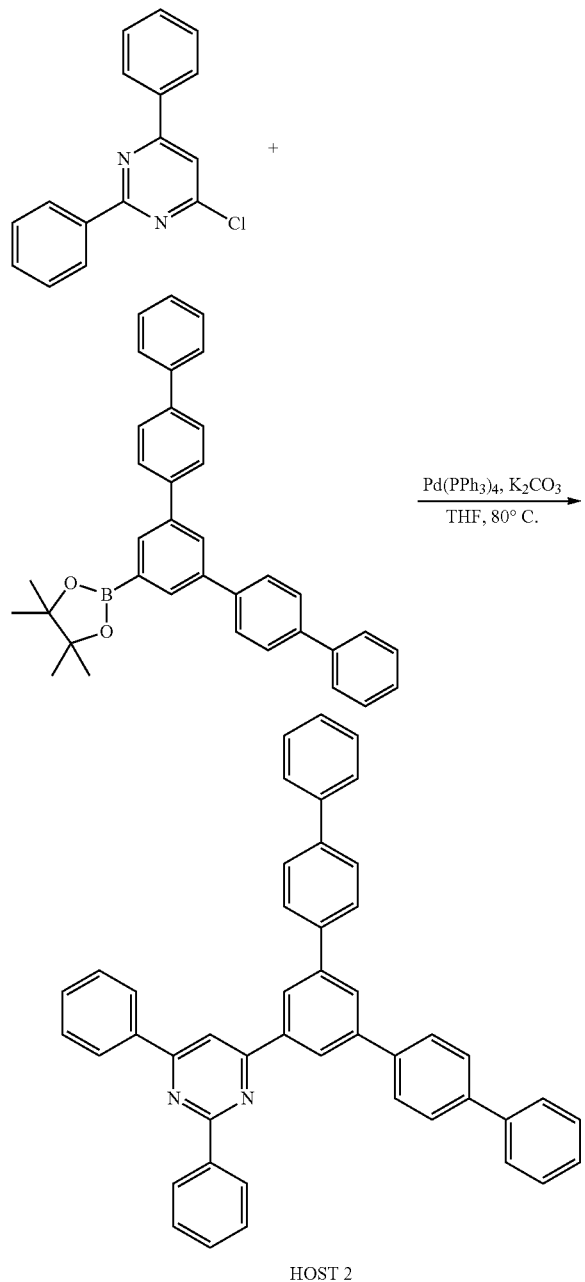

HOST 2

4-chloro-2,6-diphenylpyrimidine (10 g, 16.3 mmol) was dissolved in THF (1 L) under a nitrogen environment, Intermediate I-32 (8.3 g, 16.3 mmol) and tetrakis(triphenylphosphine)palladium (Pd(PPh$_3$)$_4$, 0.2 g, 0.16 mmol) were added thereto, and the mixture was stirred. Potassium carbonate (K$_2$CO$_3$, 5.6 g, 40 mmol) saturated in water was added thereto, and the obtained mixture was heated and refluxed at 80° C. for 12 hours. When the reaction was complete, water was added to the reaction solution, the mixture was extracted with dichloromethane(DCM), and after removing moisture with anhydrous MgSO$_4$, the resultant was filtered and concentrated under a reduced pressure. This obtained residue was separated and purified through flash column chromatography to obtain HOST 2 (7.5 g, 75%).

HRMS (70 eV, EI+): m/z calcd for C46H32N2: 612.2565, found 612 Elemental Analysis: C, 90%; H, 5%

COMPARATIVE SYNTHESIS EXAMPLE 3

HOST 3

[Reaction Scheme 36]

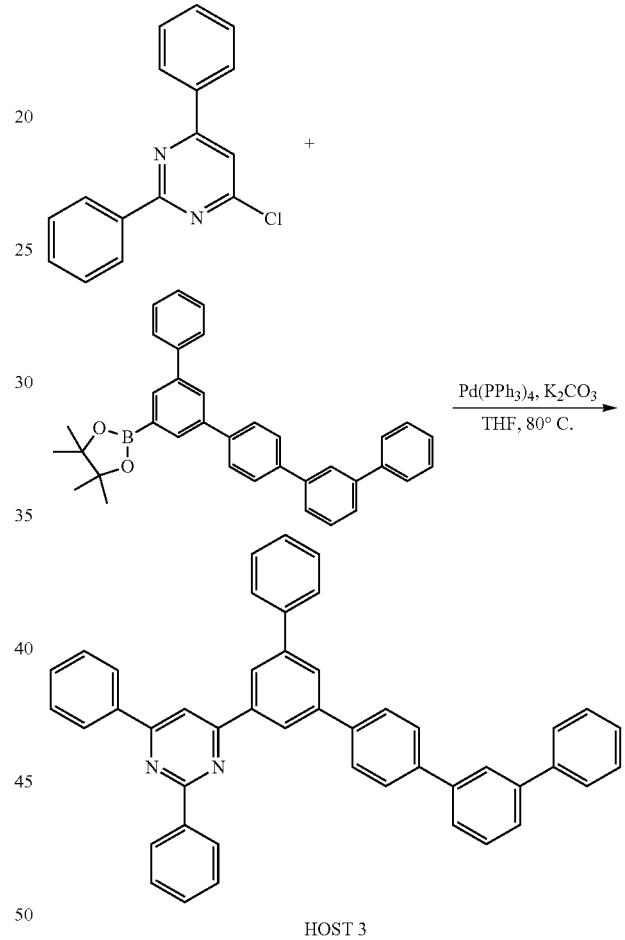

HOST 3

4-chloro-2,6-diphenylpyrimidine (10 g, 16.3 mmol) was dissolved in THF (1 L) under a nitrogen environment, Intermediate I-39 (11 g, 16.3 mmol) and tetrakis(triphenylphosphine)palladium (Pd(PPh$_3$)$_4$, 0.2 g, 0.16 mmol) were added thereto, and the mixture was stirred. Potassium carbonate (K$_2$CO$_3$, 5.6 g, 40 mmol) saturated in water was added thereto, and the obtained mixture was heated and refluxed at 80° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain HOST 3 (7.5 g, 77%).

HRMS (70 eV, EI+): m/z calcd for C46H32N2: 612.2565, found 612 Elemental Analysis: C, 90%; H, 5%

Manufacture of Organic Light Emitting Diode I

EXAMPLE 1

An organic light emitting diode was manufactured by using Compound 13 of Synthesis Example 1 as a host and Ir(PPy)$_3$ as a dopant.

As for an anode, 1000 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of a sheet resistance into a size of 50 mm×50 mm×0.7 mm, ultrasonic wave-cleaning them in each acetone, isopropylalcohol, and pure water for 15 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) (80 nm) under a vacuum degree of 650×10$^{-7}$ Pa at a deposition rate of 0.1 to 0.3 nm/s. Subsequently, a 300 Å-thick light emitting layer was formed by using Compound 13 of Synthesis Example 1 under the same vacuum deposition condition, and a phosphorescent dopant of Ir(PPy)$_3$ was simultaneously deposited. Herein, the phosphorescent dopant was deposited to be 7 wt % based on 100 wt % of the total weight of the light emitting layer by adjusting the deposition rate.

On the light emitting layer, a 50 Å-thick hole blocking layer was formed by depositing bis(2-methyl-8-quinolinolate)-4-(phenylphenolato)aluminum (BAlq) under the same vacuum deposition condition. Subsequently, a 200 Å-thick electron transport layer was formed by depositing Alq3 under the same vacuum deposition condition. On the electron transport layer, a cathode is formed by sequentially depositing LiF and Al to manufacture an organic photoelectric diode.

The organic light emitting diode has a structure of ITO/NPB (80 nm)/EML (Compound 13 (93 wt %)+Ir(PPy)$_3$ (7 wt %), 30 nm)/Balq (5 nm)/Alq3 (20 nm)/LiF (1 nm)/Al (100 nm).

EXAMPLE 2

An organic light emitting diode was manufactured according to the same method as Example 1 except for using Compound 10 according to Synthesis Example 2 instead of Compound 13 according to Synthesis Example 1.

EXAMPLE 3

An organic light emitting diode was manufactured according to the same method as Example 1 except for using Compound 1 according to Synthesis Example 3 instead of Compound 13 according to Synthesis Example 1.

EXAMPLE 4

An organic light emitting diode was manufactured according to the same method as Example 1 except for using Compound 34 according to Synthesis Example 4 instead of Compound 13 according to Synthesis Example 1.

EXAMPLE 5

An organic light emitting diode was manufactured according to the same method as Example 1 except for using Compound 37 according to Synthesis Example 5 instead of Compound 13 according to Synthesis Example 1.

COMPARATIVE EXAMPLE 1

An organic light emitting diode was manufactured according to the same method as Example 1 except for using CBP having the following structure instead of Compound 13 according to Synthesis Example 1.

COMPARATIVE EXAMPLE 2

An organic light emitting diode was manufactured according to the same method as Example 1 except for using HOST 1 according to Comparative Synthesis Example 1 instead of Compound 13 according to Synthesis Example 1.

COMPARATIVE EXAMPLE 3

An organic light emitting diode was manufactured according to the same method as Example 1 except for using HOST 2 according to Comparative Synthesis Example 2 instead of Compound 13 according to Synthesis Example 1.

COMPARATIVE EXAMPLE 4

An organic light emitting diode was manufactured according to the same method as Example 1 except for using HOST 3 according to Comparative Synthesis Example 3 instead of Compound 13 according to Synthesis Example 1.

The structures of NPB, BAlq, CBP, and Ir(PPy)$_3$ used to manufacture the organic light emitting diodes are as follows.

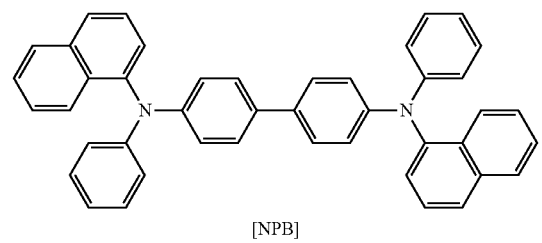

[NPB]

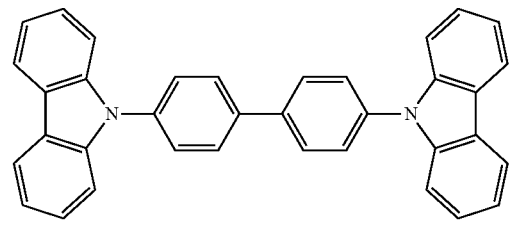

[CBP]

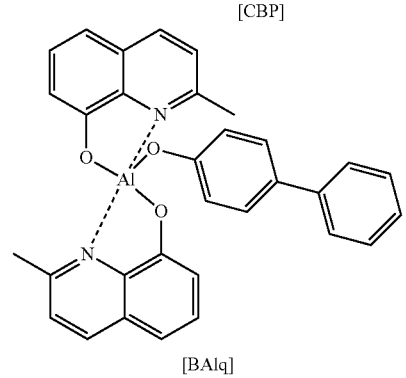

[BAlq]

-continued

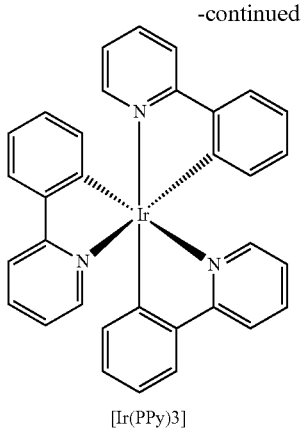

[Ir(PPy)3]

Evaluation 1

Current density and luminance changes depending on a voltage and luminous efficiency of each organic light emitting diode according to Examples 1 to 5 and Comparative Examples 1 to 4 were measured.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

Life-span was obtained by measuring time taken until current efficiency (cd/A) decreased down to 97% while current efficiency (cd/A) was maintained at 6000 cd/m$^2$.

TABLE 1

| Nos. | Compounds | Driving voltage (V) | Color (EL color) | Efficiency (cd/A) | Life-span T97 (h) |
|---|---|---|---|---|---|
| Example 1 | Compound 13 | 4.00 | Green | 32.7 | 500 |
| Example 2 | Compound 10 | 4.02 | Green | 32.4 | 270 |
| Example 3 | Compound 1 | 4.20 | Green | 31.8 | 440 |
| Example 4 | Compound 34 | 4.10 | Green | 31.0 | 310 |
| Example 5 | Compound 37 | 4.18 | Green | 33.2 | 355 |
| Comparative Example 1 | CBP | 4.80 | Green | 19.3 | 0.5 |
| Comparative Example 2 | HOST1 | 4.32 | Green | 20.8 | 190 |
| Comparative Example 3 | HOST2 | 4.35 | Green | 22.1 | 215 |
| Comparative Example 4 | HOST3 | 4.30 | Green | 22.6 | 185 |

Referring to Table 1, the organic light emitting diodes according to Examples 1 to 5 showed a low driving voltage, high efficiency, and improved life-span characteristics compared with the organic light emitting diodes according to Comparative Examples 1 to 4.

SYNTHESIS EXAMPLES OF SECOND HOST COMPOUND

SYNTHESIS EXAMPLE 1 OF SECOND HOST COMPOUND

Compound B-1

[Reaction Scheme 37]

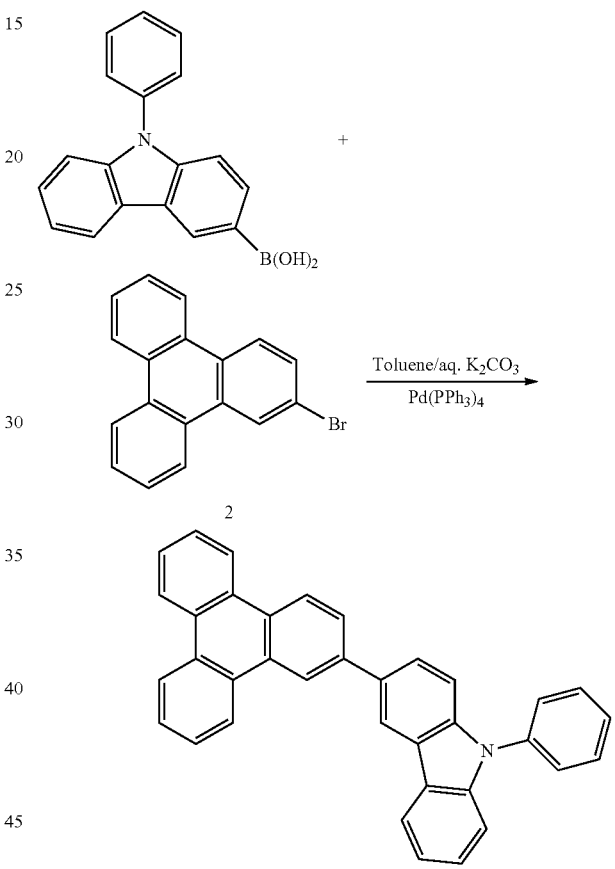

The compound of phenylcarbazolyl boronic acid (10 g, 34.83 mmol) was dissolved in Toluene (0.2 L) under a nitrogen environment, 2-bromotriphenylene (11.77 g, 38.31 mmol) and tetrakis(triphenylphosphine)palladium (0.80 g, 0.7 mmmol) were added thereto, and the mixture was stirred. Potassium carbonate (14.44 g, 104.49 mmol) saturated in water was added thereto, and the obtained mixture was heated and refluxed at 120° C. for 12 hours. When the reaction was complete, water was added to the reaction solution, the mixture was extracted with dichloromethane (DCM), and moisture was removed with anhydrous MgSO$_4$, followed by filtering and concentrating the resultant under a reduced pressure. This obtained residue was separated and purified through flash column chromatography to obtain Compound B-1 (14.4 g, 88%).

HRMS (70 eV, EI+): m/z calcd for C36H23N: 469.18, found: 469

Elemental Analysis: C, 92%; H, 5%

SYNTHESIS EXAMPLE 2 OF SECOND HOST COMPOUND

Compound B-10

[Reaction Scheme 38]

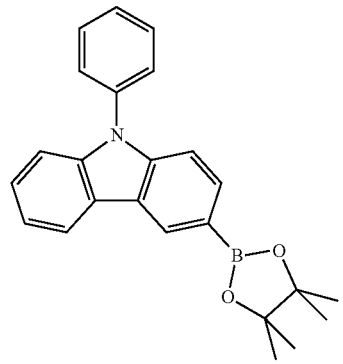

+

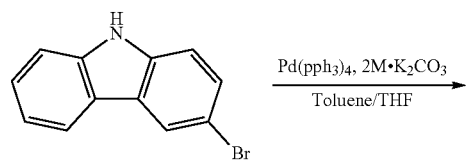

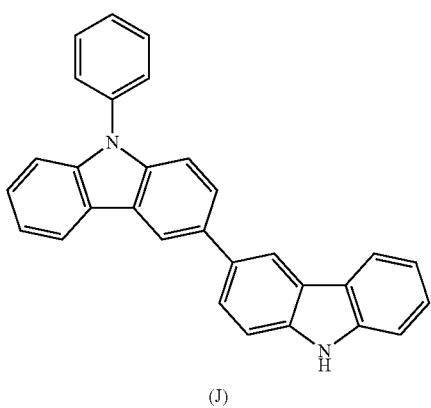

(J)

(J) + 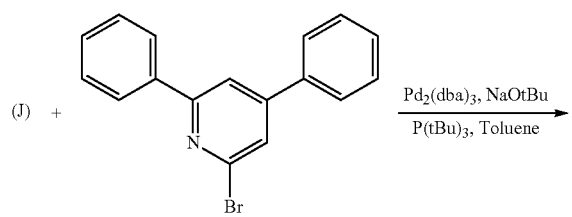

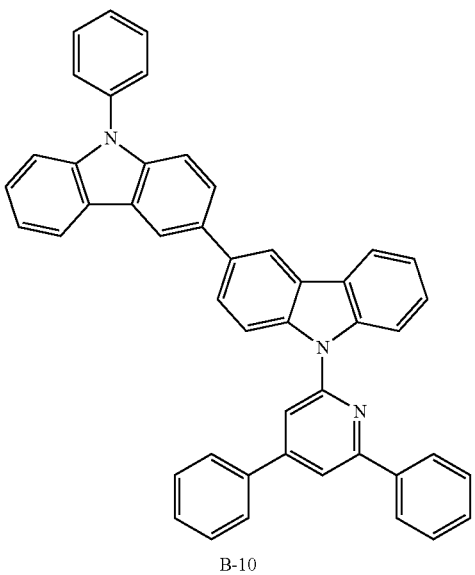

B-10

First Step: Synthesis of Compound J

The compound of 9-phenyl-3-(4,4,5,5-tetramethyl-1,3,2-dioxaborolan-2-yl)-9H-carbazole (26.96 g, 81.4 mmol) was dissolved in Toluene/THF (0.2 L) under a nitrogen environment, 3-bromo-9H-carbazole (23.96 g, 97.36 mmol) and tetrakis(triphenylphosphine)palladium (0.90 g, 0.8 mmmol) were added thereto, and the mixture was stirred. Potassium carbonate (28 g, 203.49 mmol) saturated in water was added thereto, and the obtained mixture was heated and refluxed at 120° C. for 12 hours. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Compound J (22.6 g, 68%).

HRMS (70 eV, EI+): m/z calcd for C30H2ON2: 408.16, found: 408

Elemental Analysis: C, 88%; H, 5%

Second Step: Synthesis of Compound B-10

Compound J (22.42 g, 54.88 mmol) was dissolved in toluene (0.2 L) under a nitrogen environment, 2-bromo-4,6-diphenylpyridine (20.43 g, 65.85 mmol), NaOtBu (7.92 g, 82.32 mmol), tris(dibenzylideneacetone)dipalladium (0) (1.65 g, 1.65 mmol), and tri-tert-butylphosphine (1.78 g, 4.39 mmol) were added thereto, and the mixture was heated and refluxed at 120° C. for 12 hours. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Compound B-10 (28.10 g, 80%).

HRMS (70 eV, EI+): m/z calcd for C47H31N3: 637.25, found: 637

Elemental Analysis: C, 89%; H, 5%

153
SYNTHESIS EXAMPLE 3 OF SECOND HOST COMPOUND

Compound B-31

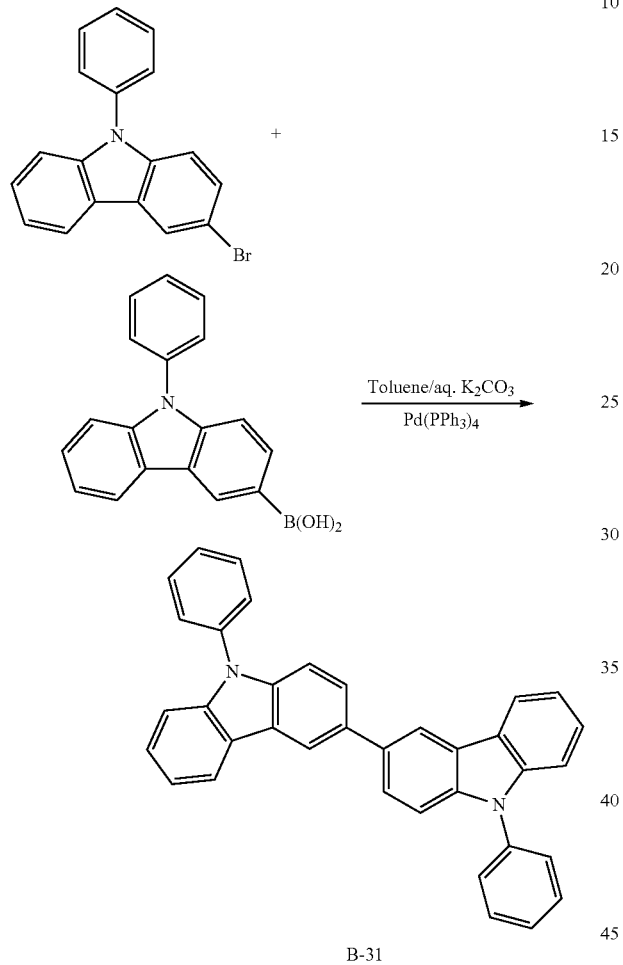

B-31

The compound of phenylcarbazolyl bromide (9.97 g, 30.95 mmol) was dissolved in toluene (0.2 L) under a nitrogen environment, phenylcarbazolylboronic acid (9.78 g, 34.05 mmol) and tetrakis(triphenylphosphine)palladium (1.07 g, 0.93 mmmol) were added thereto, and the mixture was stirred. Potassium carbonate (12.83 g, 92.86 mmol) saturated in water was added thereto, and the obtained mixture was heated and refluxed at 120° C. for 12 hours. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Compound B-31 (13.8 g, 92%).

HRMS (70 eV, EI+): m/z calcd for $C_{36}H_{24}N_2$: 484.19, found: 484

Elemental Analysis: C, 89%; H, 5%

154
SYNTHESIS EXAMPLE 4 OF SECOND HOST COMPOUND

Compound B-34

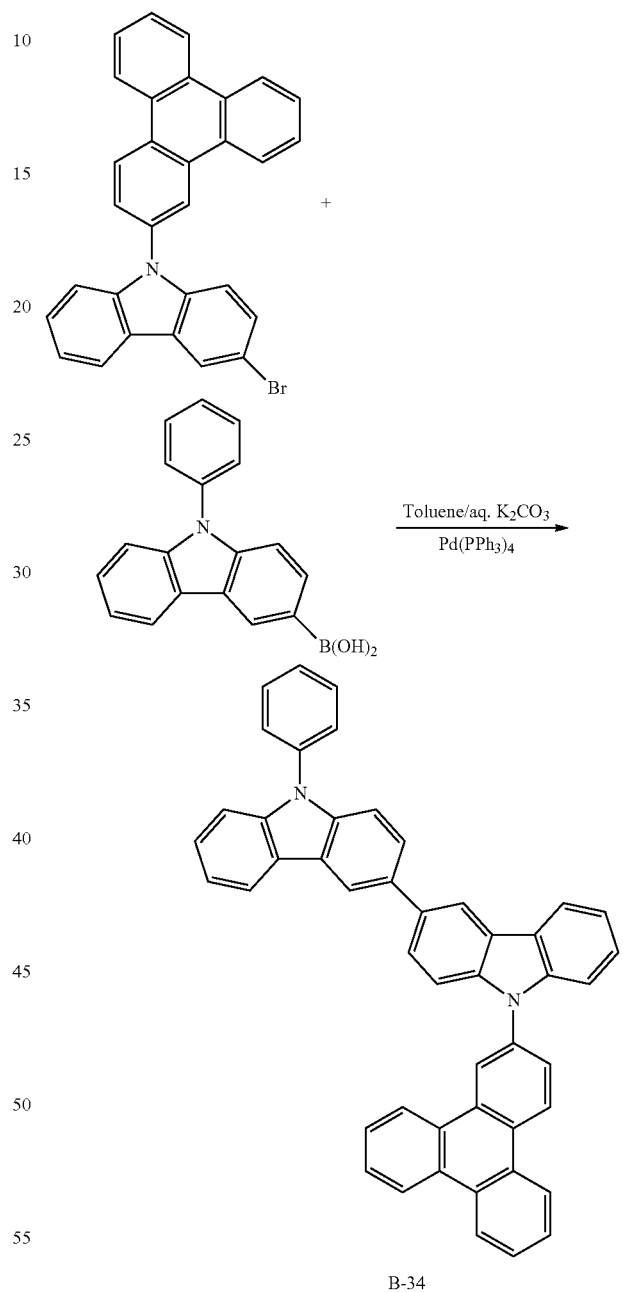

B-34

The compound of triphenylcarbazolyl bromide (14.62 g, 30.95 mmol) was dissolved in toluene (0.2 L) under a nitrogen environment, phenylcarbazolylboronic acid (9.78 g, 34.05 mmol) and tetrakis(triphenylphosphine)palladium (1.07 g, 0.93 mmmol) were added thereto, and the mixture was stirred. Potassium carbonate (12.83 g, 92.86 mmol) saturated in water was added thereto, and the obtained mixture was heated and refluxed at 120° C. for 12 hours. When the reaction was complete, water was added to the reaction solution, the mixture was extracted with dichloromethane (DCM), and after removing moisture with anhydrous MgSO₄, the resultant was filtered and concentrated under a reduced pressure. This obtained residue was separated and purified through flash column chromatography to obtain Compound B-34 (16.7 g, 85%).

HRMS (70 eV, EI+): m/z calcd for C47H29N2: 621.23, found: 621

Elemental Analysis: C, 91%; H, 5%

SYNTHESIS EXAMPLE 5 OF SECOND HOST COMPOUND

Compound B-43

[Reaction Scheme 41]

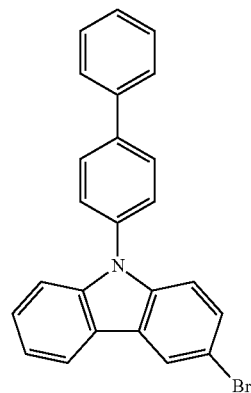

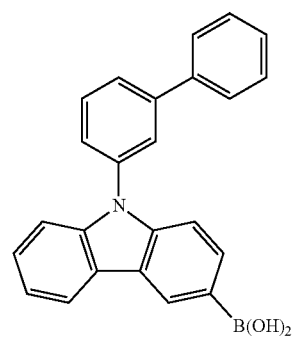

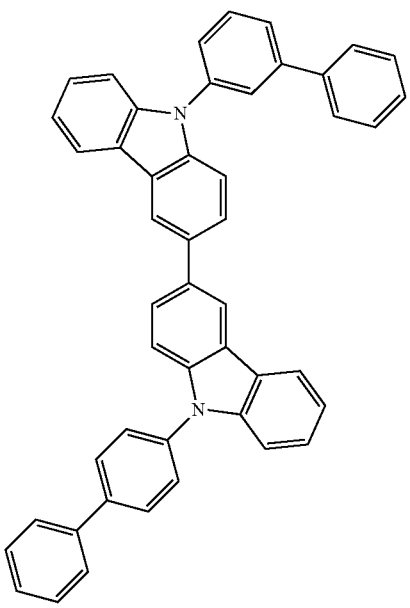

B-43

The compound of biphenylcarbazolyl bromide (12.33 g, 30.95 mmol) was dissolved in toluene (0.2 L) under a nitrogen environment, biphenylcarbazolylboronic acid (12.37 g, 34.05 mmol) and tetrakis(triphenylphosphine)palladium (1.07 g, 0.93 mmmol) were added thereto, and the mixture was stirred. Potassium carbonate (12.83 g, 92.86 mmol) saturated in water was added thereto, and the obtained mixture was heated and refluxed at 120° C. for 12 hours. When the reaction was complete, water was added to the reaction solution, the mixture was extracted with dichloromethane (DCM), and after removing moisture with anhydrous MgSO₄, the resultant was filtered and concentrated under a reduced pressure. This obtained residue was separated and purified through flash column chromatography to obtain Compound B-43 (18.7 g, 92%).

HRMS (70 eV, EI+): m/z calcd for C48H32N2: 636.26, found: 636

Elemental Analysis: C, 91%; H, 5%

SYNTHESIS EXAMPLE 6 OF SECOND HOST COMPOUND

Compound B-114

[Reaction Scheme 42]

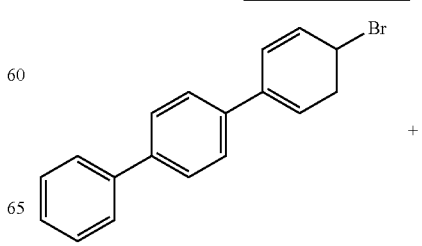

-continued

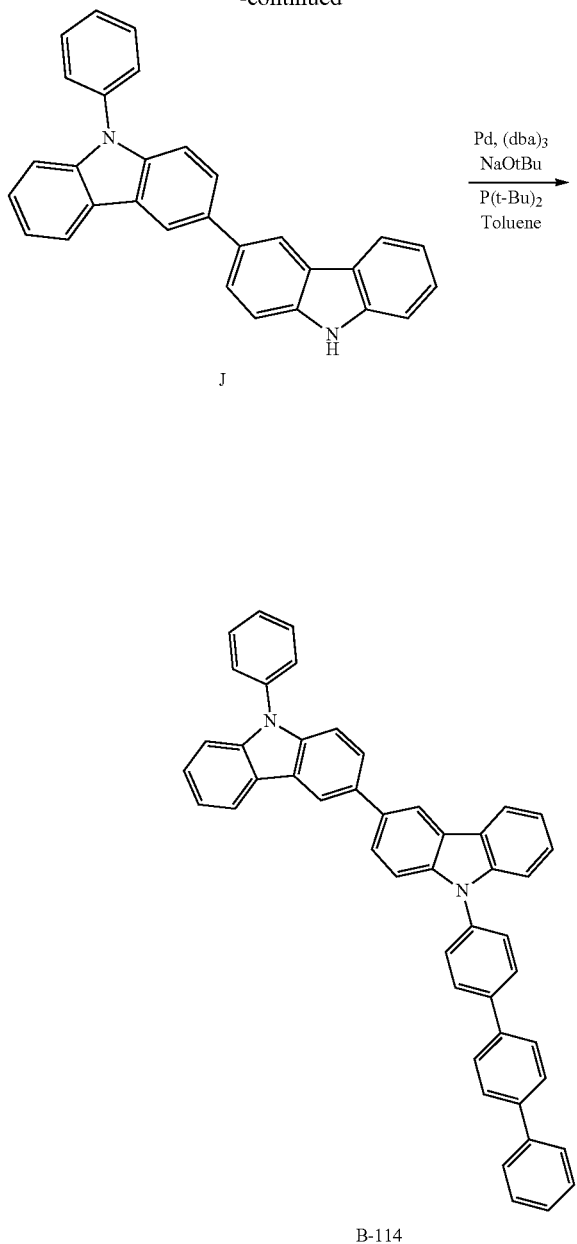

4-bromo-1,1':4',1"-terphenyl (15 g, 48.5 mmol) was dissolved in toluene (0.2 L) under a nitrogen environment, Compound J (20 g, 48.5 mmol), NaOtBu (6 g, 58.2 mmol), tris(dibenzylideneacetone)dipalladium (0) (0.439 g, 0.48 mmol), and tri-tert-butylphosphine (0.388 g, 1.92 mmol) were added thereto, and the mixture was heated and refluxed at 120° C. for 12 hours. When the reaction was complete, water was added to the reaction solution, the mixture was extracted with dichloromethane (DCM), and after removing moisture with anhydrous MgSO$_4$, the resultant was filtered and concentrated under a reduced pressure. This obtained residue was separated and purified through flash column chromatography to obtain Compound B-114 (25 g, 80%).

HRMS (70 eV, EI+): m/z calcd for C48H32N2: 636.2565, found: 636

Elemental Analysis: C, 95%; H, 5%

SYNTHESIS EXAMPLE 7 OF SECOND HOST COMPOUND

Compound E-1

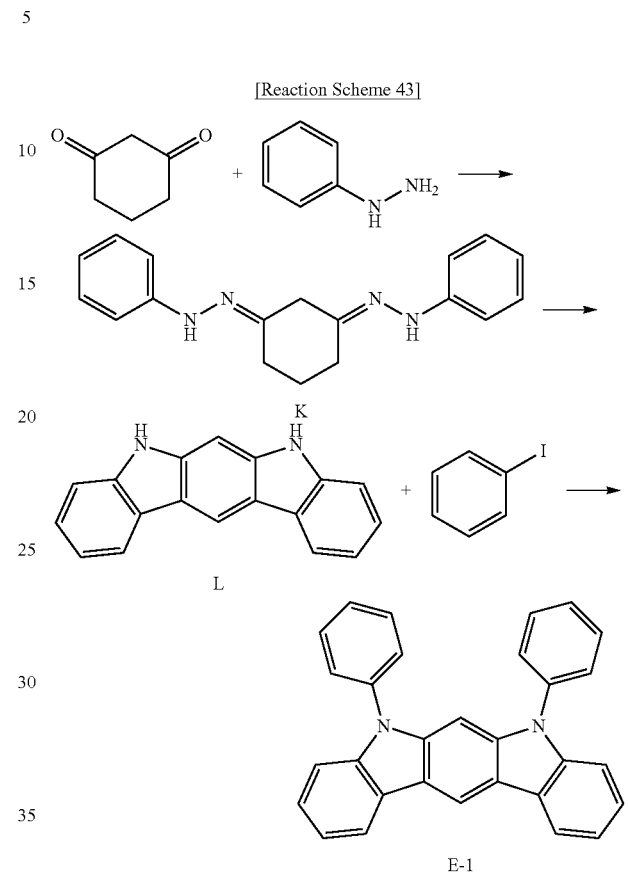

First Step: Synthesis of Compound K

Phenylhydrazine hydrochloride was dissolved in distilled water, and a 2 M NaOH aqueous solution was added thereto. A solid produced therein was filtered to obtain phenylhydrazine. The phenylhydrazine was slowly added to the compound cyclohexane-1,3-dione (30 g, 267.5 mmol) dissolved in ethanol (1000 ml) under a nitrogen environment and then, reacted for 20 minutes. When the reaction was complete, ice water was added thereto. A solid produced therein was washed with ethanol and filtered. The solid was dried under a reduced pressure to obtain Compound K (46.2 g, 38%).

HRMS (70 eV, EI+): m/z calcd for C18H2ON4: 292.3782, found: 292

Elemental Analysis: C, 74%; H, 7%

Second Step: Synthesis of Compound L

Compound K (46.2 g, 102.6 mmol) was slowly added to a mixed solution (140 ml) of acetic acid and sulfuric acid (=1:4) under a nitrogen environment at 0° C. The mixture was stirred for 5 minutes and then, heated rapidly up to 50° C. and slowly up to 110° C. After 20 minutes, the resultant was cooled down to room temperature and stirred for 12 hours. Ethanol was added thereto, and a solid produced therein after one hour was filtered under a reduced pressure and neutralized. The solid was dried under a reduced pressure to obtain Compound L (21.7 g, 51%).

HRMS (70 eV. EI+): m/z calcd for C18H12N2: 256.3013, found: 256

Elemental Analysis: C, 84%; H, 5%

Third Step: Synthesis of Compound E-1

Compound L (10 g, 39.0 mmol), iodobenzene (10.4 ml, 93.6 mmol), 18-crown-6 (4.2 g, 15.6 mmol), copper (3 g. 46.8 mmol), and potassium carbonate (48.6 g, 351 mmol) were added thereto, and the obtained mixture was heated and refluxed under a nitrogen environment at 180° C. for 20 hours. When the reaction was complete, water was added to the reaction solution, the mixture was extracted with ethyl acetate (e.a), and after removing moisture with anhydrous $MgSO_4$, the resultant was filtered and concentrated under a reduced pressure. This obtained residue was separated and purified through flash column chromatography to obtain Compound E-1 (6.7 g, 17.3%).

HRMS (70 eV, EI+): m/z calcd for C30H2ON2: 408.4932, found: 408

Elemental Analysis: C, 88%; H, 5%

SYNTHESIS EXAMPLE 8 OF SECOND HOST COMPOUND

Compound B-116

[Reaction Scheme 44]

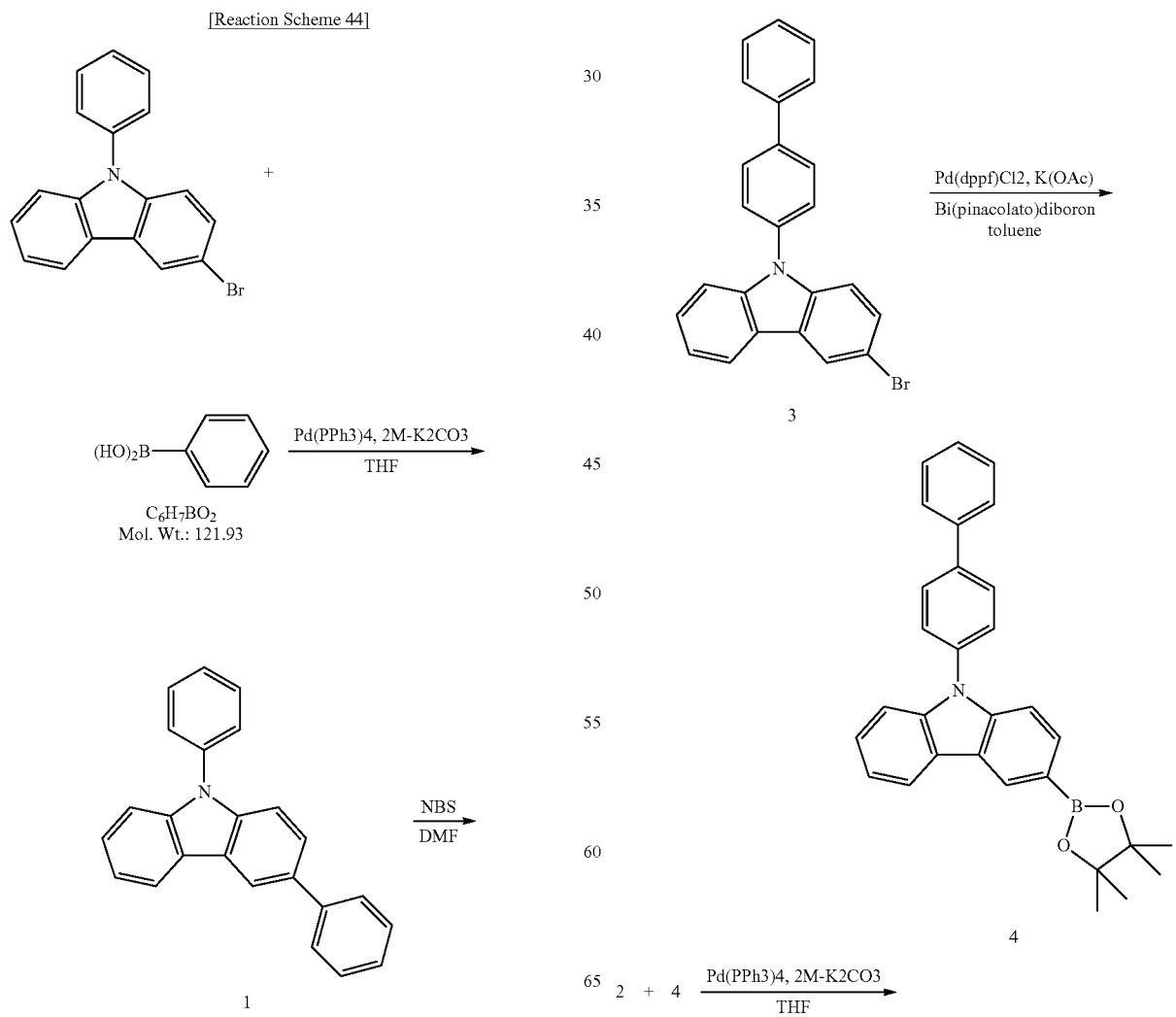

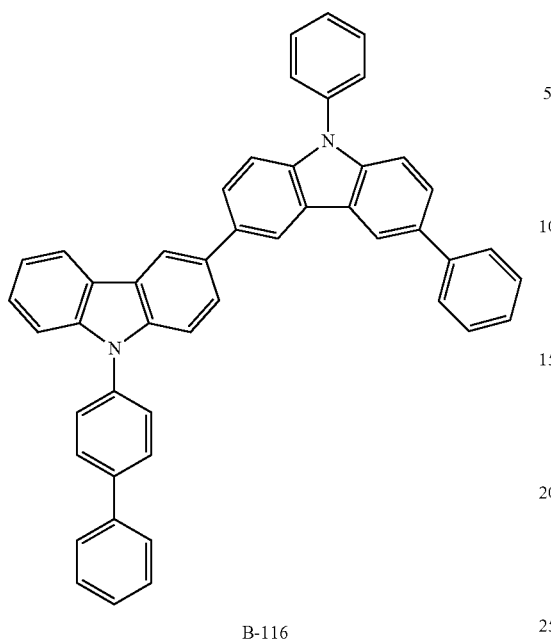

B-116

First Step: Synthesis of Compound 1

Compound 1 (32 g, 75%) was synthesized according to the same method as the synthesis method of Compound B-31 by using 3-bromo-N-phenyl carbazole (43.2 g, 134.2 mmol) and phenylboronic acid (18 g, 147.6 mmol).

Second Step: Synthesis of Compound 2

Compound 2 (35 g, 82%) was synthesized by dissolving Compound 1 (34.4 g, 107.6 mmol) in dichloromethane (500 mL), adding N-bromosuccinimide (19.2 g, 107.6 mmol) thereto, and stirring the mixture at room temperature for 8 hours.

Third Step: Synthesis of Compound 3

Compound 3 (15 g, 53%) was obtained according to the same synthesis method as the method of synthesizing Compound B-114 by using 3-bromocarbazole (17.65 g, 71.74 mmol) and 4-Iodobiphenyl (22 g, 78.91 mmol).

Fourth Step: Synthesis of Compound 4

Compound 4 (20 g, 89%) was synthesized according to the same method as the method of synthesizing Intermediate I-5 by using Compound 3 (20.1 g, 50.5 mmol) and bis(pinacolato)diboron (19.2 g, 75.8 mmol).

Fifth Step: Synthesis of Compound B-116

Compound B-116 (18 g, 84%) was synthesized according to the same method as the method of synthesizing Compound B-31 by using Compound 2 (13 g, 33.1 mmol) and Compound 4 (16.2 g, 36.4 mmol).

HRMS (70 eV, EI+): m/z calcd for $C_{48}H_{32}N_2$: 636.2565, found: 636

Elemental Analysis: C, 90%; H, 5%

SYNTHESIS EXAMPLE 9 OF SECOND HOST COMPOUND

Compound B-118

[Reaction Scheme 45]

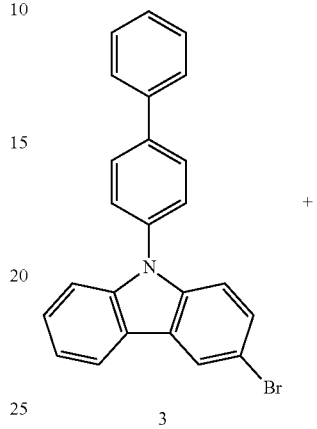

3

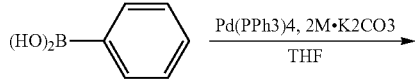

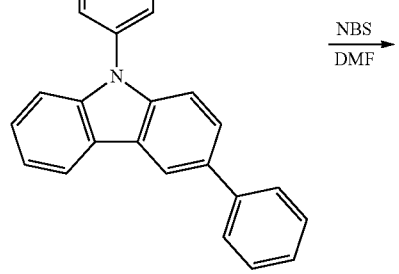

5

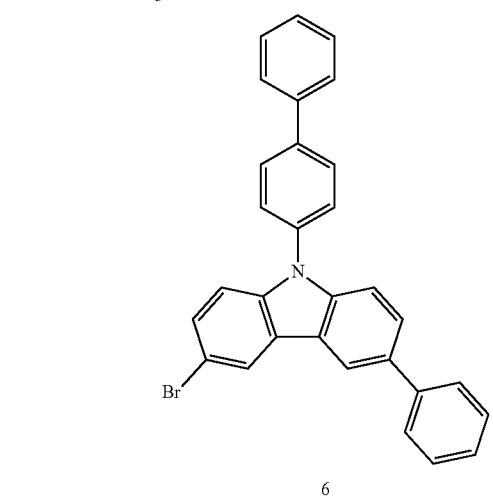

6

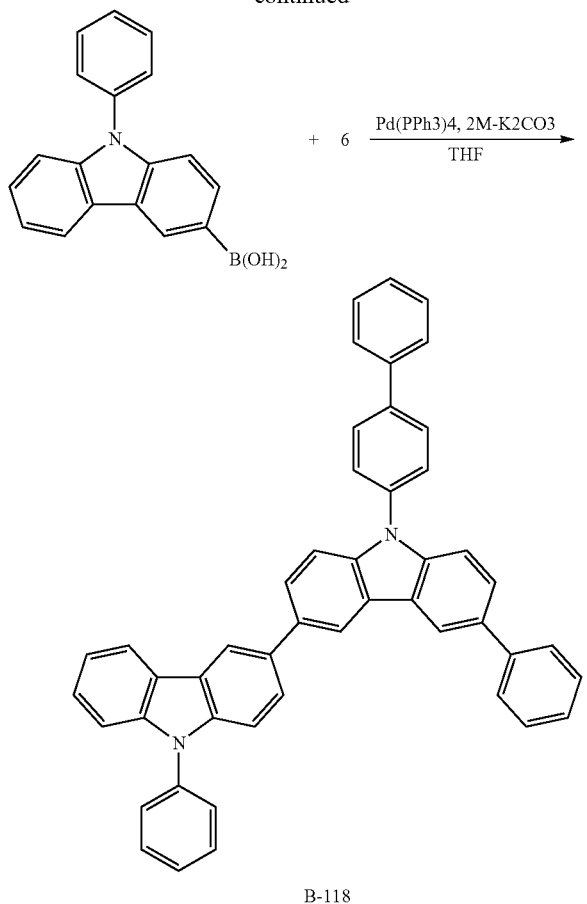

B-118

First Step: Synthesis of Compound 5

Compound 5 (33 g, 77%) was obtained according to the same synthesis method as the method of synthesizing Compound B-31 by using Compound 3 (43.2 g, 108.4 mmol) and phenylboronic acid (14.5 g, 119 mmol).

Second Step: Synthesis of Compound 6

Compound 6 (29 g, 81%) was obtained according to the same synthesis method as the method of synthesizing Compound 2 by using Compound 5 29.8 g (75.28 mmol) and N-bromosuccinimide (14 g, 75.28 mmol).

Third Step: Synthesis of Compound B-118

Compound B-118 (17 g, 79%) was obtained according to the same synthesis method as the method of synthesizing Compound B-31 by using N-phenylcarbazoe-3-yl-boronic acid (9.7 g, 33.65 mmol) and Compound 6 (16 g, 33.65 mmol).

HRMS (70 eV, EI+): m/z calcd for $C_{48}H_{32}N_2$: 636.2565, found: 636

Elemental Analysis: C, 90%; H. 5%
Manufacture of Organic Light Emitting Diode II

EXAMPLE 6

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light emitting layer was formed on the hole transport layer by vacuum-depositing Compound 13 of Synthesis Example 1 and Compound B-43 of Synthesis Example 5 that is a second host compound simultaneously as hosts and 10 wt % of tris(2-phenylpyridine)iridium(M) [Ir(ppy)$_3$] as a dopant. Herein, Compound 13 and Compound B-43 were used in a 7:3 ratio.

Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically a structure of ITO/Compound A 700 Å/Compound B 50 Å/Compound C 1020 Å/EML [Compound 13:B-43:Ir(ppy)$_3$=X:X:10%] 400 Å/Compound D:Liq 300 Å/Liq 15 Å/Al 1200 Å. (X=a weight ratio)

Compound A: N4,N4'-diphenyl-N4,N4'-bis(9-phenyl-9H-carbazol-3-yl)biphenyl-4,4'-diamine, Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine, and Compound D: 8-(4-(4,6-di(naphthalen-2-yl)-1,3,5-triazin-2-yl)phenyl)quinolone.

EXAMPLE 7

An organic light emitting diode was manufactured according to the same method as Example 6 except for using Compound 13 and Compound B-43 in a ratio of 1:1.

EXAMPLE 8

An organic light emitting diode was manufactured according to the same method as Example 6 except for using Compound 13 and Compound B-43 in a ratio of 3:7.

EXAMPLE 9

An organic light emitting diode was manufactured according to the same method as Example 6 except for using Compound 13 and Compound B-10 obtained as a second host compound according to Synthesis Example 2 in a ratio of 7:3.

EXAMPLE 10

An organic light emitting diode was manufactured according to the same method as Example 6 except for using Compound 13 and Compound B-31 obtained as a second host compound according to Synthesis Example 3 in a ratio of 1:1.

EXAMPLE 11

An organic light emitting diode was manufactured according to the same method as Example 6 except for using Compound 13 and Compound B-34 obtained as a second host compound according to Synthesis Example 4 in a ratio of 1:4.

EXAMPLE 12

An organic light emitting diode was manufactured according to the same method as Example 6 except for using Compound 13 and Compound E-1 obtained as a second host compound according to Synthesis Example 7 in a ratio of 1:1.

EXAMPLE 13

An organic light emitting diode was manufactured according to the same method as Example 6 except for using Compound 13 and Compound B-116 obtained as a second host compound according to Synthesis Example 8 in a ratio of 1:1.

EXAMPLE 14

An organic light emitting diode was manufactured according to the same method as Example 6 except for using Compound 13 and Compound B-1 obtained as a second host compound according to Synthesis Example 1 in a ratio of 1:1.

EXAMPLE 15

An organic light emitting diode was manufactured according to the same method as Example 6 except for using Compound 10 according to Synthesis Example 2 instead of Compound 13 and Compound B-43 in a ratio of 3:7.

EXAMPLE 16

An organic light emitting diode was manufactured according to the same method as Example 6 except for using Compound 10 according to Synthesis Example 2 instead of Compound 13 and Compound B-10 obtained as a second host compound according to Synthesis Example 2 instead of Compound B-43 in a ratio of 1:1.

EXAMPLE 17

An organic light emitting diode was manufactured according to the same method as Example 6 except for using Compound 10 according to Synthesis Example 2 instead of Compound 13 and Compound E-1 obtained as a second host compound according to Synthesis Example 7 instead of Compound B-43 in a ratio of 3:7.

EXAMPLE 18

An organic light emitting diode was manufactured according to the same method as Example 6 except for using Compound 1 according to Synthesis Example 3 instead of Compound 13 and Compound B-43 in a ratio of 3:7.

EXAMPLE 19

An organic light emitting diode was manufactured according to the same method as Example 6 except for using Compound 1 according to Synthesis Example 3 instead of Compound 13 and Compound B-10 obtained as a second host compound according to Synthesis Example 2 instead of Compound B-43 in a ratio of 1:1.

EXAMPLE 20

An organic light emitting diode was manufactured according to the same method as Example 6 except for using Compound 1 according to Synthesis Example 3 instead of Compound 13 and Compound B-116 obtained as a second host compound according to Synthesis Example 8 instead of Compound B-43 in a ratio of 1:1.

Reference EXAMPLE 1

An organic light emitting diode was manufactured according to the same method as Example 6 except for using Compound 13 as a single host instead of two hosts of Compound 13 and Compound B-43.

COMPARATIVE EXAMPLE 5

An organic light emitting diode was manufactured according to the same method as Example 6 except for using CBP as a single host instead of two hosts of Compound 13 and Compound B-43.

COMPARATIVE EXAMPLE 6

An organic light emitting diode was manufactured according to the same method as Example 9 except for using Compound B-10 as a single host instead of two hosts of Compound 13 and Compound B-10.

COMPARATIVE EXAMPLE 7

An organic light emitting diode was manufactured according to the same method as Example 10 except for using Compound B-31 as a single host instead of two hosts of Compound 13 and Compound B-31.

COMPARATIVE EXAMPLE 8

An organic light emitting diode was manufactured according to the same method as Example 14 except for using Compound B-1 as a single host instead of two hosts of Compound 13 and Compound B-1.

COMPARATIVE EXAMPLE 9

An organic light emitting diode was manufactured according to the same method as Example 11 except for using Compound B-34 as a single host instead of two hosts of Compound 13 and Compound B-34.

COMPARATIVE EXAMPLE 10

An organic light emitting diode was manufactured according to the same method as Example 18 except for using Compound B-43 as a single host instead of two hosts of Compound 1 and Compound B-43.

Evaluation 2

Luminous efficiency and life-span characteristics of each organic light emitting diode according to Examples 6 to 20, Reference Example 1 and Comparative Examples 5 to 10 were evaluated.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

Life-span was obtained by measuring time taken until current efficiency (cd/A) decreased down to 97% while luminance (cd/m$^2$) was maintained at 6000 cd/m$^2$.

minutes, and moved to a vacuum depositor. This obtained ITO transparent electrode was used as an anode, a 700 Å-thick hole injection layer was formed on the ITO substrate by vacuum-depositing Compound A, and a hole transport layer was formed on the injection layer by depositing Compound B to be 50 Å thick and Compound C to be 1020 Å thick. Then, a 200 Å-thick light emitting layer was formed thereon by vacuum-depositing BH113 and BD370 (Manufacturer: SFC Inc.) as a blue fluorescent luminescent host and a dopant in a dopant concentration of 5 wt %. On the light emitting layer, Compound 13 according to Synthesis Example 1 and Compound B-116 according to Synthesis Example 8 as a second host compound were vacuum-deposited in 50:50 (wt/wt) to form a 50 Å-thick electron transport auxiliary layer. On the electron transport auxiliary layer, a 300 Å-thick electron transport layer was formed by vacuum-depositing Compound D and Liq simultaneously in a ratio of 1:1, and on the electron transport layer, a cathode was formed by sequentially vacuum-depositing Liq to be 15 Å thick and Al to be 1200 Å thick, manufacturing an organic

TABLE 2

| | First host | Second host | First host:Second host | Luminous efficiency (cd/A) | Life-span T97 (h) |
|---|---|---|---|---|---|
| Example 6 | Compound 13 | B-43 | 7:3 | 37.8 | 980 |
| Example 7 | Compound 13 | B-43 | 1:1 | 46.7 | 1,000 |
| Example 8 | Compound 13 | B-43 | 3:7 | 49.8 | 1,080 |
| Example 9 | Compound 13 | B-10 | 7:3 | 46.8 | 650 |
| Example 10 | Compound 13 | B-31 | 1:1 | 43.5 | 755 |
| Example 11 | Compound 13 | B-34 | 1:4 | 45.5 | 725 |
| Example 12 | Compound 13 | E-1 | 1:1 | 47.8 | 690 |
| Example 13 | Compound 13 | B-116 | 1:1 | 48.1 | 705 |
| Example 14 | Compound 13 | B-1 | 2:8 | 47.9 | 870 |
| Example 15 | Compound 10 | B-43 | 3:7 | 50.0 | 1060 |
| Example 16 | Compound 10 | B-10 | 1:1 | 42.3 | 860 |
| Example 17 | Compound 10 | E-1 | 3:7 | 45.2 | 830 |
| Example 18 | Compound 1 | B-43 | 3:7 | 45.2 | 1020 |
| Example 19 | Compound 1 | B-10 | 1:1 | 44.6 | 645 |
| Example 20 | Compound1 | B-116 | 1:1 | 44.9 | 720 |
| Reference Example 1 | Compound 13 | | — | 32.7 | 500 |
| Comparative Example 5 | CBP | | — | 19.3 | 0.5 |
| Comparative Example 6 | B-10 | | — | 37.5 | 10 |
| Comparative Example 7 | B-31 | | — | 2.5 | — |
| Comparative Example 8 | B-1 | | — | 16.5 | 10 |
| Comparative Example 9 | B-34 | | — | 18.3 | 10 |
| Comparative Example 10 | B-43 | | — | 2.8 | 10 |

Referring to Table 2, the organic light emitting diodes according to Examples 6 to 20 showed remarkably improved luminous efficiency and life-span characteristics compared with the organic light emitting diodes according to Reference Example 1 and Comparative Examples 5 to 10.

Manufacture of Organic Light Emitting Diode III

EXAMPLE 21

ITO (indium tin oxide) was coated to be 1500 Å thick on a glass substrate, and the coated glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 light emitting diode. The organic light emitting diode had a structure of five organic thin film layers and specifically ITO/Compound A 700 Å/Compound B 50 Å/Compound C (1020 A)/EML[BH113:BD370=95:5 wt %] 200 Å/Compound 13 50 Å/Compound D:Liq 300 Å/Liq 15 Å/Al 1200 Å.

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

EXAMPLE 22

An organic light emitting diode was manufactured according to the same method as Example 21 except for using Compound 10 according to Synthesis Example 2 instead of Compound 13.

COMPARATIVE EXAMPLE 11

An organic light emitting diode was manufactured according to the same method as Example 21 except for using no electron transport auxiliary layer.

Evaluation 3

The organic light emitting diodes according to Examples 21 and 22 and Comparative Example 11 were measured about a current density change, a luminance change, and luminous efficiency depending on a voltage.

Specific measurement methods are as follows, and the results are shown in Table 3.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(5) Measurement of Life-Span

T97 life-spans of the organic light emitting diodes according to Example 1 and Comparative Example 1 were measured as a time when their luminance decreased down to 97% relative to the initial luminance (cd/m$^2$) after emitting light with 750 cd/m$^2$ as the initial luminance (cd/m$^2$) and measuring their luminance decrease depending on a time with a Polanonix life-span measurement system.

TABLE 3

| Devices | Electron transport auxiliary layer | Luminous efficiency (cd/A) | Color coordinate (x, y) | T97 life-span (h) @750 nit |
| --- | --- | --- | --- | --- |
| Example 21 | Compound 13 | 7.3 | (0.132, 0.147) | 43 |
| Example 22 | Compound 10 | 7.4 | (0.133, 0.151) | 40 |
| Comparative Example 11 | Not used | 5.8 | (0.135, 0.147) | 25 |

Referring to Table 3, the organic light emitting diodes according to Examples 21 and 22 showed remarkably improved luminous efficiency and life-span characteristics compared with the organic light emitting diode according to Comparative Example 11.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS 100, 200, 300: organic light emitting diode
105: organic layer
110: anode
120: cathode
130: light emitting layer
140: auxiliary layer
141: second auxiliary layer
142: first auxiliary layer

The invention claimed is:

1. An organic compound represented by Chemical Formula 1:

[Chemical Formula 1]

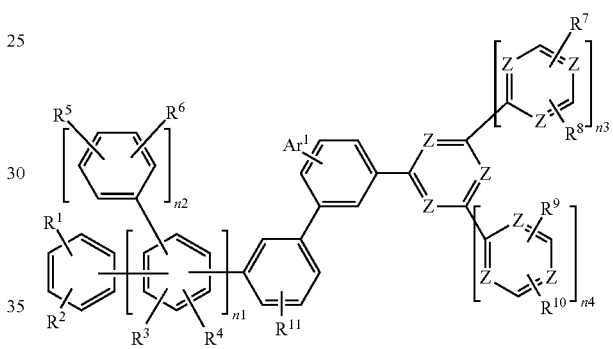

wherein, in Chemical Formula 1,

Z is independently N, C, or CR$^a$, at least one of Z's is N,

Ar$^1$ is a substituted or unsubstituted C6 to C12 aryl group or a substituted or unsubstituted C3 to C12 nitrogen-containing six-membered ring, R$^1$ to R$^6$, R$^{11}$, and R$^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof, R$^7$ to R$^{10}$ are independently hydrogen, deuterium, a substituted or unsubstituted C6 to C10 aryl group or a substituted or unsubstituted C3 to C12 heterocyclic group, R$^1$ and R$^2$ are independently present or linked with each other to form a ring, R$^5$ and R$^6$ are independently present or linked with each other to form a ring, R$^7$ and R$^8$ are independently present or linked with each other to form a ring, R$^9$ and R$^{10}$ are independently present or linked with each other to form a ring, n1 is an integer ranging from 1 to 5, n2 is an integer ranging from 0 to 2, and n3 and n4 are independently 0 or 1.

2. The organic compound of claim 1, wherein the organic compound is represented by Chemical Formula 1-I:

[Chemical Formula 1-I]

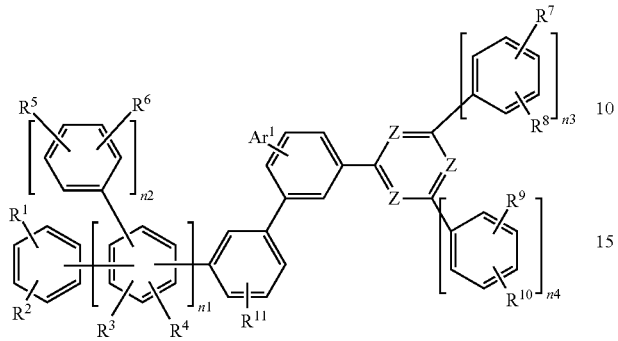

wherein, in Chemical Formula 1-I,
Z is independently N, C, or CR$^a$,
at least one of Z's is N,
Ar$^1$ is a substituted or unsubstituted C6 to C12 aryl group or a substituted or unsubstituted C3 to C12 nitrogen-containing six-membered ring,
R$^1$ to R$^6$, R$^{11}$, and R$^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof,
R$^7$ to R$^{10}$ are independently hydrogen, deuterium, a substituted or unsubstituted C6 to C10 aryl group or a substituted or unsubstituted C3 to C12 heterocyclic group,
R$^1$ and R$^2$ are independently present or linked with each other to form a ring,
R$^5$ and R$^6$ are independently present or linked with each other to form a ring,
R$^7$ and R$^8$ are independently present or linked with each other to form a ring,
R$^9$ and R$^{10}$ are independently present or linked with each other to form a ring,
n1 is an integer ranging from 1 to 5,
n2 is an integer ranging from 0 to 2, and
n3 and n4 are independently 0 or 1.

3. The organic compound of claim 1, wherein the organic compound is represented by one of Chemical Formula 1-B:

[Chemical Formula 1-B]

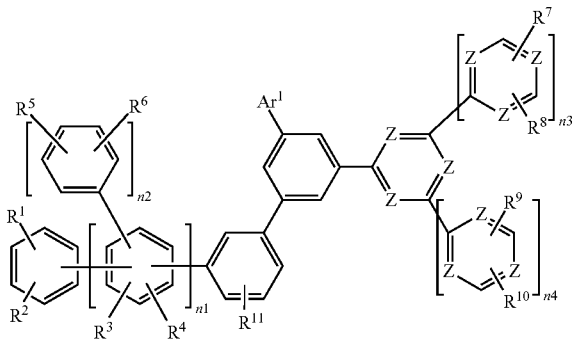

wherein, in Chemical Formula 1-B,
Z is independently N, C, or CR$^a$,
at least one of Z's is N,
Ar$^1$ is a substituted or unsubstituted C6 to C12 aryl group or a substituted or unsubstituted C3 to C12 nitrogen-containing six-membered ring,
R$^1$ to R$^6$, R$^{11}$, and R$^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof,
R$^7$ to R$^{10}$ are independently hydrogen, deuterium, a substituted or unsubstituted C6 to C10 aryl group or a substituted or unsubstituted C3 to C12 heterocyclic group,
R$^1$ and R$^2$ are independently present or linked with each other to form a ring,
R$^5$ and R$^6$ are independently present or linked with each other to form a ring,
R$^7$ and R$^8$ are independently present or linked with each other to form a ring,
R$^9$ and R$^{10}$ are independently present or linked with each other to form a ring,
n1 is an integer ranging from 1 to 5,
n2 is an integer ranging from 0 to 2, and
n3 and n4 are independently 0 or 1.

4. The organic compound of claim 1, wherein the organic compound is represented by one of Chemical Formulae 2 to 4:

[Chemical Formula 2]

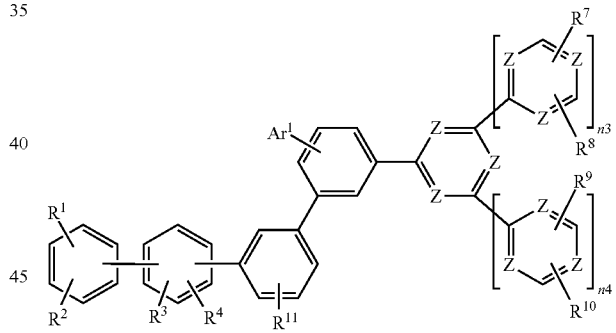

-continued

[Chemical Formula 3]

[Chemical Formula 4]

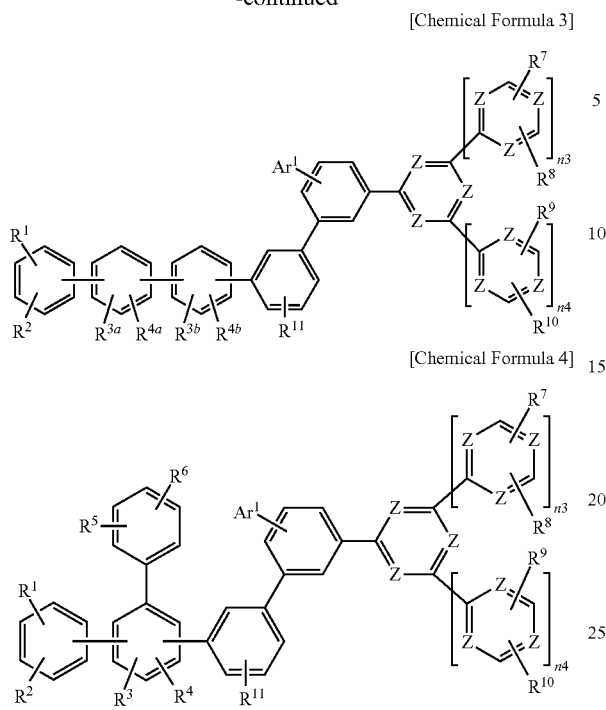

wherein, in Chemical Formulae 2 to 4,

Z is independently N, C, or CR$^a$, at least one of Z's is N,

Ar$^1$ is a substituted or unsubstituted C6 to C12 aryl group or a substituted or unsubstituted C3 to C12 nitrogen-containing six-membered ring, R$^1$, R$^2$, R$^3$, R$^4$, R$^{3a}$, R$^{4a}$, R$^{3b}$, R$^{4b}$, R$^5$, R$^6$, R$^{11}$, and R$^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof, R$^7$ to R$^{10}$ are independently hydrogen, deuterium, a substituted or unsubstituted C6 to C10 aryl group or a substituted or unsubstituted C3 to C12 heterocyclic group, R$^1$ and R$^2$ are independently present or linked with each other to form a ring, R$^5$ and R$^6$ are independently present or linked with each other to form a ring, R$^7$ and R$^8$ are independently present or linked with each other to form a ring, R$^9$ and R$^{10}$ are independently present or linked with each other to form a ring, and n3 and n4 are independently 0 or 1.

5. The organic compound of claim 4, wherein the compound represented by Chemical Formula 2 is represented by Chemical Formula 2a or 2b:

[Chemical Formula 2a]

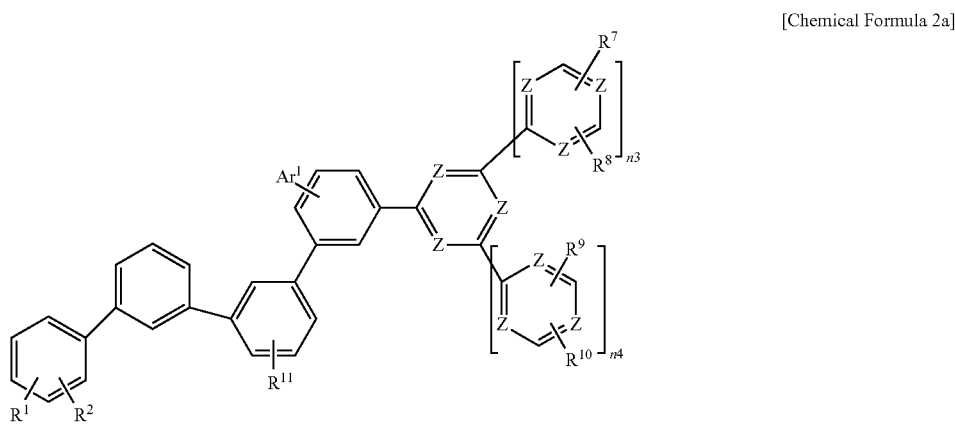

[Chemical Formula 2b]

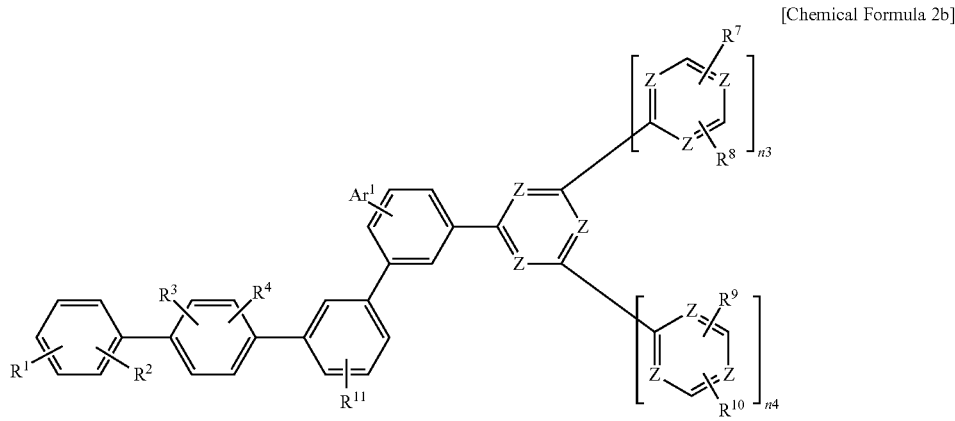

wherein, in Chemical Formulae 2a and 2b,

Z is independently N, C, or CR$^a$, at least one of Z's is N,

Ar$^1$ is a substituted or unsubstituted C6 to C12 aryl group or a substituted or unsubstituted C3 to C12 nitrogen-containing six-membered ring, R$^1$ to R$^4$, R$^{11}$, and R$^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof, R$^7$ to R$^{10}$ are independently hydrogen, deuterium, a substituted or unsubstituted C6 to C10 aryl group or a substituted or unsubstituted C3 to C12 heterocyclic group, R$^1$ and R$^2$ are independently present or linked with each other to form a ring, R$^7$ and R$^8$ are independently present or linked with each other to form a ring, R$^9$ and R$^{10}$ are independently present or linked with each other to form a ring, and n3 and n4 are independently 0 or 1.

6. The organic compound of claim 4, wherein the compound represented by Chemical Formula 3 is represented by one of Chemical Formulae 3a to 3g:

[Chemical Formula 3a]

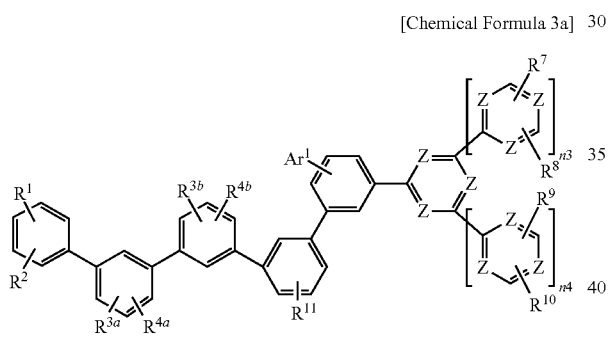

[Chemical Formula 3b]

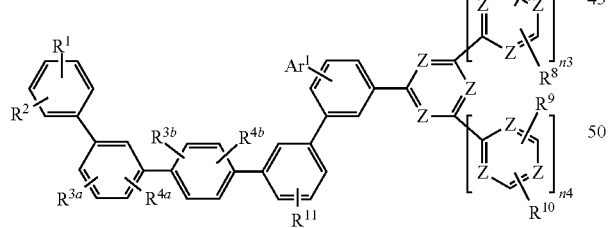

[Chemical Formula 3c]

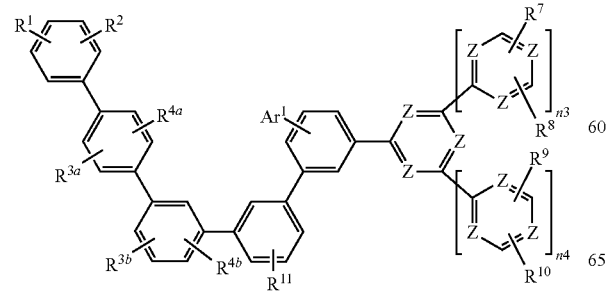

[Chemical Formula 3d]

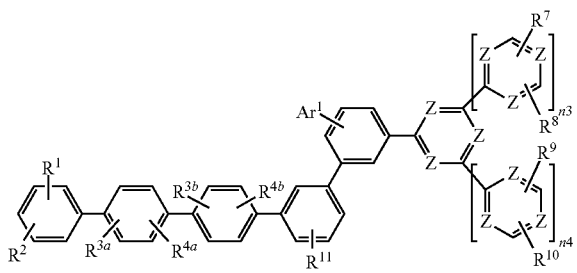

[Chemical Formula 3e]

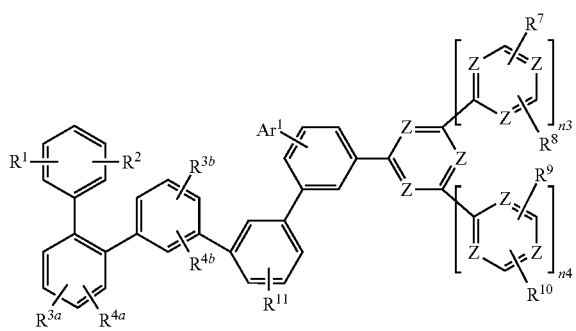

[Chemical Formula 3f]

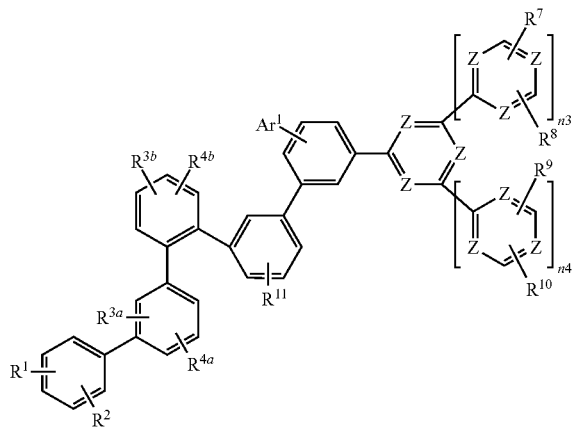

[Chemical Formula 3g]

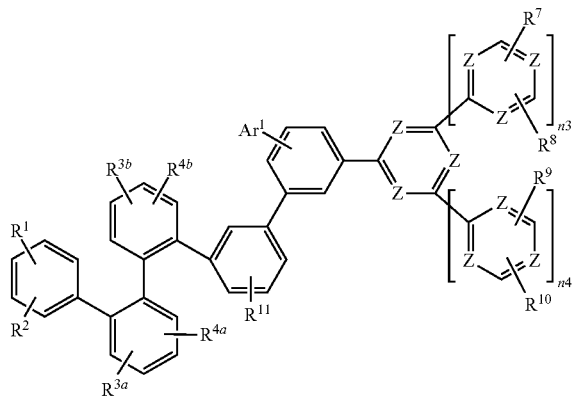

wherein, in Chemical Formulae 3a to 3g,

Z is independently N, C, or CR$^a$, at least one of Z's is N,

Ar¹ is a substituted or unsubstituted C6 to C12 aryl group or a substituted or unsubstituted C3 to C12 nitrogen-containing six-membered ring, $R^1$, $R^2$, $R^3$, $R^4$, $R^{3a}$, $R^{4a}$, $R^{3b}$, $R^{4b}$, $R^{11}$, and $R^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof, $R^7$ to $R^{10}$ are independently hydrogen, deuterium, a substituted or unsubstituted C6 to C10 aryl group or a substituted or unsubstituted C3 to C12 heterocyclic group, $R^1$ and $R^2$ are independently present or linked with each other to form a ring, $R^7$ and $R^8$ are independently present or linked with each other to form a ring, $R^9$ and $R^{10}$ are independently present or linked with each other to form a ring, and n3 and n4 are independently 0 or 1.

7. The organic compound of claim 4, wherein the compound represented by Chemical Formula 4 is represented by Chemical Formula 4a:

[Chemical Formula 4a]

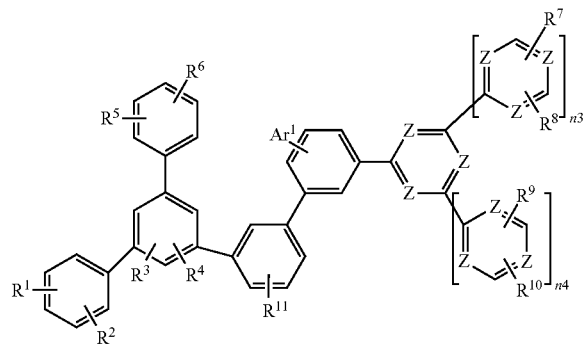

wherein, in Chemical Formula 4a,

Z is independently N, C, or $CR^a$, at least one of Z's is N,

Ar¹ is a substituted or unsubstituted C6 to C12 aryl group or a substituted or unsubstituted C3 to C12 nitrogen-containing six-membered ring, $R^1$ to $R^6$, $R^{11}$, and $R^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof, $R^7$ to $R^{10}$ are independently hydrogen, deuterium, a substituted or unsubstituted C6 to C10 aryl group or a substituted or unsubstituted C3 to C12 heterocyclic group, $R^1$ and $R^2$ are independently present or linked with each other to form a ring, $R^7$ and $R^8$ are independently present or linked with each other to form a ring, $R^9$ and $R^{10}$ are independently present or linked with each other to form a ring, and n3 and n4 are independently 0 or 1.

8. The organic compound of claim 1, wherein Ar¹ is a substituted or unsubstituted phenyl group, a substituted or unsubstituted biphenyl group, a substituted or unsubstituted naphthyl group, a substituted or unsubstituted pyridinyl group, a substituted or unsubstituted pyrimidinyl group, or a substituted or unsubstituted triazinyl group.

9. An organic compound selected from Group 1:
[Group 1]
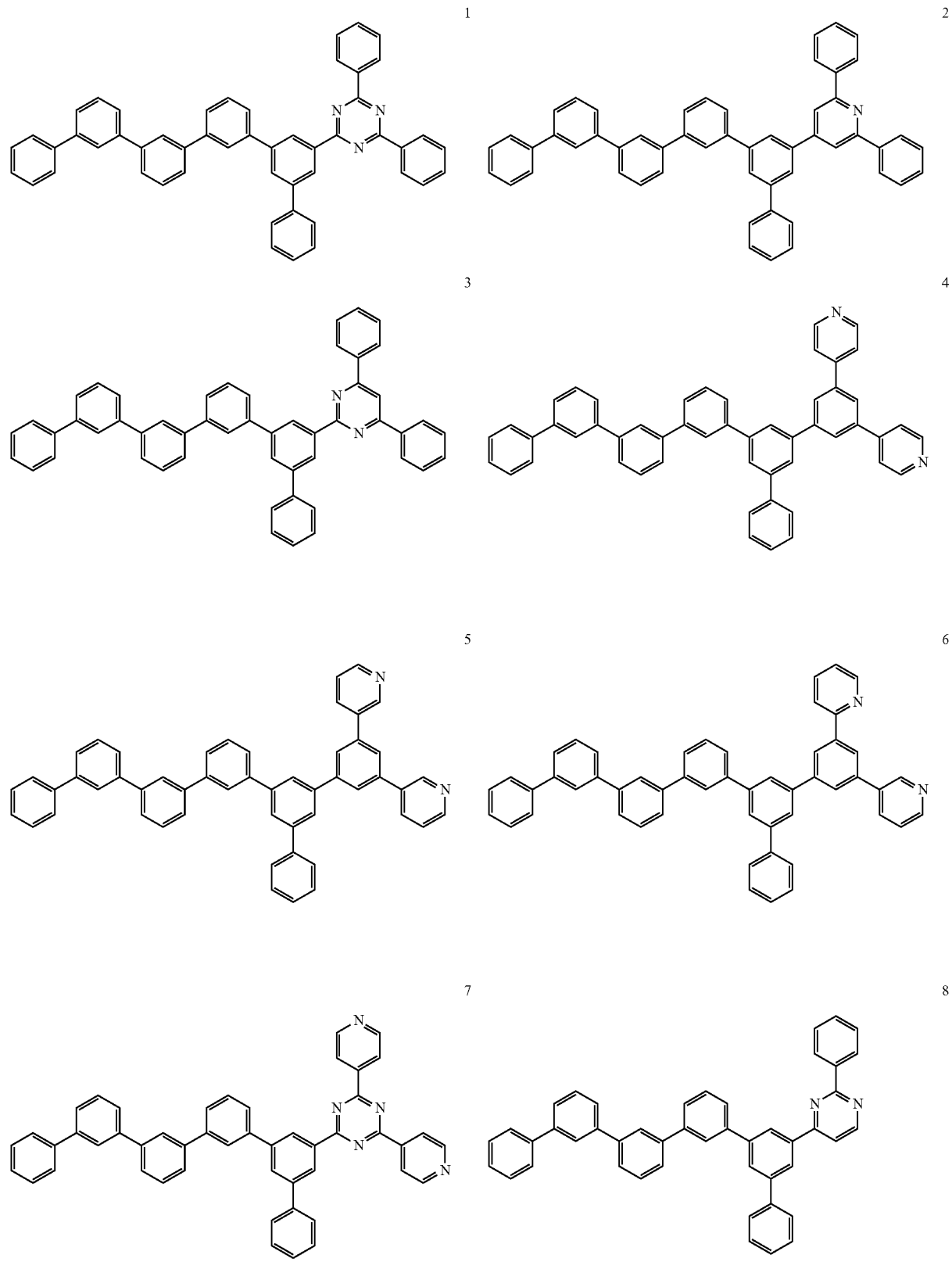

-continued
9
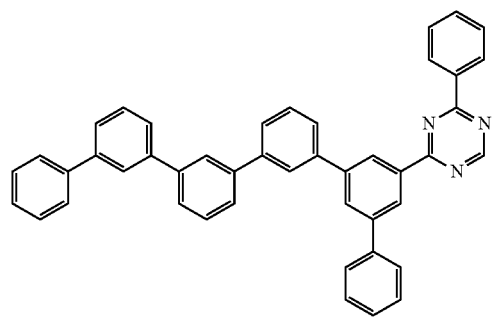
10
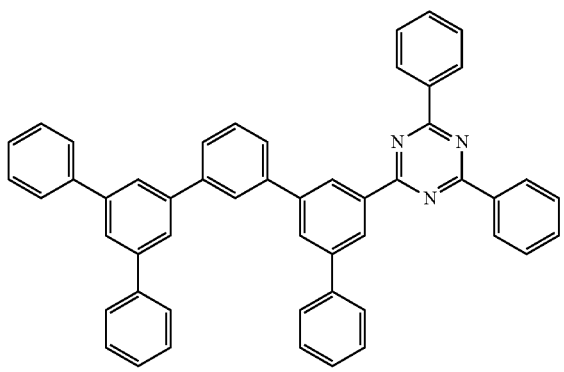
11
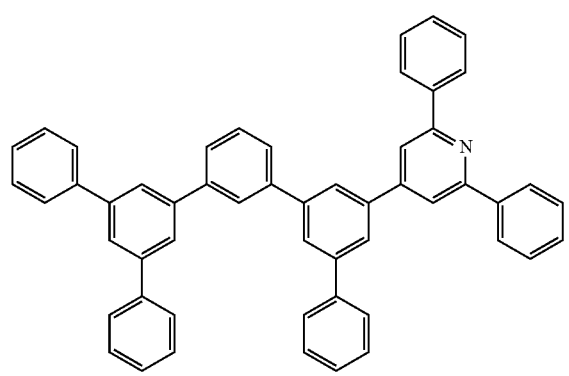
12
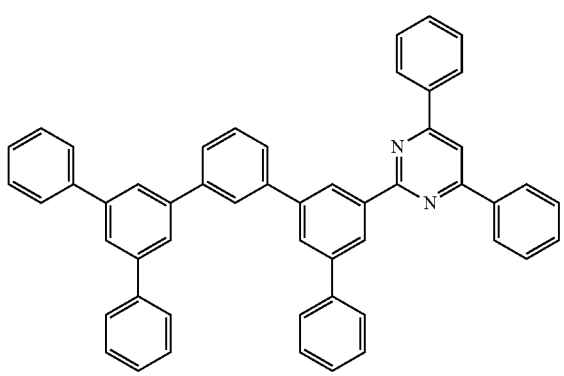
13
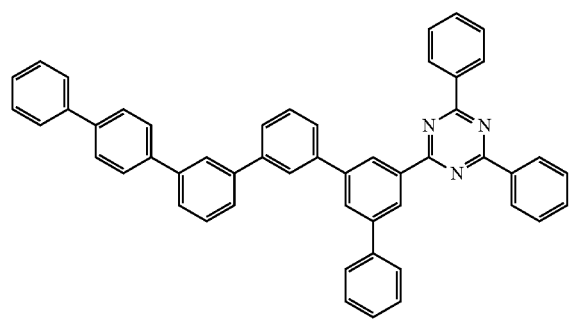
14
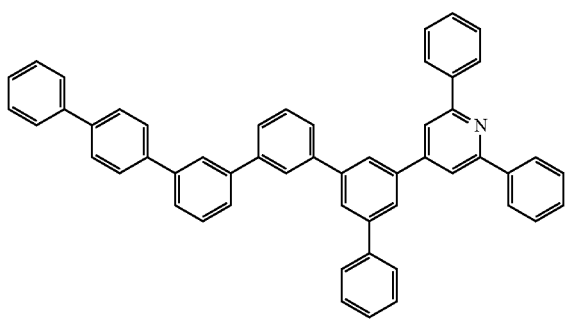
15
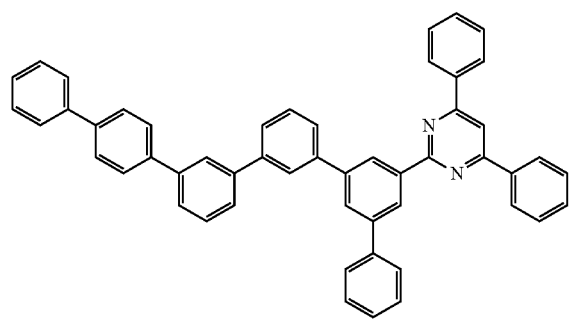
16
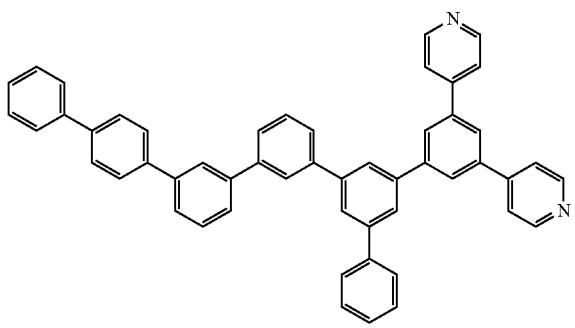

-continued
17
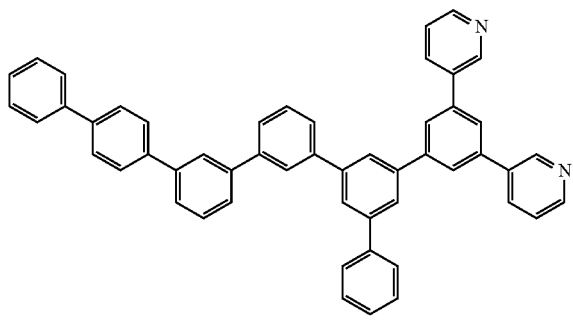
18
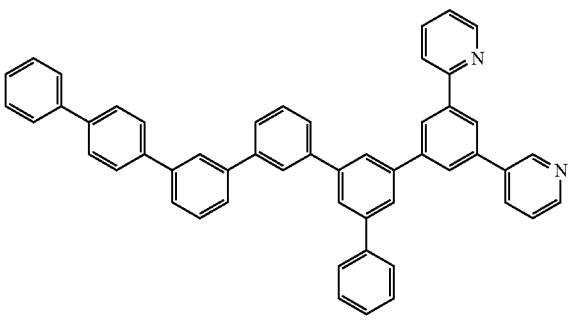
19
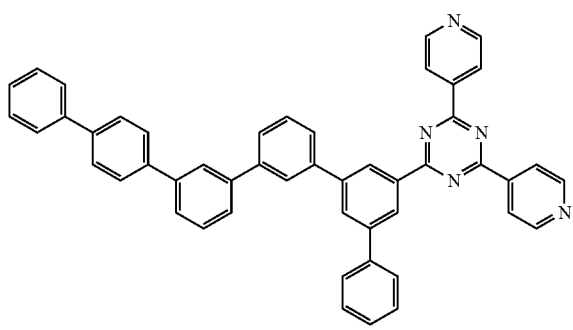
20
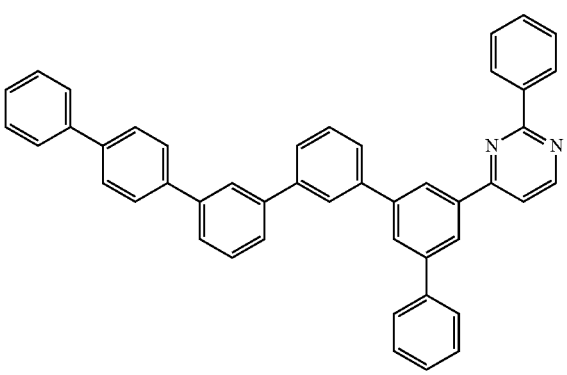
21
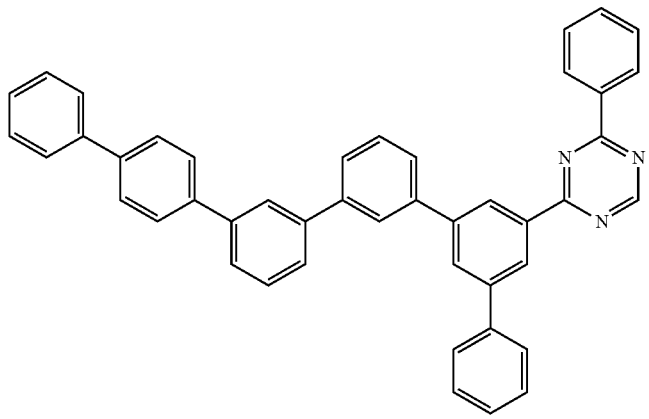
22
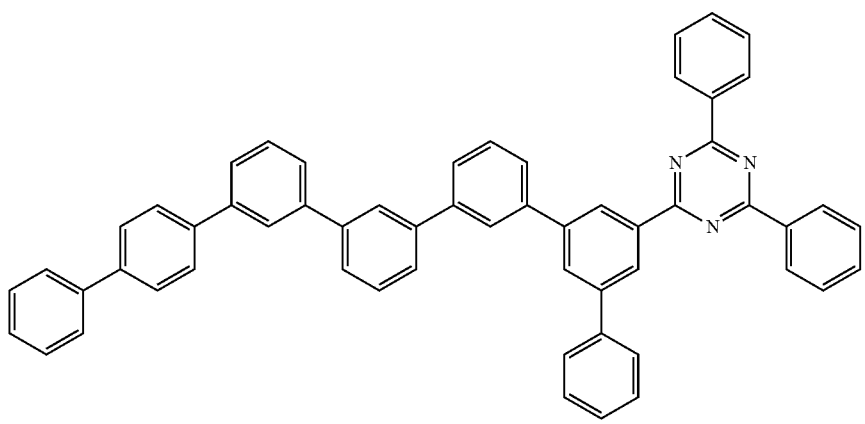

23
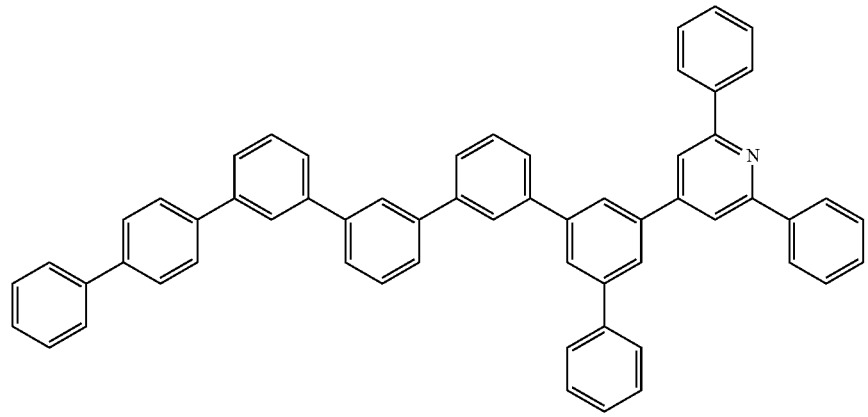
24
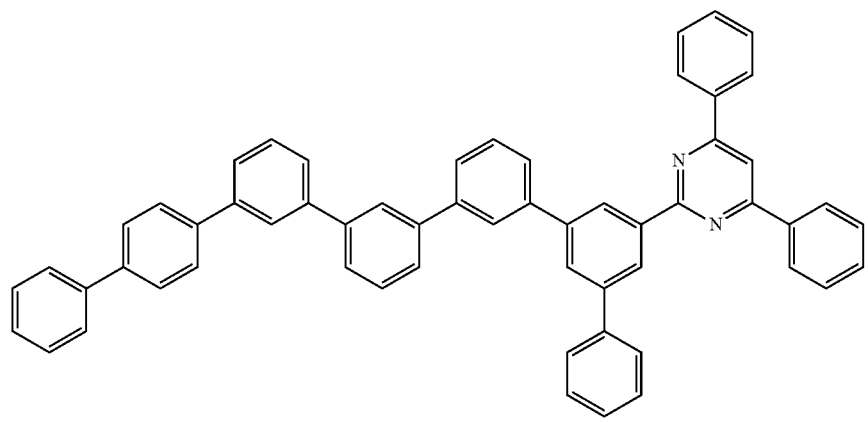
25
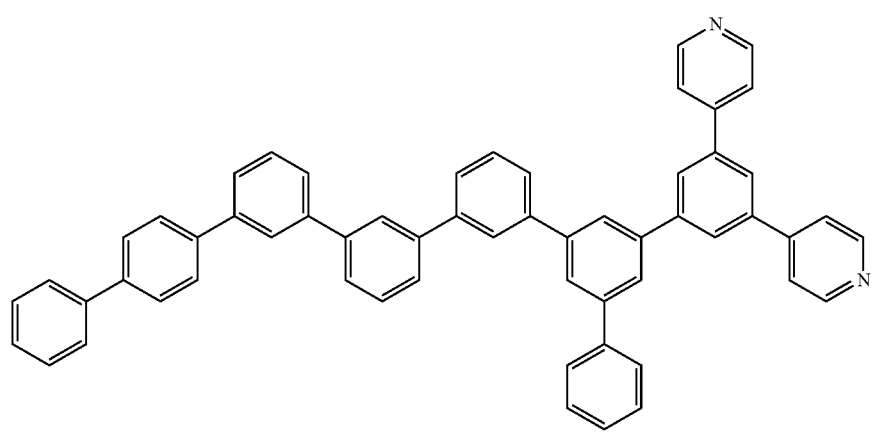

26
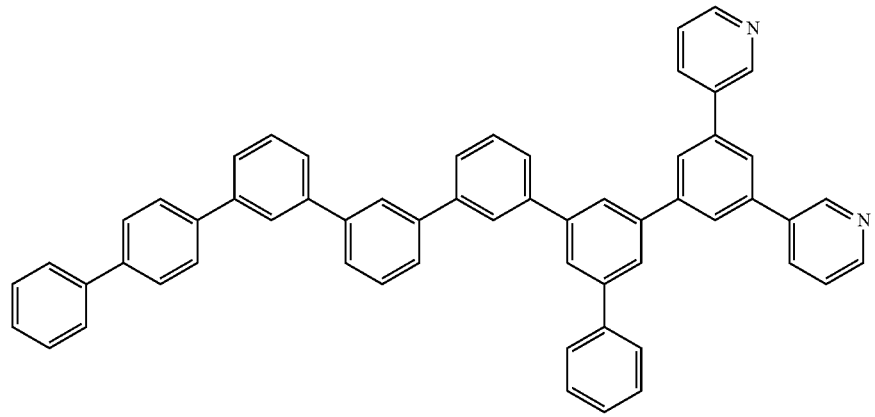
27
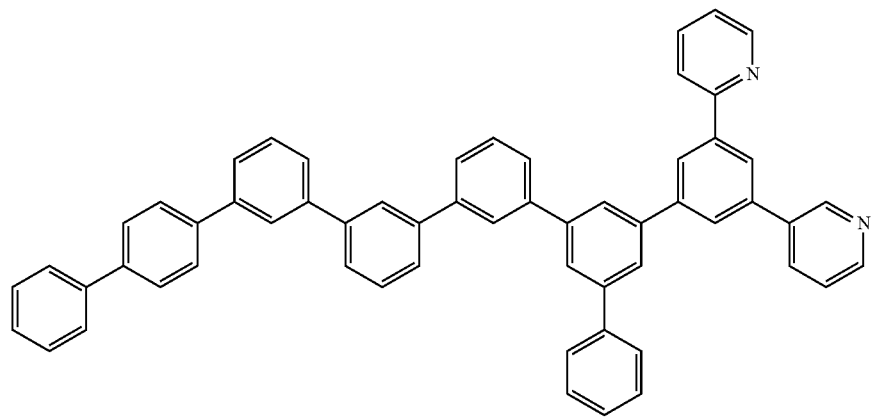
28
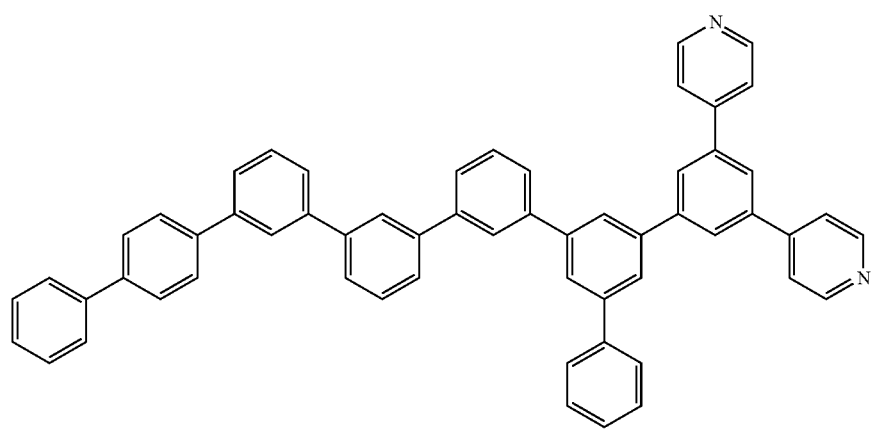

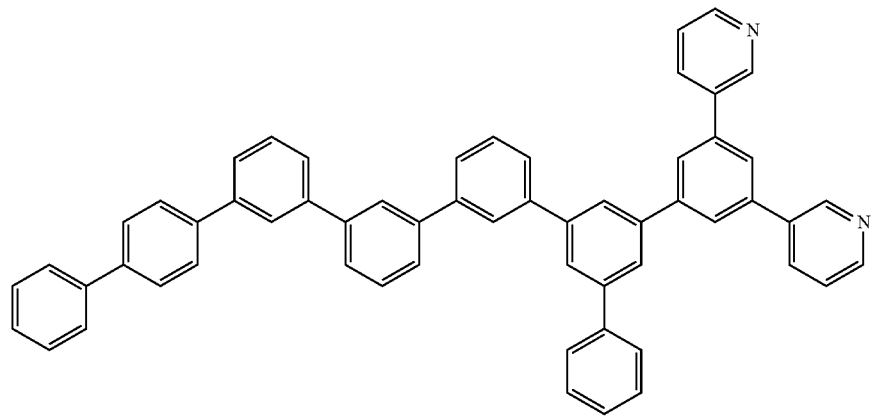
29
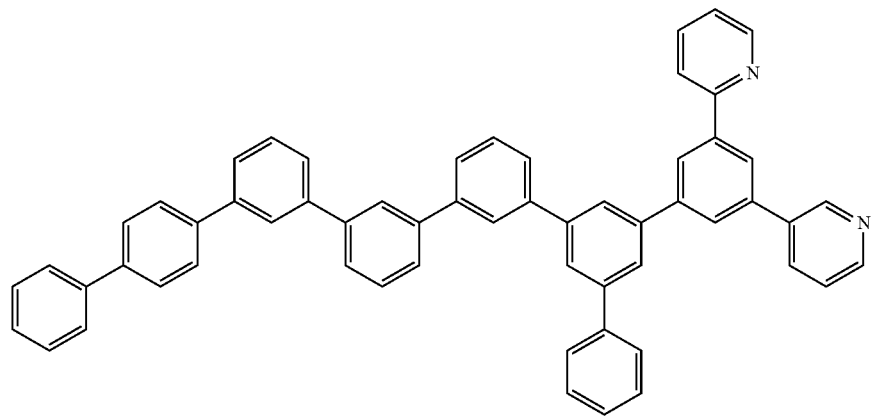
30
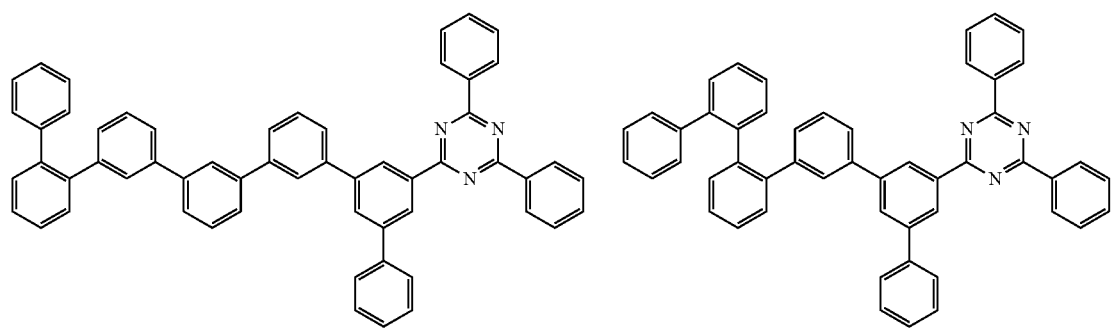
31 32
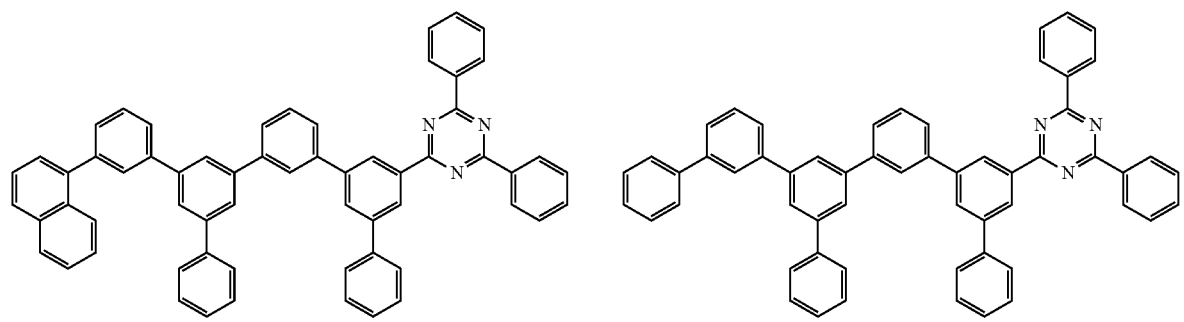
33 34

-continued
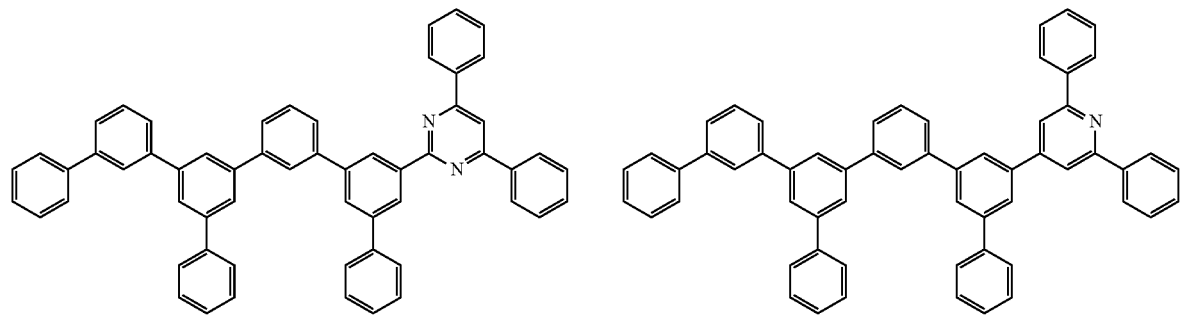
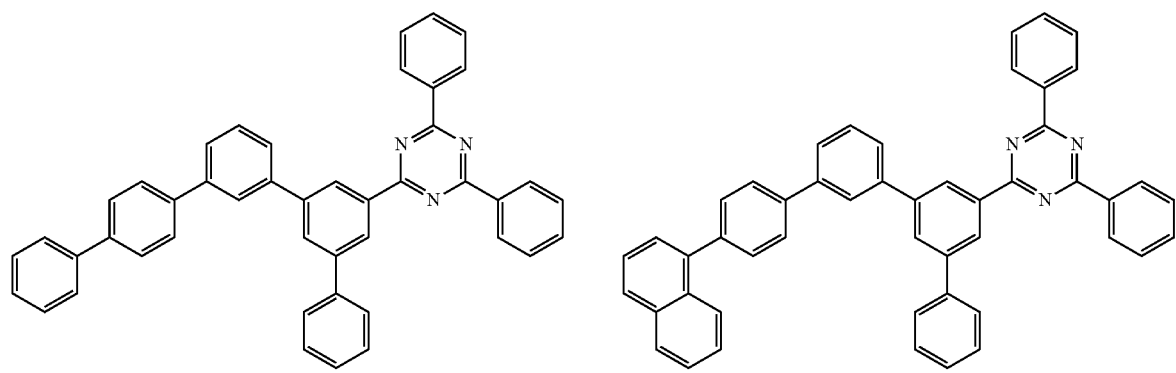
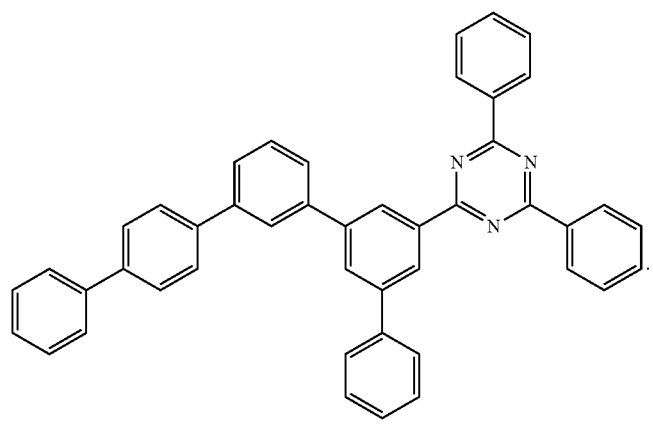

10. The organic compound of claim 1, wherein the organic compound is represented by Chemical Formula 1-II:

[Chemical Formula 1-II]

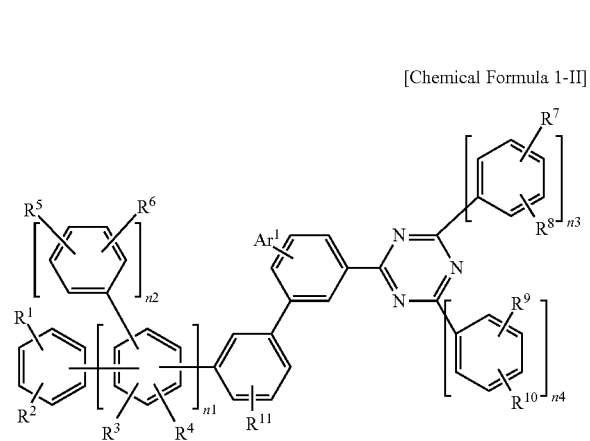

wherein, in Chemical Formula 1-II,
$Ar^1$ is a substituted or unsubstituted C6 to C12 aryl group or a substituted or unsubstituted C3 to C12 nitrogen-containing six-membered ring,
$R^1$ to $R^6$, and $R^{11}$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof,
$R^7$ to $R^{10}$ are independently hydrogen, deuterium, a substituted or unsubstituted C6 to C10 aryl group or a substituted or unsubstituted C3 to C12 heterocyclic group,
$R^1$ and $R^2$ are independently present or linked with each other to form a ring,
$R^5$ and $R^6$ are independently present or linked with each other to form a ring,
$R^7$ and $R^8$ are independently present or linked with each other to form a ring,
$R^9$ and $R^{10}$ are independently present or linked with each other to form a ring,
n1 is an integer ranging from 1 to 5,
n2 is an integer ranging from 0 to 2, and
n3 and n4 are independently 0 or 1.

11. The organic compound of claim 1, wherein the organic compound is represented by Chemical Formula 1-A:

[Chemical Formula 1-A]

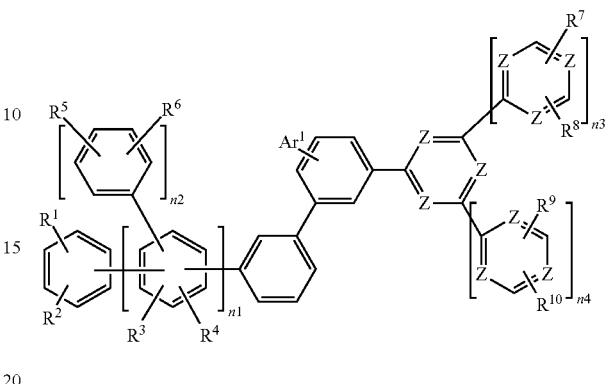

wherein, in Chemical Formula 1-A,
Z is independently N, C, or $CR^a$,
at least one of Z's is N,
$Ar^1$ is a substituted or unsubstituted C6 to C12 aryl group or a substituted or unsubstituted C3 to C12 nitrogen-containing six-membered ring,
$R^1$ to $R^6$ and $R^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof,
$R^7$ to $R^{10}$ are independently hydrogen, deuterium, a substituted or unsubstituted C6 to C10 aryl group or a substituted or unsubstituted C3 to C12 heterocyclic group,
$R^1$ and $R^2$ are independently present or linked with each other to form a ring,
$R^5$ and $R^6$ are independently present or linked with each other to form a ring,
$R^7$ and $R^8$ are independently present or linked with each other to form a ring,
$R^9$ and $R^{10}$ are independently present or linked with each other to form a ring,
n1 is an integer ranging from 1 to 5,
n2 is an integer ranging from 0 to 2, and
n3 and n4 are independently 0 or 1.

12. The organic compound of claim 1, wherein the organic compound is represented by Chemical Formula 1-C:

[Chemical Formula 1-C]

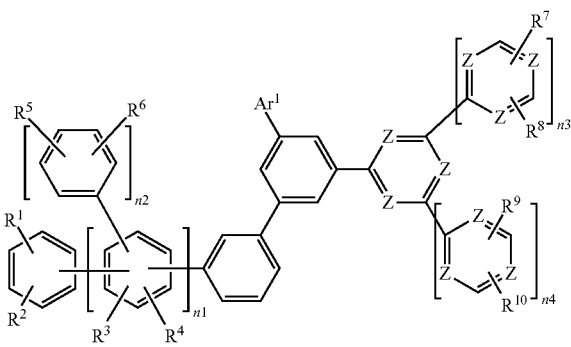

wherein, in Chemical Formula 1-C,

Z is independently N, C, or $CR^a$, at least one of Z's is N, $Ar^1$ is a substituted or unsubstituted C6 to C12 aryl group or a substituted or unsubstituted C3 to C12 nitrogen-containing six-membered ring, $R^1$ to $R^6$ and $R^a$ are independently hydrogen, deuterium, a substituted or unsubstituted C1 to C10 alkyl group, a substituted or unsubstituted C6 to C12 aryl group, a substituted or unsubstituted C3 to C12 heterocyclic group, or a combination thereof, $R^7$ to $R^{10}$ are independently hydrogen, deuterium, a substituted or unsubstituted C6 to C10 aryl group or a substituted or unsubstituted C3 to C12 heterocyclic group, $R^1$ and $R^2$ are independently present or linked with each other to form a ring, $R^5$ and $R^6$ are independently present or linked with each other to form a ring, $R^7$ and $R^8$ are independently present or linked with each other to form a ring, $R^9$ and $R^{10}$ are independently present or linked with each other to form a ring, n1 is an integer ranging from 1 to 5, n2 is an integer ranging from 0 to 2, and n3 and n4 are independently 0 or 1.

\* \* \* \* \*